United States Patent
Shen et al.

(10) Patent No.: US 7,109,019 B2
(45) Date of Patent: Sep. 19, 2006

(54) GENE CLUSTER FOR PRODUCTION OF THE ENEDIYNE ANTITUMOR ANTIBIOTIC C-1027

(75) Inventors: Ben Shen, Davis, CA (US); Wen Liu, Beijing (CN); Steven D. Christenson, Davis, CA (US); Scott Standage, Herts (GB)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/159,257

(22) Filed: May 31, 2002

(65) Prior Publication Data
US 2004/0161828 A1    Aug. 19, 2004

Related U.S. Application Data

(63) Continuation-in-part of application No. 09/478,188, filed on Jan. 5, 2000.

(60) Provisional application No. 60/115,434, filed on Jan. 6, 1999.

(51) Int. Cl.
*C12N 1/21* (2006.01)
*C12N 15/00* (2006.01)
*C07H 21/04* (2006.01)

(52) U.S. Cl. .............. 435/252.3; 435/252.35; 435/320.1; 536/23.2; 536/23.1; 536/23.7

(58) Field of Classification Search .............. 536/23.1, 536/23.2, 23.7; 435/252.3
See application file for complete search history.

(56) References Cited

U.S. PATENT DOCUMENTS 6,733,998 B1 * 5/2004 Thorson ................ 435/71.1

OTHER PUBLICATIONS

Liu et al. Genes for Production of the Enediyne Antitumor Antibiotic C-1027 in Streptomyces globisporus Are Clustered with the cagA Gene That Encodes the C-1027 Apoprotein. Antimicrobial Agents and Chemotherapy (Feb. 2000) 44(2): 382-392.*
Liu et al. Biosynthesis of the Enediyne Antitumor Antibiotic C-1027. Science (2002) 297: 1170-1173.*
Ando et al. (1998) "A New Non-Protein Enediyne Antibiotic N1999 A2: Unique Enediyne Chromophore Similar to Neocarzinostatin and DNA Cleavage" Tetra. Letts., 39: 6495-6480.
August et al. (1998) "Biosynthesis of the ansamycin antibiotic rifamycin: deductions from the molecular analysis of the *rif* biosynthetic gene cluster of *Amycolatopsis mediterranei* S699" Chem. Biol. 5: 69-79.
Bierman et al. (1992) "Plasmid cloning vectors for the conjugal transfer of DNA from *Escherichia coli* to *Streptomyces* spp" Gene 116: 43-69.

(Continued)

*Primary Examiner*—Nashaat T. Nashed
(74) *Attorney, Agent, or Firm*—Quine I.P. Law Group, PC.; Tom Hunter

(57) ABSTRACT

This invention provides nucleic acid sequences and characterization of the gene cluster responsible for the biosynthesis of the enediyne C-1027 (produced by *Streptomyces globisporus*). The pathway comprises a nonribosomal peptide synthetase (NRPS). Methods are provided for the biosynthesis of enediynes, enediyne analogs and other biological molecules.

7 Claims, 22 Drawing Sheets

C-1027 chromophore

Benzenoid diradical

OTHER PUBLICATIONS

Cane et al. (1998) "Harnessing the Biosynthetic Code: Combinations, Permutation, and Mutations" Science 282: 63-68.

Decker et al. (1996) "A general approach for cloning and characterizing dNDP-glucose dehydratase genes from actinomycetes" FEMS Lett. 141: 195-201.

Edo et al. (1985) "The Structure of Neocarzinostatin Chromophore Possessing a Novel Bicyclo[7,3,0]dodecadiyne system" Tetrahedron Lett. 26: 331-340.

Hensens et al. (1989) "Biosynthesis of NCS Chrom A, the Chromophore of the Antitumor Antibiotic Neocarzinostatin" J. Am. Chem. Soc. 111: 3295-3299.

Hopwood (1997) "Genetic Contributions to Understanding Polyketide Synthases" Chem. Rev. 97: 2465-2497.

Hu et al. (1994) "Repeated polyketide synthase modules involved in the biosynthesis of a heptaine macrolide by Streptomyces sp. FR-008" Mol. Microbiol. 14: 163-172.

Hu et al. (1988) "A New Macromelecular Antitumor Antibiotic, C-1027" J. Antibiot. 41:1575-1579.

Hutchinson and Fuji. (1995) "Polyketide Synthase Gene Manipulation: A Structure-Function Approach in Engineering Novel Antibodies" Ann. Rev. Microbiol. 49: 201-38.

Iida et al. (1993) "Synthesis and Absolute Stereochemistry of the Aminosugar Moiety of Antibiotic C-1027 Chromophore" Tetrahedron Lett. 34: 4079-4082.

Ikemoton et al. (1995) "Calicheamicin-DNA complexes: Warhead alignment and saccharide recognition of the minor groove" Proc. Natl. Acad. Sci. USA 92:10506-10510.

Katz and Donadio (1993) "Polyketide Synthesis: Prospects for Hybrid Antibodies" Ann. Rev. Microbiol. 47: 875-912.

Lam et al. (1993) "Biosynthesis of Esperamicin $A_1$, an Enediyne Antitumor Antibiotic" J. Am. Chem. Soc. 115: 12340-12345.

Lee et al. (1998) "Identification of Non Heme Diiron Proteins That Catalyze Triple Bond and Epoxy Group Formation" Science 280: 915-918.

Mao, et al. (1997) "isolation and Identification of Berberine from Cell Cultures of Coptis chinensis" Chinese J. Biotechnol. 13: 195-199.

Minami et al. (1993) "Structure of an Aromatization Product of C-1027 Chromophore" Tetrahedron Lett. 34: 2633-2636.

Myers et al. (1997) "A comparison of DNA Cleavage by Neocarzinostatin Chromophore and Its Aglycon: Evaluating the Role of the Carbohydrate Residue" J. Am. Chem. Soc. 119: 2965-2972.

Okuno et al. (1994) "Computer Modeling Analysis for Enediyne Chromophore-Apoprotein Complex of Macromolecular Antitumor Antibiotic C-1027" J. Med. Chem. 37: 2266-2273.

Otani et al. (1991) "Purification and Primary Structure of C-1027-AG, a Selective Antagonist of Antitumor Antibiotic C-1027, from Streptomyces globisporus" Agri. Biol. Chem. 55: 407-417.

Rao et al. (1987) "Cosmid Shuttle Vectors for Cloning and Analysis of Streptomyces DNA" Methods Enzymol. 153: 166-198.

Sakata et al. (1992) "Cloning and Nucleotide Sequencing of the Antitumor Antibiotic C-1027 Apoprotein Gene" Biosci. Biotech. Biochem. 56: 1592-1595.

Shen et al. (1999) "Bleomycin Biosynthesis in Streptomyces verticillus ATCC15003: A Model of Hybrid Peptide and Polyketide Biosynthesis" Bioorg. Chem. 27: 155-171.

Sievers et al. (1999) "Selective Ablation of Acute Myeloid Leukemia Using Antibody-Targeted Chemotherapy: A Phase I Study of an Anti-CD33 Calicheamicin Immunoconjugate" Blood 93: 3678-3684.

Sommer et al. (1997) "Genetic and Biochemical Characterization of a New Extracellular Lipase from Streptomyces cinnamomeus" Appl. Environ. Microbiol. 63: 3553-3560.

Spaink et al. (1991) "A novel highly unsaturated fatty acid moiety of lipo-oligosaccharide signals determines host specificity of Rizobium" Nature 354: 125-130.

Stassinopoulos et al. (1996) "Solution Structure of a Two-Base DNA Bulge Complexed with an Enediyne Cleaving Analog" Science 272: 1943-1946.

Takiff et al. (1996) "Efflux pump of the proton antiporter family confers low-level fluoroquinolone resistance in Mycobacterium smegmatis" Proc. Natl. Acad. Sci. USA 93: 362-366.

Thorson et al. (1999) "Enediyne Biosynthesis and Self-Resistance: A Progress Report" Bioorg. Chem., 27: 172-188.

Tokiwa et al. (1992) "Biosynthesis of Dynemicin A, a 3-Ene-1,5-diyne Antitumor Antibiotic" J. Am. Chem. Soc. 114: 4107-4110.

Xu et al. (1997) "Enediyne C1027 Induces the Formation of Novel Covalent DNA Interstrand Cross-Links and Monoadducts" J. Am. Chem. Soc. 119: 1133-1134.

Yoshida et al. (1993) "Structure and Cycloaromatization of a Novel Enediyne, C-1027 Chromophore" Tetrahedron Lett. 34: 2637-2640.

Zhen et al. (1989) "A New Macromolecular Antitumor Antibiotic, C-1027" J. Antibiot. 42: 1294-1298.

\* cited by examiner

```
1701  GTCACCGGCCCCGTGCTGCTCACCGAGTCCCGCGACCCTGACCTGACGCGGGGACTCTCCCTCGCGACCGTGCTGCCGGTGA  1800
       V  T  G  P  V  L  L  T  E  S  R  D  P  D  A  G  R  L  D  L  L  S  A  G  L  S  L  A  T  V  L  P  V  I

1801  TCTACGGACTGAAGGAGCTGGCCCGGACCGGGTGGGACCCGCTCGCCGCGGTGGTCCTCGGCGTGATCTTCGGCGCTGTTCGTCCAGCGCCA  1900
       Y  G  L  K  E  L  A  R  T  G  W  D  P  L  A  A  G  A  V  V  L  G  V  I  F  G  A  L  F  V  Q  R  Q

1901  GCGGCGGTTGGCCGACCCCATGCTGGACCTCGGCCTCTTCGCCGACCGGACCCTGCGCGCCGGGTCTCAGTCTGTCAACGGCGTCATCATGGGC  2000
       R  R  L  A  D  P  P  M  L  D  L  G  L  F  A  D  R  T  L  R  A  G  L  T  V  S  L  V  N  A  V  I  M  G
                                                                                                    SphI
2001  GGGACCGGACTGATGGTCGCCCTGTACCTCCAGACGATCGCCGGTCACTCCCCGTTGGCCCCGGACTGTGCCTGATCCCGGCCTGCATGCTGCTCGTCG  2100
       G  T  G  L  M  V  A  L  Y  L  Q  T  I  A  G  H  S  P  L  A  A  G  L  W  L  L  I  P  A  C  M  L  V  V

2101  TGGGCGTACAGCTGTCGAACCTGCTGGCCCGGATGCCCCTTCCCGGTGTCGTCCTCTACTTCGGCGGGCTCCTCATCGCCGCCGTCGGACAGCTCCTGATCAC  2200
       G  V  Q  L  S  N  L  L  A  Q  R  M  P  P  S  R  V  L  L  G  G  L  L  I  A  A  V  G  Q  L  L  I  T

2201  CCAGGTGGACACCGAGGACACGGCCCTCCTCATCGCGGCCACCACCCTGATCTACTTCGGCGCGGGCAGCCCGGTGGGCCCTCGGCGAGTTCGGAGTCTGG  2300
       Q  V  D  T  E  D  T  A  L  L  I  A  A  T  T  L  I  Y  F  G  A  S  P  V  G  P  I  T  T  G  A  I  M

2301  GGAGCCCGCCGCCCCCGGAGAAGGCGGGTCGCCGTGCGGCGGTCGAGTTCGGCGTGCCGCGCCATCGGCATCGCCGGGCTCGGCTCGCTGG  2400
       G  A  A  P  P  E  K  A  G  A  A  S  S  L  S  A  T  G  G  E  F  G  V  A  L  G  I  A  G  L  G  S  L  G

2401  GCACCGTCGTGTACAGCGCCGGGGTCGAGGTCCCGGACGCGGCCCTGCTGGACTCCGCGCGCGGCGCCGCGTTCACCAGCGGCGTGTCCGTGTCAGTCCGTGTGTTC  2500
       G  T  V  V  Y  S  A  G  V  E  V  P  D  A  A  G  P  A  D  A  D  A  A  Q  E  S  I  A  G  A  L  H  T  A

2501  CGGTCAGCTGGCCAGGCGCAGCGCCAGCGCCAGCGCGGGCGCCAGCGCCAGCGCCCGCCGCCGCTCTGCGCCCGTGTTC  2600
       G  Q  L  A  P  G  S  A  D  A  L  L  D  S  A  R  A  A  F  T  S  G  V  Q  S  V  A  A  V  C  A  V  F

2601  TCCCTGGCGCTCGCGTCCTCATCGCCGTGCTGCGGGACATTTCCGCTGATGGACCACGGCGAGAACGACGCTCAACCGG  2700
       S  L  A  L  A  V  L  I  G  T  R  L  R  D  I  S  A  M  D  H  G  H  G  E  E  P  A  E  N  D  A  Q  P  A

2701  CCACATGAGCGCACTTCCGGAGATGCAACGGCCGTCGAGGTATGAGGATCACCTTCCGGGGTGCACTGCACGGAGGCGTAGTGGAGTACT  2800
       C  H  M  *
       T  *

2801  GGAACAGCACGGCGGAGAACATGCCCCGCAGAACTCGAACAGTGGAAGTGCGCGCCATGACCGCCAGCTCCAGGCTTTCGCCCCTT  2900

2901  CTGGCGGGAACGACTCCCGAGAACATCACCTCCATGGCGCGACTACGGCGCGCGGTGCCCTCTCGCCAAGGCCGACCTCCTCCGCGCGAAGCCGCG  3000
                       BamHI                                                                    SacII
3001  TCTCCCCCTTACGGCCACCTGCCCTCGCCTGATCC                                                         3035
```

```
Gdh       1:~~~MFVLVTGGAGFIGSHYVRQLLGGAYPAFAGADVVVLDKLTYAGNEENLRPVADDPRF: 57
TylA2     1:~~~MFVLVTGGAGFIGSHFTGQLLTGAYPDLGATRTVVLDKLTYAGNPANLEHVAGHPDL: 57
SgcA      1:~~~MFMLVTGGAGFIGSQFVRATLHGELPGSEDARVTVLDKLTYSGNPANLTSVAAHPRY: 57
MtmE      1:MTTTSILVTGGAGFIGSHYVRTLLGPR..GVPDVTVTVLDKLTYAGTLTNLAEVSDSDRF: 58
consensus 1:   m vLVTGGAGFIGShy r  lL g  pa       v VLDKLTYaGn   NL  Va    prf:  60

Gdh       58:RFVRGDICEWDVVSEVMREVDVVHFAAETHVDRSILGASDFVVTNVVGTNTLLQGAIAA:117
TylA2     58:EFVRGDIADHGWWRRLMEGVGLVVHFAAESHVDRSIESSEAFVRTNVEGTRVLLQAAVDA:117
SgcA      58:TFVQGDTVDPRVVDEVVAGHDVIVHFAAESHVDRSIDTATRFVTNVLGTQTLLEAALRH:117
MtmE      59:RFVRGDICDAPLVDDLLAVHDQVVHFAAESHVDRSILGAADFVRTNVTGTQTLLDAALRQ:118
consensus 61:  FVrGDi  d    vv  evm    dvvVHFAAEsHVDRSI  a    FV TNV GTntLL  aAl    :120

Gdh       118:NVSKFVHVSTDEVYGTIEHGSWPEDHLLEPNSPYSAAKAGSDLIARAYHRTHGLPVCITR:177
TylA2     118:GVGRFVHISTDEVYGSIAEGSWPEDHPVAPNSPYAATKAASDLLALAYHRTYGLDVRVTR:177
SgcA      118:GVGRFVHVSTDEVYGSIASGSWTEDTPLAPNVPYAASKAGSDLMALAWHRTRGLDVVVTR:177
MtmE      119:CIETFVHISTDEVYGSIDAGSWPETAPVSPNSLYSAAKASSDLVALAYHRTHGLDVRVTR:178
consensus 121:gv kFVHvSTDEVYGsI  GSWpEd pl PNspY A KAgSDLiAlAyHRThGLdV vTR:180

Gdh       178:CSNNYGPYQFPEKVLPLFITNLMDGRRVPLYGDGLNVRDWLHVTDHCRGIQLVAESGRAG:237
TylA2     178:CSNNYGPRQYPEKAVPLFTTNLLDGLPVPLYGDGGNTREWLHVDDHCRGVALVGAGGRPG:237
SgcA      178:CTNNYGPYQYPEKVIPLFVTNLLDGLRVPLYGDGAHRRDWLHVSDHCRATQMVMNSGRAG:237
MtmE      179:CSNNYGSHQFPEKVIPLFVTSLLDGREVPLYGDGTNVRDWLHVDDHVRAIELVRTGGRAG:238
consensus 181:CsNNYGp  QfPEKvlPLFiTnllDG  VPLYGDG n RdWLHV DHcRgi  lV    GRaG:240

Gdh       238:EIYNIGGGTELTNKELTERVLELMGQDWSMVQPVTDRKGHDRRYSVDHTKISEELGYEPV:297
TylA2     238:VIYNIGGGTELTNAELTDRILELCGADRSALRRVADRPGHDRRYSVDTTKIREELGYAPR:297
SgcA      238:EVYHIGGGTELSNEELTGLLLTACGTDWSCVDRVADRQGHDRRYSLDITKIRQELGYEPL:297
MtmE      239:EVYNIGGGTELSNKELTQLLLDACGAGWDRVRYVTDRKGHDRRYSVDCTKIRRELGYRPA:298
consensus 241:eiYnIGGGTELtn ELT  vLe cG dws v  V DR GHDRRYSvD TKIr ELGY P  :300

Gdh       298:VPFERGLAETIEWYRDNRAWWEPLKSAPDGGK~~~~:329
TylA2     298:TGITEGLAGTVAWYRDNRAWWEPLKRSPGGRELERA:333
SgcA      298:VAFEDGLAATVKWYHENRSWWQPLKEAAGLLDAVG~:332
MtmE      299:REFGDALAETVAWYRHHRAWWEPLTRAYGAVAA~~~:331
consensus 301:    f  egLA Tv WYrdnRaWWePLk  a  gg         :336
```

Fig. 7

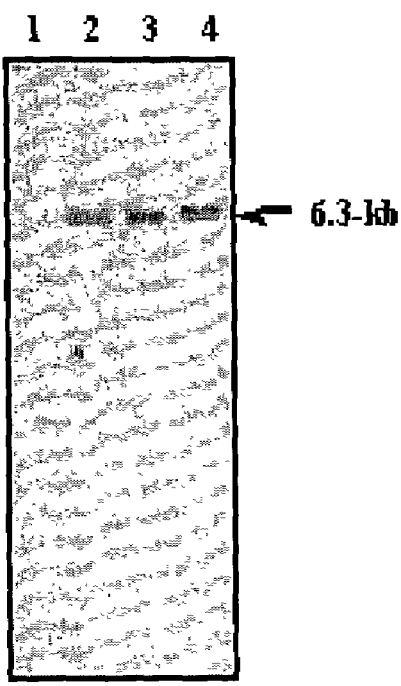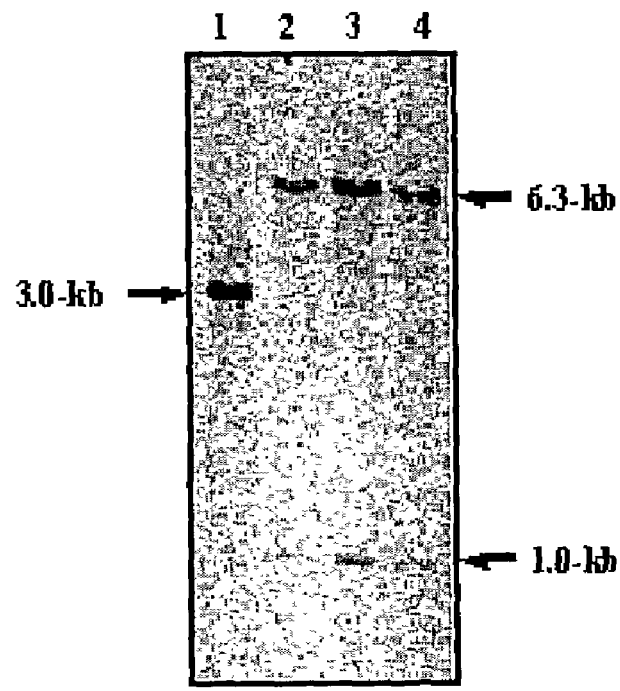
Fig. 8B                    Fig. 8C

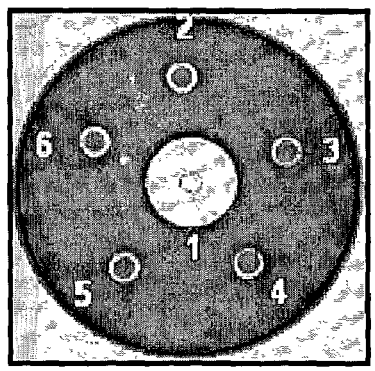 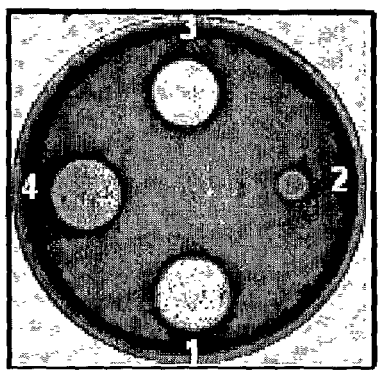 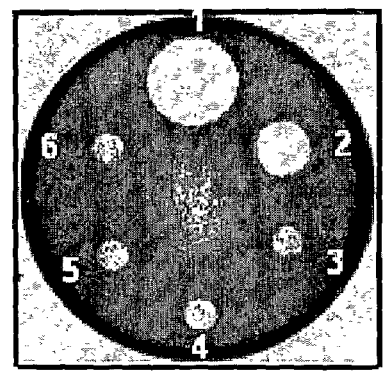
*Fig. 9A*  *Fig. 9B*  *Fig. 9C*
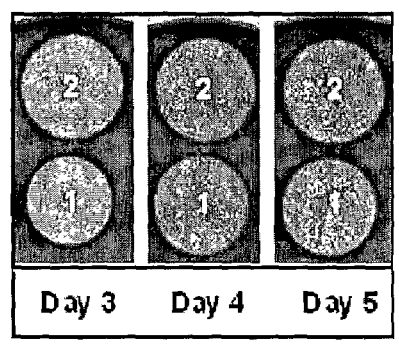
*Fig. 9D*

SEQUENCE LISTING

```
<160> NUMBER OF SEQ ID NOS: 207

<210> SEQ ID NO 1
<211> LENGTH: 42000
<212> TYPE: DNA
<213> ORGANISM: Streptomyces globisporus
<220> FEATURE:
<221> NAME/KEY: CDS
<222> LOCATION: (5982)..(7475)
<223> OTHER INFORMATION: orf(-2)
<220> FEATURE:
<221> NAME/KEY: CDS
<222> LOCATION: (13012)..(14076)
<223> OTHER INFORMATION: orf10
<220> FEATURE:
<221> NAME/KEY: CDS
<222> LOCATION: (15901)..(15960)
<223> OTHER INFORMATION: splice variant a
<220> FEATURE:
<221> NAME/KEY: CDS
<222> LOCATION: (25815)..(27167)
<223> OTHER INFORMATION: orf20
<220> FEATURE:
<221> NAME/KEY: CDS
<222> LOCATION: (27214)..(28590)
<223> OTHER INFORMATION: orf19
<220> FEATURE:
<221> NAME/KEY: CDS
<222> LOCATION: (29632)..(31194)
<223> OTHER INFORMATION: orf2
<220> FEATURE:
<221> NAME/KEY: CDS
<222> LOCATION: (31280)..(32587)
<223> OTHER INFORMATION: orf3
<220> FEATURE:
<221> NAME/KEY: CDS
<222> LOCATION: (32809)..(34389)
<223> OTHER INFORMATION: orf4
<220> FEATURE:
<221> NAME/KEY: CDS
<222> LOCATION: (36165)..(37487)
<223> OTHER INFORMATION: orf5
<220> FEATURE:
<221> NAME/KEY: CDS
<222> LOCATION: (37559)..(38935)
<223> OTHER INFORMATION: orf23
<220> FEATURE:
<221> NAME/KEY: CDS
<222> LOCATION: (38983)..(39261)
<223> OTHER INFORMATION: orf26

<400> SEQUENCE: 1
gtcgactcta gaggatcccg ggtgcggagt aggggttacg gacgaaggag gggtgcccgg      60
cgacgcctgc ggcgaagggc ggttccttga gttcgaggcc ggtggcgagg acgacgtggt     120
ccgcgtcgag gatctgcgtg tcggggagcg gcccagggcg cagcccctcg gtcaggtacg     180
gggtgaggcc cctgacggtc acctcgaagc agcggtcgtg ggaccgggcg tcgagcgcct     240
```

-continued

```
ccccgtccgc ttccacaagg acgacgccgg gacaggactc ccgtgcggcc tcgaccagtc      300
gggcgtcgag gtagtcctgg aagatgcggc ggggggcggg gccctgttcg gtgaacttcc      360
acgaagccca gcgccggggc cagtcgcgcc ggtcggcctc ctggttggcc cagttgatga      420
agtcgagcac gtcctcgcgg aacaccgaca tcctgccggc ctggatattg aagacgtggt      480 cccagggggtt gccgtcacgg tgataggcga cgccggccga gcgtaggcg gcgcgccgct      540 ccaggaggac gacttccagc ggtcttctcg cgaaatgaag caggcgtatc gcggtcgccg      600
tgcctgccag gcccgcccct acgaccagca ccctggggcg cgcacccgtc atgcccatga      660 agcctcccccc gctgactcag gcggcgcgt cgcgcgctcc cgtcggtgtc ctcgctgact      720
ggaagttccc tgacctggcg tcaactccac tgatccgtaa ggggatcgcg ggagtggata      780
cgggtcaggt cgtgcacgat cgtggcacca gacagatcac cacgtcgata ggcactcgtg      840
agccgcgccc ggggctcgac ggggcggggc accggcaggg gcggccgcgt gatcagccgg      900
agcctgtccg ggggcgtgcg tgcggggcgt cagctgtcga tgtcgggaac gccagggacg      960
tcgatctcgg tgcgggcgta gtggttgaag tagttggtgt agaggttcac ggccacgtgg     1020
acgaagacct cggcgagctc ggtgtccgtc catccctgtg ccacggccgc gttccacgag     1080
gcgtcagacg cctcgcccac ttcgccggcg atctccctgg ccacctggac cagtgcttcg     1140
agcttcacgt cgtcgccggg cgtccccgg cgaatcgcca cggtctcctc cagcgtgaaa     1200
cccgcgacct tcgccgacac cgtgtgcgcc gcctggcagt acgcgcacgc gtcgaccgcg     1260
cccacggcga gggcgatcgc ctcgcgtgtg cgggcgtcga acgttccatg ttcggcgacg     1320
gctccggtga tcgcggcgta ggtttccagg accacggggg aatgggccat tccccgtgg     1380 atgttgagca ctcgcccgaa ccgcttctcc agtcggcgca ggatgtctcc gccggctgcg     1440
ggtgcggtgt cgatggtgtg gacgggaatc cgcggcatgg gaatgcctct cctcgtagtg     1500
atgggagttc ctcgtccctc cagtctgccc aagcacctcc cccggtgagc tgtcccggcc     1560
gccctccggc cccttctagg caggtcgccc ggtggtgcgg ccccaggacg tcacctcgcc     1620
gcaccaccgg gagccccgag gggcgaggtc agaggccgag cacctcctcg gccagggcgg     1680
tgccccgaac acgggcctcg atcttggcga aggccaggtc gcgtgtggtg gaggtgtcgt     1740
cggcgaacgg ggagaagccg cagtcgtcgc aggttcccag ttgctcgacg gggatgtagc     1800
gggcggcgag caggatgcgg tcgcgtacct gctcgggggt ctcgaccact gggtcgatcg     1860
ggtcggtcac cccgaggaag acgcgggcgg caggggcag gtggtcacgg acgatgctca     1920
ggacccgctc ggggtccgct tcgccggcca gttcgagata gaagttgccc gccttgagct     1980
ggaagagctt gggcagcagt tcggcgtagt cgatgtcgag gctgtgcgtg gagtcctggt     2040
cgccgccggg gcaggtgtgt acgccgatgc gggcggtttc ctcggcgctg aagcgcccca     2100
ggacttcgtt gttgagggcg atgaagtcgt cgaggacgcc gccgctgggg tcgagcttga     2160
gggacagccg cccctcggtg aagtcgagct ggaccacgtg tgcccccgcg tccaggcagc     2220
ctcggatgtc ggcttcggcc tcgtcggcga ggtcgcgcag gaactgctcg cggggtagc     2280 cctcgatggg agtggcgggg tagaggaggc tgagggcgga gggtgcgatg accgcctgct     2340
tcagggggcg gtccgtgagc tgccgtgcgg cgcgcagata ggtttcggcc gcacctggt     2400 agcggaaggg cccttgggtg atgctgggga gctgccgggt gtgccgtctg cgaaggggga     2460
tgacagcgcc gtcgggcgag agggtgtcga ggccggtcac ggggtaggtg gcgaagctcg     2520
gcttggactg ttcaccgtcc acgaggacgg ggctgccgac tcgttccagt cgtgtcaggg     2580
tgtccgcgac ggcctgttcc tgctgtttgg ccaggtccgt ggcgtccagg gttccctggg     2640
```

-continued

```
catgcgcggc aagggcgtgc aggagtgtcg cggagcgcgg aaggctgccg atcggctcag      2700
tggcgatggt catggccgaa gagtagggaa gaggctgggt ttcgaaccac cgcaaagctt      2760
tgattgccgc tttttcaggg gaagttgatg cgaagtcgcc gagcggcgga acgtgctgat      2820
gtatgggggg cggaggagc ctgcggggtt ctaggagccg gtcgcggcca cggtggagga       2880
ggtgcccagc tgggagcggg gggtcttttc gccgacgcgg ttgggctcga tggtgcgggg      2940
gtcgacggcc tctccggggg caccttgccg gtagacgcct tcgggtcgg agtcccggtc       3000 atggggagc aggaagaaga cccggcgccg gtacagaccg ctgtccgggt ccgcttcggc       3060
gtcggccccg agttcgatgt agccgatcat gcggccgtcg cgggcgtagc gcggcttgtt      3120
cttgcgccgg ggggtcttgt ccagggcctg gcggacgtag tcgagtccct cgggatcttc     3180
gagccacacg accttcgcct cgtgaacgag atcgctgtcg gtcagtagcg agctcatggc      3240
ggcgacctct ccttcgtcgg cgtgcaccgg gtggggaagc ggtgcctgcg tgatgtgtgt      3300
tcgtctgcgg cggtgggccg cagtggtgcg gaccgcccgt ggtgccggtt ctcggccaaa     3360
gcacgggcag gtacgtcctg ggcactcac atcgtagatg gggtccgctt ccgcagggca      3420
gtgcctccgg tcggaggacg ttcattcgtc ggctgccaga gcgaggttgg ggtagaactt     3480
ccggccgttg gatttgatca tgtcggcagg tgaggcgagg cccacttcct ggcggacccg     3540
ggtggcgaag gcacgggcgg tcccggggcg gatgccttca ctgtgtgcgc accaggtgct     3600
gtaggacgtg tagagaaggc cctgttcgac gcgtagctcg ctgttctcgg ggtcgtggag     3660
gcagcactcg gcgaggaagc ggccgatgtg gtcctcggtg ttcgcgtatg cgctggtggc     3720
gatgcggacc cggtcggggc cggcgagtgt gtcgcgggtg gcgaggtagc ggcgggcccc     3780
ttcggtgagc cagtgcagga tcccggggcc ctcgtcctgg acgagttcga cagccaggtt     3840
gtcgatcttg cgttcgtcgg ggacgatccg ttcgaagggc aggaggcgga tgcggcgcca     3900
gaaggcgaag ccgccggtgg agacctcggg gcggtggttg cccagcagcc acagcttgtg     3960
cgtgggtgtg aaggagaaat agtcctgccg catgcggcgg gccttgatct tgtcaccgcc     4020
ggtcagcagg cggacgcgcg cctcgtcgaa gcggtcgttg ggcttgagct cgctgcacac     4080
gatgaggcgg cggccgtgga gttcggtgag ctcggtggag tgttcggagt atgcgccacg     4140
gtccatgagg aaacccggcg gggctgcgtc ggcgtagtcg ccgagaatct ggatcatcac     4200
gtcgaggaga acggatttgc cgttctttcc ctggccgtgg agaaagggca gcacctgcgc     4260
cccgacgtca ccggtgatgg agtagccgag aaggaggtgg aggaagtcga tcatctcccg     4320
cccttcggcg tcactgccga aggtgtcttc gaggaaacgg tgccagcggg gggtggggat     4380
gtcctggggg gaggcgctgg tggcgcggga gtggaagtcc cggtgggt cgggcttgcg       4440 catacggccg ttgcggaggt cgaccactcc gtcagggtg cacagggcgt aggggtctcc      4500
gtcgagggtg tcgggatcga gggagaggtc gggagaggcc tttgcctggg tgaggagcgc     4560
cttcataccg gtcgtcgaca gggtgcggcg tttgtggtgg tgcagttccc ggtcggtgaa     4620
cagcccgcgg ggatcgctgc cgggcatctc ctccgccatc tctccggcag cccacagggc     4680
agctttctcg cctccggccc gcttccaccg gtagccgtcc caggagtacc agcccaggcc     4740
ctccacgtgc cggaactggt cacggtagag acggacgaag agcttggcgt tgccgcggtc     4800
ggtcaggctg gcgggaatct cgcccgcctc ccaggcggtc gcggcgacgg gggcctcggg     4860
agcggcctgg acaggagga gcggcgctgg ggcggggtg gtttcgaggg ccagcatctg       4920
ctgagcggcg gcagttgcgt caaagcgagg gccctcggcg ctgctgctca tggacgtcct     4980
```

-continued

| | |
|---|---|
| tcgagatgga gcggtcgggc ggtccccgct gcgggaacgg catgaatgat cttcccggtg | 5040 |
| cggacagagt gccaggggca gcgcatgtgc gggggggacaa cggcccgttt cggacgaggg | 5100 |
| ccggccgacg gggggaagca ggggccggca accgggtggc ggggcggcgt gagcgagggc | 5160 |
| acgagcggcc cggtacgggg ggaagggctc gtctctccgt ggggcggcac gttgtggtcc | 5220 |
| tcgtccgtca gcttgcgtct ggcttcagcc tcctgacccc caataaggcg aaagctgctg | 5280 |
| gtcaagcatc tttcgtgaca ctcggcgagg gactgaaggg actgtctttc ggaatgagtg | 5340 |
| taggggttg tcgggtgggg accgcgcctc gactccccgg cggacgggat ctgttcggtc | 5400 |
| ggtcccttgg gtccctcccc ggatcgcggc agggacccaa gggggcggtg cggcgggcgg | 5460 |
| tcggtgaggg gccccggtgg agggactgag ggtctgtatg gagcgataag agggtctgaa | 5520 |
| ggggcggaga gagtttcggt ccctgcgttg agtccctggt catcaccgca ggtcagaggg | 5580 |
| gttttgaggg gtgaaaaagg gactgaaggg actcaacttc cccattatga gctgagtaga | 5640 |
| agaaagcagt atgacgatat cggcgcctac atacgcgcgc gtacatagtg agcttataat | 5700 |
| gcggaagttg agtcccttca gtccctttc gtggggtcgt atccctctg actgcgttga | 5760 |
| ccgtcgccgc tccgcgcagg gaccgaagag ggaccaagtc cctgcgcggg gcgggcgacg | 5820 |
| gtaatcgtgc agtgccccct cccccgtttc ccacagcgag tcgtcgctcc cctgtgaggc | 5880 |
| cggagagggt cctagaaccc ctcaggggcc gttctgtggc cctctgggcc tcctcctggc | 5940 |
| catttacccc atggggcgc ttgggggcgt caggagggct t gtg agg gct ctg ccg | 5996 |
|                                                                                           Met Arg Ala Leu Pro | |
|                                                                                                   1                 5 | |
| gga agt ggc gga ttg cgc atg gca gga gat gcc ccg aca gcg gcc ggg<br>Gly Ser Gly Gly Leu Arg Met Ala Gly Asp Ala Pro Thr Ala Ala Gly<br>                10                  15                  20 | 6044 |
| aat cga cga tgt ccc ccg acc cct atc cag cgt ccg ctg atc ctc agg<br>Asn Arg Arg Cys Pro Pro Thr Pro Ile Gln Arg Pro Leu Ile Leu Arg<br>            25                      30                  35 | 6092 |
| agg cag acc ttg cag gct cca gaa gcg aag aac ggc cgg tcc ccg gag<br>Arg Gln Thr Leu Gln Ala Pro Glu Ala Lys Asn Gly Arg Ser Pro Glu<br>        40                      45                  50 | 6140 |
| cag ccg cag gaa gag cgg atc gtc ctg gac gta tgg ctg gcg aac tac<br>Gln Pro Gln Glu Glu Arg Ile Val Leu Asp Val Trp Leu Ala Asn Tyr<br>        55                      60                  65 | 6188 |
| ccg ttc ccc acc tat gac ggg cgt gac ttc ctc gct ccg ctg cgc gag<br>Pro Phe Pro Thr Tyr Asp Gly Arg Asp Phe Leu Ala Pro Leu Arg Glu<br>70                      75                  80                  85 | 6236 |
| cgg gcg gcg gag ttc gag cgc gcc cac ccc cga tac cgg gtc gac atc<br>Arg Ala Ala Glu Phe Glu Arg Ala His Pro Arg Tyr Arg Val Asp Ile<br>                90                  95                  100 | 6284 |
| aac ggc cac gac ttc tgg acc atc ccc gag aag gtg gcg cgc gcc acc<br>Asn Gly His Asp Phe Trp Thr Ile Pro Glu Lys Val Ala Arg Ala Thr<br>            105                  110                115 | 6332 |
| gcg gag ggc agg cct ccg cac ata gcg ggc tac tac gcc acc gac agc<br>Ala Glu Gly Arg Pro Pro His Ile Ala Gly Tyr Tyr Ala Thr Asp Ser<br>120                      125                  130 | 6380 |
| cag ttg gcg cgg gac gcg cgc agg ccc gac ggg aag ccg gtc ttc acc<br>Gln Leu Ala Arg Asp Ala Arg Arg Pro Asp Gly Lys Pro Val Phe Thr<br>135                      140                  145 | 6428 |
| tcg gtg gag gcc gcg ttg gcc ggc cgg acg gag ata ctg gga cac ccg<br>Ser Val Glu Ala Ala Leu Ala Gly Arg Thr Glu Ile Leu Gly His Pro<br>150                      155                  160                165 | 6476 |
| gtg gtg gtg gag gac ctc gac ccc gtg gtg cgc gac tcc tac tcg ttc<br>Val Val Val Glu Asp Leu Asp Pro Val Val Arg Asp Ser Tyr Ser Phe<br>                170                  175                  180 | 6524 |

```
ggg ggc gag ttg gtg tcg ctg ccg ctc acg gtc acc acc atg ctc tgc      6572
Gly Gly Glu Leu Val Ser Leu Pro Leu Thr Val Thr Thr Met Leu Cys
            185                 190                 195 tac gcc aac tcc tcc ctc ctc gcg cgc gcc ggt gtt ccg gag ttg ccc      6620
Tyr Ala Asn Ser Ser Leu Leu Ala Arg Ala Gly Val Pro Glu Leu Pro
        200                 205                 210 cgt acc tgg gat gag gtc gaa gca gcc tgc cag gcg gtg gcc agc gtc      6668
Arg Thr Trp Asp Glu Val Glu Ala Ala Cys Gln Ala Val Ala Ser Val
    215                 220                 225 gac ggg ggc ccc ggt cac gga atc acc tgg gcc aac gac ggc tgg gtt      6716
Asp Gly Gly Pro Gly His Gly Ile Thr Trp Ala Asn Asp Gly Trp Val
230                 235                 240                 245 ttc cag cag gcc gtc gcc ctt cag aac ggg gtg ctg acc gat cag gac      6764
Phe Gln Gln Ala Val Ala Leu Gln Asn Gly Val Leu Thr Asp Gln Asp
                250                 255                 260 aac ggc cgc tcc ggc tcc gcc acg acg gtg gac gtc aca tcg gac gag      6812
Asn Gly Arg Ser Gly Ser Ala Thr Thr Val Asp Val Thr Ser Asp Glu
            265                 270                 275 atg ctg gac tgg gtc cgc tgg tgg acg cac ctc cat gag cgc ggc cat      6860
Met Leu Asp Trp Val Arg Trp Trp Thr His Leu His Glu Arg Gly His
        280                 285                 290 tac ctc tac acg ggc ggg ccc tcg gac tgg ggc ggg gcg ttc gag gct      6908
Tyr Leu Tyr Thr Gly Gly Pro Ser Asp Trp Gly Gly Ala Phe Glu Ala
    295                 300                 305 ttc gtc cag cag aag gtc gca ttc acc ttc gac tcg tcc aag gcc gcc      6956
Phe Val Gln Gln Lys Val Ala Phe Thr Phe Asp Ser Ser Lys Ala Ala
310                 315                 320                 325 cgg gaa ctc atc cag gcc ggt gca cag gcc ggt ttc gag gtc gcg gtg      7004
Arg Glu Leu Ile Gln Ala Gly Ala Gln Ala Gly Phe Glu Val Ala Val
                330                 335                 340 ttc ccg ttg ccc agg aac gcg aag gcc ccg gta gcg ggc cag ccc gtc      7052
Phe Pro Leu Pro Arg Asn Ala Lys Ala Pro Val Ala Gly Gln Pro Val
            345                 350                 355 tcg gga gac tcc ctg tgg ctg gcc gcg gga ctc gac gag acc acg cag      7100
Ser Gly Asp Ser Leu Trp Leu Ala Ala Gly Leu Asp Glu Thr Thr Gln
        360                 365                 370 gac ggg ctg ctc gct ctc acc cag tac ctg atc agc ccg gcc aac gcc      7148
Asp Gly Leu Leu Ala Leu Thr Gln Tyr Leu Ile Ser Pro Ala Asn Ala
    375                 380                 385 gcg gac tgg cac cgc acc aac ggt ttc gta ccg gtg acc ggc gcg gcc      7196
Ala Asp Trp His Arg Thr Asn Gly Phe Val Pro Val Thr Gly Ala Ala
390                 395                 400                 405 ggg gaa ctg ctg gaa gcg aca ggc tgg ttc gac cgc cgg ccg cag caa      7244
Gly Glu Leu Leu Glu Ala Thr Gly Trp Phe Asp Arg Arg Pro Gln Gln
                410                 415                 420 cgg gtg gcc ggg gag cag ttg aag gcg tcc gac cgg tca ccg gcg gcg      7292
Arg Val Ala Gly Glu Gln Leu Lys Ala Ser Asp Arg Ser Pro Ala Ala
            425                 430                 435 ctc ggc gcg ctg ctc ggc gac ttc gcg gcc gtc aac gag gtc atc acc      7340
Leu Gly Ala Leu Leu Gly Asp Phe Ala Ala Val Asn Glu Val Ile Thr
        440                 445                 450 gca gcg atg gac gat gtc ctg cgc agt gga gcg gac ccc gcg aag gcc      7388
Ala Ala Met Asp Asp Val Leu Arg Ser Gly Ala Asp Pro Ala Lys Ala
    455                 460                 465 ttc gcc gaa gcc ggc gtg gcc gcc cag caa ctg ctc gat gcc tac aac      7436
Phe Ala Glu Ala Gly Val Ala Ala Gln Gln Leu Leu Asp Ala Tyr Asn
470                 475                 480                 485 gcc cgg aac cgc tcc gga tcc ggg acc ccc tcc gcc gtc tgagatccgg      7485
Ala Arg Asn Arg Ser Gly Ser Gly Thr Pro Ser Ala Val
```

-continued

|     | 490 | | 495 | | |     |
|---|---|---|---|---|---|---|
| taccggggca | caggggcgcc | gccgcccgct | ttcccggcgg | ggcactggcc | ggggggacatg | 7545 |
| ctctcccgcc | cccggcagga | cgtagggtca | acccgcctgc | gccttcaggt | ggcggcgcag | 7605 |
| atactcaccg | gtcagggagg | aatccgcggc | gagcaggtcc | ttcggtgtgc | cggtgaagac | 7665 |
| gatctcgccg | ccctcccgtc | ccccgtcggg | acccaggtcg | atgatccagt | cggcctgctg | 7725 |
| caccacatcg | aggttgtgct | cgatgaccac | gacggtgttc | ccggcctcga | cgagcccgtc | 7785 |
| caggagcttc | agcagggtgt | caacgtccga | catgtgcagc | ccggtggtgg | gctcgtccag | 7845 |
| gacatagacc | gtgcccgtgc | ggtgcagctg | gtcggcaagt | ttgatccgct | gcagttcacc | 7905 |
| gccggagagg | ctggaaagcg | gctggcccag | gctgaggtac | ccaagaccga | cgtcgacgag | 7965 |
| agcgcgcagt | ttcggcagca | gggccttctc | ggtgaagaac | tcgacggcct | cgtcggcggg | 8025 |
| cagctccagg | acgtccgcga | tcgacttccc | gcgaagctgg | tgctccagga | cctcgggctt | 8085 |
| gaagcggcgc | ccctcacaga | caccgcagtg | cgtggtcacc | ggatccatga | aggccagctc | 8145 |
| ggtgatgatg | accccgcggc | cctggcactc | ctcgcacgac | cccttggagt | tgaagctgaa | 8205 |
| cagcgaggcg | ttcgcgccgg | tctccttcgc | gaacagcttg | cgcagcgggt | ccatcaggcc | 8265 |
| gaggtaggag | accggtgtgg | agcgcgacga | ggcggcgatc | gcggactggt | cgacaaagac | 8325 |
| cgcgtcgggg | tgcgcctcca | tgaatgcccc | ggagatcagg | ctgctcttgc | cggaacccgc | 8385 |
| caccccggtc | accgcggtca | gcacaccggt | gggcacggcc | acggagacct | gcttcaggtt | 8445 |
| gtggagatcc | gcgttctcca | cggtcagctc | ccccgtgggc | gggcggacct | cctccttcac | 8505 |
| gcgggccccc | cgccgcagag | cctccccggt | ccgggtcttc | gccttccgca | gcttcgcgaa | 8565 |
| ggaccccctcg | aacacgatct | cgcccccgtg | cactcccgcc | ccgggaccga | catcgacgat | 8625 |
| gtggtcggcg | atctcgatca | catcggggtc | gtgctcgacg | accagcacgg | tgttcccctt | 8685 |
| gtcgcgcagc | gcgcgcagca | ggtcgttgag | ccgccccacg | tcgcgcgggt | gcaggccgat | 8745 |
| gctgggctcg | tcgaagatgt | acgtgagccc | ggccagacca | ctgccgaggt | ggcgcaccat | 8805 |
| cttcagccgc | tgcccctcgc | ccccccgagag | gtcggccgtg | ggcctgtcca | gggtcaggta | 8865 |
| gccgagcccg | atggacacga | tccgctccag | ggccgtgcgc | gcggctttcg | cgagaggggc | 8925 |
| agcggccggc | tccgtgacgc | cggcgagcac | ctccgtgagg | tcgcggacct | ccatgctcga | 8985 |
| gtagtcggcg | atgttcttgc | cgtcgatccg | gacgtcgagc | gcggcggcgt | tgagccgcgc | 9045 |
| gccccggcag | gagggacaga | ctccgtcggt | gacgaaacgt | tcgatgacct | cgcgcttgcg | 9105 |
| gtcgctcagc | gcgctgaggt | cgcgcttgag | gttgagccgc | tcgaaccggt | cggccaaccc | 9165 |
| ctcgtagttc | gtctgaaact | cggtgctctt | ggtcttcagc | gtcaccttcc | cgccggtgcc | 9225 |
| gcgcagcagc | gtgtccagct | cctcggcgct | gtactcggcg | atcggcttgg | ccggatccag | 9285 |
| acggccggac | ttcgcccaga | tctgccagtc | cgggctaccc | accttgtact | cggggaaaag | 9345 |
| gaccgccccg | tcgtccaggg | acttcgagcg | gtccagcatc | ttgtccaggt | cgagggcgat | 9405 |
| gctctggccg | agaccgtcgc | agtccgggca | catgccctgg | gggtcgttga | acgagaacgc | 9465 |
| ggagacgccg | agcgaggacg | gcccgtcgtc | cttcgtcgtg | ccgaaccgtg | cgaacagggc | 9525 |
| ccggatcatc | ggctgtacgt | ccgtcatggt | ccccaccgtg | gaccgggcgt | gccccccac | 9585 |
| gggcttctgg | tcgacgatca | ccggggtggt | gaggttctcg | atcgcctcgg | cctgaggacg | 9645 |
| ttcgtacttc | ggaagctggt | tgcggatgta | ccagctgaag | gtggagttca | gctgtcgctg | 9705 |
| ggcctccacg | gccaccgtgt | cgaagacgat | cgacgacttg | cccgaacccg | agaccccccgt | 9765 |
| gaagaccgtg | atctggttgc | ggggaatcgt | cagggagaca | tctttgaggt | tgtggatccg | 9825 |

```
cgcgcccgcg atgcggatgc cgtctcccgg gccggatgtt tttcccgcgc cggcggtggg      9885
gtcggtgacg ctcacagagt tttcctcctg gcttccgtac atgatttacc cgtgtcagccg     9945
ggcaaaccgg cggaacggta accacctagc ttgtactcag gaggtgtccg gggtcttctc     10005
ctcccgtgct gacttggggg ccggcccgcc ggacagggcc ggctccgtgt tccaccccgc     10065
cagccgatcc ccccgctccg tctcgtcctc ctcgagaacg atccggctgc tcgcccagcg     10125
caggatcggc ggcgccgtca ccgaggtgat gagggcgacc agcacgatga tcgtgaaggt     10185
cacggtgtcc agtacgccga tacgcaggcc gaccagggcg atcaccacct cgatcattcc     10245
acgcgagttc atccccgctc cgagcgccag cccctcgtag cggctcatcc cgccactacg     10305
ggcggcgacg tacgcaccgg cgaacttgcc gaaagtggcc accaacagca ccccgaggcc     10365
cgtgagcagc accgacggct ccgcgagtgc ggtcaggtcc atgcgaagcc ccacactgcc     10425
caggaacacc ggtgcgaaca cggccatgac cagcgtgcgc agcggggcga gccgtaccgg     10485
ggcgatgtgc ctcagcaggg tcgcaccggc cacgaacgcc ccgaacaacg cctccatccc     10545
ggccgccgcg gtcagcgccc cgtacaggac gaccacggcc acgccgacgg tgacggccga     10605
tacggggacc cggctgtcac ccgtacggga cagccgcctg ccgatcgggc cgcccaccgc     10665
acacgccgcg gcgacgaaga cggtcgtcca ggccatcgtg gtcaggacca cgggcccccc     10725
ggccgcccca ctcgccagcg ccgtcaccag agcgagcagc agccagccca ccgcgtcgtc     10785
gaacaccgct gccgcgatga gcagctggcc gacgttgcgg tgcgtcagat tcaggtcggc     10845
gagcgtcttg gcgatcaccg ggagggccgt gacacacatc gcgaccccga ggaacagcgc     10905
gaagacgccc cgctctccgg agtccgcgag cagcgaggcg gcaccaggt agccggtggc      10965
gatgcccagc cccagaggaa tcagaagacc cgccaggctg acccgggcgg ccagacccc       11025
gcgcttgcgc aggatccggg ggtcgaactg ggcacctgcg atggccacca gcagaaggac     11085
gccgaactgg cagaacgcgt cgagcaggtg cgcctgcgag atgtcctcgg gaaacagcct     11145
gccggaaagt cccggcgaga tctgccccag cagggtcggc ccgagcagta ccccgcggt      11205
cagctccccc accagcggcg gcagaccgat ccgggtcccc agccgtccca gaccgtaggc     11265
acaggcgagc aggaggccga cctggagcag gaagaccgtc agcggctccc cgcccagcgg     11325
cgacgtggct gcgagcacag ccacgtcagg accgcgcacc gggaacccag cccagcccgt     11385
ccgtcgacgc ggccagaccc ccctgcctca ccggtcgctc ggcccccgcc tcatccccca     11445
gaagagcccg tgcctgcagt gcggcgctct gctccatgag gcggcccacc acctttcccg     11505
gcacggcgcc gtgcggcccg tcggcgtcgc ccgcagcggt gtgcgtcatg ccggccatct     11565
cgtcggacgc ctcggagaac cgctgcctgg cccgggccgt gtcggcgaac tcgtcggagg     11625
agaccccgcc gatcagttcg acgaaggact gcaggtcgga gtccgcggtg ttggagatct     11685
tccgggcctg ccagaaatag gagtcctccg aatggtgcat gtcgtagaag ccgaccagga     11745
actcgtagaa gcggccgtac tccagccggt agcgggcctc gaactcctcg aacgcgctgg     11805
tctcgtcgac cgaccgtcc aggcaggagt tgagcgagcg cgctgccagc agtccgctgt      11865
aggtggcgag gtgcacccccg gaggagaaca ccgggtcgac gaagcacgcg gcatcccga     11925
ccagggccat gccggcgcc cagaacttcg tgttgctgta cgaccagtcc ttgcggaccc      11985
ggagctcgcc gtaggggccc tcggtcaccc gggtggcctc ggagagcttc tccgcgatca     12045
gcgggcaggc cgcgatgaac gactccatcg ccttctcggg gtcgcctgc accaggctcg      12105
ccgagtcccg gttcaccact gcgccgacac tcgtcagctc gggagacagg ggtatgtacc     12165
```

-continued

```
agaaccaccc gtgctcgaag gtgcaggtga agatgttccc ggagttcggc ttcggaagcc    12225
gcttgccgcc gttgaagtag ccgaacaggg ccaggttgcg gaagaagggc gagtactcgc    12285
gcttggcgcc cgacttcttg tacagccac cggtgttgcc ggaggcgtcc acgacgaaac     12345
gggagcccac ctcgtgctcg cgccctcgg agtcccggta cgcacgccc cgcacccggc      12405 cgtcctcggc cttgagcacg tcgaggacat cgctgttctc ccgcacctcg acaccgtgcc    12465
tgcgagcgtt gtcgagcagg atctggtcga acttcatgcg ctcgacctgg tacgcgtacc    12525
ccgtcgcccc cggcatccgg cgcgagacgg cgaagtcgaa cgtccacggt cggggttgg     12585 caccccactt gaacgtcccg ccgtgcttga tcgtgaaggc tgccttcttc agctcgtcgg    12645
agacaccgag gaggtgtgcg atgccgtgga cggtggaggg gaggagcgac tcaccgatct    12705
ggtagcgcgg gaaggtctcc ttctccagct ggagtacgcg atggcccgc ttgcggacca    12765 gcgtggagac ggtcgagccc gccggacctc cgccgaccac gatgacgtcg tactgcgctg    12825
acacgtccac ggactctcct tctcgcacat cgggcgtctc atattcccag gaatcctctg    12885
gcccgcccag gtgctgccgc atcttcggta ttgcgaagtc gtgggcattc tgcgagaagc    12945
atgaaccgcg tggcccggtc tacagtggcg tggaatttca gtgattgcgc tgaagggcgg    13005 cacacg atg aag gca ctt gta ctg tcg ggt ggt tcg ggg acc cgc ctg         13053
       Met Lys Ala Leu Val Leu Ser Gly Gly Ser Gly Thr Arg Leu
           500             505                 510 cgc ccg atc agt tac gcc atg ccg aag cag ctc gtt ccg atc gcc ggg       13101
Arg Pro Ile Ser Tyr Ala Met Pro Lys Gln Leu Val Pro Ile Ala Gly
    515             520                 525 aag cca gtc ctt gaa tat gtt ctg gat aat atc cgg aac ctc gat atc       13149
Lys Pro Val Leu Glu Tyr Val Leu Asp Asn Ile Arg Asn Leu Asp Ile
530             535                 540 aaa gag gtc gcc att gtc gtc ggt gac tgg gct cag gaa att att gag       13197
Lys Glu Val Ala Ile Val Val Gly Asp Trp Ala Gln Glu Ile Ile Glu
545             550                 555                 560 gca atg ggt gac ggc agc cgt ttc ggt ctg cgc ctc acc tac ata cgc       13245
Ala Met Gly Asp Gly Ser Arg Phe Gly Leu Arg Leu Thr Tyr Ile Arg
            565                 570                 575 cag gag caa cct ctg ggc atc gcg cac tgc gtg aaa ctg gcc cga gac       13293
Gln Glu Gln Pro Leu Gly Ile Ala His Cys Val Lys Leu Ala Arg Asp
        580                 585                 590 ttc ctc gac gag gac gac ttc gtc ctc tac cta ggc gac atc atg ctg       13341
Phe Leu Asp Glu Asp Asp Phe Val Leu Tyr Leu Gly Asp Ile Met Leu
    595                 600                 605 gac gga gac ctg tcc gcg cag gcg ggg cac ttc ctc cac acc cgc ccc       13389
Asp Gly Asp Leu Ser Ala Gln Ala Gly His Phe Leu His Thr Arg Pro
610                 615                 620 gcc gcg cgg atc gtc gtg cgc cag gtg ccc gac ccc cgg gcc ttc ggg       13437
Ala Ala Arg Ile Val Val Arg Gln Val Pro Asp Pro Arg Ala Phe Gly
625                 630                 635                 640 gtg atc gag ctg gac ggc gaa ggg cgt gtg ctg cgc ctg gtc gag aaa       13485
Val Ile Glu Leu Asp Gly Glu Gly Arg Val Leu Arg Leu Val Glu Lys
                645                 650                 655 ccc cgt gaa ccg cgc agc gac ctc gcg gcg gtc ggc gtg tac ttc ttc       13533
Pro Arg Glu Pro Arg Ser Asp Leu Ala Ala Val Gly Val Tyr Phe Phe
            660                 665                 670 acc gcg gac gtg cac cgc gcc gtc gac gcg att agc ccg agc cga cgg       13581
Thr Ala Asp Val His Arg Ala Val Asp Ala Ile Ser Pro Ser Arg Arg
        675                 680                 685 ggc gag ctg gaa atc acc gac gcc atc cag tgg ctg ctg gag cag ggc       13629
Gly Glu Leu Glu Ile Thr Asp Ala Ile Gln Trp Leu Leu Glu Gln Gly
    690                 695                 700
```

| | | | | | | | | | | | | | | |
|---|---|---|---|---|---|---|---|---|---|---|---|---|---|---|
| ctg | ccg | gtc | gag | gcc | ggc | cgc | tac | acg | gac | tac | tgg | aag | gac | acc | ggc | 13677 |
| Leu | Pro | Val | Glu | Ala | Gly | Arg | Tyr | Thr | Asp | Tyr | Trp | Lys | Asp | Thr | Gly |
| 705 | | | | 710 | | | | | 715 | | | | | 720 |

```
ctg ccg gtc gag gcc ggc cgc tac acg gac tac tgg aag gac acc ggc    13677
Leu Pro Val Glu Ala Gly Arg Tyr Thr Asp Tyr Trp Lys Asp Thr Gly
705                 710                 715                 720 cgg gtc gag gac gtc gtg gag tgc aac cgg cgg atg ctc ggc cgt ctg    13725
Arg Val Glu Asp Val Val Glu Cys Asn Arg Arg Met Leu Gly Arg Leu
                725                 730                 735 gcg ctc cag gtg tcg ggc gag gtg gac ccg gag agc gaa ctg gtg ggt    13773
Ala Leu Gln Val Ser Gly Glu Val Asp Pro Glu Ser Glu Leu Val Gly
        740                 745                 750 gcg gtg gtc gtc gag gag ggc gcc cgg gtg acg cgt tcg cgg gtc gtg    13821
Ala Val Val Val Glu Glu Gly Ala Arg Val Thr Arg Ser Arg Val Val
            755                 760                 765 gga cca gcg gtg atc ggc gcg ggc acg gtc gtc gag gac agc cag atc    13869
Gly Pro Ala Val Ile Gly Ala Gly Thr Val Val Glu Asp Ser Gln Ile
770                 775                 780 gga ccg tac gcc tcc atc ggc cgg cgc tgc acc gtg cgg gcg tcc cgg    13917
Gly Pro Tyr Ala Ser Ile Gly Arg Arg Cys Thr Val Arg Ala Ser Arg
785                 790                 795                 800 ctc tcc gac tcc atc gtc ctt gac gac gcc tcg atc ctc gcg gtg agc    13965
Leu Ser Asp Ser Ile Val Leu Asp Asp Ala Ser Ile Leu Ala Val Ser
                805                 810                 815 gga ctg cac ggc tcg ctg atc gga agg ggc gcg cgg atc gcg ccc ggg    14013
Gly Leu His Gly Ser Leu Ile Gly Arg Gly Ala Arg Ile Ala Pro Gly
        820                 825                 830 gcc cgg ggc gag gcc cgg cac cgg ctg gtc gtc ggc gac cac gtg cag    14061
Ala Arg Gly Glu Ala Arg His Arg Leu Val Val Gly Asp His Val Gln
            835                 840                 845 atc gag atc gcg gcc tgacgcaccc accggagcac cgggggagg ctcggcaggg     14116
Ile Glu Ile Ala Ala
    850 gcgtcaggcc gtaagaaggg ctgccggggc gggacggacc cgccccggca gcccacaggt  14176 ccccggtccg cggatatggg ggactcgagg ttcgatcagc cgaaggtcag agccacgtgg  14236 ccgaggtcga gcccggagtt gccggcgccg aggttacagg cggccgtggc gcagtcgacg  14296 ctgccgaccg gcgtgccttc gggcgtggag cccgtgtacg acttgcgcac gacgaagctg  14356 aacgacgccg ctccggacgc gtccgtggtg aaggacgtcg cggtcgccgg gttgcacgcg  14416 tcctggccac cgaccggagc gcactgggcg atgtagtagg tctcgccggc ggcggcaccg  14476 ctgaccgaca ccgacacgct ctgtccgtca ctcagacccg aggcgggact gacggagaag  14536 gcgggcgcgg cgaaggcgac ggactgtgcg gcggcggcca ggccgatgga tgcgacggcc  14596 acgacgccga acctggaagc acggcgggac atgtgacgta acgacatgcg taggctccga  14656 ttcgaggagg gggttgatca ctccatgaaa ggatcacctc gccggacggc cgcctgcatc  14716 tccctctgtg ctctcgtgga tttccggcac ggcactcccg tcgacggccg cccgcagaat  14776 gcggcagacc ccccgcacct cctccggccc caccgccgta ccgtgggca gcgacagcac  14836 ccgctcggtg agcgcctcca ccttcgggag cggatcgggc gcgtggcgcg cgaggtcgga  14896 ccggtagggc tcgcagctgt ggcagccggg gctgaagtag gcgcgggcca ggacgttgtg  14956 ccgttggagc accgcctgga gttcgtcgcg gtgcagcccg gcgcggacgg cgtccacctc  15016 gatgacgacg tactggcagt tcgacagctc gttcggatcc tgcggcgga cccggacgcc  15076 gggcagtccg tcgaggtact gctcgtacag acggtagttg cgccggttga tcgcggtgaa  15136 gtgatcggcg gactccaggg aggtgaggcc catggccgcg ctgatctcgt gcatccgcgc  15196 gaccgttccg ctcccggtga tctcatgcgc ggcgttgagc cctggtggc gcatggcccg   15256
```

-continued

```
gagccggtcg gccagggcgt cgtcgtcggt gacgatcgcc ccgccctcga agctgttcac    15316
gaacttcgtc gcctggaagc tgaagatctc cgccgtgccg aagccgccga tcggcttcga    15376
ccggtaggtg cagccgaagg cgtgggcggc atcgaagagc aggtgcagcc cgtgctcggc    15436
ggccagcttg gtcagctcgt cgatccgggc cggtctgccg aagacgtgca cgtccaggat    15496
ggcgcgggta cgcgggccga tgagccgctc cacgtgtgcc acgtccgcgg ttccggtctc    15556
ctcgtccagt tcgcagaaga caggcaccgc accgatccag tccagtgcgt gggcggtggc    15616
gacccaggtg aaggagggca cgatcacctc gtccccagga ccgatgccca gggccttcgc    15676
ggcgacctgg atgccggtgg tggcgttcga tacggcgacg cagtgcctga cctgggtcag    15736
ctcggccaca cgggcctcga actcccggac caggggccg tcattggtga accacaggcg    15796
ctccagcgcc ccgtcgatcc gttccatcaa acggtcgcgg gagcccacgt tcgggcgtcc    15856
cacgtgcagc ggttcgctga agtagggcgt gggtagggag tcca gac gca ccg ggc    15912
                                              Asp Ala Pro Gly
                                                      855 cgc cgc tca tgc cgt gcg cac gcc gac gaa gag gcc ggg gct gtt ggg     15960
Arg Arg Ser Cys Arg Ala His Ala Asp Glu Glu Ala Gly Ala Val Gly
        860                 865                 870 ccggccgtcg gccagccgga agccgggcac gaaccgcacc gagagcccca ccgattcgaa    16020
ggcgtcggtg tactgctcgc gggtgaagag gctggaggtc aggacctcgg agaactctct    16080
gaagccggag gcgtccgcga cccggaaccg gacctccaga cgtgacttgt cgccctggcg    16140
cacggagtgc gtcatccgcg tgatgacacg gccctcctcc tggtgcagat ggccgccgac    16200
atgcccgtcg aggaagttct cggggaaata ccagggttcg gcgacgagga ctcccccggg    16260
gttcaggtgg tgggccatgg ccgacaccgc ggccttgagc tcggtgacgg accccatctc    16320
gccgagcgcg ttgcccatgc aggtgatcgc gtcgaaggtg cggcccaggt cgaacgaacg    16380
catgtcaccg gcgtgcagcg ggacgccggg aagccggccc gccgcctgct ccagcatcgc    16440
gggcgcgtac tcgaggccct ccacatggcc gaagagcgtg gcgagcgtct ccagatgggc    16500
tccggtgccg caggcgacgt ccaggagcga cacggcgtcg gggcgggcgg cgaggatcag    16560
ctcggtgagc ccgcgggcct ccaggtcgaa gtccttgccg cggctgcgga acacgaggtc    16620
gtagaacttc gcgtgctcgg ggccgtactc catcagacga gctccttcgc agactgggcg    16680
gagatgattc tgggctccgg gatgggaacg atgaacttcc ctcccgcctc caggaagcgg    16740
cgctccttgc ggacgacctc gtcggtgtag ttccaggcga ggaggaggta gtagtccggc    16800
tcggtggcag cgacctcctc cggaggaagg accgggatgc ggttcccggg cagcagtttg    16860
ccgtgcttga ggctggtggt gtcgccgcag acgtgatgt cctgatccgt cagaccgcag    16920
gccatcagca actgggtccc cttggacggt gctccgtagc cggccacgcg gtggccgtcc    16980
gcggccagac cgcgaacgag cgtacggatc gcttcggtca cgcgcgtcac ccgctcggcg    17040
aacgcccggt aggggcatc cgtcagcagt ccgcgctcct cctccaggcc gagcagcgcc    17100
gcgaccgagg gctccgggac ccgtgcggcc gactcgcgcg cggcgacgac cgcgatcgaa    17160
ccgccgtgca cggcgacccg ctccacgtcg atgatccgca ggccgtgcgc gccgaagagg    17220
tggcgcagtg tgtgcaggga gaagtacgac aggtgctcgt ggtagatcgt gtcgaactgg    17280
ttctcgtcga gcaggttcag caggtacggc acctcgatga ccaggacgcc gtcgtcgtcg    17340
agcactgcgt cgacgccgtc caggatgcgg tgcacgtcgt cgatgtgcgc gaagcactgg    17400
cggccgatga cggccttggc cctgcccctgc tcaaggggca tgcggcccgc gggctccggg    17460
ccgaagaagt ccgggtccgt ggggatcccc cgggcgttgg cgatctcggc gaggttggcc    17520
```

-continued

| | | | | |
|---|---|---|---|---|
| gccgggtcga | ccccggccac | ccgcatgccc | gccgcccgga | acatcgcgag ctgggtgccg 17580 |
| acgttgctgc | ccagctccac | gaccaggtcg | ccggaggcga | ggcttgcccg gcgggtcgcc 17640 |
| agcccgacga | tgtgcgccat | gtgctcgcgg | atctggtcgg | agtcggagga gacgtagacg 17700 |
| tagtgcttga | acagtgtccc | ggggtcgacg | acatggcgaa | gcgtcatcag ccggcacgac 17760 |
| cggcacacga | tgacgtcgag | cgggaagacg | tcctgcgcct | catcggcgtc ggccggatcg 17820 |
| acgaacccgt | tggccagcgg | cagcgagccg | aaggagatca | cctcggtcca gtcgtccgca 17880 |
| ccgcatacac | ggcacgtctc | gtcccgcctg | catttctcca | gcatgaagtc tcctgacggc 17940 |
| gaatgccgac | gcatcgggcc | cgtcggtccg | ggacggtca | atctagggtt ccggccgacg 18000 |
| ggcgctccac | ttcgtatgtg | ccctactggt | tcagcggagc | ggacgggtga acgcccgtac 18060 |
| gtcctcgatg | aggagctgcg | gctgctccat | ggccgcgaag | tgcccgccgc ggtcgaactc 18120 |
| ggtccaccgc | gtcagggtcg | gcaggatgcc | ctcggcgaac | gaccggatcg gccgggtggc 18180 |
| gtcgtccggg | aacaccgcga | cgccgacggg | ggccgtcagc | ggccagggcc cgccccaggt 18240 |
| gcgggcgaag | tccgccatgc | cgcgagccga | ctcgtagtac | aactgagcgc tggaaccggc 18300 |
| cgtcgcggtc | agccagtaga | tcatcacgtg | ggtgagcagc | cggtcccggg agatggcctc 18360 |
| ctccacgttc | ttgccgccgc | tccactcctg | gaacttgtcg | agaatccagg cgagctggcc 18420 |
| gaccggggag | tcggtgaggc | cgtaggccag | ggtctgcggg | cgggtggcct ggatgcgctg 18480 |
| ccagccgatg | ccggtgtcgg | cgaactcccc | gctgtgcgcc | agcttgccca ggtcgctctc 18540 |
| gtccaggcgc | ccgatggcct | ccggggcgtc | ctggggcggg | aaggtcacca gcatgttcag 18600 |
| gtggacgccg | gccacgtgct | cggggtcggc | cagccccagc | tccagcgaga cgacctttcc 18660 |
| ccagtcgccg | ccctgggcga | cgtaacgctc | gtagccgagc | cggttcatca gctccgccca 18720 |
| ggcgcgtgcg | atccgccgca | cgtcccagcc | cggctcggca | gtcgggccgg agaagccgta 18780 |
| gcccggcatg | gaggggacga | cgacgtggaa | ggcgtccgcc | gggtcgccgc cgtgcgcgcg 18840 |
| cgggtcgctc | agcggcccga | tgacgtcgag | gaactcggcg | accgagcccg gccagccgtg 18900 |
| ggtgaggatc | agcgggatcg | cgtccggctc | gggcgaacgc | acgtgaagga agtgcacgtc 18960 |
| ggcgccgtcg | atcgtggtga | cgaactgggg | gaacgcgttc | agctcggcct ccgcggcacg 19020 |
| ccagtcgtag | ccgtggcgcc | agtggtcggt | gagctccttg | aggtaggaca gcggcactcc 19080 |
| gcggtcccat | ccggatccgg | gtatctcgga | cggccaccgg | gtcgcgtcga tccgccgggt 19140 |
| taaggtcgtc | gaatgtcgga | ctgggtcgat | ctcgatacgg | aagggacgca cagtgaatcc 19200 |
| accctcgtga | ttgtgggagc | ggggcggcgc | gaggcggccg | ccccgatgtg atccggggac 19260 |
| cgtgtctcag | gccggttcgg | ccggcgcggc | cgcgccttcc | cgtgcggaga aggaccgcac 19320 |
| ggaggacagg | aagttgcgga | tcatcggcat | gccgtgttcg | gtccggaagc tctccggatg 19380 |
| gaactggacg | gactccaccg | gcagcgaacg | gtggcgcagg | cccatcacgt acccgtcgtc 19440 |
| cgtggagcgc | ccggtgacct | cgagggacgg | cgggaccgtg | ccctccggca cgatcagtga 19500 |
| gtggtagcgg | gtcgcgaaga | accccgcggg | cagcccggtg | aacactccgc gcccgtcgtg 19560 |
| cgtgatccgg | ctcgtcttcc | cgtgcatgag | atgccgggcg | gggacggtgg cggcgccgta 19620 |
| ggcgcgggcg | acggcctgat | gccccagaca | gaccccgagc | agcgggaccc ggccggcgaa 19680 |
| ggcctggacg | atctcgacgt | gcccggaggt | gtcgggtgg | ccggggccg gccccagcag 19740 |
| gaccgcgtcc | ggccgcatca | gccccatctc | gtccggggtc | atgagatgcg accgcaccat 19800 |
| gacgggctcc | gcgccggcgg | acatcagata | ctggcgcagg | atgtcgacga agctgtcgaa 19860 |

-continued

```
cgcgtcgacc accaggaccc gcggggcctc ggtgcctgcg ccggatccgt cgggagacca     19920
caagctcaca gcaactcctc tccggtgacc gcccagtgag tggcgctcat cttggccagc     19980
gtctcggtcc actccgcccc cggttcggaa tcggcgacga ttccggccga ggcccgggtg     20040
cggtagacgc cctcgtggtg gaaaagggtc cggatgcaca gcgcgaggtt ggtgtacccg     20100
cccacgtcga ggaggccgag cgccccggcg tacaggccgc ggcggctgcg ttcgacggac     20160
tcgatgatct ccatggcgcg gatcttcggc gcgcccgtca tggtgccggc ggggaacagg     20220
gcggcgatgg tgtcgaaggc atcggtgtcc acccgcgccc ggccgacgac cgtggagacc     20280
aggtgcagca cgtgggagta gccctccacg tccagctggt cgggtacgtc gagcgtgttc     20340
ggccgggcga tccgtccgat gtcgttgcgg cagaggtcca ccagcatggt gtgctcggcg     20400
atctccttgg gatccgacct cagccggact cccgcggcga tgccgccgtc cgcgccggac     20460
cgcggcaccg tgcccgcgat cggccgcatc gtgacctcgc cgtcctcgat gcgtacgaac     20520
agctcggggc tggcgccgat cagacggtgc ccgtcgatgc ccgccagata catgtacggg     20580
gaggcgttcc gcccgcgcag gcgctggtag acgtccgcgg ggtcggccgt cgagcggatg     20640
gagagctcgt gaccgatctg cacctggtag atgtcgccga cggcgatgtg cttcagacac     20700
cgctcgacgt cgttcgcgaa cacttcgggg gcgctgtcgt cggtgaccgc ggaggcgggg     20760
aagccgtctg cggacggatc gggccaggcc tgctccacgt cggcgaggag cccggtgacg     20820
gtctccggcg cgaggccggg ccagtacggg gactcgtgga gcagcagttc gcatcggccg     20880
gtggcgagat cggtgaccac gctgcccgg tgcaggacca tgcgtacgtc cggcaggcca     20940
ggccggttct cgatgaggtg gggcaggtcc tcgatgtagc gggccgtgtc gtacccgaag     21000
aacccgagga acccgaagcg gaagccggac gcggaccect cggcgtcgaa catgtcccgc     21060
atggcccgca gcagcggcca caacccgccc gcggtacgca gccgcagccc ctggggccg     21120 tcctccagga gcgcgccggc ccgctccagg agcaggcccc gcagggcggg tacgccctcg     21180
acgcgcacca cccggtcggt gaccgagagc gagagcagcg cgccgaagcc gacgaactgg     21240
tgcctgcggt cgcggggccgg gccggccgcg gactccagga ggtagacctc gtcggggccg     21300
aagtgctcgg ccagcgcgcg gtaggcgggc agggcgcccg tctccttcac atcgaggcgt     21360
cgtgtccgca cccgcaccgg ggccgagacc acgcactggt cggtcatcct gggtcctccc     21420
ggatcacgtg gtgatggcgt agcggtgtgc cacctgacgg gcggtcagca ccgcccggtc     21480
ggggccggag cggttgtcga cgacgcgcgc ggccttccag ctgacgaagg agccggtgtg     21540
ggtcacgggg tcgaggtcgg tgtccacgac gatgccggcg tgcgcgccgg tccgctccct     21600
gagccgggcg gcgacggcct cgccgatgcc ctgccgttcc ccctcggcgc cggccagcag     21660
gtccatgcgc acgtgacgg cgtcgctgcc gtcgtcctgc cggtcgatga cgacctggta     21720
gccgaggcag ccgccgaccc cgtcgaggat cgcggcctcc agctcggcgg gctggagggt     21780
cacgtcgccc aggggatgc ggtccgcgac ccggccgatg acctggatcc gcggtcccgg     21840
cagcggctcc ccggggcccg ccgggaggat gcggaccagg tccccggtgc ggtagcggat     21900
cagtggtttg atgccgtcca ccagcatggt gaggacgagt tcgccctctc ccgtgtcgcc     21960
gaccacggcg ccggtgtccg gttcgacgag ttcggtcaag tagttgggct gggcgaggtg     22020
gagcgctccg gtgtccgctc cggtggcgat gcacagggct tcctgggagc cgtagagcgt     22080
gggccgcacg acggcttgcg gccagagggt cgccacgttg tcggcgaact gcggggtgca     22140
gatctcaccc agcgtgagga agagcttcac gggaagccgg gccaggtcgt agccgtagtg     22200
cagggccgcc ttggcaaggc tcaggcacag cgccggagca cagacgacga cctcgacctc     22260
```

```
cagctcctcg atcagccgca gcgccttacg gaatcccacc ctgggggact cgggccagat    22320
cttgacgtga caggccccca gctccgctgc caccgcggtg aacacgtccc cgaacgcgta    22380
cagctccgac ggccccatca ggcccacgac gggcatccgc cccccgaacc tcgcttccag    22440
catgcggcgc caggactccc ggacggcgat gttgctggtc gcgatgtcct tctcgccgcg    22500
tgggcacggg gtggccgccc cggtggtccc ggtggtctcg tagtagatgc gtgcttcgtg    22560
cagcgggccc gacaggacgt cgtgcatctc ccgccgcagg tcgtccttgg tggtgaaggg    22620
caggtccgcc aggttcgcgg gggtgacggc ctcgacgtcc acgcctgcca gatggcggcg    22680
gtagaacggc gagcggcggg tgacgtggcg cagtacggcc gtcagccgtt cgccctccca    22740
gcgctcgcgg tcggcggcgg tgagttcgcc gcggtagaac gcgtcgctca cctgcccgta    22800
ggcggaccag aactcgctgt ccgcgtcggg gtccagcggc ccggtcccgc cgggaccggg    22860
ccgccggccg tctctcacgg ctgtgcctgg agttcgttga gcgcgaggcc gacccgctcg    22920
ttgacctcgt tggaggccag cacgtccgaa cggccggtga gccgacggtg ttcgtcgagc    22980
agttcgatca tgtccgtcat cctctcgacc aggcgcgaga cgttggtgag gccctcctcg    23040
tccttgagcg cgtcgccccg gtgcagcgcg tgcaccgtcg ccgggaagcc gctgcccacc    23100
aggatcatcc ggttgagcag ggcattgacg gtcagctgag cccatacctc gccgcgctg     23160 tagcggcggg cgaccgagat gatccccgcg accttgttgc tcagcggccg gtcgaagcgc    23220
agataaccga ctccggcacg ctcgatgaag gtctgcatga ggctggccgt gccgaatccg    23280
tgcacgggcg ccgcgaagat gatcccgtcc gccgcgacca tcttcgccac gacctcgggc    23340
accccgtcgg ccagggtgca ggccaccggc ctgtcgttgc agtccccgca gggcccgcac    23400
cgctccatcc tgatcgagcg caggtcgacg gcctcgaagt cgacgccgcg gttctctgct    23460
acgcgtgccg cgtgccgcag tacgtcggcg gtgttgccgt cacgttccga accgttgatc    23520
gcgaggatct tgagttgtgc gctcacgagg ggcctccttg gtgagtcagg tgcgctcggc    23580
ggtcggctcg ggggaactgt ctggccgccg ctggtccggg agccgcaggg ccggctcggc    23640
gggggcggga ggaagaccgc cccgcggcgg gccgccacgc tcgccgaacc ggatgagggg    23700
cttctcgacg agatagaagc tgatggtcgc cagcacgacg ctgatcgaga tcgtgaagag    23760
gaacagttcc cagaacccca tgtcaccccg gaattccggc gttggcacgg gagacttgcc    23820
gaagatgctg ccgttcctga gccagaggtt gatcacgatc tcgtgccaga ggtagacgcc    23880
gagggagatc tggccgagga agaggatcgg cttgctggtg aagagcgcgt ccgagaaccg    23940
ggactcggcg ccggggaccg tcatcggtgc caggagcagc agggtgaagg aggtcaggat    24000
gaagtggtcg acgagctcct gggccagggc gcgttgtcg cccatgcccg ggatgccgat     24060
gggcttggtg gcgtagagga ggtacagcgg gatgagcggg acccagcaga tcagcgggcg    24120
ccggatcacg aaacggtaga agcccggggt ccctggcgtc gcctcggcgt acgcggagta    24180
gatggccagt gccatgcccg cggcgaagca gccggcgtag tagggcggcc agtaccactg    24240
catcgtcgcg ccggtggagg ggaggttggt gtacgtgacc cagccgatgg ccatgacttc    24300
cagcgcggcc agcggcagca ggaggcggcg tgccttctgc ccgggagtgc tgccgccccg    24360
cgcgagccgg tggccgatcc aggcgatcag cggcagggcg aggtagaacg tgaactcggc    24420
ggggaccgtc caggtgggct cgatgccgtg catcggctgg ccctcgggca gatagaagtg    24480
catgagcagc acgggccgca ggacgtcgct gacgctgtcg atctcgaacc agttgtagcc    24540
ggggattgcg aagacgagca acaggtagta ggcgggcagg atgcgcaggg cccggcgttt    24600
```

```
gaggaaccgt ccggtggcgg gccgcttcgt cccactgatg gtgacgcggg cgtagggctt    24660
gtacagcatc attccggaca gagcgaagaa gggggaaggc ataccccag accgtccgcg     24720 aggacgcccc agaacggttt gcccggctca ccgacgaagc tgcccactcc ggcctggaag    24780
gcgacgtggt agacgaccac acccagcgcg aggacacctc gcagtccctc gaacttcggt   24840
attcgcttgc tttttgcgcc acctgcgtcg cgaaggacgt cccccatgga acagtcccct   24900
ttcccttggc acttgctcgt tgacttcccg aaatagtcgg gtctgcggag tgtgagccgc   24960
atctccaatc gtgctgttcc ggtgctcagg acgacttgtt tcggcctgag tgggaaggca   25020 gccaccccg ccgcccgcc tcggccagac cgggggccga ggagtccgt tccgagagga      25080 tcggagtgat ctccggcggc caggcgatgc ccacctccgg atccagcgga ttcaagccat   25140
gttcgagccg ggggtcgtag gccgccgagc acaggtagac gatcaccgcc tcgtcgctca   25200
gcgtgaggaa tccgaagccc agccccgcgg agacgtacag cgcccgtccg ttctcctcgc   25260
cgagctccac ggtccgccag ccgccgaagg tgggcgaccc cacccggatg tcgaccacgg   25320
cgccgaacac gctgccgcgc aggcagctga agtacttggc ctggccgggt acgccccgg   25380 cgaagtggat gccccgcagc accccgtggg aggagatcgc gcagttcgcc tgccgcaggt   25440
cgaaggagtg gcctacggtg cggcggaagg gctcgccctg gaaccactcg cgaaacgagc   25500
cccgttcgtc acgaagacc tgcttctcct ccgtccacgc tcccgagatc ccgatcggct    25560
tcatcgctgg ccccttctct cgacttctct cgacgactcg cgggaggcgg ccgaggggtc   25620
cgccgggccc gtgggaacgc cgcagtctag atgcggcggc accggggca ggggggtgcg     25680 gacgacgtcc gccccacctc agcacaccgg gagatgcagg tcggtgacgg gcgacgtgac   25740
gatgcaacgg tccgaggccc ggttgccgg acgacggccc acagagccat cggagcaacg    25800
gaggcggacc gcag atg acc aag cac gcc cgt gac cgc gcg gta gtc ctc     25850
            Met Thr Lys His Ala Arg Asp Arg Ala Val Val Leu
                875             880             885 ggc gca ggg atg gcg ggg ctg ctc gcc gcg cgc gtc ctg tcc gag acg    25898
Gly Ala Gly Met Ala Gly Leu Leu Ala Ala Arg Val Leu Ser Glu Thr
                890             895             900 tac aag gaa gtg ctg gtg atc gac cgg gac cgg ttg ggc ggc acg gag    25946
Tyr Lys Glu Val Leu Val Ile Asp Arg Asp Arg Leu Gly Gly Thr Glu
            905             910             915 cag cgc cgc ggt gtc ccg cac gga cgc cac gcc cat gcg ctg ctg gcc   25994
Gln Arg Arg Gly Val Pro His Gly Arg His Ala His Ala Leu Leu Ala
            920             925             930 aag gga cag cag atc ctc aac gaa ctc ttc ccc gga ctc gac acc gaa   26042
Lys Gly Gln Gln Ile Leu Asn Glu Leu Phe Pro Gly Leu Asp Thr Glu
            935             940             945 ctc acc tcg gcc gga atc ccc gcc ggg gac atc gcc ggg aac ctg cgg   26090
Leu Thr Ser Ala Gly Ile Pro Ala Gly Asp Ile Ala Gly Asn Leu Arg
950             955             960             965 tgg tac ttc aac ggc cgc cgg ctc cag ccc ttc gac acc ggg ctg atc   26138
Trp Tyr Phe Asn Gly Arg Arg Leu Gln Pro Phe Asp Thr Gly Leu Ile
                970             975             980 agc gtc tcg gcg acg agg ccc gag ctg gag tcc cac gtg cgc gca cgg   26186
Ser Val Ser Ala Thr Arg Pro Glu Leu Glu Ser His Val Arg Ala Arg
            985             990             995 gtc gcc gcg ctg cca cag gtg aag atc atg gac ggg tgc gtg atc cgg   26234
Val Ala Ala Leu Pro Gln Val Lys Ile Met Asp Gly Cys Val Ile Arg
            1000            1005            1010 ggc ctg acc gcc tcg gcc gac cgc agc cgc gtc acc ggt gtc gag gtg   26282
Gly Leu Thr Ala Ser Ala Asp Arg Ser Arg Val Thr Gly Val Glu Val
            1015            1020            1025
```

-continued

| | |
|---|---|
| gtc gac gag tcg ggt acg gac acc ccg acg cgc ctg gag gcc gac ctc<br>Val Asp Glu Ser Gly Thr Asp Thr Pro Thr Arg Leu Glu Ala Asp Leu<br>1030                       1035                       1040                       1045 | 26330 |
| gtc gtc gac gtc acg ggg cgc ggc tcg cgg act ccc gcc tgg ctg gag<br>Val Val Asp Val Thr Gly Arg Gly Ser Arg Thr Pro Ala Trp Leu Glu<br>               1050                       1055                       1060 | 26378 |
| gag ttc gga tac gag cgg ccc gcg gag gac cgc ttc aag atc gat ctg<br>Glu Phe Gly Tyr Glu Arg Pro Ala Glu Asp Arg Phe Lys Ile Asp Leu<br>1065                       1070                       1075 | 26426 |
| gcg tac acc acg cgc cac ttc aag ctc aag gaa gac ccc tac ggc acg<br>Ala Tyr Thr Thr Arg His Phe Lys Leu Lys Glu Asp Pro Tyr Gly Thr<br>               1080                       1085                       1090 | 26474 |
| gac ctg tcg atc aac ccg gtg gca tcg ccg agc aac ccg cgc ggc gcg<br>Asp Leu Ser Ile Asn Pro Val Ala Ser Pro Ser Asn Pro Arg Gly Ala<br>1095                       1100                       1105 | 26522 |
| ttc ttc ccc cgg ctc gcg gac ggc agc tcc cag ctc tcc ctc acc gga<br>Phe Phe Pro Arg Leu Ala Asp Gly Ser Ser Gln Leu Ser Leu Thr Gly<br>1110                       1115                       1120                       1125 | 26570 |
| atc ctc ggc gac cac ccg ccc acc gac gac gag ggc ttc ctg gcg ttc<br>Ile Leu Gly Asp His Pro Pro Thr Asp Asp Glu Gly Phe Leu Ala Phe<br>               1130                       1135                       1140 | 26618 |
| gcc aag tcg ctt gcc gcg ccg gag atc tac cgg gcc gtc cgc gat gcc<br>Ala Lys Ser Leu Ala Ala Pro Glu Ile Tyr Arg Ala Val Arg Asp Ala<br>1145                       1150                       1155 | 26666 |
| gaa cct ctc gac gaa ccg gtc acc ttc cgc ttc ccg gcg agc gtc cgc<br>Glu Pro Leu Asp Glu Pro Val Thr Phe Arg Phe Pro Ala Ser Val Arg<br>               1160                       1165                       1170 | 26714 |
| cgc cgt tac gag agg ctg cgc cgt ttc ccc ggc ggg ttc ctc gtc atg<br>Arg Arg Tyr Glu Arg Leu Arg Arg Phe Pro Gly Gly Phe Leu Val Met<br>1175                       1180                       1185 | 26762 |
| ggc gac ggc gtg tgc agc ttc aac ccc gtc tac ggc cag ggc atg acg<br>Gly Asp Gly Val Cys Ser Phe Asn Pro Val Tyr Gly Gln Gly Met Thr<br>1190                       1195                       1200                       1205 | 26810 |
| gtc gcc gcc ctg gag gcc gtg gcg ctg cgg gac cac ttg cgc gac gcc<br>Val Ala Ala Leu Glu Ala Val Ala Leu Arg Asp His Leu Arg Asp Ala<br>               1210                       1215                       1220 | 26858 |
| ccg gac ccc gac gcc ctg cgc ttc ttc cgg cgt atc tcc acg gtc atc<br>Pro Asp Pro Asp Ala Leu Arg Phe Phe Arg Arg Ile Ser Thr Val Ile<br>1225                       1230                       1235 | 26906 |
| gac gtt ccg tgg gac atc gcc gcc gga gcg gat ctg aac ttc ccc ggg<br>Asp Val Pro Trp Asp Ile Ala Ala Gly Ala Asp Leu Asn Phe Pro Gly<br>               1240                       1245                       1250 | 26954 |
| gtg gag ggc ccc cgc acc atg aag gtg aag atg gcc aac gcc tac atg<br>Val Glu Gly Pro Arg Thr Met Lys Val Lys Met Ala Asn Ala Tyr Met<br>1255                       1260                       1265 | 27002 |
| gcc cgc ctg cac gca gcg gca gcc gtc gac ggc gcg gtg acc ggg gcg<br>Ala Arg Leu His Ala Ala Ala Ala Val Asp Gly Ala Val Thr Gly Ala<br>1270                       1275                       1280                       1285 | 27050 |
| ttc ttc cgg gtg gcc ggg ctg gtg gac ccc ccg cag gcc ctg atg cgc<br>Phe Phe Arg Val Ala Gly Leu Val Asp Pro Pro Gln Ala Leu Met Arg<br>               1290                       1295                       1300 | 27098 |
| ccc tcc ctc gcc ctg cgg gtc atg cgc aac tcc tcg gcg aag ccg tcg<br>Pro Ser Leu Ala Leu Arg Val Met Arg Asn Ser Ser Ala Lys Pro Ser<br>1305                       1310                       1315 | 27146 |
| gtc cct tcg ggc gcc gcc gta tgaccgcgcg gcccgtccgg ggcggctgcc<br>Val Pro Ser Gly Ala Ala Val<br>               1320 | 27197 |
| ggggccagga gccgac atg cgg gtg atg atc acg gtg ttc ccg gcg cgg gcg<br>                     Met Arg Val Met Ile Thr Val Phe Pro Ala Arg Ala | 27249 |

```
                1325            1330            1335
cac ttc ctg ccg ctg gtg ccc tat gcc tgg gcc ctg cag agc gcg ggc    27297
His Phe Leu Pro Leu Val Pro Tyr Ala Trp Ala Leu Gln Ser Ala Gly
            1340            1345            1350 cac gag gta tgt gtc gtg gcg ccc ccg ggc tat ccc acc ggg gtg gcc    27345
His Glu Val Cys Val Val Ala Pro Pro Gly Tyr Pro Thr Gly Val Ala
            1355            1360            1365 gac ccc gac ttc cac gag gcc gtc acc gcg gcc ggc ctg aag tcg gtg    27393
Asp Pro Asp Phe His Glu Ala Val Thr Ala Ala Gly Leu Lys Ser Val
    1370            1375            1380 acc tgc ggg cag ccg cag ccg ctg gcg gtc cac gac cgc gac gac ccc    27441
Thr Cys Gly Gln Pro Gln Pro Leu Ala Val His Asp Arg Asp Asp Pro
1385            1390            1395            1400 ggc tac gcg gcg atg ctg ccg acc gcg gcg gag tcg gag cgc tac gtg    27489
Gly Tyr Ala Ala Met Leu Pro Thr Ala Ala Glu Ser Glu Arg Tyr Val
                1405            1410            1415 gcg gcc ctc ggg atc agc gag aag gag cgc ccc acc tgg gac gtc ttc    27537
Ala Ala Leu Gly Ile Ser Glu Lys Glu Arg Pro Thr Trp Asp Val Phe
            1420            1425            1430 tac cac ttc acc ttg ctg gcg atc cgc gac tac cat ccg ccg cgg ccg    27585
Tyr His Phe Thr Leu Leu Ala Ile Arg Asp Tyr His Pro Pro Arg Pro
    1435            1440            1445 cgg cag gac gtg gac cag gtg atc gag ttc gcc cgg atc tgg cag ccc    27633
Arg Gln Asp Val Asp Gln Val Ile Glu Phe Ala Arg Ile Trp Gln Pro
1450            1455            1460 gat ctg gtg ctg tgg gac gcc tgg ttc ccc tcg ggc gcg atc gcg gcg    27681
Asp Leu Val Leu Trp Asp Ala Trp Phe Pro Ser Gly Ala Ile Ala Ala
1465            1470            1475            1480 cgg gtc agc ggc gcc gcg cac gcg cgg gtg ctc gta gcc ccc gac tac    27729
Arg Val Ser Gly Ala Ala His Ala Arg Val Leu Val Ala Pro Asp Tyr
                1485            1490            1495 acc ggc tgg gtc acc gag cgg ttc gcc gcc gcg ggc ccc gcg gcg ggg    27777
Thr Gly Trp Val Thr Glu Arg Phe Ala Ala Ala Gly Pro Ala Ala Gly
            1500            1505            1510 gcc gac ctc ctg gcc gag acg atg cgg ccg ctg gcc gag cgg tac ggc    27825
Ala Asp Leu Leu Ala Glu Thr Met Arg Pro Leu Ala Glu Arg Tyr Gly
        1515            1520            1525 gtg gag gtc gac gac gat ctt ctg ctc gga cag tgg acg gtc aat ccg    27873
Val Glu Val Asp Asp Asp Leu Leu Leu Gly Gln Trp Thr Val Asn Pro
    1530            1535            1540 ttc ccg gcg ccg atg aac ccg ccg acc cgg ctc acg aac gtt ccg gtg    27921
Phe Pro Ala Pro Met Asn Pro Pro Thr Arg Leu Thr Asn Val Pro Val
1545            1550            1555            1560 cgc tac gtg ccc tac acc ggt gcc agc gtc atg ccc gcg tgg ctg tac    27969
Arg Tyr Val Pro Tyr Thr Gly Ala Ser Val Met Pro Ala Trp Leu Tyr
                1565            1570            1575 gcg cgg ccg tcg cgg ccg cgg gtg gcg ctg tcg ctc gga gtg tcc gcg    28017
Ala Arg Pro Ser Arg Pro Arg Val Ala Leu Ser Leu Gly Val Ser Ala
            1580            1585            1590 cgg gcg ttc ctc aag ggt gac tgg ggg cgt acc gcc aaa ctg ctg gaa    28065
Arg Ala Phe Leu Lys Gly Asp Trp Gly Arg Thr Ala Lys Leu Leu Glu
        1595            1600            1605 gcg gtc gcg gag ctg gac atc gag gtg atc gcc acg ctc aac gac aac    28113
Ala Val Ala Glu Leu Asp Ile Glu Val Ile Ala Thr Leu Asn Asp Asn
    1610            1615            1620 caa ctg gcg gag agc ggg ccg ctg ccg gac aac gtc cac acc ctc gac    28161
Gln Leu Ala Glu Ser Gly Pro Leu Pro Asp Asn Val His Thr Leu Asp
1625            1630            1635            1640 tac gta ccg ctc gac cag ttg ctg ccc acc tgc tcg gcc gtc atc cac    28209
```

-continued

| | |
|---|---|
| Tyr Val Pro Leu Asp Gln Leu Leu Pro Thr Cys Ser Ala Val Ile His<br>                1645                   1650                  1655 | |
| cac gga tcg acg ggc acc ttc gcc gcg gcg agc gcg gcc ggg ctg ccc<br>His Gly Ser Thr Gly Thr Phe Ala Ala Ala Ser Ala Ala Gly Leu Pro<br>           1660                  1665                  1670 | 28257 |
| cag gtg gtc tgc gac acc gac gag ccc ctc ctg ctc ttc ggc gag gac<br>Gln Val Val Cys Asp Thr Asp Glu Pro Leu Leu Leu Phe Gly Glu Asp<br>1675                  1680                  1685 | 28305 |
| acc ccc gac ggc atc gcg tgg gac ttc acc tgc cag aag cag ctc acc<br>Thr Pro Asp Gly Ile Ala Trp Asp Phe Thr Cys Gln Lys Gln Leu Thr<br>           1690                  1695                  1700 | 28353 |
| gcg acg ctc acc tcc cgc gtg gtc acc gac tac ggg gcg ggg gtg cgc<br>Ala Thr Leu Thr Ser Arg Val Val Thr Asp Tyr Gly Ala Gly Val Arg<br>1705                  1710                  1715                  1720 | 28401 |
| gtc gac cac cag aag cag tcc gcc gga cag atc cgt gag caa cta cgc<br>Val Asp His Gln Lys Gln Ser Ala Gly Gln Ile Arg Glu Gln Leu Arg<br>           1725                  1730                  1735 | 28449 |
| agg gtg ctc acc gaa cct tcc ttc cgc gag ggc gct cga cgg atc cgg<br>Arg Val Leu Thr Glu Pro Ser Phe Arg Glu Gly Ala Arg Arg Ile Arg<br>           1740                  1745                  1750 | 28497 |
| gaa gac cgg aat tcc gcc ccc agc ccg gtc gaa ctc gta tcg ctc ctg<br>Glu Asp Arg Asn Ser Ala Pro Ser Pro Val Glu Leu Val Ser Leu Leu<br>           1755                  1760                  1765 | 28545 |
| gta gaa ctg acg aag cgt cat cgc cgt gac aag gag gcg gac cga<br>Val Glu Leu Thr Lys Arg His Arg Arg Asp Lys Glu Ala Asp Arg<br>1770                  1775                  1780 | 28590 |
| tgaggatgct ggtgacgggc ggagcgggtt tcatcggctc gcagttcgtg cgggccacac | 28650 |
| tgcacggcga gctgccgggt tccgaggacg cccgggtgac ggtcctggac aagctgacgt | 28710 |
| actccggcaa tccggccaac ctcacctccg tcgcggccca tccgcggtac accttcgtcc | 28770 |
| agggcgacac cgtcgacccg cgcgtcgtcg acgaggtggt cgccggccac gacgtcatcg | 28830 |
| tccacttcgc ggcggagtcg cacgtggacc gctcgatcga caccgccacc cggttcgtca | 28890 |
| cgaccaacgt gctcgggacc cagacgctgc tggaagcggc tctccggcac ggggtcggcc | 28950 |
| ggttcgtgca cgtgtcgacc gacgaggtct acgggtcgat cgcctccggc tcatggaccg | 29010 |
| aggacacccc gctcgccccc aacgtcccct acgcggcgtc gaaggcgggt tcggacctga | 29070 |
| tggcgctcgc ctggcaccgc acccgggggcc tggacgtcgt cgtcacccgg tgcaccaaca | 29130 |
| actacggtcc ctaccagtac cccgagaagg tgatcccgct cttcgtcacc aacatcctcg | 29190 |
| acggcttgcg ggtgccccctg tacgggacg gcgcccaccg ccgggactgg ctgcacgtgt | 29250 |
| ccgaccactg ccgggccatc cagatggtca tgaactccgg ccgggccggg gaggtctacc | 29310 |
| acatcggcgg cggcaccgaa ctctccaacg aggaactcac cggcctgttg ctcacggcgt | 29370 |
| gcggcaccga ctggtcctgc gtggaccggg tggccgaccg gcaggggcac gaccgccgct | 29430 |
| actcgctcga catcacgaag atccggcagg aactgggcta cgagcccctg gtcgccttcg | 29490 |
| aggacggcct ggccgcgacg gtgaagtggt accacgagaa ccgttcgtgg tggcagccgc | 29550 |
| tgaaggaagc ggccggcctc ctggacgccg tcggctgacg gcagccaccg ctaggaacac | 29610 |
| cccaggaaag gagccaccctc c gtg aca gca gtc aag gag ccg acg tcc cgc<br>                                Met Thr Ala Val Lys Glu Pro Thr Ser Arg<br>                                    1785                  1790 | 29661 |
| gca gga cgg cgg gag tgg atc gct ctc gtc gtc ctc tcc ttg ccc acg<br>Ala Gly Arg Arg Glu Trp Ile Ala Leu Val Val Leu Ser Leu Pro Thr<br>1795                  1800                  1805 | 29709 |
| atg ctg ttg atg ctg gac atc aac gtc ctc atg ctg gcc ttg ccg cag<br>Met Leu Leu Met Leu Asp Ile Asn Val Leu Met Leu Ala Leu Pro Gln | 29757 |

|     |     |
| --- | --- |
| ttg agc gag gat ctc ggc gcg agc agc acg caa cag ctg tgg atc acc<br>Leu Ser Glu Asp Leu Gly Ala Ser Ser Thr Gln Gln Leu Trp Ile Thr<br>            1830                1835                1840 | 29805 |
| gac atc tac gga ttc gcg atc gcc ggc ttc ctg gtg acc atg ggc acc<br>Asp Ile Tyr Gly Phe Ala Ile Ala Gly Phe Leu Val Thr Met Gly Thr<br>        1845                1850                1855 | 29853 |
| ctc ggc gac cgg atc ggc cgc gcg agg ctc ctc ctc ggg ggc gcg gcc<br>Leu Gly Asp Arg Ile Gly Arg Arg Arg Leu Leu Leu Gly Gly Ala Ala<br>    1860                1865                1870 | 29901 |
| gtc ttc gcg gtc gtg tcc gtc gtc gcc gcg ttc tcc gac agc gcg gcg<br>Val Phe Ala Val Val Ser Val Val Ala Ala Phe Ser Asp Ser Ala Ala<br>1875                1880                1885 | 29949 |
| atg ctc gtc gtc agc cgc gcc gtg ctc ggc gtc gcc ggg gcc acg gtg<br>Met Leu Val Val Ser Arg Ala Val Leu Gly Val Ala Gly Ala Thr Val<br>1890                1895                1900                1905 | 29997 |
| atg ccc tcg acg ctc gcg ctc atc agc aac atg ttc gag gac ccc aag<br>Met Pro Ser Thr Leu Ala Leu Ile Ser Asn Met Phe Glu Asp Pro Lys<br>                1910                1915                1920 | 30045 |
| gag cgg ggc acc gcc atc gcc atg tgg gcg agc gcc atg atg gcc gga<br>Glu Arg Gly Thr Ala Ile Ala Met Trp Ala Ser Ala Met Met Ala Gly<br>            1925                1930                1935 | 30093 |
| gtc gcc ctc ggg ccc gcc gtc ggc ggc ctg gtc ctc gcc gcg ttc tgg<br>Val Ala Leu Gly Pro Ala Val Gly Gly Leu Val Leu Ala Ala Phe Trp<br>        1940                1945                1950 | 30141 |
| tgg gga tcg gtg ttc ctc atc gcc gtt ccg gtg atg ctg ctg gtg gtg<br>Trp Gly Ser Val Phe Leu Ile Ala Val Pro Val Met Leu Leu Val Val<br>    1955                1960                1965 | 30189 |
| gtc acc ggc ccc gtg ctg ctc acc gag tcc cgc gac ccg gac gcc gga<br>Val Thr Gly Pro Val Leu Leu Thr Glu Ser Arg Asp Pro Asp Ala Gly<br>1970                1975                1980                1985 | 30237 |
| cgg ctg gac ctg ctg agc gcg ggg ctc tcc ctc gcg acc gtg ctg ccg<br>Arg Leu Asp Leu Leu Ser Ala Gly Leu Ser Leu Ala Thr Val Leu Pro<br>                1990                1995                2000 | 30285 |
| gtg atc tac gga ctg aag gag ctg gcc cgg acc ggg tgg gac ccg ctc<br>Val Ile Tyr Gly Leu Lys Glu Leu Ala Arg Thr Gly Trp Asp Pro Leu<br>            2005                2010                2015 | 30333 |
| gcc gcc ggc gcg gtg gtc ctc ggc gtg atc ttc ggc gcg ctg ttc gtc<br>Ala Ala Gly Ala Val Val Leu Gly Val Ile Phe Gly Ala Leu Phe Val<br>        2020                2025                2030 | 30381 |
| cag cgc cag cgg cgg ttg gcc gac ccc atg ctg gac ctc ggc ctc ttc<br>Gln Arg Gln Arg Arg Leu Ala Asp Pro Met Leu Asp Leu Gly Leu Phe<br>    2035                2040                2045 | 30429 |
| gcc gac cgc acc ctg cgg gcg ggt ctg acg gtc agt ctg gtc aac gcc<br>Ala Asp Arg Thr Leu Arg Ala Gly Leu Thr Val Ser Leu Val Asn Ala<br>2050                2055                2060                2065 | 30477 |
| gtc atc atg ggc ggg acc gga ctg atg gtc gcc ctg tac ctc cag acg<br>Val Ile Met Gly Gly Thr Gly Leu Met Val Ala Leu Tyr Leu Gln Thr<br>                2070                2075                2080 | 30525 |
| atc gcc ggt cac tcc ccg ttg gcc gcc ggg ctg tgg ctg ctc atc ccg<br>Ile Ala Gly His Ser Pro Leu Ala Ala Gly Leu Trp Leu Leu Ile Pro<br>            2085                2090                2095 | 30573 |
| gcc tgc atg ctc gtc gtg ggc gta cag ctg tcg aac ctg ctg gcc cag<br>Ala Cys Met Leu Val Val Gly Val Gln Leu Ser Asn Leu Leu Ala Gln<br>        2100                2105                2110 | 30621 |
| cgg atg ccc cct tcc cgg gtg ctg ctg ggg gga ctg ctg atc gcg gcc<br>Arg Met Pro Pro Ser Arg Val Leu Leu Gly Gly Leu Leu Ile Ala Ala<br>    2115                2120                2125 | 30669 |
| gtc gga cag ctc ctg atc acc cag gtg gac acc gag gac acc gcc ctc | 30717 |

```

Val Gly Gln Leu Leu Ile Thr Gln Val Asp Thr Glu Asp Thr Ala Leu
2130                2135                2140                2145 ctc atc gcg gcc acc acc ctg atc tac ttc ggc gcc tca ccg gtg ggg       30765
Leu Ile Ala Ala Thr Thr Leu Ile Tyr Phe Gly Ala Ser Pro Val Gly
                2150                2155                2160 ccg atc acc acg ggc gcg atc atg gga gcc gcg ccc ccg gag aag gcg       30813
Pro Ile Thr Thr Gly Ala Ile Met Gly Ala Ala Pro Pro Glu Lys Ala
            2165                2170                2175 ggt gcc gcc tcg tcg ctg tcc gcc acc ggc ggc gag ttc gga gtg gcg       30861
Gly Ala Ala Ser Ser Leu Ser Ala Thr Gly Gly Glu Phe Gly Val Ala
            2180                2185                2190 ctc ggc atc gcg ggc ctg ggg agt ctg ggc acc gtc gtg tac agc gcc       30909
Leu Gly Ile Ala Gly Leu Gly Ser Leu Gly Thr Val Val Tyr Ser Ala
            2195                2200                2205 ggg gtc gag gtg ccg gac gcg gcc ggg ccc gcc gac gcc gac gcc gcg       30957
Gly Val Glu Val Pro Asp Ala Ala Gly Pro Ala Asp Ala Asp Ala Ala
2210                2215                2220                2225 cag gag agc atc gcc ggc gcc ctg cac acg gcc ggt cag ctg gca ccg       31005
Gln Glu Ser Ile Ala Gly Ala Leu His Thr Ala Gly Gln Leu Ala Pro
                2230                2235                2240 ggc agc gcc gac gcc ctg ctg gac tcc gcg cgc gcg gcc ttc acc agc       31053
Gly Ser Ala Asp Ala Leu Leu Asp Ser Ala Arg Ala Ala Phe Thr Ser
            2245                2250                2255 ggc gtg cag tcc gtc gcc gcc gtc tgc gcc gtg ttc tcc ctg gcg ctc       31101
Gly Val Gln Ser Val Ala Ala Val Cys Ala Val Phe Ser Leu Ala Leu
            2260                2265                2270 gcc gtc ctc atc ggc acc cgg ctg cgg gac att tcc gcg atg gac cac       31149
Ala Val Leu Ile Gly Thr Arg Leu Arg Asp Ile Ser Ala Met Asp His
            2275                2280                2285 ggg cac ggc gag gaa ccg gcc gag aac gac gct caa ccg gcc aca           31194
Gly His Gly Glu Glu Pro Ala Glu Asn Asp Ala Gln Pro Ala Thr
2290                2295                2300 tgagcgcact tccggagatg caacggccgc cgtcgaggta tgaggatcac cttccggggt     31254
gcacctgcac ggcaacggag gcgta gtg gag tac tgg aac agc acg gcg gag       31306
                           Met Glu Tyr Trp Asn Ser Thr Ala Glu
                           2305                2310 acc atg ccc cgc cag gaa ctc gaa cag tgg aag tgg cgc agg ctc cag       31354
Thr Met Pro Arg Gln Glu Leu Glu Gln Trp Lys Trp Arg Arg Leu Gln
2315                2320                2325 gcc gcc atg gac cac gcc aga agg ctt tcg ccc ttc tgg cgg gaa cga       31402
Ala Ala Met Asp His Ala Arg Arg Leu Ser Pro Phe Trp Arg Glu Arg
2330                2335                2340                2345 ctc ccc gag aac atc acc tcc atg gcg gac tac gcg gcg cgg gtg cct       31450
Leu Pro Glu Asn Ile Thr Ser Met Ala Asp Tyr Ala Ala Arg Val Pro
            2350                2355                2360 ctc ctg cgc aag gcc gac ctc ctc gcc gcg gaa gcc gcg tct ccc cct       31498
Leu Leu Arg Lys Ala Asp Leu Leu Ala Ala Glu Ala Ala Ser Pro Pro
            2365                2370                2375 tac ggc acc tgg ccc tcg ctg gat ccg gcg ctc gga gtg cgc cat cac       31546
Tyr Gly Thr Trp Pro Ser Leu Asp Pro Ala Leu Gly Val Arg His His
            2380                2385                2390 cag acc agc ggc acc agc ggt aac ccc ccc atc cgg acg ttc gac acc       31594
Gln Thr Ser Gly Thr Ser Gly Asn Pro Pro Ile Arg Thr Phe Asp Thr
            2395                2400                2405 gaa cgc gac tgg gcc tgg tgc gtg gac acg ttc tgc acg gcg ctc cac       31642
Glu Arg Asp Trp Ala Trp Cys Val Asp Thr Phe Cys Thr Ala Leu His
2410                2415                2420                2425 agc atg ggc gtg cgc ccg cac cac aag ggt ctg gtg gcg ttc ggc tac       31690
Ser Met Gly Val Arg Pro His His Lys Gly Leu Val Ala Phe Gly Tyr
```

-continued

```
                 2430                2435                2440
ggg ctg ttc gcc ggt ttc tgg ggc atg cac tac ggc ctc gag cgc atg    31738
Gly Leu Phe Ala Gly Phe Trp Gly Met His Tyr Gly Leu Glu Arg Met
            2445                2450                2455 ggc gcc acg gtc atc ccg gcc ggc ggc ctc gac tcc cgc tcc cgg gta    31786
Gly Ala Thr Val Ile Pro Ala Gly Gly Leu Asp Ser Arg Ser Arg Val
            2460                2465                2470 cgg ctg ctg gtc gac tac cag atc gag gtg ctc ggc ctc aca ccg agc    31834
Arg Leu Leu Val Asp Tyr Gln Ile Glu Val Leu Gly Leu Thr Pro Ser
            2475                2480                2485 tat gcg atg cgg ctg atc gag acg gcc cgc gag atg ggc atc gac ctc    31882
Tyr Ala Met Arg Leu Ile Glu Thr Ala Arg Glu Met Gly Ile Asp Leu
2490                2495                2500                2505 gcc cgc gag gct aac gtc cag atc atc ctg gcc ggg gcg gag ccg cgc    31930
Ala Arg Glu Ala Asn Val Gln Ile Ile Leu Ala Gly Ala Glu Pro Arg
            2510                2515                2520 tcc gcg ttc acc acc cgc acc atc gag gag gcc ttc ggc gcc cgg gtc    31978
Ser Ala Phe Thr Thr Arg Thr Ile Glu Glu Ala Phe Gly Ala Arg Val
            2525                2530                2535 ttc aac gcc gcg ggc acc act gag ttc ggg ggg gtg ttc atg ttc gag    32026
Phe Asn Ala Ala Gly Thr Thr Glu Phe Gly Gly Val Phe Met Phe Glu
            2540                2545                2550 tgc acc gcc cgg cgc gag gcc tgc cac atc atc gaa ccc tcg tgc atc    32074
Cys Thr Ala Arg Arg Glu Ala Cys His Ile Ile Glu Pro Ser Cys Ile
            2555                2560                2565 gag gag gtg ctc gac ccg gtg acg gaa cag ccc gtc ggc tac ggc gag    32122
Glu Glu Val Leu Asp Pro Val Thr Glu Gln Pro Val Gly Tyr Gly Glu
2570                2575                2580                2585 gag ggc gtc cga gtc acc acc ggg ctg aac cgt gag ggg atg cag ctc    32170
Glu Gly Val Arg Val Thr Thr Gly Leu Asn Arg Glu Gly Met Gln Leu
            2590                2595                2600 ttc cgg cac tgg acc gag gac gtc gtg gtc aag cgg ccc cac acc gag    32218
Phe Arg His Trp Thr Glu Asp Val Val Val Lys Arg Pro His Thr Glu
            2605                2610                2615 tgc ggc tgc ggc cgg acg tgg gac ttc tac gac ggc ggc atc ctt cgg    32266
Cys Gly Cys Gly Arg Thr Trp Asp Phe Tyr Asp Gly Gly Ile Leu Arg
            2620                2625                2630 cgc gtg gac gac atg cgc aag ata cgc ggg gtc tcg atc acc ccg gtg    32314
Arg Val Asp Asp Met Arg Lys Ile Arg Gly Val Ser Ile Thr Pro Val
            2635                2640                2645 atg atc gag gat gtg ctg cgc ggc ttc gac gag gtg aac gag ttc cac    32362
Met Ile Glu Asp Val Leu Arg Gly Phe Asp Glu Val Asn Glu Phe His
2650                2655                2660                2665 tcg tcc atc cgg acc gtc cgc gga ctc gat acg atc cac gtc aag gtc    32410
Ser Ser Ile Arg Thr Val Arg Gly Leu Asp Thr Ile His Val Lys Val
            2670                2675                2680 gag gcg gga gac atc tcg ggt gag gcg gcc gag agc ctg tgc ggc cgc    32458
Glu Ala Gly Asp Ile Ser Gly Glu Ala Ala Glu Ser Leu Cys Gly Arg
            2685                2690                2695 atc acc gag gag ttc aag cgt gag ata ggc ata cgg ccc cag gtg gag    32506
Ile Thr Glu Glu Phe Lys Arg Glu Ile Gly Ile Arg Pro Gln Val Glu
            2700                2705                2710 ctg acc ccc gcg ggc agc ctc ccc cga tcg aag tgg aag gcg gca cga    32554
Leu Thr Pro Ala Gly Ser Leu Pro Arg Ser Lys Trp Lys Ala Ala Arg
            2715                2720                2725 ctt cat gac gag cgc gaa ctc gcc cct cag gcc tgagcaggtg gagcagctcc   32607
Leu His Asp Glu Arg Glu Leu Ala Pro Gln Ala
2730                2735                2740 tggtgagcta ccggagcctg ggcctgctgg agcagagctg cgcggtcccg gccgtgctcg   32667
```

-continued

```
ccgcggtcag ggccgcccgt gcggaactcc gtatcgccct ggacggccag ggcgtggagt     32727
tcgagtacta ccgggggcac gacgacagcc tcgtggcctg aacccacccc cggtccgccg     32787
ggtcagacga aagggagacc g gtg ccc cac ggt gca gag cgc gaa gcg agc       32838
                         Met Pro His Gly Ala Glu Arg Glu Ala Ser
                                         2745                2750 ccg gcc gag gag agc gcc ggc acc cgg ccg ctg acc ggc gag gag tat       32886
Pro Ala Glu Glu Ser Ala Gly Thr Arg Pro Leu Thr Gly Glu Glu Tyr
                2755                2760                2765 ctg gag agc ctg cgg gac gcg cgg gag gtg tac ctc gac ggc agc cgc       32934
Leu Glu Ser Leu Arg Asp Ala Arg Glu Val Tyr Leu Asp Gly Ser Arg
            2770                2775                2780 gtc aag gac gtc acc gcg cat ccc gcg ttc cac aac ccg gcc cgg atg       32982
Val Lys Asp Val Thr Ala His Pro Ala Phe His Asn Pro Ala Arg Met
        2785                2790                2795 acg gcc cgg ctg tac gac agc ctg cac gac ccc gcc cag aaa gcg gtc       33030
Thr Ala Arg Leu Tyr Asp Ser Leu His Asp Pro Ala Gln Lys Ala Val
    2800                2805                2810 ctg acg gcg ccc acc gat gcc ggt gac ggt ttc acc cac cgc ttc ttc       33078
Leu Thr Ala Pro Thr Asp Ala Gly Asp Gly Phe Thr His Arg Phe Phe
2815                2820                2825                2830 acc gca ccg cgc agc gtc gac gac ctg gtc aag gac cag gcc gcc atc       33126
Thr Ala Pro Arg Ser Val Asp Asp Leu Val Lys Asp Gln Ala Ala Ile
                2835                2840                2845 gca tcc tgg gcg cgc aag agc tac ggc tgg atg ggg cgc agc ccc gac       33174
Ala Ser Trp Ala Arg Lys Ser Tyr Gly Trp Met Gly Arg Ser Pro Asp
            2850                2855                2860 tac aag gcg tcg ttc ctc ggc acg ctg ggg gcc aac gcc gac ttc tac       33222
Tyr Lys Ala Ser Phe Leu Gly Thr Leu Gly Ala Asn Ala Asp Phe Tyr
        2865                2870                2875 gag ccc ttc gcg gac aac gcc cgg cgc tgg tac cgg gag tcg cag gag       33270
Glu Pro Phe Ala Asp Asn Ala Arg Arg Trp Tyr Arg Glu Ser Gln Glu
    2880                2885                2890 aag gtg ctg tac tgg aac cat gcc ttc ctt cac ccg ccg gtc gac cgc       33318
Lys Val Leu Tyr Trp Asn His Ala Phe Leu His Pro Pro Val Asp Arg
2895                2900                2905                2910 tcg ctg ccc gcc gac gag gtg ggc gac gtc ttc atc cac gtc gag cgg       33366
Ser Leu Pro Ala Asp Glu Val Gly Asp Val Phe Ile His Val Glu Arg
                2915                2920                2925 gag acc gac gcg ggc ctg gtg gtg agc ggg gcc aag gtc gtc gcg acc       33414
Glu Thr Asp Ala Gly Leu Val Val Ser Gly Ala Lys Val Val Ala Thr
            2930                2935                2940 gga tcg gcc ctc acc cac gcg gcg ttc atc tcg cac tgg gga ctt ccc       33462
Gly Ser Ala Leu Thr His Ala Ala Phe Ile Ser His Trp Gly Leu Pro
        2945                2950                2955 atc aag gac cgg aag ttc gcc ctg gtg gcc acc gtg ccg atg gac gcg       33510
Ile Lys Asp Arg Lys Phe Ala Leu Val Ala Thr Val Pro Met Asp Ala
    2960                2965                2970 gac ggc ctc aag gtg atc tgc cgt ccc tcc tac tcc gca aac gcg gcg       33558
Asp Gly Leu Lys Val Ile Cys Arg Pro Ser Tyr Ser Ala Asn Ala Ala
2975                2980                2985                2990 acc acg ggc agc ccg ttc gac aac ccg ctg tcc tca cgg ctg gac gag       33606
Thr Thr Gly Ser Pro Phe Asp Asn Pro Leu Ser Ser Arg Leu Asp Glu
                2995                3000                3005 aac gac gcc atc ctc gta ctc gac cag gtg ctg atc ccc tgg gag aac       33654
Asn Asp Ala Ile Leu Val Leu Asp Gln Val Leu Ile Pro Trp Glu Asn
            3010                3015                3020 gtg ttc gtc tac ggc aac ctg ggc aag gta cat ctc ctc gcc gga cag       33702
Val Phe Val Tyr Gly Asn Leu Gly Lys Val His Leu Leu Ala Gly Gln
```

```
                       3025                  3030                  3035
tcc ggg atg atc gaa cgc gcc acc ttc cac ggg tgc acc cgg ctc gcc        33750
Ser Gly Met Ile Glu Arg Ala Thr Phe His Gly Cys Thr Arg Leu Ala
    3040                  3045                  3050 gtg aag ctg gag ttc atc gcc ggg ctg ctg gcc aag gcg ctg gac atc        33798
Val Lys Leu Glu Phe Ile Ala Gly Leu Leu Ala Lys Ala Leu Asp Ile
3055                  3060                  3065                  3070 acc ggg gcg aag gac ttc cgc ggt gtg cag acc cgg ctc gga gaa gtc        33846
Thr Gly Ala Lys Asp Phe Arg Gly Val Gln Thr Arg Leu Gly Glu Val
                3075                  3080                  3085 ctg gcc tgg cgc aac ctc ttc tgg tca ctg tcg gac gcg gcg gcc cgc        33894
Leu Ala Trp Arg Asn Leu Phe Trp Ser Leu Ser Asp Ala Ala Ala Arg
                3090                  3095                  3100 aac ccc gtc ccc tgg aag aac ggc acg ctc ctg ccc aac cct cag gcg        33942
Asn Pro Val Pro Trp Lys Asn Gly Thr Leu Leu Pro Asn Pro Gln Ala
            3105                  3110                  3115 ggt atg gcc tac cgc tgg ttc atg cag atc ggc tac ccg cgg gtc ctg        33990
Gly Met Ala Tyr Arg Trp Phe Met Gln Ile Gly Tyr Pro Arg Val Leu
    3120                  3125                  3130 gag atc gtc caa cag gac gtg gcc agc ggc ctc atg tac gtc aac tcc        34038
Glu Ile Val Gln Gln Asp Val Ala Ser Gly Leu Met Tyr Val Asn Ser
3135                  3140                  3145                  3150 tcc acg gag gac ttc cgc aac ccc gag acc ggc ccc tac ttg gag aag        34086
Ser Thr Glu Asp Phe Arg Asn Pro Glu Thr Gly Pro Tyr Leu Glu Lys
                3155                  3160                  3165 tac ctc cgg ggc agc gac ggc gca ggc gcc gtc gag cgt gtc aag gtg        34134
Tyr Leu Arg Gly Ser Asp Gly Ala Gly Ala Val Glu Arg Val Lys Val
                3170                  3175                  3180 atg aag ctg ctg tgg gac gcg gtg gga tcc gac ttc ggc ggc cgg cac        34182
Met Lys Leu Leu Trp Asp Ala Val Gly Ser Asp Phe Gly Gly Arg His
                3185                  3190                  3195 gaa ctc tac gag cgg aac tac tcc ggg aac cac gag aac acc cgg atc        34230
Glu Leu Tyr Glu Arg Asn Tyr Ser Gly Asn His Glu Asn Thr Arg Ile
        3200                  3205                  3210 gag ttg ctg ctg tcg cag acg gcg agc ggc aaa ctg gac tcg tac atg        34278
Glu Leu Leu Leu Ser Gln Thr Ala Ser Gly Lys Leu Asp Ser Tyr Met
3215                  3220                  3225                  3230 gac ttc gcc cag gca tgc atg gac gag tac gac ctg gac ggc tgg acc        34326
Asp Phe Ala Gln Ala Cys Met Asp Glu Tyr Asp Leu Asp Gly Trp Thr
                3235                  3240                  3245 gct ccc gac ctg gag tcg ttt cac gcg atg cgt tcc gcc tcc cgc gac        34374
Ala Pro Asp Leu Glu Ser Phe His Ala Met Arg Ser Ala Ser Arg Asp
                3250                  3255                  3260 ctt ctc gga ggg ctg tagttccccg acggtgtact gcggcccccg atccgggggc        34429
Leu Leu Gly Gly Leu
        3265 cgcagtacac cgtcggggcg gctggtgctc agccgcgcag gaatccgatg agctcggggg     34489 cgagcttctt gggcgccatg gcgacggcac cgtggttgag cccgttcagg gtgcggtggc     34549 tcgcgtcggg gaggactccg gtgagttcct tcgcggcacg ctggaaaccg tcgggctct     34609 tggaaccggt cagcaccagg gtcggggccg acgccgccga ccacggctcg gcggggagcg     34669 gcttgccctg ctgggtgtcg cccatcaccg cgatgtcgta gggaagcgtg ttggccagac     34729 ccttgaggtt ggaccagaca ccgggcatca ggcgcatggc gccgaccatg aaggagggca     34789 tgccctgtgc cttgaccatg aaggccttga ccgcgtcgct cgtcggtcc tccgccagaa      34849 ggctgtcgat ctgaccgccg aagccggcgg cgggccgaa gccgtccgag gtgacggaga      34909 acggcggctc gtagaccgcg agcttgttca ccttcaggcc ggcggcggcg gctcgcaggg     34969
```

-continued

```
cgagcaccgc gccggaagag ctgccgaaca gggaggccga accgccgacc tggtcgatca    35029
gcgccgcgat gtcctcgatc tcgcgctcga ccgcgtacgc cggaccgtcg gcgctggcgc    35089
cgcggccccg acggtcgtag ttgacgaccg tgaagtgctc ggcgaggaga ccggcgagct    35149
tcttggcgtc ggagcggtcg gccaaggcgg aggccaccag gatcaccgcc ggcccctcgc    35209
ccgacttgtc gaaggcgatc gtggtgccgt cggccgatac cgtcgttgat tccaccttgg    35269
ctgctttctc acgggttgaa gacatagctt ccctcagatc acattgtggg gcgtgctgcc    35329
gacagtggag accggcgtcc ggaggaaaag taatcggtcc tgccagaatt gggggttccg    35389
gagggcacgc cgaccgctgc acgacggcgc gccccgacct tccggacatt gtcgtgccct    35449
cagatgtgtt tcgcatcttc aggagtgctc agtgatccgt gaggtgagaa agggacggtg    35509
gtccggtcag tcgttgccgc gcgggctgtt ctggtaagcg gccagacgcc actgcccgtc    35569
ctgttcgacg gccagccagg aggcccggac ggcgccgtcg ccgctcgcct cggtctcccc    35629
cggggcgagg atgccgccct cggtgatgag cagggcgatg ccgtcgccga gcaggcgcgc    35689
gtcgatgggg ctgccgatga cacgggtgcc cttgtacggg cccgcgaagg cggccgccat    35749
gtgggtgcgg atgttctcgc ggcccttgcg gaagaggccg gggaggatca tcgtcccgtc    35809
ctcggcgaag acgtcggcga accggtcggc gtcgtggtcg gccaggcgg ccacgatgcg    35869 cgccggcaga gcggctaccg ctgccagggc ggcgtcggga gcggaggtgg tcgagtcggt    35929
gctggtcata tcgcggttcc cgtccgttgg ttggcggttt cggcacggcc cgcagccctg    35989
cccgagcccg acgctggcag gcggccccgt catcaggcat ctcctgcgtt gcgccccacg    36049
ccagtcactt cacggccaga acaagtcgcg cattctggaa gaagctgagg cccgcgaccc    36109
ggtgcgacga tctgcggtgt cacggagttc gcacacgttt acgcacggag gctcg atg    36167
                                                                  Met
```

| | | |
|---|---|---|
| ccc gct gtc aat gga tcg gtg cag tca ggc cag tcg cac cga cgc tcc<br>Pro Ala Val Asn Gly Ser Val Gln Ser Gly Gln Ser His Arg Arg Ser<br>           3270                        3275                        3280 | | 36215 |
| gtc gtg gcg acg gtg gtg ggc aac ttc gtg gag tcg ttc gac tgg ctc<br>Val Val Ala Thr Val Val Gly Asn Phe Val Glu Ser Phe Asp Trp Leu<br>3285                      3290                        3295                      3300 | | 36263 |
| gcc tac ggg ctc ttc gct cct ctc ttc gcg gct cag ttc ttc ccc tcg<br>Ala Tyr Gly Leu Phe Ala Pro Leu Phe Ala Ala Gln Phe Phe Pro Ser<br>           3305                        3310                        3315 | | 36311 |
| tcc aac cag ttc acc tcc ctg ctc ggc gcg ttc gcg gtc ttc ggc acg<br>Ser Asn Gln Phe Thr Ser Leu Leu Gly Ala Phe Ala Val Phe Gly Thr<br>           3320                        3325                        3330 | | 36359 |
| ggc atg ctc ttc cgg ccg atc ggc ggg gtc ctg ctg ggc cgc ctc gcc<br>Gly Met Leu Phe Arg Pro Ile Gly Gly Val Leu Leu Gly Arg Leu Ala<br>           3335                        3340                        3345 | | 36407 |
| gac cgg cgc ggc cgg cgc ccc gcc ctg atg ctg gcg atc gga ctg atg<br>Asp Arg Arg Gly Arg Arg Pro Ala Leu Met Leu Ala Ile Gly Leu Met<br>           3350                        3355                        3360 | | 36455 |
| acc ggc ggc tcg acc ctg atc gcc gtc gtc ccc acc tac gag cac atc<br>Thr Gly Gly Ser Thr Leu Ile Ala Val Val Pro Thr Tyr Glu His Ile<br>3365                      3370                        3375                      3380 | | 36503 |
| ggg atc ctc gcc ccg ctg ctt ctg ctc ctc gcc cgg ctc gcc cag gga<br>Gly Ile Leu Ala Pro Leu Leu Leu Leu Leu Ala Arg Leu Ala Gln Gly<br>           3385                        3390                        3395 | | 36551 |
| gtc tcc tcg ggc ggg gaa tgg aca gcg gcg gcc acc tac ctg atg gag<br>Val Ser Ser Gly Gly Glu Trp Thr Ala Ala Ala Thr Tyr Leu Met Glu<br>           3400                        3405                        3410 | | 36599 |
| atc gcg ccg aag aac cgc cgg tgc ctc tac agc agc ctc ttc tcc gtg | | 36647 |

```
                Ile Ala Pro Lys Asn Arg Arg Cys Leu Tyr Ser Ser Leu Phe Ser Val
                        3415                3420                3425 acg acc atg gcg ggc ccc ttc gtc gca tcg ctg ctg ggc gcg ggc ctc            36695
Thr Thr Met Ala Gly Pro Phe Val Ala Ser Leu Leu Gly Ala Gly Leu
        3430                3435                3440 ggc gtg tgg ctg gga acc gcg acg atg gag gcc tgg ggc tgg cgg gtg            36743
Gly Val Trp Leu Gly Thr Ala Thr Met Glu Ala Trp Gly Trp Arg Val
3445                3450                3455                3460 ccg ttc ctc ctc ggc ggc gtc ttc ggc gtg atc ctg ctg ttc ctg cgc            36791
Pro Phe Leu Leu Gly Gly Val Phe Gly Val Ile Leu Leu Phe Leu Arg
                3465                3470                3475 cgt cgg ctc acc gag acc gag gtc ttc cgc cgg gag gtg cgg ccc cgg            36839
Arg Arg Leu Thr Glu Thr Glu Val Phe Arg Arg Glu Val Arg Pro Arg
        3480                3485                3490 gcc cgg cgc ggc tca ctg ggc cag ctg atc gga gcc cac cgc ccc cag            36887
Ala Arg Arg Gly Ser Leu Gly Gln Leu Ile Gly Ala His Arg Pro Gln
            3495                3500                3505 gtg ctg ctg gcc gtg atg ctg gtg gcc gga ctg ggc gtc atc ggc gga            36935
Val Leu Leu Ala Val Met Leu Val Ala Gly Leu Gly Val Ile Gly Gly
        3510                3515                3520 acg tgg tcg acc gcg gtc ccg gcg atg ggc cac cgt ctg atc ggc tcg            36983
Thr Trp Ser Thr Ala Val Pro Ala Met Gly His Arg Leu Ile Gly Ser
3525                3530                3535                3540 cag acg atg ttc tgg gtg gtg gtc tgt gtg acc ggc tcg gtc atc ctg            37031
Gln Thr Met Phe Trp Val Val Val Cys Val Thr Gly Ser Val Ile Leu
                3545                3550                3555 ctg cag gta ccc ata ggg ctg ctc gcc gac cgg gtg gaa ccg ggc agg            37079
Leu Gln Val Pro Ile Gly Leu Leu Ala Asp Arg Val Glu Pro Gly Arg
        3560                3565                3570 ttc ctg atc gtc tcc agc gtc gtc ttc gcc gct gtg ggc tcg tac gcc            37127
Phe Leu Ile Val Ser Ser Val Val Phe Ala Ala Val Gly Ser Tyr Ala
            3575                3580                3585 tac ctc acc gtc cag gac tcc ttc gcg agc ctg gcg ttc acg tac agc            37175
Tyr Leu Thr Val Gln Asp Ser Phe Ala Ser Leu Ala Phe Thr Tyr Ser
        3590                3595                3600 acc gga gtg atc ttc ctc ggc tgc gtc acc atg gtg ctg ccg aag atg            37223
Thr Gly Val Ile Phe Leu Gly Cys Val Thr Met Val Leu Pro Lys Met
3605                3610                3615                3620 ctc tcc aga atc ttc cct ccg cag ata cgc ggc ctg ggc atc ggg ctg            37271
Leu Ser Arg Ile Phe Pro Pro Gln Ile Arg Gly Leu Gly Ile Gly Leu
                3625                3630                3635 ccg cac gcc tcg acc acc gca ctc ctc ggc ggg gcg ggg cca ctg ctg            37319
Pro His Ala Ser Thr Thr Ala Leu Leu Gly Gly Ala Gly Pro Leu Leu
            3640                3645                3650 gcc gcc tac tcc gac gag cga ggc gcc tcg ggc tgg ttc atc gcc gcc            37367
Ala Ala Tyr Ser Asp Glu Arg Gly Ala Ser Gly Trp Phe Ile Ala Ala
        3655                3660                3665 gtg atg gcc gcg gtc ctg ctc gcc tgg ccg gcc acc ctg tgg gag cga            37415
Val Met Ala Ala Val Leu Leu Ala Trp Pro Ala Thr Leu Trp Glu Arg
        3670                3675                3680 cgg ctg ttc cgc gcc cgg acg gcc ccg gga agc gag ccg gtt ccc gaa            37463
Arg Leu Phe Arg Ala Arg Thr Ala Pro Gly Ser Glu Pro Val Pro Glu
3685                3690                3695                3700 tcc gcc gtc gcc cgc ccc gtc ggg tgaccgtccg cacttctgca tcccgtccgg           37517
Ser Ala Val Ala Arg Pro Val Gly
                3705 caccgagcgc cggcgaccct cccgactgag aggttgacat c atg acg acg tcc gac          37573
                                            Met Thr Thr Ser Asp
                                                3710
```

```
acc acc gac cgg tcc cag gac ggc gtg ccg ccg ctc tcc ttc cac cag         37621
Thr Thr Asp Arg Ser Gln Asp Gly Val Pro Pro Leu Ser Phe His Gln
        3715                3720                3725 gag ttc ctg tgc atg ttc gac agc ggg aac gac ggc gcc gac gtg ggg         37669
Glu Phe Leu Cys Met Phe Asp Ser Gly Asn Asp Gly Ala Asp Val Gly
3730                3735                3740                3745 ccg ttc ggc ccc atg tac cac atc gtc gga gcc tgg cgg ctg acc ggc         37717
Pro Phe Gly Pro Met Tyr His Ile Val Gly Ala Trp Arg Leu Thr Gly
                3750                3755                3760 ggg atc gac gag gag acc ctg cgc gag gcg ctg ggt gac gtc gtc gtg         37765
Gly Ile Asp Glu Glu Thr Leu Arg Glu Ala Leu Gly Asp Val Val Val
        3765                3770                3775 cgc cac gag gcc ctg cgc aca tcg ctg gtc cgc gaa ggt ggc acg cac         37813
Arg His Glu Ala Leu Arg Thr Ser Leu Val Arg Glu Gly Gly Thr His
            3780                3785                3790 cgg ccg gag atc ctg cct gcg ggg ccc gcc gcg ctg gag gtc cgt gat         37861
Arg Pro Glu Ile Leu Pro Ala Gly Pro Ala Ala Leu Glu Val Arg Asp
3795                3800                3805 ctc ggc gac gtc gac gag tcg gag cgg gtg cgg cgc ggt gag gaa ctg         37909
Leu Gly Asp Val Asp Glu Ser Glu Arg Val Arg Arg Gly Glu Glu Leu
3810                3815                3820                3825 ctc aac gag gtg gag tcg acc ggt ctg agc gtg cgg gag ctg ccc ctg         37957
Leu Asn Glu Val Glu Ser Thr Gly Leu Ser Val Arg Glu Leu Pro Leu
            3830                3835                3840 ctg cgg gcc gtg ctc gga cgc ttc gac cag aag gac gcg gtg ctg gtc         38005
Leu Arg Ala Val Leu Gly Arg Phe Asp Gln Lys Asp Ala Val Leu Val
                3845                3850                3855 ctc atc gcc cac cac acc gcc gcg gac gcc tgg gcc atg cac gtc atc         38053
Leu Ile Ala His His Thr Ala Ala Asp Ala Trp Ala Met His Val Ile
            3860                3865                3870 gcc cgc gac ctg ctc aac ctg tac gcc gcc agg cgc ggg aac ccg gtt         38101
Ala Arg Asp Leu Leu Asn Leu Tyr Ala Ala Arg Arg Gly Asn Pro Val
3875                3880                3885 ccc ccg ctc ccc gag ccg gcc cag cat gcc gag ttc gcc cgc tgg gag         38149
Pro Pro Leu Pro Glu Pro Ala Gln His Ala Glu Phe Ala Arg Trp Glu
3890                3895                3900                3905 cgc gag gcg gcc gag gca ccg cgg gtc gcg gtc tcg aag gaa ttc tgg         38197
Arg Glu Ala Ala Glu Ala Pro Arg Val Ala Val Ser Lys Glu Phe Trp
            3910                3915                3920 cgc aag cgc ctc cag ggc gcg cgg atc atc ggg ctg gag acg gac ata         38245
Arg Lys Arg Leu Gln Gly Ala Arg Ile Ile Gly Leu Glu Thr Asp Ile
                3925                3930                3935 ccg cgc tcg gcg ggg ctg ccc aag ggc acc gcg tgg cag cgc ttc gcc         38293
Pro Arg Ser Ala Gly Leu Pro Lys Gly Thr Ala Trp Gln Arg Phe Ala
            3940                3945                3950 gta cgc ggg gaa ctg gcc gac gcc gtg gtg gag ttc tca cgg gcc gcc         38341
Val Arg Gly Glu Leu Ala Asp Ala Val Val Glu Phe Ser Arg Ala Ala
        3955                3960                3965 aag tgc tcc ccg ttc atg acc atg ttc gcc gcc tac cag gtg ctg ctg         38389
Lys Cys Ser Pro Phe Met Thr Met Phe Ala Ala Tyr Gln Val Leu Leu
3970                3975                3980                3985 cac cgc agg acg ggc gag ctg gac atc acc gtg ccg acc ttc tcc ggg         38437
His Arg Arg Thr Gly Glu Leu Asp Ile Thr Val Pro Thr Phe Ser Gly
            3990                3995                4000 ggg cgc aac aac tcg cgg ttc gag gac acc gtc ggt tcc ttc atc aac         38485
Gly Arg Asn Asn Ser Arg Phe Glu Asp Thr Val Gly Ser Phe Ile Asn
            4005                4010                4015 ttc ctg ccg ctg cgt acc gac ctc tcc gga tgc gca tcc ttc cgc gag         38533
Phe Leu Pro Leu Arg Thr Asp Leu Ser Gly Cys Ala Ser Phe Arg Glu
            4020                4025                4030
```

```
                                                                     -continued gtc gtg ctg cgc acc cgc acc acc tgc gga gag gcg ttc acc cac gag    38581
Val Val Leu Arg Thr Arg Thr Thr Cys Gly Glu Ala Phe Thr His Glu
    4035               4040                4045 ctg ccc ttc tcc cgg ctg atc ccg gag gtg ccg gag ctg atg gcg tcg    38629
Leu Pro Phe Ser Arg Leu Ile Pro Glu Val Pro Glu Leu Met Ala Ser
4050                4055                4060                4065 gcg gcc tcc gac aac cac cag atc tcc gtc ttc cag gcc gtg cac gcg    38677
Ala Ala Ser Asp Asn His Gln Ile Ser Val Phe Gln Ala Val His Ala
            4070                4075                4080 ccc gcg tcc gag ggg ccc gag cag gcc ggg gac ctg acg tac tcg aag    38725
Pro Ala Ser Glu Gly Pro Glu Gln Ala Gly Asp Leu Thr Tyr Ser Lys
    4085                4090                4095 atc tgg gag cgg cag ctg tcg cag gcg gag ggc tcc gac atc ccc gac    38773
Ile Trp Glu Arg Gln Leu Ser Gln Ala Glu Gly Ser Asp Ile Pro Asp
4100                4105                4110 ggg gtg ctg tgg tcg atc cac atc gac ccc tcg ggc tcc atg gcc ggc    38821
Gly Val Leu Trp Ser Ile His Ile Asp Pro Ser Gly Ser Met Ala Gly
            4115                4120                4125 agc ctc ggg tac aac acc aac cgc ttc aag gac gag acg atg gcg gcc    38869
Ser Leu Gly Tyr Asn Thr Asn Arg Phe Lys Asp Glu Thr Met Ala Ala
4130                4135                4140                4145 ttc ctg gcc gac tac ctc gac gtg ctc gag aac gcg gtg gcc cgg ccg    38917
Phe Leu Ala Asp Tyr Leu Asp Val Leu Glu Asn Ala Val Ala Arg Pro
            4150                4155                4160 gac gcc ccc ttc acc tcc tgagacagtt ccggcggcgg cgaacccgcc           38965
Asp Ala Pro Phe Thr Ser
                4165 cgaagaaagg aaagcca gtg tcc acc gtt tcc gac aca gcg gcc ggc tcc     39015
                Met Ser Thr Val Ser Asp Thr Ala Ala Gly Ser
                    4170                4175 tcc ctg gag gag aag gtc acc cgg atc tgg acg ggt gtt ctc ggc acg    39063
Ser Leu Glu Glu Lys Val Thr Arg Ile Trp Thr Gly Val Leu Gly Thr
    4180                4185                4190 tcc ggt gag gaa ggc gcg acg ttc atc gag ctc gga ggg cag tcg gtc    39111
Ser Gly Glu Glu Gly Ala Thr Phe Ile Glu Leu Gly Gly Gln Ser Val
4195                4200                4205                4210 tcg gcc gtg cgc atc gcc acg cgt atc cag gag gag ctc gac atc tgg    39159
Ser Ala Val Arg Ile Ala Thr Arg Ile Gln Glu Glu Leu Asp Ile Trp
            4215                4220                4225 gtc gac atc ggc gtc ctc ttc gac gac ccg gat ctg cct acc ttc atc    39207
Val Asp Ile Gly Val Leu Phe Asp Asp Pro Asp Leu Pro Thr Phe Ile
                4230                4235                4240 gcg gcg gtc gtc cgg acg gcc gac gcc gcg ggc ggc gag ggc tcc gga    39255
Ala Ala Val Val Arg Thr Ala Asp Ala Ala Gly Gly Glu Gly Ser Gly
    4245                4250                4255 acg cag tgagactcgc cgggcgccgt ctccccgcgg cgcccggttt cacatggctg     39311
Thr Gln
    4260 aggcggttca cccggtaccg ggtgaaccgc ctcagccatg tgaaaccggg cctggtcagc  39371 gcagctggat gtccgtctcc cgggcgatcg cccggaggaa ctcgccgcgg acagcgcgt   39431 cggcgaccag ctcgatgtcg tcggccatgt accggtcgac gcccagcgtc ggaaccagcc  39491 ggcgcaccgc ttcgtacgtg gccttcgccg ccgggctcaa gccgtcgaac cggcggaga   39551 tgtcgaccgc ctgggcggcg gccaggtact ccaccgcgag gatcttgttg ttgttcgaca  39611 ggacccggcg ggcgttgcgg gccgagatca ggcccatgct caccacgtcc tggttgtcgc  39671 cgttggacgg gacgctctgg gtgctggccg ggccgatcgt ccggttctcg gccaccagtg  39731
```

-continued

```
cggtggccgg gtactgggcg ccggcgaatc cgctgtgcag ccccgggtcc cggagacga    39791
ggaactccgg gaggccgtag ctgaggtgcc ggttcaggac ccggttgatc tgccgctcgg   39851
ccaggacgcc gagctggtg agcgcgatgg tcacgaagtc catcgcgaac gcgatcggct    39911
gaccgtggaa gttcgccccg tggaagatct ccttgccctc gaagaagagc gggttgtcgt   39971
tggccgagtt gagctcgatg cgcagcttgt gccgcgcgtg gtacaaggtg tcgcgcaccg   40031
ccccgacgac ctgggggatg gcccgcagcg agtaggcctt ctgcaggtag atctccgagc   40091
gctggacgtc cttgccggcc tccttgtcct tctggagttc tcggcgcagg tcggcgtgct   40151
cgaccgtcag tccgctgccc cgcatcaggg cccgcatgtt ggcggcggtg tcgatctggc   40211
cctcgtgcgg gcgggctatg tcgtgcccct ccgcgaggaa ggggctggtc gatccgcgta   40271
ccgcctcgat gagcagagcc gtcacgatct cggcctgctg ggcctgctcc agggcccgtc   40331
cgacgaccag ggagcccaga ccggtcatcc cggacgtgcc gttgatcagt gcgaggccct   40391
ccttgaagcg cagttcgagc ggctcgatgc ccgctcggc cagcacctgg gcggtctcca   40451
ccggccgtcc gtcgcgcagg acgtagccct ctccgatgag ggtgctcgcg acgtgggaga   40511
ggggagccag gtcgccgctc gccccgagtg acccgatctc gggtatggcc ggggtgatgc   40571
cctcgttcag gtactgcgcg aggcgttcga ggatgatggg gcgcaccgcg gagtggccct   40631
tggcgagggt gttcagccgg gcggcgacga tcgcccgcgc ctcgtcctcg gcgaacagcg   40691
gaccgactcc cgcgctgtgg ctacggacga gattggtctg cagttcgact tccttcgact   40751
tgtcgacctg catgtagatc atctcgccgt acccggtggt cacccgtag atggggatgt    40811
tctgttcggc gatcccttcg aagatctccc ggctcttctg ggccttcgcg atggattcgg   40871
ccggtacgtc gaccgtcgcg cgttcctccg cgacgcggcg tacggcttcg acggtcaggg   40931
tctcgccgtc gacggaaacc gggacgatct cggtctcgac ttgagtcaat gccatcactc   40991
catgggtagc ggccgaggcc ggtgtacgac aggtcagggg gtgggttcgt gaggcgcggc   41051
tcagcgggtg agccgggagc ggtccacctt ccccgcggcg ttgcgcggca ggcgtgaagt   41111
caggcgggtg aagacggcgg gcagtgcgag ggggccgaac tggccgcgca gatgggaacg   41171
ccaggcccgg atgtccgcgc gcacgtcctc ccggccctct ccttgtggca ccacgtacac   41231
ggcgaggcgg gtcaccaggc cctggccgtt gacgtggggg aggaccgcgc actccaggac   41291
cgagggtca cggttcagcg cggcctcgat ctcggtgagt ccaagcggt tcccgaacag     41351
cttgacctgg aagtccttgc ggccccggaa ttccagggct ccgtcgaacc gtacccgcgc   41411
cagatccccg gtccggtacc accggtcacc gtccggggcg aggccggcga ggggcgcgaa   41471
cagcgcgctg tggtccgggc cgccctcgac ggcgagataa cccggcgtca cgtacgggga   41531
gcggatcacc agttcgccgg tgacgccggc ggggctcggc cggtcgtccg cgtccacgac   41591
gagtacctgg cggccgggga gcgggtaccc gatcggggcc gggcccgtga ccggcccggt   41651
gatctcgtgc caggtcgcgg cgatcgtctc ggtgggcccg tagaggttga tcaggcgggt   41711
ccggggcagg gccgcgcgca gtccgtccac gagttcgccg ggcagcgcct cgcccatcag   41771
gagcaggtgg cccagggtgc cgggccgatc gcccgggtcg gaggcggtga tcactcccag   41831
gaggtcccgg gcgaagctgg gcacggtctg gagatgagtg atccgctcct ggacgagcca   41891
cggcaccagc ttgtcggggt tcaccctgac gcgctccggc accggacaca gcgtcccgcc   41951
ggccacgagc gtcgcgaaga cctcggccag cgccgggtcg tgctccggg                42000
```

<210> SEQ ID NO 2
<211> LENGTH: 21185

-continued

```
<212> TYPE: DNA
<213> ORGANISM: Streptomyces globisporus
<220> FEATURE:
<221> NAME/KEY: CDS
<222> LOCATION: (1966)..(4041)
<223> OTHER INFORMATION: orf27
<220> FEATURE:
<221> NAME/KEY: CDS
<222> LOCATION: (4188)..(5189)
<223> OTHER INFORMATION: orf28
<220> FEATURE:
<221> NAME/KEY: CDS
<222> LOCATION: (5249)..(6502)
<223> OTHER INFORMATION: orf29
<220> FEATURE:
<221> NAME/KEY: CDS
<222> LOCATION: (8371)..(9408)
<223> OTHER INFORMATION: orf31
<220> FEATURE:
<221> NAME/KEY: CDS
<222> LOCATION: (11262)..(12092)
<223> OTHER INFORMATION: orf33
<220> FEATURE:
<221> NAME/KEY: CDS
<222> LOCATION: (12252)..(13397)
<223> OTHER INFORMATION: orf34
<220> FEATURE:
<221> NAME/KEY: CDS
<222> LOCATION: (14047)..(14898)
<223> OTHER INFORMATION: orf35
<220> FEATURE:
<221> NAME/KEY: CDS
<222> LOCATION: (18961)..(20037)
<223> OTHER INFORMATION: orf40
<220> FEATURE:
<221> NAME/KEY: CDS
<222> LOCATION: (20066)..(20917)
<223> OTHER INFORMATION: orf41

<400> SEQUENCE: 2
agcgccgggt cgtgctccgg ggagacccac tgcgccaccc gcgcgcccgg ccccatcgcg      60
aaccgttcgc ccatccagcc cgcgaactgg cccagcgcgg catgcgactg ggcgatcccc     120
ttgggccgcc cggtcgaacc cgaggtgaac gccacgtagg ccaggtctgc caggcccggc     180
cccgccgcgc tcgtcgcgtc cgggccggcg gcgggtcgag ggccgagcac agaggaggcg     240
tccagcaggg tggcgcccgg ttcaccggcg taccagagcg ccagcggatc ctcctgcgga     300
tcgccgtcga ggaccaggca cgccgggcgc agatcgctga gcatcgaccg gtgtcgttcg     360
cccgcgccgt ccggagcgaa ccacgccagg tgggcgcccg cctccaggac tcccagcagc     420
accgcgatcc ggcgggcgcc cggctgcatc cgcaccgcca ccggcgagcc gtgccccgcg     480
ccggccgcgg tgagggccga ggcgacgcgg gccgcgtccg cggtcagttc ggcggtcagt     540
tcggcgtagc ttgtgcgcgt gccgccgaac gagacggcga caccgtcgtg ttccgcgtgg     600
cggcggaccg aggcgtgcac cggccgcgtc atgtccccgc cggacgcccg gcggtccgaa     660
gcgcgcaggg cgtggtcccg gtggcggtcg tcgtccagcg gcagagcgcc cacgggtgtg     720
tccggatccg tggtcgcggc ggtcaggagg acggccagct gatccagcat ccgccgggcc     780
gaagcgggct cgaacagagc ttcgcggtac tccaggtagc cggtgaccga gggcgcggtg     840
tcctgcagca ccagggtcag gtcggcggcg gcagtgccgt tgtgcacgga cagccgcctc     900
acctcggcgc ctggtatccg caggcccggc cgctcctcgt ggacgaacac ggcgtcggcc     960
ccctcgatcc ggcacggccc gggggccggg gccggcgtcg tgtgcagcag ctcccggaag    1020
gcggtggccg gcgtgccgtc gtcctgtccg gcgtagcgct ggaccagggc tcggaatccg    1080
gccagcacca cggccgcggc ggtgacccct tccgcttcgg cgagccgggc cgtacggaag    1140
```

-continued

```
ccgaggtccg gactccagcc gaaggcgacg gtgctccccg cgtgcgaggg caggtgcggg    1200
cggttccggt cggcgggcag gacctgtccg gaggcggtcg ccgaagactc ctcgctcccg    1260
ggcgcccggg gcgtttgcgg cgcgggcgca gtgggaggcc ggccgccggt ggtgacggcg    1320
aggtacgcgt tcgacaacgc ggccggcagg ggcccggacg gcccgtccca ggctccggag    1380
tgcgaggcca ccaggagaag caggtgcgcg cgtgggcctc tgcgggcgat gtggagccgt    1440
gcgggcgcgt caccctcggc gaagggacgg gccgcccagc gagcgcagag ttcctcctcc    1500
ccgcactcct cgtcggcact cggcccgtcc acggcggccc cgtctccggc ggcggcccgc    1560
caggccgtcc gcagggcctc caggtcgagt ccgccgctca cgtggtaggc cgcgtacggg    1620
tgcaacaccg cagatccgga ggccggcgaa ggccccggt ccggctcggt cacagtcacg     1680
tcattcgcca cgacgcccat cttggggcgg cggcgcacag gacgcttctc cttgagtgcg    1740
gagctccgcg tacggcgccg aagcgttcgg tcaaaccttg ttcgaccaac tgcgcaatct    1800
ggaagttgac gtcttccagg tggagttggg aacgatggag gccccgccg gccgcgtcgg     1860 aacggccgtg cagtgcggcc ctctccaaca ctcccggcca tcgcggaatc cgagacgtgc    1920
ccgaaggagc ccccttgca agcctggttc aagcgcacca gtggt gtg ccc ggt gac    1977
                                                  Val Pro Gly Asp
                                                    1 aga cgt gga aag tgg ctg gtc ctg gcc gcc tgg ctc atc atc gcg atg     2025
Arg Arg Gly Lys Trp Leu Val Leu Ala Ala Trp Leu Ile Ile Ala Met
  5              10                  15                  20 gcg ctg ggc ccg ctg gcg ggg aag ctc gcc gac gtc cag gac tcc agc     2073
Ala Leu Gly Pro Leu Ala Gly Lys Leu Ala Asp Val Gln Asp Ser Ser
          25                  30                  35 gcc aac gcc ttc ctt ccg cgc agc tcg gag tcc gcg aag ctg aac aag     2121
Ala Asn Ala Phe Leu Pro Arg Ser Ser Glu Ser Ala Lys Leu Asn Lys
      40                  45                  50 gaa ctg gag aag ttc cgc gcc gac gag ctg atg ccg gcc gtg gtg gtc     2169
Glu Leu Glu Lys Phe Arg Ala Asp Glu Leu Met Pro Ala Val Val Val
  55                  60                  65 tac agc gcc gac ggc tcg ctg ccc gcc gag ggg cgg gcc aag gcc gag     2217
Tyr Ser Ala Asp Gly Ser Leu Pro Ala Glu Gly Arg Ala Lys Ala Glu
          70                  75                  80 aag gac ata gcc gcc ttc cag gag ctg gcc gcc gag ggc gag aag gtc     2265
Lys Asp Ile Ala Ala Phe Gln Glu Leu Ala Ala Glu Gly Glu Lys Val
 85                  90                  95                 100 gaa gcg ccc ctg gag tcg gag gac ggc cag gcg ctc atg gtc gtc gtt     2313
Glu Ala Pro Leu Glu Ser Glu Asp Gly Gln Ala Leu Met Val Val Val
              105                 110                 115 ccg ctg atc agc gac gcc gac atc gtc gcc acg acg aag aag gtc cgc     2361
Pro Leu Ile Ser Asp Ala Asp Ile Val Ala Thr Thr Lys Lys Val Arg
          120                 125                 130 gat gtc gcg gac gcc aac gcc ccc ccg ggc gtc gcc atc gag gtg ggc     2409
Asp Val Ala Asp Ala Asn Ala Pro Pro Gly Val Ala Ile Glu Val Gly
      135                 140                 145 ggg ccc gcc ggg tcg acg acc gac gcc gcc ggc gct ttc gag tcc ctc     2457
Gly Pro Ala Gly Ser Thr Thr Asp Ala Ala Gly Ala Phe Glu Ser Leu
150                 155                 160 gac tcc atg ctg atg atg gtc acc ggc ctt gtg gtc gcc atc ctg ctg     2505
Asp Ser Met Leu Met Met Val Thr Gly Leu Val Val Ala Ile Leu Leu
165                 170                 175                 180 ctg atc acc tac cgc tcc ccc atc ctg tgg ctg ctg ccc ctg ctc tcc     2553
Leu Ile Thr Tyr Arg Ser Pro Ile Leu Trp Leu Leu Pro Leu Leu Ser
              185                 190                 195 gtc ggc ttc gcc tcc gtg ctg acc cag gtc ggc acc tac atg ctc gcc     2601
```

```
                                                   -continued

Val Gly Phe Ala Ser Val Leu Thr Gln Val Gly Thr Tyr Met Leu Ala
            200                 205                 210 aag tac gcc ggg ctg ccg gtc gac ccg cag agc tcc ggc gtc ctg atg     2649
Lys Tyr Ala Gly Leu Pro Val Asp Pro Gln Ser Ser Gly Val Leu Met
            215                 220                 225 gtc ctc gtg ttc ggt gtc ggc acc gac tac gcc ctg ctg ctc atc gcc     2697
Val Leu Val Phe Gly Val Gly Thr Asp Tyr Ala Leu Leu Leu Ile Ala
            230                 235                 240 cgc tac cgt gag gaa ctg cgc cgc gag cag gac cgg cac gtg gcc atg     2745
Arg Tyr Arg Glu Glu Leu Arg Arg Glu Gln Asp Arg His Val Ala Met
245                 250                 255                 260 aag acc gcg ttg cga cgg tcg ggc ccg gcc atc ctg gcc tcg gcc ggc     2793
Lys Thr Ala Leu Arg Arg Ser Gly Pro Ala Ile Leu Ala Ser Ala Gly
            265                 270                 275 acc atc gcc atc ggc ctc gtc tgc ctg gtc ctc gcg gac gtc aac tcc     2841
Thr Ile Ala Ile Gly Leu Val Cys Leu Val Leu Ala Asp Val Asn Ser
            280                 285                 290 tcc cgc tcc atg ggc ctg gtc ggc gcg atc ggc gtg gtc tgc gcc ctc     2889
Ser Arg Ser Met Gly Leu Val Gly Ala Ile Gly Val Val Cys Ala Leu
            295                 300                 305 ctc gcc atg gtc acg atc ctg ccc gcg ctg ctg gtc atc ctg ggc cgc     2937
Leu Ala Met Val Thr Ile Leu Pro Ala Leu Leu Val Ile Leu Gly Arg
            310                 315                 320 tgg gtg ttc tgg ccc ttc gtt ccc cgc tgg acg ccg gag tcg gcc gcg     2985
Trp Val Phe Trp Pro Phe Val Pro Arg Trp Thr Pro Glu Ser Ala Ala
325                 330                 335                 340 gcc ccc gag gca ccg gcg tcc cac agc cgc tgg gag cgc atc ggc tcc     3033
Ala Pro Glu Ala Pro Ala Ser His Ser Arg Trp Glu Arg Ile Gly Ser
            345                 350                 355 gtc acg gcc gcc cgg ccg cgc cgc gcc tgg gtg ctg tcc ttg gcc gcg     3081
Val Thr Ala Ala Arg Pro Arg Arg Ala Trp Val Leu Ser Leu Ala Ala
            360                 365                 370 acg ggg ctt ctc gcc ctc agt tcc ctc ggc ctc gac atg gga ctc acc     3129
Thr Gly Leu Leu Ala Leu Ser Ser Leu Gly Leu Asp Met Gly Leu Thr
            375                 380                 385 cag agc gaa ctg ctc cag acg aag ccc gag tcc gtc gtc gcc cag gag     3177
Gln Ser Glu Leu Leu Gln Thr Lys Pro Glu Ser Val Val Ala Gln Glu
            390                 395                 400 cgg atc tcc gcc cac tac ccg tcc ggc tcc tcc gac ccc gcc acc gtc     3225
Arg Ile Ser Ala His Tyr Pro Ser Gly Ser Ser Asp Pro Ala Thr Val
405                 410                 415                 420 gtc gca ccc agc gcg gac gtg gcc gag gtc cgc cgg gcc gcc gag ggg     3273
Val Ala Pro Ser Ala Asp Val Ala Glu Val Arg Arg Ala Ala Glu Gly
            425                 430                 435 acc gac gga gtg gtc tcc gtc cag gac ggc ccc acc act ccc gac gga     3321
Thr Asp Gly Val Val Ser Val Gln Asp Gly Pro Thr Thr Pro Asp Gly
            440                 445                 450 gag ctg acc atg ctg tcc gtg gtg ctg aag gac gtt ccc gac agc agc     3369
Glu Leu Thr Met Leu Ser Val Val Leu Lys Asp Val Pro Asp Ser Ser
            455                 460                 465 ggg gcc aag gac acc atc gat gca ctg cgg gac aac acg gat gct ctc     3417
Gly Ala Lys Asp Thr Ile Asp Ala Leu Arg Asp Asn Thr Asp Ala Leu
            470                 475                 480 gtg ggg ggt acg acg gcc cag agc ctg gac acc cag cgc gcc tcg gtc     3465
Val Gly Gly Thr Thr Ala Gln Ser Leu Asp Thr Gln Arg Ala Ser Val
485                 490                 495                 500 cgt gac ctc tgg gtc acc gtc ccc gcg gtc ctg ctg gtg gtc ctg ctc     3513
Arg Asp Leu Trp Val Thr Val Pro Ala Val Leu Leu Val Val Leu Leu
            505                 510                 515
```

-continued

| | |
|---|---|
| gtc ctg atc tgg ctg ctg cgc tcg gtc acc gga ccg ctg atc atg ctc<br>Val Leu Ile Trp Leu Leu Arg Ser Val Thr Gly Pro Leu Ile Met Leu<br>520                          525                      530 | 3561 |
| ggc acc gtg gtc gtg tcg ttc ttc gcg gcc ctg ggg gcg tcc aac ctg<br>Gly Thr Val Val Val Ser Phe Phe Ala Ala Leu Gly Ala Ser Asn Leu<br>535                          540                      545 | 3609 |
| ctc ttc gag tac gtg atg ggg cac gcc ggc gtc gac tgg tcg gtg ccg<br>Leu Phe Glu Tyr Val Met Gly His Ala Gly Val Asp Trp Ser Val Pro<br>550                          555                      560 | 3657 |
| ctt ctc ggg ttc gtg tac ctg gtc gcc ctc gga atc gac tac aac atc<br>Leu Leu Gly Phe Val Tyr Leu Val Ala Leu Gly Ile Asp Tyr Asn Ile<br>565                      570                      575                      580 | 3705 |
| ttc ctc atg cac cgg gtg aag gag gag gtc gct ctg cac ggc cat gcc<br>Phe Leu Met His Arg Val Lys Glu Glu Val Ala Leu His Gly His Ala<br>                 585                      590                      595 | 3753 |
| aag ggc gtg ctc acc ggc ctg acc acc acc ggg ggc gtc atc acc agt<br>Lys Gly Val Leu Thr Gly Leu Thr Thr Thr Gly Gly Val Ile Thr Ser<br>        600                      605                      610 | 3801 |
| gcc ggc gtg gtc ctg gcc gcg acg ttc gcc gtc atc gcc aca ctg ccg<br>Ala Gly Val Val Leu Ala Ala Thr Phe Ala Val Ile Ala Thr Leu Pro<br>615                          620                      625 | 3849 |
| ctg gtc ccg atg gcc cag atg ggt gtc gtg gtc ggc ctg ggc att ctg<br>Leu Val Pro Met Ala Gln Met Gly Val Val Val Gly Leu Gly Ile Leu<br>630                          635                      640 | 3897 |
| ctg gac acc ttc ctc gtc cgg acg att ctt ctg ccg gcc ctg gcg ctc<br>Leu Asp Thr Phe Leu Val Arg Thr Ile Leu Leu Pro Ala Leu Ala Leu<br>645                      650                      655                      660 | 3945 |
| gat ctg ggg ccc cgg ttc tgg tgg ccg ggc gcg ctg tcg aag acg tcc<br>Asp Leu Gly Pro Arg Phe Trp Trp Pro Gly Ala Leu Ser Lys Thr Ser<br>                 665                      670                      675 | 3993 |
| ggg gga ccg gcc ccc gtc cgc gag gac cgc acg tcc cag ccc gtg ggc<br>Gly Gly Pro Ala Pro Val Arg Glu Asp Arg Thr Ser Gln Pro Val Gly<br>        680                      685                      690 | 4041 |
| tgagacccgt cccgacgaga cccgtacggc gggcggccgg ttcccccggg ccgtacgact | 4101 |
| gagcaaccca gaagatgggc cgcccgcgac caggcgtcac gatggtggcc caccggccgc | 4161 |
| aggccgatct cccggaagga agcgcc gtg ttg ggc gat gag gac ggc aag gcc<br>                                            Val Leu Gly Asp Glu Asp Gly Lys Ala<br>                                                            695                      700 | 4214 |
| gcc gag ctg tgg tcg atg gcg aac ctg ggt aca ccg atg gcc gtg cgc<br>Ala Glu Leu Trp Ser Met Ala Asn Leu Gly Thr Pro Met Ala Val Arg<br>                 705                      710                      715 | 4262 |
| gtc gcg gcg acc ctg cgc atc gcc gac cac atc acg gcc gga gcg cac<br>Val Ala Ala Thr Leu Arg Ile Ala Asp His Ile Thr Ala Gly Ala His<br>720                          725                      730 | 4310 |
| acc gcc ggc gaa atc gcc gaa gcg gcc gcc gtg cac gag gaa tcc ctc<br>Thr Ala Gly Glu Ile Ala Glu Ala Ala Ala Val His Glu Glu Ser Leu<br>        735                      740                      745 | 4358 |
| gac cgg ctg ctg cgc tac ctc acc gtc cgg ggc ctg ctg gac cgt gac<br>Asp Arg Leu Leu Arg Tyr Leu Thr Val Arg Gly Leu Leu Asp Arg Asp<br>750                          755                      760                      765 | 4406 |
| ggg ctc ggc cgg tac acg ctg acc ccc ctg ggc cgg ccg ctg tgc gag<br>Gly Leu Gly Arg Tyr Thr Leu Thr Pro Leu Gly Arg Pro Leu Cys Glu<br>                 770                      775                      780 | 4454 |
| gac cac ccc gcc ggc gtc cgg gcc tgg ttc gac atg gag gga gcg ggg<br>Asp His Pro Ala Gly Val Arg Ala Trp Phe Asp Met Glu Gly Ala Gly<br>                 785                      790                      795 | 4502 |
| cgg ggc gag ctg tcg ttc gtc gac ctg ctg cac agc gta cgg acc ggg<br>Arg Gly Glu Leu Ser Phe Val Asp Leu Leu His Ser Val Arg Thr Gly<br>        800                      805                      810 | 4550 |

| | | |
|---|---|---|
| aag gcc gcc ttc ccc ctg cgc tac ggc cgc ccc ttc tgg gag gac ctg<br>Lys Ala Ala Phe Pro Leu Arg Tyr Gly Arg Pro Phe Trp Glu Asp Leu<br>815               820                  825 | | 4598 |
| gcg gag gac ccc cgc cgc gcg gag tcc ttc aac cgg ctg ctc ggc cag<br>Ala Glu Asp Pro Arg Arg Ala Glu Ser Phe Asn Arg Leu Leu Gly Gln<br>830               835              840              845 | | 4646 |
| gac gtc gcc act cgc gcc ccg gcc gtg gtg gcc ggc ttc gac tgg gcg<br>Asp Val Ala Thr Arg Ala Pro Ala Val Val Ala Gly Phe Asp Trp Ala<br>850               855              860 | | 4694 |
| agc acc ggt cat gtc atc gac ctc gga ggc ggc gac ggc tcc ctg ctg<br>Ser Thr Gly His Val Ile Asp Leu Gly Gly Gly Asp Gly Ser Leu Leu<br>865               870              875 | | 4742 |
| acc gca ctg ctg acc gcc tgt ccg tca ctg cgc ggc acg gtc ctg gac<br>Thr Ala Leu Leu Thr Ala Cys Pro Ser Leu Arg Gly Thr Val Leu Asp<br>880               885              890 | | 4790 |
| ctg ccc gaa gcg gtg cag cgt gcc aag gag tcg ttc gcc gtg tcc gga<br>Leu Pro Glu Ala Val Gln Arg Ala Lys Glu Ser Phe Ala Val Ser Gly<br>895               900              905 | | 4838 |
| ctg gac gac cgg gcg aac gcg gtc gcg ggc agc ttc ttc gac gcc ctc<br>Leu Asp Asp Arg Ala Asn Ala Val Ala Gly Ser Phe Phe Asp Ala Leu<br>910               915              920              925 | | 4886 |
| ccc gcc ggc gcg ggc gcc tac gtc ctg tcc ctg gtc ctg cac gac tgg<br>Pro Ala Gly Ala Gly Ala Tyr Val Leu Ser Leu Val Leu His Asp Trp<br>930               935              940 | | 4934 |
| gac gac gag gcg tcc gtc gcg atc ctg cgg cgc tgc gcc gag gcg gcg<br>Asp Asp Glu Ala Ser Val Ala Ile Leu Arg Arg Cys Ala Glu Ala Ala<br>945               950              955 | | 4982 |
| ggg cag acg gga tcg gtg ttc gtc atc gag tcg acc ggc tcg gcg ggg<br>Gly Gln Thr Gly Ser Val Phe Val Ile Glu Ser Thr Gly Ser Ala Gly<br>960               965              970 | | 5030 |
| gac gcc ccg cac aca ggt atg gac ctg cgc atg ctg tgc atc tac gga<br>Asp Ala Pro His Thr Gly Met Asp Leu Arg Met Leu Cys Ile Tyr Gly<br>975               980              985 | | 5078 |
| gcc aag gag cgc cgc gtg gag gag ttc gag gaa ctc gcc ggc cgg gcc<br>Ala Lys Glu Arg Arg Val Glu Glu Phe Glu Glu Leu Ala Gly Arg Ala<br>990               995             1000           1005 | | 5126 |
| ggg ctc cgg gtc gtc gcc gtc cac ccc gcg ggc cct tcc gcg atc atc<br>Gly Leu Arg Val Val Ala Val His Pro Ala Gly Pro Ser Ala Ile Ile<br>1010             1015            1020 | | 5174 |
| cag atg tcc gcg gtc tgaccgcccg gagccccggc ccatcgcggc gcgggccacg<br>Gln Met Ser Ala Val<br>1025 | | 5229 |
| gcagacaagg agagagcgt atg gcc ggc ctg gtc atg tcg ccg gtg gag gcg<br>                               Met Ala Gly Leu Val Met Ser Pro Val Glu Ala<br>                                        1030                1035 | | 5281 |
| ctc gac gcg ctg ggc acg gtg cag ggg cgt cag gac ccc tat ccc ttc<br>Leu Asp Ala Leu Gly Thr Val Gln Gly Arg Gln Asp Pro Tyr Pro Phe<br>           1040                1045                1050 | | 5329 |
| tac gag gcg atc cgc gcg cac ggg cag gcg gtc ccc acg aag ccc ggc<br>Tyr Glu Ala Ile Arg Ala His Gly Gln Ala Val Pro Thr Lys Pro Gly<br>           1055                1060                1065 | | 5377 |
| cgc ttc gtg gtg gtc ggc cac gac gcg tgc gac cgg gcg ctg cgg gaa<br>Arg Phe Val Val Val Gly His Asp Ala Cys Asp Arg Ala Leu Arg Glu<br>1070             1075                1080                1085 | | 5425 |
| ccg gcc ctg cgc gtc cag gac gcc agg agc tac gac gtc gtc ttc ccc<br>Pro Ala Leu Arg Val Gln Asp Ala Arg Ser Tyr Asp Val Val Phe Pro<br>           1090                1095                1100 | | 5473 |
| tcg tgg cgg tcg cac tcc tcg gtc cgg ggg ttc acc agc tcc atg ctc<br>Ser Trp Arg Ser His Ser Ser Val Arg Gly Phe Thr Ser Ser Met Leu | | 5521 |

-continued

```
                     1105                 1110                  1115
tac agc aac ccg ccc gat cac ggc cgg ttg cgc cag gtg gtg agc ttc    5569
Tyr Ser Asn Pro Pro Asp His Gly Arg Leu Arg Gln Val Val Ser Phe
            1120                 1125                 1130 gcg ttc acc ccg ccc aag gtg cgc cgg atg cac ggg gtg atc gag gac    5617
Ala Phe Thr Pro Pro Lys Val Arg Arg Met His Gly Val Ile Glu Asp
        1135                 1140                 1145 atg acc gac cgg ctc ctc gac cgg atg gcc cgg ctc ggc tcc ggc ggc    5665
Met Thr Asp Arg Leu Leu Asp Arg Met Ala Arg Leu Gly Ser Gly Gly
1150                 1155                 1160                 1165 tcc ccg gtc gac ctc ata gcc gag ttc gcc gcc cgg ctg ccc gtc gcg    5713
Ser Pro Val Asp Leu Ile Ala Glu Phe Ala Ala Arg Leu Pro Val Ala
                1170                 1175                 1180 gtg atc agc gag atg atc ggc ttt ccg gcg aag gac cag gtg tgg ttc    5761
Val Ile Ser Glu Met Ile Gly Phe Pro Ala Lys Asp Gln Val Trp Phe
            1185                 1190                 1195 cgc gac atg gcc tcc cgg gtc gcc gtg gcg acg gac ggt ttc acc gac    5809
Arg Asp Met Ala Ser Arg Val Ala Val Ala Thr Asp Gly Phe Thr Asp
        1200                 1205                 1210 ccc ggc gcg ctc acg ggg gcc gac gcc gcc atg gac gag atg agc gcc    5857
Pro Gly Ala Leu Thr Gly Ala Asp Ala Ala Met Asp Glu Met Ser Ala
    1215                 1220                 1225 tac ttc gac gac ctc ctg gac cgt cgc cgc cgc acc ccg gcc gac gac    5905
Tyr Phe Asp Asp Leu Leu Asp Arg Arg Arg Thr Pro Ala Asp Asp
1230                 1235                 1240                 1245 ctg gtc acc ctg ctc gcc gag gcc cac gac ggc tcc ccc ggg cgc ctg    5953
Leu Val Thr Leu Leu Ala Glu Ala His Asp Gly Ser Pro Gly Arg Leu
                1250                 1255                 1260 gac cac gac gaa ctg atg ggc acc atg atg gtg ctg ctc aca gcc ggg    6001
Asp His Asp Glu Leu Met Gly Thr Met Met Val Leu Leu Thr Ala Gly
            1265                 1270                 1275 ttc gag acc acg agc ttt ctg atc ggc cac ggg gcg atg atc gcc ctc    6049
Phe Glu Thr Thr Ser Phe Leu Ile Gly His Gly Ala Met Ile Ala Leu
        1280                 1285                 1290 gaa caa cgg gcg cac gcg gcc cgg ctg cgg gcc gaa ccc gac ttc gcc    6097
Glu Gln Arg Ala His Ala Ala Arg Leu Arg Ala Glu Pro Asp Phe Ala
    1295                 1300                 1305 gac ggc tac gtc gag gag atc ctc agg ttc gag ccg ccg gtc cac gtc    6145
Asp Gly Tyr Val Glu Glu Ile Leu Arg Phe Glu Pro Pro Val His Val
1310                 1315                 1320                 1325 acc agc cgg tgg gct gcc gag gac ctc gac ctg ctg ggc ctg tcc gta    6193
Thr Ser Arg Trp Ala Ala Glu Asp Leu Asp Leu Leu Gly Leu Ser Val
                1330                 1335                 1340 ccg gcg ggc tcc aag ctg gtc ctg atc ctg gcc gcc gcg aat cgc gat    6241
Pro Ala Gly Ser Lys Leu Val Leu Ile Leu Ala Ala Ala Asn Arg Asp
            1345                 1350                 1355 ccc ggc cgc tac ccc gag ccc ggc cgc ttc gac ccc gac cgc tac gcg    6289
Pro Gly Arg Tyr Pro Glu Pro Gly Arg Phe Asp Pro Asp Arg Tyr Ala
        1360                 1365                 1370 ccc cgg ccg ggc ggg ccg gag gcc acc aga ccg ctg agc ttc ggc gcg    6337
Pro Arg Pro Gly Gly Pro Glu Ala Thr Arg Pro Leu Ser Phe Gly Ala
    1375                 1380                 1385 ggc ggc cac ttc tgc ctc ggc gct ccg ctg gcg cgg ctg gaa gcc cgg    6385
Gly Gly His Phe Cys Leu Gly Ala Pro Leu Ala Arg Leu Glu Ala Arg
1390                 1395                 1400                 1405 atc gcg ctg ccg cgt ctg ctg cgc cgc ttc ccg gac ctg gcc gtg tcc    6433
Ile Ala Leu Pro Arg Leu Leu Arg Arg Phe Pro Asp Leu Ala Val Ser
                1410                 1415                 1420 gag ccc ccc gtc tac cgc gac cgc tgg gtc gtc cgc ggc ctc gaa acc    6481
```

```
Glu Pro Pro Val Tyr Arg Asp Arg Trp Val Val Arg Gly Leu Glu Thr
        1425                1430                1435 ttt ccc gtg acc ctc ggg tcc tgagccccg ccggccggaa cacgtgaccg          6532
Phe Pro Val Thr Leu Gly Ser
        1440 tcccggccgg cgggtgcgcg ccctctcaga cgtacagggt gttgggcccc tgaccacaca    6592 gcacccggcc gtacagctcc aggttggtgc tcgggttcat gcaggtgcag cgtgatgctc    6652 tgggcatcgc tgcacgcgct ggatcgggac gtcgttgtag atcgaggacc cgccgctcgc    6712 ctgggcgagt atgtccaccg actccttgcc cagtcggcac gccgccccca gcaggccgcg    6772 gcacagcacc cgctcctcca cgtccaggc ctcgcccgaa gccccttgg agtcgacgag      6832 gtcggccagc cgatgggcgt ggaaccgtgc tcgtcggcc agcagggtcg cctcgccgag     6892 ctgcaggtgg gtgatcggcg ccgagccctg ctcctcgtac tcggtgtagg tgatcttgcg    6952 gccgggcagc ctcccgcgga agacgtcctg agcggccgcg gccagtccgg tcatggtgcc    7012 gaccgacgag gccgaggcca cggccagcat cggcgcccgg aacatcggtg atccggcgtt    7072 gagttcggag cgtactgct gctggagcac cgcgcccagc ggaaggacgc gctcctgggg     7132 aacgaagacg tccgcggcga tggtgctgac gcttcccgag ccccggagcc ccgaggtgtg    7192 ccagtcgtcg acgatctgca gctggtcggt cggcaccagg gccatcacgg gctgcatgcc    7252 gccgtcgggg gtcggtgaga cggcgatcag aacctgccag tgactgtgcc aggcaccgct    7312 gatgaagccc cacttgccgt tcactacgac accgccgtcg accggggccg ccatgccgcc    7372 gggactgagg gtgccggaga cccggacatc cggccgggga acacctcgt cctgcacgtg     7432 gtcggggaag aggcccgcca tccaggtggg tatccaccac accgaggccg tccaggcggc    7492 cgatccgtcg ccgcgcgcca gctcggcggc cacgtccacc agggtgcggg cgtcggactc    7552 gaagccgccg taacgggccg gcacgcgcat gcggaagatc ccggcttcgg ccatcgcctc    7612 gaccgactcc tcgtgcagcc gccggttctc ctcggtccag gccgcgtggg actggagcag    7672 cggcctcagc ttcgaggccc gttccaccag ttcggtacgg gcgggcgtag acgtctggtc    7732 cactcgatcc tccaggaatc atgagacgcc ctgtccgcgg tatgcggaag caggcgtctg    7792 cgcgcatcgg tcaggacggc gtcgccctgc tcccgcatgg ttcaccgagt tccgcggacg    7852 tcgcatctcc ttgattgccg gtcacctacc ccgatgccga tcgggctggt gcgacagcgc    7912 atcccacgag aagtccacga acggtccggg aagccagaat gtgcttctcg gccggagtca    7972 cggccggcgc cggcgcccgt cgccggtcac gccggaccac gcccgaccg gtcatggagg      8032 cagcccatga gtgacaacga cagtccgtcc cgggtgccgg ccgcggtggc acccgccacc    8092 gcgaaaccgt cggccggcac ggtcctcggc gccgcggtgg cttcgcccgc cgcctacacc    8152 gcggcgaccg cccaggaagc ggcgaccgcg ctggtccgca tgctgatgga acagatggtg    8212 ctcggtcccg gcgcggtcgg tcccgagacc cgcgcggacg gccgcgcg cggaccggc       8272 tccggccacg gcccggcgcc gcagaccgga ccggacgcgc cgggcgaacc cccgcccacg    8332 tgggcgccga acctcgacga cgggaaggta ggaggacg atg agg ccg ctc gtt cgg    8388
                                        Met Arg Pro Leu Val Arg
                                        1445                1450 gca gtg ctg cgg ggt tcc ctg cgg cag gtg agg tac gtg gac gtg gtc      8436
Ala Val Leu Arg Gly Ser Leu Arg Gln Val Arg Tyr Val Asp Val Val
                1455                1460                1465 tcc ccg cgc cgg gcg cgc tcc ctg gtg gcg cgg gtg tac cgg gag acc      8484
Ser Pro Arg Arg Ala Arg Ser Leu Val Ala Arg Val Tyr Arg Glu Thr
                1470                1475                1480
```

-continued

| | |
|---|---|
| gag gag cag ttc ggc gtg ctc gcg ccc ccc ctg gcc ctc cac tcg ccc<br>Glu Glu Gln Phe Gly Val Leu Ala Pro Pro Leu Ala Leu His Ser Pro<br>            1485                                  1490                              1495 | 8532 |
| gcc gcg gcg tcg ctg gcc gcg acg tgg ctc atg ctg cgg gag aca ctg<br>Ala Ala Ala Ser Leu Ala Ala Thr Trp Leu Met Leu Arg Glu Thr Leu<br>1500                                1505                              1510 | 8580 |
| ctg gtc gac ggg cgg gtg agc cgg gcg gtg aag gag acg gtc gcc acc<br>Leu Val Asp Gly Arg Val Ser Arg Ala Val Lys Glu Thr Val Ala Thr<br>1515                      1520                      1525                      1530 | 8628 |
| gag gtc tcc cgt gcc aac gac tgt ccg tac tgc gtc cag gtc cat cag<br>Glu Val Ser Arg Ala Asn Asp Cys Pro Tyr Cys Val Gln Val His Gln<br>            1535                                  1540                              1545 | 8676 |
| gcg gta ctc ggg aca ctg cct ccg gac ggc ggc cag gcc ggg ctc ctg<br>Ala Val Leu Gly Thr Leu Pro Pro Asp Gly Gly Gln Ala Gly Leu Leu<br>1550                                1555                              1560 | 8724 |
| cgg tgg gtc cgg gag gca ggc cga cgg ccc ggc ggt gcg gtg ggc<br>Arg Trp Val Arg Glu Ala Gly Arg Arg Pro Gly Gly Gly Ala Val Gly<br>            1565                                  1570                              1575 | 8772 |
| ggc ggg cgg ccg ctt ccg ttc agc ggt gaa cag gca ccg gaa ctg tgc<br>Gly Gly Arg Pro Leu Pro Phe Ser Gly Glu Gln Ala Pro Glu Leu Cys<br>1580                                1585                              1590 | 8820 |
| ggc gtc gtg gtc acg ttc cac tac atc aac cgc atg gtc tcc ctc ttc<br>Gly Val Val Val Thr Phe His Tyr Ile Asn Arg Met Val Ser Leu Phe<br>1595                      1600                      1605                      1610 | 8868 |
| ctc gac gac tcc ccc atg ccg acc cgg acg ccg aca ccg ttg cgc ggg<br>Leu Asp Asp Ser Pro Met Pro Thr Arg Thr Pro Thr Pro Leu Arg Gly<br>            1615                                  1620                              1625 | 8916 |
| ccc atc atg agg acc acc gca ctg gcc atg cgt ccc gtc ggc ccg ggg<br>Pro Ile Met Arg Thr Thr Ala Leu Ala Met Arg Pro Val Gly Pro Gly<br>            1630                                  1635                              1640 | 8964 |
| ctg ctg aca ccg ggc gca tcg ctc ggc ctg ctg cct ccg gct ccc ctg<br>Leu Leu Thr Pro Gly Ala Ser Leu Gly Leu Leu Pro Pro Ala Pro Leu<br>1645                                1650                              1655 | 9012 |
| ccg ccc gga ctg gag tgg gcc gag ggc aac cct ttc gtg gcc cag gcg<br>Pro Pro Gly Leu Glu Trp Ala Glu Gly Asn Pro Phe Val Ala Gln Ala<br>            1660                                  1665                              1670 | 9060 |
| ctg ggg cgt gcc gtc gcc gct gtg gac cag gga gcg cac tgg gtg ccc<br>Leu Gly Arg Ala Val Ala Ala Val Asp Gln Gly Ala His Trp Val Pro<br>1675                      1680                      1685                      1690 | 9108 |
| gaa ccg gtc cgg gag cgg ctg cgc aca cgt ctg gac acc tgg gac gga<br>Glu Pro Val Arg Glu Arg Leu Arg Thr Arg Leu Asp Thr Trp Asp Gly<br>            1695                                  1700                              1705 | 9156 |
| tcg gcg ccg ggc ctc ggc cgg gga tgg ctc gac gag gcc gtg tcc ggc<br>Ser Ala Pro Gly Leu Gly Arg Gly Trp Leu Asp Glu Ala Val Ser Gly<br>            1710                                  1715                              1720 | 9204 |
| ctg ccg ccc cag gac gtg ccc gcg gca cgg ctg gcg ctg ctg acg gcc<br>Leu Pro Pro Gln Asp Val Pro Ala Ala Arg Leu Ala Leu Leu Thr Ala<br>            1725                                  1730                              1735 | 9252 |
| ttc gcc ccc tac cag gtg ctc ccg gac gac gtc gag gag ttc aga cgg<br>Phe Ala Pro Tyr Gln Val Leu Pro Asp Asp Val Glu Glu Phe Arg Arg<br>1740                                1745                              1750 | 9300 |
| cgt cgg ccc acc gac cgc gaa ctc gtc gag ctc acg tcc tac gcc gcg<br>Arg Arg Pro Thr Asp Arg Glu Leu Val Glu Leu Thr Ser Tyr Ala Ala<br>1755                      1760                      1765                      1770 | 9348 |
| ctg acc acg gcc gtc cgt gtc ggt cgc acg ctc gtc gtg ccc gac gcc<br>Leu Thr Thr Ala Val Arg Val Gly Arg Thr Leu Val Val Pro Asp Ala<br>            1775                                  1780                              1785 | 9396 |
| gcc ggg ccg gga tgaacggccc cgcaacggct cgggaaggct gtctcacggc<br>Ala Gly Pro Gly<br>            1790 | 9448 |

-continued

| | |
|---|---|
| cggaggcgta cgccggtgag gtgctcggac tcctcccaga ggcggcgccg ggccctgggg | 9508 |
| tcgacggctg ctccgccggg gcgcacgagc ccgggtgcgc cccgggtctc ggtcacgccg | 9568 |
| aggggcccgt agaactcgcc cccgcgcgcg ccgggatcgg tggccgcccg cagaccaggc | 9628 |
| agcatccccg ccgcggcggg ctgcaggaac aacggggcga gcggggagcc gagcctgcgc | 9688 |
| acgggcgcgg gaaagtcccg gcccagaccg gtcgcggtca gcccgggatg agcggcgagc | 9748 |
| gaggccagtt ccgcgccgga ctccgccagt ctgtgatgga gttccagcgc gaacatgagg | 9808 |
| ttggccagct tggactggtt gtaggccggg taccggctgt agcggcgttc gccgtgaagg | 9868 |
| tcgctgaagt cgatgcgccc cagccggtgc agatagctgc tgatcgtcac gacccgcgcg | 9928 |
| cccggcgcgg cccgcaggct gtccaggagc aggccggtga gggcgaagtg ccccaggtgg | 9988 |
| ttcgtggcga actggagttc gtgaccgtcc ggggtgcggg cccggtcggt ccacatcacg | 10048 |
| cccgcgttgt tgaccagcag gtggatgcgc gggaagcggt cgcgcagttc ctcggcgccg | 10108 |
| gcacgcaccg acgcgagacg ggaaagatcc agccgtctga ccgtcagttg cgccgacggc | 10168 |
| acccggcttt ggatgcgggc cgccgcggcg acccgcgcgt ccggatcgcg cacggccagc | 10228 |
| accacgtggg cgccgtgccg ggcgagctcc tgcgccaggt gcagtccgat gccggagctg | 10288 |
| gcaccggtga ccaccgcggt ggttccggta cggtccggga catcggcggc gctccagcgt | 10348 |
| cgccgcgttc tcatcggtcg tccctcccgg gggatgcgtc agccggcctg ggccatcgcg | 10408 |
| gcccggtagc cgttggcgac gatctgccgg gcggagtgct cgtagtactc gtcgtccttc | 10468 |
| ggcagctccg tggcgagacc gctgacgtac cggttgaaca tgcagaacgc ggcggcgatc | 10528 |
| agaacggtgt cgtgcagagc ggtgtcgtcc gctccctcgg cccgcgccga ggcgatcacc | 10588 |
| cctgcggaga ccgggcgcgc cgcgctctgg acctcggcgg cgacgccag cagcgcgcgc | 10648 |
| gtcctgccgt cgatgggcgc ggtggcgggg tcggcgagga cggcctcgac gagctgccgg | 10708 |
| cctcccggca gctgcgcggc ggcgaaggcc cgtgggagg cggcgcagaa ctcggtggag | 10768 |
| ttgagatgcg agacgtacgc cgcgatgagc tcgcgttgcc ccggttccag cgaggacggc | 10828 |
| gcccgcagca gggcgttcgc gagatcgccc agcggtgctg cggtgccggg gtggtgagcc | 10888 |
| atcagaccac tgatgccggg gaggtcgttg tcgagtgcta tgtggggcac ggctcttcct | 10948 |
| tccgggtgga cgaggggcgg acggcggcg atcagggcca ttcgacttcg tcgtcggcg | 11008 |
| ccgcgcagat gcgggtgaag ggccattcca cgtcttcccc tcccgttgcg gagtgggcgg | 11068 |
| aggccgtggt gaagagggtg acgagtccga acgtgccgaa gaggagggac agtcgggcaa | 11128 |
| cgtgaagtgc ggtacccatg cgagctccta gcgagggcgg cgtgaccgcg ggacggtgag | 11188 |
| acctcgtgat gccaggaagc tagcgaatcg gactgagggt ggcaacgata tgccagactt | 11248 |

| | | |
|---|---|---|
| tggcaacttg cct gtg tat cag ccg gac tgt cgg ccg ctg gta aag acg<br>     Val Tyr Gln Pro Asp Cys Arg Pro Leu Val Lys Thr<br>         1795        1800 | | 11297 |
| gaa cgg cga gat ccc gcg acc gcg tcg cag agc agc agg gtc tgc tca<br>Glu Arg Arg Asp Pro Ala Thr Ala Ser Gln Ser Ser Arg Val Cys Ser<br>      1805      1810      1815 | | 11345 |
| ccc agc gtc ggg gcg gcc agc atg tcg cgt acc ggg agc gtg acg ccc<br>Pro Ser Val Gly Ala Ala Ser Met Ser Arg Thr Gly Ser Val Thr Pro<br> 1820      1825      1830 | | 11393 |
| agc tcg cgg ttg atc ctg cgg acc agc cgg gtg atg agc agg gag tcg<br>Ser Ser Arg Leu Ile Leu Arg Thr Ser Arg Val Met Ser Arg Glu Ser<br>1835      1840      1845      1850 | | 11441 |
| ccg ccg tgg gcg aag aaa tca gca cct tcg gag ggg tcc ggg aag ccg<br>Pro Pro Trp Ala Lys Lys Ser Ala Pro Ser Glu Gly Ser Gly Lys Pro | | 11489 |

-continued

| | |
|---|---|
| agc agg tca ccc cag ccg cgc acc agt acc tgg cgg atg tcg ccg gtg<br>Ser Arg Ser Pro Gln Pro Arg Thr Ser Thr Trp Arg Met Ser Pro Val<br>1870     1875     1880 | 11537 |
| gtg acg acc gtg cgc cgg gag ccc cga cgt gcc gag cgc agc cgc gag<br>Val Thr Thr Val Arg Arg Glu Pro Arg Arg Ala Glu Arg Ser Arg Glu<br>1885     1890     1895 | 11585 |
| gca tgc acc agc gcc acc tgg tcg ccg agg ttg cgc cgc gac agc tcg<br>Ala Cys Thr Ser Ala Thr Trp Ser Pro Arg Leu Arg Arg Asp Ser Ser<br>1900     1905     1910 | 11633 |
| cgc agc gac acc gtg acg ccg aac ctc tcg gtg atc ctg cgg acc agc<br>Arg Ser Asp Thr Val Thr Pro Asn Leu Ser Val Ile Leu Arg Thr Ser<br>1915     1920     1925     1930 | 11681 |
| cgc gtg atc agc agc gtg tcc ccg ccg cgc gcg aag aaa tcc gaa tgc<br>Arg Val Ile Ser Ser Val Ser Pro Pro Arg Ala Lys Lys Ser Glu Cys<br>1935     1940     1945 | 11729 |
| tcg gtg agg tcg gag cgg ccg agg agc tcg ctc cac gcg ccg acc atg<br>Ser Val Arg Ser Glu Arg Pro Arg Ser Ser Leu His Ala Pro Thr Met<br>1950     1955     1960 | 11777 |
| aac tcc ccc acg tca ccg agc cgg tgc tcg tcg ccg tcg ggg ccc ttc<br>Asn Ser Pro Thr Ser Pro Ser Arg Cys Ser Ser Pro Ser Gly Pro Phe<br>1965     1970     1975 | 11825 |
| ggc gcg ccg gat ccc gcg gaa cgg ttc cgg ccg gag acg gca gag cgg<br>Gly Ala Pro Asp Pro Ala Glu Arg Phe Arg Pro Glu Thr Ala Glu Arg<br>1980     1985     1990 | 11873 |
| tca ctg gtc act ttc gcc acc tcc agg ggc atg tgt cgg ctg cat cgg<br>Ser Leu Val Thr Phe Ala Thr Ser Arg Gly Met Cys Arg Leu His Arg<br>1995     2000     2005     2010 | 11921 |
| ctt ccc gcc acg gta cgg gag cac atg ttg cat ggc aat acc ttt cca<br>Leu Pro Ala Thr Val Arg Glu His Met Leu His Gly Asn Thr Phe Pro<br>2015     2020     2025 | 11969 |
| agt cgg tgg caa ccc tcc ttg cca tcc acc cac tgc agt tgg gcg aga<br>Ser Arg Trp Gln Pro Ser Leu Pro Ser Thr His Cys Ser Trp Ala Arg<br>2030     2035     2040 | 12017 |
| tgt gta ggc att cga ggt ccg cag gtt tgc caa gcc gcg cgc gac cgg<br>Cys Val Gly Ile Arg Gly Pro Gln Val Cys Gln Ala Ala Arg Asp Arg<br>2045     2050     2055 | 12065 |
| cat act ctc tgg cac aac tgg aat gag tagcgtggca ggccacgggg<br>His Thr Leu Trp His Asn Trp Asn Glu<br>2060     2065 | 12112 |
| accgggccgg gccaggaacc ttcgtcctcc atctattcgc tggggcgtgc acgtgttgga | 12172 |
| gcagccatct ttcggccgtc gcctgaggca gctgaggacc gagcggggtc tttcccaggc | 12232 |
| cgcgctcgcg ggggacggc atg tct acg ggc tat ctc tcg cgc ctg gag tcg<br>          Met Ser Thr Gly Tyr Leu Ser Arg Leu Glu Ser<br>              2070     2075 | 12284 |
| ggc gcc cgg cag ccc tcc gat cgc gcc gtc gcc cac ctg gcc gga caa<br>Gly Ala Arg Gln Pro Ser Asp Arg Ala Val Ala His Leu Ala Gly Gln<br>2080     2085     2090 | 12332 |
| ctc ggc atc agc ccg tcg gag ttc gaa ggg tcc cgg gcc acc tcg ctc<br>Leu Gly Ile Ser Pro Ser Glu Phe Glu Gly Ser Arg Ala Thr Ser Leu<br>2095     2100     2105     2110 | 12380 |
| gcc cag atc ctc tcc ctc tcc act tcc ctg gag tcc gac gag acc agt<br>Ala Gln Ile Leu Ser Leu Ser Thr Ser Leu Glu Ser Asp Glu Thr Ser<br>2115     2120     2125 | 12428 |
| gag ctt ctc gcc gag gcg gta cgt tcc gcg cat ggc cag gat ccg atg<br>Glu Leu Leu Ala Glu Ala Val Arg Ser Ala His Gly Gln Asp Pro Met<br>2130     2135     2140 | 12476 |
| ctc cgc tgg cag gcc ctg tgg ctg ctg gga cag tgg aag cgc cgg cac | 12524 |

```
                Leu Arg Trp Gln Ala Leu Trp Leu Leu Gly Gln Trp Lys Arg Arg His
                                2145                2150                2155 ggc gac tcg gcc ggc gag cac ggc tac ctc cag cgt ctg gtg acg ctg         12572
Gly Asp Ser Ala Gly Glu His Gly Tyr Leu Gln Arg Leu Val Thr Leu
        2160                2165                2170 agt gag gag atc ggc ctg gcc gag ttg cgc gca cgg gcc ctg acc cag         12620
Ser Glu Glu Ile Gly Leu Ala Glu Leu Arg Ala Arg Ala Leu Thr Gln
2175                2180                2185                2190 ttc gcc cgg tcg ctg cgg gta ctg ggc gag atc gtt ccg gcg gtg gag         12668
Phe Ala Arg Ser Leu Arg Val Leu Gly Glu Ile Val Pro Ala Val Glu
                2195                2200                2205 gct gcc gcc gcc gcc cac cgg ctc gcg gtg gac cat gcg ctg tcc agc         12716
Ala Ala Ala Ala Ala His Arg Leu Ala Val Asp His Ala Leu Ser Ser
            2210                2215                2220 cag gac agg gcc gct tcg ctg ctg gtt ctg gtg tcg gtg gag gcc gag         12764
Gln Asp Arg Ala Ala Ser Leu Leu Val Leu Val Ser Val Glu Ala Glu
        2225                2230                2235 gcg gga cgg atg ccc gac gcc cgg cgc cac gcc gac gaa ctg acc gtc         12812
Ala Gly Arg Met Pro Asp Ala Arg Arg His Ala Asp Glu Leu Thr Val
    2240                2245                2250 ctg gtg agg gga cgg tcc gac act ctg tgg gcc gag gcg ttg tgg acg         12860
Leu Val Arg Gly Arg Ser Asp Thr Leu Trp Ala Glu Ala Leu Trp Thr
2255                2260                2265                2270 gcg ggt gcg ttg aag gtg cgg cag ggc gag ttc gcc gcg gcc gag gtc         12908
Ala Gly Ala Leu Lys Val Arg Gln Gly Glu Phe Ala Ala Ala Glu Val
                2275                2280                2285 ctt ttc cag gag gct ctg gac ggg ttc gac agc cgg gag aac ctg acg         12956
Leu Phe Gln Glu Ala Leu Asp Gly Phe Asp Ser Arg Glu Asn Leu Thr
            2290                2295                2300 atc tgg ctg cgg ctg cgc atc gcg atg gcc gaa ctc cac ctg cag aaa         13004
Ile Trp Leu Arg Leu Arg Ile Ala Met Ala Glu Leu His Leu Gln Lys
        2305                2310                2315 ctt cct ccc gag ccc gac gcc gcg cag ctc tgc atc gag gcg gcg gag         13052
Leu Pro Pro Glu Pro Asp Ala Ala Gln Leu Cys Ile Glu Ala Ala Glu
    2320                2325                2330 gcg gcc ctt ccc ttt gcc cgc aca tcc gct ctg gaa cag tcc ctc gcc         13100
Ala Ala Leu Pro Phe Ala Arg Thr Ser Ala Leu Glu Gln Ser Leu Ala
2335                2340                2345                2350 gct ctg cgg gcg cgc ctc gcc ttc cat gag ggc agg ttc gcc gat gcc         13148
Ala Leu Arg Ala Arg Leu Ala Phe His Glu Gly Arg Phe Ala Asp Ala
                2355                2360                2365 cgc gcg ttg ttg gag agg ctc ggc agg acc gag ctc cgg ctg ccc tat         13196
Arg Ala Leu Leu Glu Arg Leu Gly Arg Thr Glu Leu Arg Leu Pro Tyr
            2370                2375                2380 cag agc cgg atc cgc ctg gag gtc ctc ggt cat cag ctg cgc atc ctg         13244
Gln Ser Arg Ile Arg Leu Glu Val Leu Gly His Gln Leu Arg Ile Leu
        2385                2390                2395 agc ggg gag gag gag gaa ggc ctg gcc ggc ctc cag ctc ctg gcc gag         13292
Ser Gly Glu Glu Glu Glu Gly Leu Ala Gly Leu Gln Leu Leu Ala Glu
    2400                2405                2410 gag gcg cag gag aac tcc aac atc aac ctc gcc gcg gag atc tgg cgg         13340
Glu Ala Gln Glu Asn Ser Asn Ile Asn Leu Ala Ala Glu Ile Trp Arg
2415                2420                2425                2430 ctc gcg gcg gaa tgc ctg atg cgg gcg cgc ggg aag gtc cgc ggc gcc         13388
Leu Ala Ala Glu Cys Leu Met Arg Ala Arg Gly Lys Val Arg Gly Ala
                2435                2440                2445 acc ggc ggc tgacgccgcg ccggttcgcg aggtccaccg cgccgccgtg                 13437
Thr Gly Gly gccaccgccg tcggcgtgag cgccggcgt gtgccgcccc ccacggttgc tcgcccttgg        13497
```

```
tggtgcatct gttggcacat gtgtacctcc tacacagtca attgttgcca aaattgtcga    13557
accgaatggc aattgcttgc ctttgctgaa gaggcgtgct gatatgcaag tcaagtagcc    13617
tcctccgatc tcgggcggcc atatgggaaa catcgagttg agcggcgatg gcgttcgtca    13677
gtgctgccgt tctggccagg caactgatgt cgatggggat ggcaagattt tgccgaaaac    13737
cgatacatct ctgtccgtcc cggacagcct tcgccccccg ggtgacactg ctccggcatg    13797
gctccggttt ctcgtcgccc ggccgacgga ccgcaccgtc cggaacgagg cgccggtgtg    13857
cgtccgctga tgggcacagc ggcctcggcc gcagcaggtt cccaccgaga agaatgccga    13917
ggcccagccg tgaaccacga catgtcccag cgtgccttgc tggaggcggc ggccgagggg    13977
ctgcggcggc tggccggcga cgcgcggtgc cggagcgcgt cggccgcgcc ctcctcggca    14037
```

| | | |
|---|---|---|
| ttgagggac atg ttc tcc ccc gcc gcc cgc cgg tac gtg ctc gcc tcg gac | | 14088 |
| Met Phe Ser Pro Ala Ala Arg Arg Tyr Val Leu Ala Ser Asp | | |
| 2450 2455 2460 | | |
| cgc gcg ggg ttc ttc gag cag gct gtc cgg ctg cgc tcc cgg ggg tac | | 14136 |
| Arg Ala Gly Phe Phe Glu Gln Ala Val Arg Leu Arg Ser Arg Gly Tyr | | |
| 2465 2470 2475 | | |
| cgg gtg agc gcg gag ttc gtc ggc ccc gat cag gga gcc acc gac gcc | | 14184 |
| Arg Val Ser Ala Glu Phe Val Gly Pro Asp Gln Gly Ala Thr Asp Ala | | |
| 2480 2485 2490 2495 | | |
| ctc cac gcg gag cac gtg gtc gaa gag cac ctg agg ctg ctc gat cag | | 14232 |
| Leu His Ala Glu His Val Val Glu Glu His Leu Arg Leu Leu Asp Gln | | |
| 2500 2505 2510 | | |
| gag ccg gcc cct gac cgg atc ggt gtg gac gtc tcc cgg atc ggc ctc | | 14280 |
| Glu Pro Ala Pro Asp Arg Ile Gly Val Asp Val Ser Arg Ile Gly Leu | | |
| 2515 2520 2525 | | |
| gcc cac tcg gcg cag act gcc ctg cgc aac acc ggg cgg ctg gct gcc | | 14328 |
| Ala His Ser Ala Gln Thr Ala Leu Arg Asn Thr Gly Arg Leu Ala Ala | | |
| 2530 2535 2540 | | |
| gct gcg gcg ctc cgc ggg agc gag gtc gtc ctc ctc atg gag ggg tcc | | 14376 |
| Ala Ala Ala Leu Arg Gly Ser Glu Val Val Leu Leu Met Glu Gly Ser | | |
| 2545 2550 2555 | | |
| gag gac atc gac acc gtg ctg gcc gtc cat gac gcc ctg gtg aac cgt | | 14424 |
| Glu Asp Ile Asp Thr Val Leu Ala Val His Asp Ala Leu Val Asn Arg | | |
| 2560 2565 2570 2575 | | |
| tac gac aac gtg ggg atc acc ctt cag gcg cac ctg cac cgc acc gtg | | 14472 |
| Tyr Asp Asn Val Gly Ile Thr Leu Gln Ala His Leu His Arg Thr Val | | |
| 2580 2585 2590 | | |
| gac gac gcc atg gcg gtc gcg ggt cct ggc cgc acc gtg cgg ctg gtc | | 14520 |
| Asp Asp Ala Met Ala Val Ala Gly Pro Gly Arg Thr Val Arg Leu Val | | |
| 2595 2600 2605 | | |
| atg ggc tcc tcg gcc gag cct gcc ggc acc gct ctg tcc cgg ggc ccc | | 14568 |
| Met Gly Ser Ser Ala Glu Pro Ala Gly Thr Ala Leu Ser Arg Gly Pro | | |
| 2610 2615 2620 | | |
| gct ctg gag gac cgg tac ctt gac ctc gcg gag ctt ctc gtg gac cgt | | 14616 |
| Ala Leu Glu Asp Arg Tyr Leu Asp Leu Ala Glu Leu Leu Val Asp Arg | | |
| 2625 2630 2635 | | |
| ggc gtc cgg ctg agt ctg gcc act ccg gac gcc gag gtc ctg gcc ggg | | 14664 |
| Gly Val Arg Leu Ser Leu Ala Thr Pro Asp Ala Glu Val Leu Ala Gly | | |
| 2640 2645 2650 2655 | | |
| gcg cag gag cgt ggt ctg ctc gaa cgc gtc cag gac atc gag atg ctc | | 14712 |
| Ala Gln Glu Arg Gly Leu Leu Glu Arg Val Gln Asp Ile Glu Met Leu | | |
| 2660 2665 2670 | | |
| tac ggt gtg cgg ccc gag ctg ctg cgc cgc cac cgg gcg gcg ggc cgc | | 14760 |
| Tyr Gly Val Arg Pro Glu Leu Leu Arg Arg His Arg Ala Ala Gly Arg | | |
| 2675 2680 2685 | | |

| | | | | | | | | | | | | | | | |
|---|---|---|---|---|---|---|---|---|---|---|---|---|---|---|---|
| ccc | tgt | cgc | atc | cac | gcg | gcc | tac | ggg | atg | aac | tgg | tgg | ctt | ccc | ctg |
| Pro | Cys | Arg | Ile | His | Ala | Ala | Tyr | Gly | Met | Asn | Trp | Trp | Leu | Pro | Leu |
| | | 2690 | | | | 2695 | | | | | 2700 | | | | |

14808

| | | | | | | | | | | | | | | | |
|---|---|---|---|---|---|---|---|---|---|---|---|---|---|---|---|
| ctg | cgg | agg | ctg | gcc | gac | aac | ccg | ccg | atg | gtg | ctc | aac | gcc | ctg | gcc |
| Leu | Arg | Arg | Leu | Ala | Asp | Asn | Pro | Pro | Met | Val | Leu | Asn | Ala | Leu | Ala |
| | 2705 | | | | | 2710 | | | | | 2715 | | | | |

14856

| | | | | | | | | | | |
|---|---|---|---|---|---|---|---|---|---|---|
| gac | atc | ggc | cgg | gac | cgg | gag | ccc | gtc | gcc | cac | cag | gcg | tac |
| Asp | Ile | Gly | Arg | Asp | Arg | Glu | Pro | Val | Ala | His | Gln | Ala | Tyr |
| 2720 | | | | | 2725 | | | | | 2730 | | | |

14898

| | |
|---|---|
| tgacccgccc cgggccgcga tccgcggggc accggccccg gggcgccggt cagctcccgg | 14958 |
| tcgccgcgaa ctgcccgggc ctgcgcccct cgcccgccgg ccccggtag gcctgggcga | 15018 |
| tgtccagcca cttctccgcc tcctgaccag acgcggtcag ggcgaggtcg tcgcggtggc | 15078 |
| ggcgccgggt gaccagcagg cagaagtcgt gcgcgggacc gctgaccgtc tcggtggcgt | 15138 |
| cctcggggcc gaccgtccag acctcgcccg aggggggcggt gagctcgaag cggaacggcg | 15198 |
| cggccggcgg ggtcagaccg tgggactcgt agccgaagtc gcgtgtcagc caggcgaagt | 15258 |
| cgacgatgtt gcgaagccgc tcggtgggcg tgcgccggac acccagggcg tcggcgacgt | 15318 |
| cctggccgtg ggcgaacacc tccatgatcc cggcgcagcc cagaacgacc ggcggcagcg | 15378 |
| ggttgaccag ccacggaacc acctggccgg cggggaccgc ggcgagcgcc tcgaccgagg | 15438 |
| cccgccccat gccccggaag cgggtgagca gttcctgcgg cgggaagccc ttgaactgct | 15498 |
| gcagagccgc gttgaccgct ccgtcgaagt tgcctgccgc ggcggccgtg acggccttga | 15558 |
| actcctccgg cgccgccgcc gcggtcctgg ccaggttgaa gacgaaggtg aggtgggcga | 15618 |
| tctggtcggt gacggtccag ccgggcgccg gcgtcggagt gttccaggct tcgtcgtcga | 15678 |
| tcttctcgac cagctgcgcc agctcctcga tgtcggtggc caggtgcttg aggacgtcgt | 15738 |
| cgagcgaatt catctcgtac ttccttcact gggggtgttc cgggctggga cggatgtccc | 15798 |
| gccgggtggg ccggcggccg gcggaagcgc cgtcgcggag cgtcggcgac agtcgctagg | 15858 |
| cggcgcgtcc cgcgtaggag ccggcccggt cggaataggg cgcgagcgcc tcggccaggg | 15918 |
| cttcgggtat cagggtcggc acggtcgccg tgttggggcc gcgcatgcag gcgatgcgct | 15978 |
| ggcgtccccg cgccaccagg gtctcgccgc cgtcgtcgcc cagcttgatg tagtcgaagg | 16038 |
| tgaactccag ctgggtctgc cgcagctccg agagcctcat ccggatcgac agttcgtcga | 16098 |
| aggcggtgat ctccgcgaag aactcgcagt ccaccttgag ggtgaagagc ttgaggtcct | 16158 |
| cctggacctc ggcgagcacc gaaggcgccc tctccttgag aaagagttcc cggcaacgcc | 16218 |
| cctgccaacg aaggtagttg acgtagtaga cgttgccgac gaggttcgtc tcctcgaagc | 16278 |
| cgacggtgtg gcggagctcg aagtagtcag gattcgtcgc ggtcataggt ctgtgcccct | 16338 |
| cgtcgtcggg gccggtcgtc gcaccgagtt gcgtgaagca actcactggt cgcgatggcc | 16398 |
| tgcggggtcg gtggcccgcg ctccgggcgg agagtgcggg cggggtgccg gccggcgcgg | 16458 |
| ggtcagccgc gcgccgacgg cagcagggga agaaccctct cgcggccgct cgtggagccg | 16518 |
| tcggggccg gtgcgccgta ggtgacggag ataccccggc tctgcgcggc gcgcacgatc | 16578 |
| cccggcatcg cgcgttcggc gagcgccgcg atggtcatcg cggattgac cgtcagcgcg | 16638 |
| ccgggaaccg acgatccgtc ggtgacgaag atccccgggt ggtcgcggag ctcgttgctg | 16698 |
| tcgtccaggg cggatgtgtg ggggtcgtcg cccatccggc aggaggagag cgggtggacg | 16758 |
| gtgtaggcgc cgacgaggtc gttggtccag ggcatgacct tggccaggcc gtccttctcc | 16818 |
| aggatctcct tgacctcggc gtcggatgcg gcccaggcgc ccaggtgtt cttcgtcggg | 16878 |
| tcgtagcgca ggttgccccg gccgagcatc tgctgggaga tgcggtgggc gttaccggtg | 16938 |

-continued

```
gcgggaggggg ggccgaagac gccttcgttg tcgtcctcga tcatcgtgaa gatcgtgagc      16998
caggaggtcc actgcttcag gatctccttc ttctccttgc cgaaccagga ggggcccgtg      17058
gcgccgggca cctgggcgag gatcgtgccg aggcccggcg ggaagtagag ctgttccagg      17118
gagtagcggg agtactcggg caacgagccg tccagcctgt cccagctcgc cacggtgggc      17178
cccttgccga tctggttggc cgcgtaggcg agcccgtcgc cccggtccag gccgaacagc      17238
tcggccgcct tggcctcgtc gatgatggcg gtgttgagcc gctcgccgtt gccggagaag      17298
tagcgtccga ccgctcgtgg catggtgccc aggtgggcct cgctgcgctg gaggatcacc      17358
ggggtcgcgc ccgcgccggc cgccatcacc acgatcttcg cctcgatgac gccgctgccc      17418
gcctggaggc ggtagtcgtc gtcgtgcacg acgttgtagt gcacccggta ggagccgtcg      17478
ggggtgcgcg agaggtgctg gacctcgtgc agcgggcgga tgcgcgcccc atgggcgatg      17538
gcggcgggca ggtagttgac cagcaaggac tgcttggcct cgaagcggca gccggccatc      17598
atccagttgc agttcacgca cttggtgttg tcgatggcga cggcgagggg gttggcggtg      17658 cggccgcgt ggttgcacgc gcggcccac agtccgccgg cgtagctcac gtcgttccag       17718
tcctgccggg tcacggagag ggactcctcg acacggtcgt accaggggtc cagggtttcg      17778
cggctcaccg cctgcggcca catccggcgt cctatggacc cctgccggtc gaagacgaag      17838
cgcggggcgc ggggcatcgc ggcgaagtag acgacgctgc cgccgcccac acagttcccg      17898
ccgaggatgc tcatgccgtc cccgaccgtg aagtcgaacg ccctcgtgta cgaggagccg      17958
agtttgtagt cgtgctcgaa ctccttgctc tccagccacg gccgcgttc caggacggtg       18018 acgtcggcgc ccccgccgc caggtggtag gcggcgatgg caccgccgaa tccgctgccg       18078
atgacgagga cgtccgtgcg ctcggccgtg gtgctcatgc ggggctcccg gtggacgtgg      18138
tgtcggggtg gaggcgggcg aactcacgcc cgtagctgta atccttgaag cgccacaggc      18198
cgtcggcgtc cggcatgctc aggcccatgg cctccagtcc cggatggccg tcctccatcg      18258
cctgtgccgt gttgaggtgc gcggccgaat cgaaggccat gttgcagaag agggacagca      18318
gcacccagaa ctccttctcg gggtggcctg gtgtcgtcag ccgctggatc agcgcggccc      18378
ggtccgggta gtcgagcgcc acgaagggcg ggaccgtcgg gtcgggagcc aggcggcgct      18438
ccgccgcgta ggccagcgcg tgctcgttca ccaggcgcac caggtcgtcc agaccctcgt      18498
ggatgccggt cgcatcccat gcaggagct ccagggctcc cgcctggacg gcgccaccgc        18558
cggtggacac ccccgcgatg gcccggtcgt ccgcgaagcg cttctggccc ggcacgatcg      18618
tgtccgcgta ggcctccagg gtcatggtcc ggatatcgcc ggccggcgcc cctcgctcat      18678
tgtcgtcgcg caactcgctc tccattctcg cagtccggag tgggatgcct tgtggcgagg      18738
agaaagctag gttcgttcga ccggttcaag caactagcca aagtcgaggc gaccttgaaa      18798
ccgactccac ggagttggcg cgaagcggcg gatggattac acgcgcgggc gagcggctca      18858
ctagtctggc cgcacggatg tcttcatcac ctgcacgtgg aaaagcttct gcacgggcac      18918
cgcatgtgga agtgagccct ggtctcatgt cttgggggaa ac gtg aaa agt gac          18972
                                              Val Lys Ser Asp
                                                          2735 tct gcc caa cgc gcc gtg gag cga tca cgc cgt gtc gta cgg atc gat        19020
Ser Ala Gln Arg Ala Val Glu Arg Ser Arg Arg Val Val Arg Ile Asp
        2740                 2745                 2750 gaa ctc att ccc gcc gat tcc ccg cgc ctg aac gga atc gat cgt tcc        19068
Glu Leu Ile Pro Ala Asp Ser Pro Arg Leu Asn Gly Ile Asp Arg Ser
        2755                 2760                 2765
```

-continued

| | |
|---|---|
| cat gtg cag cgc ctc gcg acc gtg tac gcg tcc ctg ccg ccg gtc ctg<br>His Val Gln Arg Leu Ala Thr Val Tyr Ala Ser Leu Pro Pro Val Leu<br>2770                  2775                  2780                  2785 | 19116 |
| gtg cac cgc ccg acc atg cgg gtc gtc gac ggc atg cac cgc atc ggc<br>Val His Arg Pro Thr Met Arg Val Val Asp Gly Met His Arg Ile Gly<br>                2790                  2795                  2800 | 19164 |
| gcg gcc cgc ctg aag ggg ctg gac acg gtc gag gtc acc ttc ttc gag<br>Ala Ala Arg Leu Lys Gly Leu Asp Thr Val Glu Val Thr Phe Phe Glu<br>2805                  2810                  2815 | 19212 |
| ggc gcc gag gag cag gtg ttc ctg cgt tcc gtc gcg gcg aac atc acc<br>Gly Ala Glu Glu Gln Val Phe Leu Arg Ser Val Ala Ala Asn Ile Thr<br>                2820                  2825                  2830 | 19260 |
| aac ggc ctg ccg ttg tcg gtg gcc gac cgc aag acc gcc gcg gcc cgc<br>Asn Gly Leu Pro Leu Ser Val Ala Asp Arg Lys Thr Ala Ala Ala Arg<br>2835                  2840                  2845 | 19308 |
| att ctg gcc tcc cac ccg acc ctg tcc gac cgc gcg gtc gcc gca cac<br>Ile Leu Ala Ser His Pro Thr Leu Ser Asp Arg Ala Val Ala Ala His<br>2850                  2855                  2860                  2865 | 19356 |
| gtc ggc ctc gac gcc aag acc gtg gcg ggg gta cgg acg tgt tca gcc<br>Val Gly Leu Asp Ala Lys Thr Val Ala Gly Val Arg Thr Cys Ser Ala<br>                2870                  2875                  2880 | 19404 |
| gcg ggt tct ccg ctg ctg aac atg cgc acc ggg gcg gac ggc cgc gtc<br>Ala Gly Ser Pro Leu Leu Asn Met Arg Thr Gly Ala Asp Gly Arg Val<br>2885                  2890                  2895 | 19452 |
| cac ccg ttg gac cgc acc gcc gaa cgc ctg cac gcg gcc gcg ctg ctg<br>His Pro Leu Asp Arg Thr Ala Glu Arg Leu His Ala Ala Ala Leu Leu<br>                2900                  2905                  2910 | 19500 |
| acc cag gac ccg gga ctc ccg ttg cgc tcc gtc gtc gag cag acg ggg<br>Thr Gln Asp Pro Gly Leu Pro Leu Arg Ser Val Val Glu Gln Thr Gly<br>2915                  2920                  2925 | 19548 |
| ctg tcg ctg ggc acg gcc cac gac gtc cgc cgt cgg ctg ctg cgg ggc<br>Leu Ser Leu Gly Thr Ala His Asp Val Arg Arg Arg Leu Leu Arg Gly<br>2930                  2935                  2940                  2945 | 19596 |
| gag gac ccg gtc ccg cag aac cgg cag agc gcg atg ctg gag ccg gga<br>Glu Asp Pro Val Pro Gln Asn Arg Gln Ser Ala Met Leu Glu Pro Gly<br>                2950                  2955                  2960 | 19644 |
| ctc gcc ccg cag aag aag gcg acg gcc aag ccc ccc gtc ggc ccg gcc<br>Leu Ala Pro Gln Lys Lys Ala Thr Ala Lys Pro Pro Val Gly Pro Ala<br>2965                  2970                  2975 | 19692 |
| gcc cgt ccg gtc ccg aag gtg ccg ccc gcc gtc gcc ggc agg ccg ccg<br>Ala Arg Pro Val Pro Lys Val Pro Pro Ala Val Ala Gly Arg Pro Pro<br>                2980                  2985                  2990 | 19740 |
| gtg tca ccg cgg tcc cgg gcc ccg ctg gag gcg ctg cgc aag ctc tcc<br>Val Ser Pro Arg Ser Arg Ala Pro Leu Glu Ala Leu Arg Lys Leu Ser<br>2995                  3000                  3005 | 19788 |
| aac gac ccc tcc ctg cgc cac tcc gac cag ggg cgc gaa ctc atg cgc<br>Asn Asp Pro Ser Leu Arg His Ser Asp Gln Gly Arg Glu Leu Met Arg<br>3010                  3015                  3020                  3025 | 19836 |
| tgg ctg cac aac cgg ttc gtc gtc gac gag gcg tgg cgc cgg cgc gcg<br>Trp Leu His Asn Arg Phe Val Val Asp Glu Ala Trp Arg Arg Arg Ala<br>                3030                  3035                  3040 | 19884 |
| gac gcg gtc ccg gcc cac tgc gtc gac tcg atg gcg gag ctg gcg cag<br>Asp Ala Val Pro Ala His Cys Val Asp Ser Met Ala Glu Leu Ala Gln<br>3045                  3050                  3055 | 19932 |
| cac tgc tcg gac gcc tgg cac cgg ttc gcc gag gag atg gtt cgg cgc<br>His Cys Ser Asp Ala Trp His Arg Phe Ala Glu Glu Met Val Arg Arg<br>                3060                  3065                  3070 | 19980 |
| cgg cac agc gcc gcg gcc gac ggc tcc gga ctc cgc acg act cag cca<br>Arg His Ser Ala Ala Ala Asp Gly Ser Gly Leu Arg Thr Thr Gln Pro<br>3075                  3080                  3085 | 20028 |

| | | |
|---|---|---|
| act cgc cgt tgacggccta cttcgacagg gagttacg gtg acc acg aac acc<br>Thr Arg Arg                                                           Val Thr Thr Asn Thr<br>3090                                                                       3095 | 20080 |

```
atc gag gac gcg gtc cgc cgg gtc gtc gag tac atg cac gtc aac ctg      20128
Ile Glu Asp Ala Val Arg Arg Val Val Glu Tyr Met His Val Asn Leu
    3100                3105                3110 ggt cag aac ctc acg atc gat gac atg gcg cgc acg gcg atg ttc agc      20176
Gly Gln Asn Leu Thr Ile Asp Asp Met Ala Arg Thr Ala Met Phe Ser
3115                3120                3125 aag ttc cat ttc acc cgc atc ttc cgc gaa gtc acc ggt acc tct ccc      20224
Lys Phe His Phe Thr Arg Ile Phe Arg Glu Val Thr Gly Thr Ser Pro
3130                3135                3140                3145 ggg cgt ttc ctg tcc gcc tta cgg att cag gag gcc aag aga ctt ctc      20272
Gly Arg Phe Leu Ser Ala Leu Arg Ile Gln Glu Ala Lys Arg Leu Leu
        3150                3155                3160 gtg cac act gca ctc agt gtg gcc gat atc agc agt cag gtc ggc tac      20320
Val His Thr Ala Leu Ser Val Ala Asp Ile Ser Ser Gln Val Gly Tyr
            3165                3170                3175 agc agt gtc ggt act ttc agt tct cgc ttc aag gcc tgt gtg ggg ctt      20368
Ser Ser Val Gly Thr Phe Ser Ser Arg Phe Lys Ala Cys Val Gly Leu
                3180                3185                3190 tcc ccg agc gcc tat cgc gac ttc ggg ggt gtg cag ccg ggt ttt ccc      20416
Ser Pro Ser Ala Tyr Arg Asp Phe Gly Gly Val Gln Pro Gly Phe Pro
                    3195                3200                3205 tcc gcc gcg gcc cgt ctc act ccc acc gcg cac aat ccc tcc gtg cgc      20464
Ser Ala Ala Ala Arg Leu Thr Pro Thr Ala His Asn Pro Ser Val Arg
3210                3215                3220                3225 ggc cgc att cac tcc gcc ccg ggt gac agg ccc gga agg atc ttc gtg      20512
Gly Arg Ile His Ser Ala Pro Gly Asp Arg Pro Gly Arg Ile Phe Val
        3230                3235                3240 ggc ctg ttc ccc ggc agg atg cgc cag ggc cgc ccg gcg cgc tgg acc      20560
Gly Leu Phe Pro Gly Arg Met Arg Gln Gly Arg Pro Ala Arg Trp Thr
            3245                3250                3255 gtc atg gag agt ccc ggg gcc ttc gag ctc cgg gac gtg ccc gtg ggc      20608
Val Met Glu Ser Pro Gly Ala Phe Glu Leu Arg Asp Val Pro Val Gly
                3260                3265                3270 acc tgg cac atc ctg gtc cac tcc ttc ccc gcc gga cac cgg ccg cac      20656
Thr Trp His Ile Leu Val His Ser Phe Pro Ala Gly His Arg Pro His
3275                3280                3285 cag ctc gac tcc gaa ccg ctg ttg ctc ggg cac agc gga ccg ctc gtg      20704
Gln Leu Asp Ser Glu Pro Leu Leu Leu Gly His Ser Gly Pro Leu Val
3290                3295                3300                3305 gtg cac ccc ggt gcc ctg ctc cgg ccg gcg gac atc ctc ctg cgc gcg      20752
Val His Pro Gly Ala Leu Leu Arg Pro Ala Asp Ile Leu Leu Arg Ala
        3310                3315                3320 gtg gac gcc ctc gat cca ccg gtc ctg ctg gcc cac ttc gcg ctg gag      20800
Val Asp Ala Leu Asp Pro Pro Val Leu Leu Ala His Phe Ala Leu Glu
            3325                3330                3335 agc cgc ctc acc tcg ccg tac tca ccg tca tcg gta gcc ctc cgc gca      20848
Ser Arg Leu Thr Ser Pro Tyr Ser Pro Ser Ser Val Ala Leu Arg Ala
                3340                3345                3350 tcc gca ggg aga gca tgg gtt cgg caa ccg ccc ggt gtc cgg cga cgg      20896
Ser Ala Gly Arg Ala Trp Val Arg Gln Pro Pro Gly Val Arg Arg Arg
                    3355                3360                3365 tac gca gat cga gat cgc ggg tgaccagggc cgtgacgaac accgcctcca         20947
Tyr Ala Asp Arg Asp Arg Gly
3370                3375 tcatcccgag gttgctgccg acgcagaacc ggggcccccgc gccgaacggg atgtacgcgt   21007
```

```
accgcggccg gtcggcggtc tgccggggtt cgaaccgctc ggggtcgaag cgctcggggt    21067
cctcccacag ccccggatgg cggtgcatga tgtacgggca gaccagcaca tccgatccgg    21127
cggacaccgt gtagccgccg accacatcgc gttgctgggc caccctgggc aggatccc     21185
```

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 3

```
atgggcatga cgggt                                                        15
```

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 4

```
ctagaggatc ccggg                                                        15
```

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 5

```
atgccgcgga ttccc                                                        15
```

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 6

```
tcagctgtcg atgtc                                                        15
```

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 7

```
atgaccatcg ccact                                                        15
```

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 8

```
tcagaggccg agcac                                                        15
```

```
<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 9
atgagctcgc tactg                                                15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 10
ctaggagccg gtcgc                                                15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 11
atgagcagca gcgcc                                                15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 12
tcattcgtcg gctgc                                                15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 13
gtgagggctc tgccg                                                15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 14
tcagacggcg gaggg                                                15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Primer
```

```
<400> SEQUENCE: 15
gtgagcgtca ccgac                                              15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 16
tcaacccgcc ctgcg                                              15

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 17
atgaggatgc tggtg                                              15

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 18
gtggctgtgc tcgca                                              15

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 19
atgaggatgc tggtg                                              15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 20
tcagccgacg gcgtc                                              15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 21
gtgacagcag tcaag                                              15

<210> SEQ ID NO 22
<211> LENGTH: 15
```

```
<212> TYPE: DNA
<213> ORGANISM: Artificial Sequence
<220> FEATURE:
<223> OTHER INFORMATION: Description of Artificial Sequence: Primer

<400> SEQUENCE: 22
tcatgtggcc ggttg                                                            15

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 23
gtggagtact ggaac                                                            15

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 24
tcaggcctga ggggc                                                            15

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 25
gtgccccacg gtgca                                                            15

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 26
ctacagccct ccgag                                                            15

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 27
atgtcttcaa cccgt                                                            15

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 28
```
tcagccgcgc aggaa                                                    15

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 29
atgctggaga aatgc                                                    15

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 30
tcagacgagc tcctt                                                    15

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 31
atggagtacg gcccc                                                    15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 32
tcatgccgtg cgcac                                                    15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 33
atgagcggcg gcccg                                                    15

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 34
tcacctcgcc ggacg                                                    15

<210> SEQ ID NO 35
<211> LENGTH: 15
<212> TYPE: DNA
<213> ORGANISM: Artificial Sequence

```
<220> FEATURE:
<223> OTHER INFORMATION: Description of Artificial Sequence: Primer

<400> SEQUENCE: 35
atgtcgttac gtcac                                                          15

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 36
tcagccgaag gtcag                                                          15

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 37
atgaaggcac ttgta                                                          15

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 38
tcaggccgcg atctc                                                          15

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 39
gtggacgtgt cagcg                                                          15

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 40
tcaggaccgc gcacc                                                          15

<210> SEQ ID NO 41
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 41
atgaagccga tcggg                                                          15
```

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 42
tcaggacgac ttgtt                                                15

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 43
atgccttccc ccttc                                                15

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 44
tcaggtgcgc tcggc                                                15

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 45
gtgagagacg gccgg                                                15

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 46
tcacgtggtg atggc                                                15

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 47
atgaccgacc agtgc                                                15

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: Primer

```
<400> SEQUENCE: 48
tcacagcaac tcctc                                                          15

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 49
gtgagcttgt ggtct                                                          15

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 50
tcaggccggt tcggc                                                          15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 51
gtgcgtccct tccgt                                                          15

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 52
tcagcggagc ggacg                                                          15

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 53
atgccagcac cgact                                                          15

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 54
tcagtcgttg ccgcg                                                          15

<210> SEQ ID NO 55
```

```
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 55
atgcgggtga tgatc                                                    15

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 56
tcatcggtcc gcctc                                                    15

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 57
atgaccaagc acgcc                                                    15

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 58
tcatacggcg gcgcc                                                    15

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 59
gtgagcgcac aactc                                                    15

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 60
tcacggctgt gcctg                                                    15

<210> SEQ ID NO 61
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 61
```
atgtcttcaa cccgt                                           15

<210> SEQ ID NO 62
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 62
tcagccgcgc aggaa                                           15

<210> SEQ ID NO 63
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 63
atgacgacgt ccgac                                           15

<210> SEQ ID NO 64
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 64
tcaggaggtg aaggg                                           15

<210> SEQ ID NO 65
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 65
atggcattga ctcaa                                           15

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 66
tcagcgcagc tggat                                           15

<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 67
atgacgcggc cggtg                                           15

<210> SEQ ID NO 68
<211> LENGTH: 15
<212> TYPE: DNA

```
<213> ORGANISM: Artificial Sequence
<220> FEATURE:
<223> OTHER INFORMATION: Description of Artificial Sequence: Primer

<400> SEQUENCE: 68
tcagcgggtg agccg                                                    15

<210> SEQ ID NO 69
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 69
gtgtccaccg tttcc                                                    15

<210> SEQ ID NO 70
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 70
tcactgcgtt ccgga                                                    15

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 71
gtgtgcccgg tgacagac                                                 18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 72
tcagcccacg ggctggga                                                 18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 73
gtgttgggcg atgaggac                                                 18

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 74
tcagaccgcg gacatctg                                                 18
```

```
<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 75
atggccggcc tggtcatg                                                 18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 76
tcaggacccg agggtcac                                                 18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 77
gtggaccaga cgtctacg                                                 18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 78
tcatgcaggt gcagcgtg                                                 18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 79
atgaggccgc tcgttcgg                                                 18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 80
tcatcccggc ccggcggc                                                 18

<210> SEQ ID NO 81
<211> LENGTH: 18
<212> TYPE: DNA
<213> ORGANISM: Artificial Sequence
<220> FEATURE:
```

<223> OTHER INFORMATION: Description of Artificial Sequence: Primer

<400> SEQUENCE: 81
atgagaacgc ggcgacgc                                      18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 82
tcacggccgg aggcgtac                                      18

<210> SEQ ID NO 83
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 83
atgtgctccc gtacc                                         15

<210> SEQ ID NO 84
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 84
tcagccggac tgtcg                                         15

<210> SEQ ID NO 85
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 85
atggcccttc acccg                                         15

<210> SEQ ID NO 86
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 86
tcagccggcc tgggc                                         15

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 87
atgtctacgg gctatctc                                      18

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 88
tcagccgccg gtggcgcc                                                18

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 89
atgttctccc ccgccgcc                                                18

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 90
tcagtacgcc tggtgggc                                                18

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 91
atgaattcgc tcgacgac                                                18

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 92
tcagctcccg gtcgccgc                                                18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 93
atgaccgcga cgaatcct                                                18

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Primer

```
<400> SEQUENCE: 94
ctaggcggcg cgtcccgc                                                 18

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 95
atgagcacca cggccgag                                                 18

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 96
tcagccgcgc gccgacgg                                                 18

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 97
atgaccctgg aggcctac                                                 18

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 98
tcatgcgggg ctcccggt                                                 18

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 99
gtgaaaagtg actctgcc                                                 18

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 100
tcaacggcga gttggctg                                                 18

<210> SEQ ID NO 101
<211> LENGTH: 18
```

```
<212> TYPE: DNA
<213> ORGANISM: Artificial Sequence
<220> FEATURE:
<223> OTHER INFORMATION: Description of Artificial Sequence: Primer

<400> SEQUENCE: 101
gtgaccacga acaccatc                                              18

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 102
tcacccgcga tctcgatc                                              18

<210> SEQ ID NO 103

<400> SEQUENCE: 103

000

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 104
tcacctcgcc gtactcac                                              18

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 105
atcatcccga tcatc                                                 15

<210> SEQ ID NO 106
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 106
tcatgccgcc cttcc                                                 15

<210> SEQ ID NO 107
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 107
atgagccgca tagcc                                                 15

<210> SEQ ID NO 108
<211> LENGTH: 15
```

```
<212> TYPE: DNA
<213> ORGANISM: Artificial Sequence
<220> FEATURE:
<223> OTHER INFORMATION: Description of Artificial Sequence: Primer

<400> SEQUENCE: 108
tcacgcgcgg gcgct                                                    15

<210> SEQ ID NO 109
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 109
gtgaccgtgc ccggt                                                    15

<210> SEQ ID NO 110
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 110
tcatacaggc accgt                                                    15

<210> SEQ ID NO 111
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 111
atggcggaga gtttc                                                    15

<210> SEQ ID NO 112
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 112
tcacttctcc ttcac                                                    15

<210> SEQ ID NO 113
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 113
gtgccccggg cctt                                                     15

<210> SEQ ID NO 114
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 114
```
tcatgcgacg gcgcc 15

<210> SEQ ID NO 115
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 115
gtggcatcgg taccg 15

<210> SEQ ID NO 116
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 116 tcagggtat gtgag 15

<210> SEQ ID NO 117
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 117
atgctgccac ggacg 15

<210> SEQ ID NO 118
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 118
tcagcgcgtc cggcg 15

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 119
gtgatgaccc actgc 15

<210> SEQ ID NO 120
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 120
tcaggccttc ggggc 15

<210> SEQ ID NO 121
<211> LENGTH: 15
<212> TYPE: DNA
<213> ORGANISM: Artificial Sequence

```
<220> FEATURE:
<223> OTHER INFORMATION: Description of Artificial Sequence: Primer

<400> SEQUENCE: 121
gtgacgacga gcggc                                                    15

<210> SEQ ID NO 122
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 122
tcagctcgcc gccgg                                                    15

<210> SEQ ID NO 123
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 123
atcgcggcac acgac                                                    15

<210> SEQ ID NO 124
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 124
tcagctcccc tcctg                                                    15

<210> SEQ ID NO 125
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 125
gtggacgagg ccggc                                                    15

<210> SEQ ID NO 126
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 126
tcacccggat gtcgt                                                    15

<210> SEQ ID NO 127
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 127
gtgagtgctc tgatc                                                    15
```

<210> SEQ ID NO 128
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 128
tcaccgcgga acgga                                                    15

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 129
gtgccgcttc tacgc                                                    15

<210> SEQ ID NO 130
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 130
ctactggaca ctgtg                                                    15

<210> SEQ ID NO 131
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 131
atgccgcaca ggacc                                                    15

<210> SEQ ID NO 132
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 132
tcagccggtg agagc                                                    15

<210> SEQ ID NO 133
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 133
gtgagtgctc tgatc                                                    15

<210> SEQ ID NO 134
<211> LENGTH: 15
<212> TYPE: DNA
<213> ORGANISM: Artificial Sequence
<220> FEATURE:
<223> OTHER INFORMATION: Description of Artificial Sequence: Primer

```
<400> SEQUENCE: 134
tcaccccggc acagg                                              15

<210> SEQ ID NO 135
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 135 atcaccccg gaggc                                               15

<210> SEQ ID NO 136
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 136
tcactccgcc tcctc                                              15

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 137
agctccatca agtcsatgrt cgg                                     23

<210> SEQ ID NO 138
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 138
ccggtgttsa csgcgtagaa ccaggcg                                 27

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (9)
<223> OTHER INFORMATION: a, t, c or g

<400> SEQUENCE: 139
gacacvgcnt gytcbtcv                                           18

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (13)
```

-continued

<223> OTHER INFORMATION: a, t, c or g

<400> SEQUENCE: 140
rtgsgcrttv gtnccrct                                                    18

<210> SEQ ID NO 141
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 141
gcstcccgsg acctgggctt cgactc                                           26

<210> SEQ ID NO 142
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 142
agsgasgasg agcaggcggt stcsac                                           26

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 143
csggsgssgc sggsttcatc gg                                               22

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 144
gggwrctggy rsggsccgta gttg                                             24

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 145
aggtggaggc gctcaccgag                                                  20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 146
gggcgtcagg ccgtaagaag                                                  20

-continued

```
<210> SEQ ID NO 147
<211> LENGTH: 3035
<212> TYPE: DNA
<213> ORGANISM: Streptomyces globisporus
<220> FEATURE:
<221> NAME/KEY: CDS
<222> LOCATION: (101)..(1096)
<223> OTHER INFORMATION: sgcA
<220> FEATURE:
<221> NAME/KEY: CDS
<222> LOCATION: (1143)..(2705)
<223> OTHER INFORMATION: sgcB

<400> SEQUENCE: 147
```

| | | |
|---|---|---|
| ggatccggga agaccggaat tccgccccca gcccggtcga actcgtatcg ctcctggtag | | 60 |
| aactgacgaa gcgtcatcgc cgtgacaagg aggcggaccg atg agg atg ctg gtg | | 115 |
| | Met Arg Met Leu Val | |
| | 1                  5 | |
| acg ggc gga gcg ggt ttc atc ggc tcg cag ttc gtg cgg gcc aca ctg | | 163 |
| Thr Gly Gly Ala Gly Phe Ile Gly Ser Gln Phe Val Arg Ala Thr Leu | | |
|           10                  15                  20 | | |
| cac ggc gag ctg ccg ggt tcc gag gac gcc cgg gtg acg gtc ctg gac | | 211 |
| His Gly Glu Leu Pro Gly Ser Glu Asp Ala Arg Val Thr Val Leu Asp | | |
|           25                  30                  35 | | |
| aag ctg acg tac tcc ggc aat ccg gcc aac ctc acc tcc gtc gcg gcc | | 259 |
| Lys Leu Thr Tyr Ser Gly Asn Pro Ala Asn Leu Thr Ser Val Ala Ala | | |
|             40                  45                  50 | | |
| cat ccg cgg tac acc ttc gtc cag ggc gac acc gtc gac ccg cgc gtc | | 307 |
| His Pro Arg Tyr Thr Phe Val Gln Gly Asp Thr Val Asp Pro Arg Val | | |
|     55                  60                  65 | | |
| gtc gac gag gtg gtc gcc ggc cac gac gtc atc gtc cac ttc gcg gcg | | 355 |
| Val Asp Glu Val Val Ala Gly His Asp Val Ile Val His Phe Ala Ala | | |
| 70                  75                  80                  85 | | |
| gag tcg cac gtg gac cgc tcg atc gac acc gcc acc cgg ttc gtc acg | | 403 |
| Glu Ser His Val Asp Arg Ser Ile Asp Thr Ala Thr Arg Phe Val Thr | | |
|                   90                  95                  100 | | |
| acc aac gtg ctc ggg acc cag acg ctg ctg gaa gcg gct ctc cgg cac | | 451 |
| Thr Asn Val Leu Gly Thr Gln Thr Leu Leu Glu Ala Ala Leu Arg His | | |
|           105                  110                  115 | | |
| ggg gtc ggc cgg ttc gtg cac gtg tcg acc gac gag gtc tac ggg tcg | | 499 |
| Gly Val Gly Arg Phe Val His Val Ser Thr Asp Glu Val Tyr Gly Ser | | |
|         120                  125                  130 | | |
| atc gcc tcc ggc tca tgg acc gag gac acc ccg ctc gcc ccc aac gtc | | 547 |
| Ile Ala Ser Gly Ser Trp Thr Glu Asp Thr Pro Leu Ala Pro Asn Val | | |
| 135                  140                  145 | | |
| ccc tac gcg gcg tcg aag gcg ggt tcg gac ctg atg gcg ctc gcc tgg | | 595 |
| Pro Tyr Ala Ala Ser Lys Ala Gly Ser Asp Leu Met Ala Leu Ala Trp | | |
| 150                  155                  160                  165 | | |
| cac cgc acc cgg ggc ctg gac gtc gtc gtc acc cgg tgc acc aac aac | | 643 |
| His Arg Thr Arg Gly Leu Asp Val Val Val Thr Arg Cys Thr Asn Asn | | |
|                   170                  175                  180 | | |
| tac ggt ccc tac cag tac ccc gag aag gtg atc ccg ctc ttc gtc acc | | 691 |
| Tyr Gly Pro Tyr Gln Tyr Pro Glu Lys Val Ile Pro Leu Phe Val Thr | | |
|                 185                  190                  195 | | |
| aac atc ctc gac ggc ttg cgg gtg ccc ctg tac ggg gac ggc gcc cac | | 739 |
| Asn Ile Leu Asp Gly Leu Arg Val Pro Leu Tyr Gly Asp Gly Ala His | | |
|         200                  205                  210 | | |
| cgc cgg gac tgg ctg cac gtg tcc gac cac tgc cgg gcc atc cag atg | | 787 |
| Arg Arg Asp Trp Leu His Val Ser Asp His Cys Arg Ala Ile Gln Met | | |
| 215                  220                  225 | | |
| gtc atg aac tcc ggc cgg gcc ggg gag gtc tac cac atc ggc ggc ggc | | 835 |
| Val Met Asn Ser Gly Arg Ala Gly Glu Val Tyr His Ile Gly Gly Gly | | |

```
                                        -continued
   230            235             240              245
acc gaa ctc tcc aac gag gaa ctc acc ggc ctg ttg ctc acg gcg tgc    883
Thr Glu Leu Ser Asn Glu Glu Leu Thr Gly Leu Leu Leu Thr Ala Cys
                250             255              260 ggc acc gac tgg tcc tgc gtg gac cgg gtg gcc gac cgg cag ggg cac    931
Gly Thr Asp Trp Ser Cys Val Asp Arg Val Ala Asp Arg Gln Gly His
            265             270              275 gac cgc cgc tac tcg ctc gac atc acg aag atc cgg cag gaa ctg ggc    979
Asp Arg Arg Tyr Ser Leu Asp Ile Thr Lys Ile Arg Gln Glu Leu Gly
        280             285              290 tac gag ccc ctg gtc gcc ttc gag gac ggc ctg gcc gcg acg gtg aag   1027
Tyr Glu Pro Leu Val Ala Phe Glu Asp Gly Leu Ala Ala Thr Val Lys
    295             300              305 tgg tac cac gag aac cgt tcg tgg tgg cag ccg ctg aag gaa gcg gcc   1075
Trp Tyr His Glu Asn Arg Ser Trp Trp Gln Pro Leu Lys Glu Ala Ala
310             315              320              325 ggc ctc ctg gac gcc gtc ggc tgacggcagc caccgctagg aacaccccag      1126
Gly Leu Leu Asp Ala Val Gly
                330 gaaaggagcc acctcc gtg aca gca gtc aag gag ccg acg tcc cgc gca gga 1178
               Met Thr Ala Val Lys Glu Pro Thr Ser Arg Ala Gly
                               335                 340 cgg cgg gag tgg atc gct ctc gtc gtc ctc tcc ttg ccc acg atg ctg   1226
Arg Arg Glu Trp Ile Ala Leu Val Val Leu Ser Leu Pro Thr Met Leu
345             350              355              360 ttg atg ctg gac atc aac gtc ctc atg ctg gcc ttg ccg cag ttg agc   1274
Leu Met Leu Asp Ile Asn Val Leu Met Leu Ala Leu Pro Gln Leu Ser
                365             370              375 gag gat ctc ggc gcg agc agc acg caa cag ctg tgg atc acc gac atc   1322
Glu Asp Leu Gly Ala Ser Ser Thr Gln Gln Leu Trp Ile Thr Asp Ile
            380             385              390 tac gga ttc gcg atc gcc ggc ttc ctg gtg acc atg ggc acc ctc ggc   1370
Tyr Gly Phe Ala Ile Ala Gly Phe Leu Val Thr Met Gly Thr Leu Gly
        395             400              405 gac cgg atc ggc cgc cgc agg ctc ctg ctc ggg ggc gcg gcc gtc ttc   1418
Asp Arg Ile Gly Arg Arg Arg Leu Leu Leu Gly Gly Ala Ala Val Phe
    410             415              420 gcg gtc gtg tcc gtc gtc gcc gcg ttc tcc gac agc gcg gcg atg ctc   1466
Ala Val Val Ser Val Val Ala Ala Phe Ser Asp Ser Ala Ala Met Leu
425             430              435              440 gtc gtc agc cgc gcc gtg ctc ggc gtc gcc ggg gcc acg gtg atg ccc   1514
Val Val Ser Arg Ala Val Leu Gly Val Ala Gly Ala Thr Val Met Pro
                445             450              455 tcg acg ctc gcg ctc atc agc aac atg ttc gag gac ccc aag gag cgg   1562
Ser Thr Leu Ala Leu Ile Ser Asn Met Phe Glu Asp Pro Lys Glu Arg
                460             465              470 ggc acc gcc atc gcc atg tgg gcg agc gcc atg atg gcc gga gtc gcc   1610
Gly Thr Ala Ile Ala Met Trp Ala Ser Ala Met Met Ala Gly Val Ala
            475             480              485 ctc ggg ccc gcc gtc ggc ggc ctg gtc ctc gcc gcg ttc tgg tgg gga   1658
Leu Gly Pro Ala Val Gly Gly Leu Val Leu Ala Ala Phe Trp Trp Gly
        490             495              500 tcg gtg ttc ctc atc gcc gtt ccg gtg atg ctg ctg gtg gtg gtc acc   1706
Ser Val Phe Leu Ile Ala Val Pro Val Met Leu Leu Val Val Val Thr
505             510              515              520 ggc ccc gtg ctg ctc acc gag tcc cgc gac ccg gac gcc gga cgg ctg   1754
Gly Pro Val Leu Leu Thr Glu Ser Arg Asp Pro Asp Ala Gly Arg Leu
                525             530              535 gac ctg ctg agc gcg ggg ctc tcc ctc gcg acc gtg ctg ccg gtg atc   1802
```

```
                                    -continued

Asp Leu Leu Ser Ala Gly Leu Ser Leu Ala Thr Val Leu Pro Val Ile
                540                 545                 550 tac gga ctg aag gag ctg gcc cgg acc ggg tgg gac ccg ctc gcc gcc     1850
Tyr Gly Leu Lys Glu Leu Ala Arg Thr Gly Trp Asp Pro Leu Ala Ala
            555                 560                 565 ggc gcg gtg gtc ctc ggc gtg atc ttc ggc gcg ctg ttc gtc cag cgc     1898
Gly Ala Val Val Leu Gly Val Ile Phe Gly Ala Leu Phe Val Gln Arg
570                 575                 580 cag cgg cgg ttg gcc gac ccc atg ctg gac ctc ggc ctc ttc gcc gac     1946
Gln Arg Arg Leu Ala Asp Pro Met Leu Asp Leu Gly Leu Phe Ala Asp
585                 590                 595                 600 cgc acc ctg cgg gcg ggt ctg acg gtc agt ctg gtc aac gcc gtc atc     1994
Arg Thr Leu Arg Ala Gly Leu Thr Val Ser Leu Val Asn Ala Val Ile
                605                 610                 615 atg ggc ggg acc gga ctg atg gtc gcc ctg tac ctc cag acg atc gcc     2042
Met Gly Gly Thr Gly Leu Met Val Ala Leu Tyr Leu Gln Thr Ile Ala
                620                 625                 630 ggt cac tcc ccg ttg gcc gcc ggg ctg tgg ctg ctg atc ccg gcc tgc     2090
Gly His Ser Pro Leu Ala Ala Gly Leu Trp Leu Leu Ile Pro Ala Cys
                635                 640                 645 atg ctc gtc gtg ggc gta cag ctg tcg aac ctg ctg gcc cag cgg atg     2138
Met Leu Val Val Gly Val Gln Leu Ser Asn Leu Leu Ala Gln Arg Met
    650                 655                 660 ccc cct tcc cgg gtg ctg ctg ggg gga ctg ctg atc gcg gcc gtc gga     2186
Pro Pro Ser Arg Val Leu Leu Gly Gly Leu Leu Ile Ala Ala Val Gly
665                 670                 675                 680 cag ctc ctg atc acc cag gtg gac acc gag gac acc gcc ctc ctc atc     2234
Gln Leu Leu Ile Thr Gln Val Asp Thr Glu Asp Thr Ala Leu Leu Ile
                685                 690                 695 gcg gcc acc acc ctg atc tac ttc ggc gcc tca ccg gtg ggg ccg atc     2282
Ala Ala Thr Thr Leu Ile Tyr Phe Gly Ala Ser Pro Val Gly Pro Ile
                700                 705                 710 acc acg ggc gcg atc atg gga gcc gcg ccc ccg gag aag gcg ggt gcc     2330
Thr Thr Gly Ala Ile Met Gly Ala Ala Pro Pro Glu Lys Ala Gly Ala
                715                 720                 725 gcc tcg tcg ctg tcc gcc acc ggc ggc gag ttc gga gtg gcg ctc ggc     2378
Ala Ser Ser Leu Ser Ala Thr Gly Gly Glu Phe Gly Val Ala Leu Gly
730                 735                 740 atc gcg ggc ctg ggg agt ctg ggc acc gtc gtg tac agc gcc ggg gtc     2426
Ile Ala Gly Leu Gly Ser Leu Gly Thr Val Val Tyr Ser Ala Gly Val
745                 750                 755                 760 gag gtg ccg gac gcg gcc ggg ccc gcc gac gcc gac gcc gcg cag gag     2474
Glu Val Pro Asp Ala Ala Gly Pro Ala Asp Ala Asp Ala Ala Gln Glu
                765                 770                 775 agc atc gcc ggc gcc ctg cac acg gcc ggt cag ctg gca ccg ggc agc     2522
Ser Ile Ala Gly Ala Leu His Thr Ala Gly Gln Leu Ala Pro Gly Ser
                780                 785                 790 gcc gac gcc ctg ctg gac tcc gcg cgc gcg gcc ttc acc agc ggc gtg     2570
Ala Asp Ala Leu Leu Asp Ser Ala Arg Ala Ala Phe Thr Ser Gly Val
            795                 800                 805 cag tcc gtc gcc gcc gtc tgc gcc gtg ttc tcc ctg gcg ctc gcc gtc     2618
Gln Ser Val Ala Ala Val Cys Ala Val Phe Ser Leu Ala Leu Ala Val
810                 815                 820 ctc atc ggc acc cgg ctg cgg gac att tcc gcg atg gac cac ggg cac     2666
Leu Ile Gly Thr Arg Leu Arg Asp Ile Ser Ala Met Asp His Gly His
825                 830                 835                 840 ggc gag gaa ccg gcc gag aac gac gct caa ccg gcc aca tgagcgcact     2715
Gly Glu Glu Pro Ala Glu Asn Asp Ala Gln Pro Ala Thr
                845                 850
```

-continued

```
tccggagatg caacggccgc cgtcgaggta tgaggatcac cttccggggt gcacctgcac    2775
ggcaacggag gcgtagtgga gtactggaac agcacggcgg agaccatgcc ccgccaggaa    2835
ctcgaacagt ggaagtggcg caggctccag gccgccatgg accacgccag aaggctttcg    2895
cccttctggc gggaacgact ccccgagaac atcacctcca tggcggacta cgcggcgcgg    2955
gtgcctctcc tgcgcaaggc cgacctcctc gccgcggaag ccgcgtctcc cccttacggc    3015 acctggcccct cgctggatcc                                               3035
```

<210> SEQ ID NO 148
<211> LENGTH: 332
<212> TYPE: PRT
<213> ORGANISM: Streptomyces globisporus

<400> SEQUENCE: 148

```
Met Arg Met Leu Val Thr Gly Gly Ala Gly Phe Ile Gly Ser Gln Phe
 1               5                  10                  15

Val Arg Ala Thr Leu His Gly Glu Leu Pro Gly Ser Glu Asp Ala Arg
                20                  25                  30

Val Thr Val Leu Asp Lys Leu Thr Tyr Ser Gly Asn Pro Ala Asn Leu
            35                  40                  45

Thr Ser Val Ala Ala His Pro Arg Tyr Thr Phe Val Gln Gly Asp Thr
        50                  55                  60

Val Asp Pro Arg Val Val Asp Glu Val Val Ala Gly His Asp Val Ile
 65                  70                  75                  80

Val His Phe Ala Ala Glu Ser His Val Asp Arg Ser Ile Asp Thr Ala
                85                  90                  95

Thr Arg Phe Val Thr Thr Asn Val Leu Gly Thr Gln Thr Leu Leu Glu
            100                 105                 110

Ala Ala Leu Arg His Gly Val Gly Arg Phe Val His Val Ser Thr Asp
        115                 120                 125

Glu Val Tyr Gly Ser Ile Ala Ser Gly Ser Trp Thr Glu Asp Thr Pro
    130                 135                 140

Leu Ala Pro Asn Val Pro Tyr Ala Ala Ser Lys Ala Gly Ser Asp Leu
145                 150                 155                 160

Met Ala Leu Ala Trp His Arg Thr Arg Gly Leu Asp Val Val Thr
                165                 170                 175

Arg Cys Thr Asn Asn Tyr Gly Pro Tyr Gln Tyr Pro Glu Lys Val Ile
            180                 185                 190

Pro Leu Phe Val Thr Asn Ile Leu Asp Gly Leu Arg Val Pro Leu Tyr
        195                 200                 205

Gly Asp Gly Ala His Arg Arg Asp Trp Leu His Val Ser Asp His Cys
    210                 215                 220

Arg Ala Ile Gln Met Val Met Asn Ser Gly Arg Ala Gly Glu Val Tyr
225                 230                 235                 240

His Ile Gly Gly Gly Thr Glu Leu Ser Asn Glu Leu Thr Gly Leu
                245                 250                 255

Leu Leu Thr Ala Cys Gly Thr Asp Trp Ser Cys Val Asp Arg Val Ala
            260                 265                 270

Asp Arg Gln Gly His Asp Arg Arg Tyr Ser Leu Asp Ile Thr Lys Ile
        275                 280                 285

Arg Gln Glu Leu Gly Tyr Glu Pro Leu Val Ala Phe Glu Asp Gly Leu
    290                 295                 300

Ala Ala Thr Val Lys Trp Tyr His Glu Asn Arg Ser Trp Trp Gln Pro
305                 310                 315                 320
```

```
Leu Lys Glu Ala Ala Gly Leu Leu Asp Ala Val Gly
            325                 330
```

<210> SEQ ID NO 149
<211> LENGTH: 521
<212> TYPE: PRT
<213> ORGANISM: Streptomyces globisporus

<400> SEQUENCE: 149

```
Met Thr Ala Val Lys Glu Pro Thr Ser Arg Ala Gly Arg Arg Glu Trp
 1               5                  10                  15

Ile Ala Leu Val Val Leu Ser Leu Pro Thr Met Leu Met Leu Asp
                20                  25                  30

Ile Asn Val Leu Met Leu Ala Leu Pro Gln Leu Ser Glu Asp Leu Gly
            35                  40                  45

Ala Ser Ser Thr Gln Gln Leu Trp Ile Thr Asp Ile Tyr Gly Phe Ala
    50                  55                  60

Ile Ala Gly Phe Leu Val Thr Met Gly Thr Leu Gly Asp Arg Ile Gly
 65                  70                  75                  80

Arg Arg Arg Leu Leu Leu Gly Gly Ala Ala Val Phe Ala Val Val Ser
                85                  90                  95

Val Val Ala Ala Phe Ser Asp Ser Ala Ala Met Leu Val Val Ser Arg
            100                 105                 110

Ala Val Leu Gly Val Ala Gly Ala Thr Val Met Pro Ser Thr Leu Ala
        115                 120                 125

Leu Ile Ser Asn Met Phe Glu Asp Pro Lys Glu Arg Gly Thr Ala Ile
    130                 135                 140

Ala Met Trp Ala Ser Ala Met Met Ala Gly Val Ala Leu Gly Pro Ala
145                 150                 155                 160

Val Gly Gly Leu Val Leu Ala Ala Phe Trp Trp Gly Ser Val Phe Leu
                165                 170                 175

Ile Ala Val Pro Val Met Leu Leu Val Val Thr Gly Pro Val Leu
            180                 185                 190

Leu Thr Glu Ser Arg Asp Pro Asp Ala Gly Arg Leu Asp Leu Leu Ser
        195                 200                 205

Ala Gly Leu Ser Leu Ala Thr Val Leu Pro Val Ile Tyr Gly Leu Lys
    210                 215                 220

Glu Leu Ala Arg Thr Gly Trp Asp Pro Leu Ala Ala Gly Ala Val Val
225                 230                 235                 240

Leu Gly Val Ile Phe Gly Ala Leu Phe Val Gln Arg Gln Arg Arg Leu
                245                 250                 255

Ala Asp Pro Met Leu Asp Leu Gly Leu Phe Ala Asp Arg Thr Leu Arg
            260                 265                 270

Ala Gly Leu Thr Val Ser Leu Val Asn Ala Val Ile Met Gly Gly Thr
        275                 280                 285

Gly Leu Met Val Ala Leu Tyr Leu Gln Thr Ile Ala Gly His Ser Pro
    290                 295                 300

Leu Ala Ala Gly Leu Trp Leu Leu Ile Pro Ala Cys Met Leu Val Val
305                 310                 315                 320

Gly Val Gln Leu Ser Asn Leu Leu Ala Gln Arg Met Pro Pro Ser Arg
                325                 330                 335

Val Leu Leu Gly Gly Leu Leu Ile Ala Ala Val Gly Gln Leu Leu Ile
            340                 345                 350

Thr Gln Val Asp Thr Glu Asp Thr Ala Leu Leu Ile Ala Ala Thr Thr
```

```
                355                 360                 365
Leu Ile Tyr Phe Gly Ala Ser Pro Val Gly Pro Ile Thr Thr Gly Ala
    370                 375                 380

Ile Met Gly Ala Ala Pro Pro Glu Lys Ala Gly Ala Ala Ser Ser Leu
385                 390                 395                 400

Ser Ala Thr Gly Gly Glu Phe Gly Val Ala Leu Gly Ile Ala Gly Leu
                405                 410                 415

Gly Ser Leu Gly Thr Val Val Tyr Ser Ala Gly Val Glu Val Pro Asp
            420                 425                 430

Ala Ala Gly Pro Ala Asp Ala Asp Ala Ala Gln Glu Ser Ile Ala Gly
            435                 440                 445

Ala Leu His Thr Ala Gly Gln Leu Ala Pro Gly Ser Ala Asp Ala Leu
    450                 455                 460

Leu Asp Ser Ala Arg Ala Ala Phe Thr Ser Gly Val Gln Ser Val Ala
465                 470                 475                 480

Ala Val Cys Ala Val Phe Ser Leu Ala Leu Ala Val Leu Ile Gly Thr
                485                 490                 495

Arg Leu Arg Asp Ile Ser Ala Met Asp His Gly His Gly Glu Glu Pro
            500                 505                 510

Ala Glu Asn Asp Ala Gln Pro Ala Thr
            515                 520

<210> SEQ ID NO 150
<211> LENGTH: 329
<212> TYPE: PRT
<213> ORGANISM: Saccharopolyspora erythraea

<400> SEQUENCE: 150

Met Arg Val Leu Val Thr Gly Gly Ala Gly Phe Ile Gly Ser His Tyr
  1               5                  10                  15

Val Arg Gln Leu Leu Gly Gly Ala Tyr Pro Ala Phe Ala Gly Ala Asp
                 20                  25                  30

Val Val Val Leu Asp Lys Leu Thr Tyr Ala Gly Asn Glu Glu Asn Leu
             35                  40                  45

Arg Pro Val Ala Asp Pro Arg Phe Arg Phe Val Arg Gly Asp Ile
     50                  55                  60

Cys Glu Trp Asp Val Val Ser Glu Val Met Arg Glu Val Asp Val Val
 65                  70                  75                  80

Val His Phe Ala Ala Glu Thr His Val Asp Arg Ser Ile Leu Gly Ala
                 85                  90                  95

Ser Asp Phe Val Val Thr Asn Val Val Gly Thr Asn Thr Leu Leu Gln
                100                 105                 110

Gly Ala Leu Ala Ala Asn Val Ser Lys Phe Val His Val Ser Thr Asp
            115                 120                 125

Glu Val Tyr Gly Thr Ile Glu His Gly Ser Trp Pro Glu Asp His Leu
    130                 135                 140

Leu Glu Pro Asn Ser Pro Tyr Ser Ala Ala Lys Ala Gly Ser Asp Leu
145                 150                 155                 160

Ile Ala Arg Ala Tyr His Arg Thr His Gly Leu Pro Val Cys Ile Thr
                165                 170                 175

Arg Cys Ser Asn Asn Tyr Gly Pro Tyr Gln Phe Pro Glu Lys Val Leu
            180                 185                 190

Pro Leu Phe Ile Thr Asn Leu Met Asp Gly Arg Arg Val Pro Leu Tyr
    195                 200                 205
```

```
Gly Asp Gly Leu Asn Val Arg Asp Trp Leu His Val Thr Asp His Cys
    210                 215                 220

Arg Gly Ile Gln Leu Val Ala Glu Ser Gly Arg Ala Gly Glu Ile Tyr
225                 230                 235                 240

Asn Ile Gly Gly Gly Thr Glu Leu Thr Asn Lys Glu Leu Thr Glu Arg
                245                 250                 255

Val Leu Glu Leu Met Gly Gln Asp Trp Ser Met Val Gln Pro Val Thr
                260                 265                 270

Asp Arg Lys Gly His Asp Arg Arg Tyr Ser Val Asp His Thr Lys Ile
                275                 280                 285

Ser Glu Glu Leu Gly Tyr Glu Pro Val Val Pro Phe Glu Arg Gly Leu
    290                 295                 300

Ala Glu Thr Ile Glu Trp Tyr Arg Asp Asn Arg Ala Trp Trp Glu Pro
305                 310                 315                 320

Leu Lys Ser Ala Pro Asp Gly Gly Lys
                325

<210> SEQ ID NO 151
<211> LENGTH: 333
<212> TYPE: PRT
<213> ORGANISM: Streptomyces fradiae

<400> SEQUENCE: 151

Met Arg Val Leu Val Thr Gly Gly Ala Gly Phe Ile Gly Ser His Phe
  1               5                  10                  15

Thr Gly Gln Leu Leu Thr Gly Ala Tyr Pro Asp Leu Gly Ala Thr Arg
                20                  25                  30

Thr Val Val Leu Asp Lys Leu Thr Tyr Ala Gly Asn Pro Ala Asn Leu
            35                  40                  45

Glu His Val Ala Gly His Pro Asp Leu Glu Phe Val Arg Gly Asp Ile
        50                  55                  60

Ala Asp His Gly Trp Trp Arg Arg Leu Met Glu Gly Val Gly Leu Val
 65                  70                  75                  80

Val His Phe Ala Ala Glu Ser His Val Asp Arg Ser Ile Glu Ser Ser
                85                  90                  95

Glu Ala Phe Val Arg Thr Asn Val Glu Gly Thr Arg Val Leu Leu Gln
                100                 105                 110

Ala Ala Val Asp Ala Gly Val Gly Arg Phe Val His Ile Ser Thr Asp
                115                 120                 125

Glu Val Tyr Gly Ser Ile Ala Glu Gly Ser Trp Pro Glu Asp His Pro
                130                 135                 140

Val Ala Pro Asn Ser Pro Tyr Ala Ala Thr Lys Ala Ala Ser Asp Leu
145                 150                 155                 160

Leu Ala Leu Ala Tyr His Arg Thr Tyr Gly Leu Asp Val Arg Val Thr
                165                 170                 175

Arg Cys Ser Asn Asn Tyr Gly Pro Arg Gln Tyr Pro Glu Lys Ala Val
                180                 185                 190

Pro Leu Phe Thr Thr Asn Leu Leu Asp Gly Leu Pro Val Pro Leu Tyr
            195                 200                 205

Gly Asp Gly Gly Asn Thr Arg Glu Trp Leu His Val Asp Asp His Cys
    210                 215                 220

Arg Gly Val Ala Leu Val Gly Ala Gly Arg Pro Gly Val Ile Tyr
225                 230                 235                 240

Asn Ile Gly Gly Gly Thr Glu Leu Thr Asn Ala Glu Leu Thr Asp Arg
                245                 250                 255
```

-continued

```
Ile Leu Glu Leu Cys Gly Ala Asp Arg Ser Ala Leu Arg Arg Val Ala
            260                 265                 270

Asp Arg Pro Gly His Asp Arg Arg Tyr Ser Val Asp Thr Thr Lys Ile
        275                 280                 285

Arg Glu Glu Leu Gly Tyr Ala Pro Arg Thr Gly Ile Thr Glu Gly Leu
    290                 295                 300

Ala Gly Thr Val Ala Trp Tyr Arg Asp Asn Arg Ala Trp Trp Glu Pro
305                 310                 315                 320

Leu Lys Arg Ser Pro Gly Gly Arg Glu Leu Glu Arg Ala
                325                 330

<210> SEQ ID NO 152
<211> LENGTH: 332
<212> TYPE: PRT
<213> ORGANISM: Streptomyces globisporus

<400> SEQUENCE: 152

Met Arg Met Leu Val Thr Gly Ala Gly Phe Ile Gly Ser Gln Phe
  1               5                  10                  15

Val Arg Ala Thr Leu His Gly Glu Leu Pro Gly Ser Glu Asp Ala Arg
                 20                  25                  30

Val Thr Val Leu Asp Lys Leu Thr Tyr Ser Gly Asn Pro Ala Asn Leu
             35                  40                  45

Thr Ser Val Ala Ala His Pro Arg Tyr Thr Phe Val Gln Gly Asp Thr
         50                  55                  60

Val Asp Pro Arg Val Val Asp Glu Val Val Ala Gly His Asp Val Ile
 65                  70                  75                  80

Val His Phe Ala Ala Glu Ser His Val Asp Arg Ser Ile Asp Thr Ala
                 85                  90                  95

Thr Arg Phe Val Thr Thr Asn Val Leu Gly Thr Gln Thr Leu Leu Glu
            100                 105                 110

Ala Ala Leu Arg His Gly Val Gly Arg Phe Val His Val Ser Thr Asp
        115                 120                 125

Glu Val Tyr Gly Ser Ile Ala Ser Gly Ser Trp Thr Glu Asp Thr Pro
    130                 135                 140

Leu Ala Pro Asn Val Pro Tyr Ala Ala Ser Lys Ala Gly Ser Asp Leu
145                 150                 155                 160

Met Ala Leu Ala Trp His Arg Thr Arg Gly Leu Asp Val Val Thr
                165                 170                 175

Arg Cys Thr Asn Asn Tyr Gly Pro Tyr Gln Tyr Pro Glu Lys Val Ile
            180                 185                 190

Pro Leu Phe Val Thr Asn Ile Leu Asp Gly Leu Arg Val Pro Leu Tyr
        195                 200                 205

Gly Asp Gly Ala His Arg Arg Asp Trp Leu His Val Ser Asp His Cys
    210                 215                 220

Arg Ala Ile Gln Met Val Met Asn Ser Gly Arg Ala Gly Glu Val Tyr
225                 230                 235                 240

His Ile Gly Gly Gly Thr Glu Leu Ser Asn Glu Leu Thr Gly Leu
                245                 250                 255

Leu Leu Thr Ala Cys Gly Thr Asp Trp Ser Cys Val Asp Arg Val Ala
            260                 265                 270

Asp Arg Gln Gly His Asp Arg Arg Tyr Ser Leu Asp Ile Thr Lys Ile
        275                 280                 285

Arg Gln Glu Leu Gly Tyr Glu Pro Leu Val Ala Phe Glu Asp Gly Leu
```

```
                    290                 295                 300
Ala Ala Thr Val Lys Trp Tyr His Glu Asn Arg Ser Trp Trp Gln Pro
305                 310                 315                 320

Leu Lys Glu Ala Ala Gly Leu Leu Asp Ala Val Gly
                325                 330

<210> SEQ ID NO 153
<211> LENGTH: 331
<212> TYPE: PRT
<213> ORGANISM: Streptomyces argillaceus

<400> SEQUENCE: 153

Met Thr Thr Thr Ser Ile Leu Val Thr Gly Gly Ala Gly Phe Ile Gly
  1               5                  10                  15

Ser His Tyr Val Arg Thr Leu Leu Gly Pro Arg Gly Val Pro Asp Val
                 20                  25                  30

Thr Val Thr Val Leu Asp Lys Leu Thr Tyr Ala Gly Thr Leu Thr Asn
             35                  40                  45

Leu Ala Glu Val Ser Asp Ser Asp Arg Phe Arg Phe Val Arg Gly Asp
 50                  55                  60

Ile Cys Asp Ala Pro Leu Val Asp Asp Leu Leu Ala Val His Asp Gln
 65                  70                  75                  80

Val Val His Phe Ala Ala Glu Ser His Val Asp Arg Ser Ile Leu Gly
                 85                  90                  95

Ala Ala Asp Phe Val Arg Thr Asn Val Thr Gly Thr Gln Thr Leu Leu
            100                 105                 110

Asp Ala Ala Leu Arg Gln Gly Ile Glu Thr Phe Val His Ile Ser Thr
            115                 120                 125

Asp Glu Val Tyr Gly Ser Ile Asp Ala Gly Ser Trp Pro Glu Thr Ala
130                 135                 140

Pro Val Ser Pro Asn Ser Leu Tyr Ser Ala Ala Lys Ala Ser Ser Asp
145                 150                 155                 160

Leu Val Ala Leu Ala Tyr His Arg Thr His Gly Leu Asp Val Arg Val
                165                 170                 175

Thr Arg Cys Ser Asn Asn Tyr Gly Ser His Gln Phe Pro Glu Lys Val
            180                 185                 190

Ile Pro Leu Phe Val Thr Ser Leu Leu Asp Gly Arg Glu Val Pro Leu
            195                 200                 205

Tyr Gly Asp Gly Thr Asn Val Arg Asp Trp Leu His Val Asp Asp His
210                 215                 220

Val Arg Ala Ile Glu Leu Val Arg Thr Gly Gly Arg Ala Gly Glu Val
225                 230                 235                 240

Tyr Asn Ile Gly Gly Gly Thr Glu Leu Ser Asn Lys Glu Leu Thr Gln
                245                 250                 255

Leu Leu Leu Asp Ala Cys Gly Ala Gly Trp Asp Arg Val Arg Tyr Val
            260                 265                 270

Thr Asp Arg Lys Gly His Asp Arg Arg Tyr Ser Val Asp Cys Thr Lys
            275                 280                 285

Ile Arg Arg Glu Leu Gly Tyr Arg Pro Ala Arg Glu Phe Gly Asp Ala
290                 295                 300

Leu Ala Glu Thr Val Ala Trp Tyr Arg His His Arg Ala Trp Trp Glu
305                 310                 315                 320

Pro Leu Thr Arg Ala Tyr Gly Ala Val Ala Ala
                325                 330
```

-continued

<210> SEQ ID NO 154
<211> LENGTH: 216
<212> TYPE: PRT
<213> ORGANISM: Streptomyces globisporus
<220> FEATURE:
<223> OTHER INFORMATION: orf(-7)

<400> SEQUENCE: 154

```
Met Gly Met Thr Gly Ala Arg Pro Arg Val Leu Val Gly Ala Gly
 1               5                  10                  15

Leu Ala Gly Thr Ala Thr Ala Ile Arg Leu Leu His Phe Ala Arg Arg
                20                  25                  30

Pro Leu Glu Val Val Leu Leu Glu Arg Arg Ala Ala Tyr Arg Ser Ala
            35                  40                  45

Gly Val Ala Tyr His Arg Asp Gly Asn Pro Trp Asp His Val Phe Asn
    50                  55                  60

Ile Gln Ala Gly Arg Met Ser Val Phe Arg Glu Asp Val Leu Asp Phe
65                  70                  75                  80

Ile Asn Trp Ala Asn Gln Glu Ala Asp Arg Arg Asp Trp Pro Arg Arg
                85                  90                  95

Trp Ala Ser Trp Lys Phe Thr Glu Gln Gly Pro Ala Pro Arg Arg Ile
            100                 105                 110

Phe Gln Asp Tyr Leu Asp Ala Arg Leu Val Glu Ala Ala Arg Glu Ser
        115                 120                 125

Cys Pro Gly Val Val Leu Val Glu Ala Asp Gly Glu Ala Leu Asp Ala
    130                 135                 140

Arg Ser His Asp Arg Cys Phe Glu Val Thr Val Arg Gly Leu Thr Pro
145                 150                 155                 160

Tyr Leu Thr Glu Gly Leu Arg Pro Gly Pro Leu Pro Asp Thr Gln Ile
                165                 170                 175

Leu Asp Ala Asp His Val Val Leu Ala Thr Gly Leu Glu Leu Lys Glu
            180                 185                 190

Pro Pro Phe Ala Ala Gly Val Ala Gly His Pro Ser Phe Val Arg Asn
        195                 200                 205

Pro Tyr Ser Ala Pro Gly Ile Leu
    210                 215
```

<210> SEQ ID NO 155
<211> LENGTH: 181
<212> TYPE: PRT
<213> ORGANISM: Streptomyces globisporus
<220> FEATURE:
<223> OTHER INFORMATION: orf(-6)

<400> SEQUENCE: 155

```
Met Pro Arg Ile Pro Val His Thr Ile Asp Thr Ala Pro Ala Ala Gly
 1               5                  10                  15

Gly Asp Ile Leu Arg Arg Leu Glu Lys Arg Phe Gly Arg Val Leu Asn
                20                  25                  30

Ile His Gly Gly Met Ala His Ser Pro Val Val Leu Glu Thr Tyr Ala
            35                  40                  45

Ala Ile Thr Gly Ala Val Ala Glu His Gly Thr Phe Asp Ala Arg Thr
    50                  55                  60

Arg Glu Ala Ile Ala Leu Ala Val Gly Ala Val Asp Ala Cys Ala Tyr
65                  70                  75                  80

Cys Gln Ala Ala His Thr Val Ser Ala Lys Val Ala Gly Phe Thr Leu
                85                  90                  95
```

-continued

```
Glu Glu Thr Val Ala Ile Arg Arg Gly Thr Pro Gly Asp Asp Val Lys
                100                 105                 110

Leu Glu Ala Leu Val Gln Val Ala Arg Glu Ile Ala Gly Glu Val Gly
        115                 120                 125

Glu Ala Ser Asp Ala Ser Trp Asn Ala Ala Val Ala Gln Gly Trp Thr
    130                 135                 140

Asp Thr Glu Leu Ala Glu Val Phe Val His Val Ala Val Asn Leu Tyr
145                 150                 155                 160

Thr Asn Tyr Phe Asn His Tyr Ala Arg Thr Glu Ile Asp Pro Gly Val
                165                 170                 175

Pro Asp Ile Asp Ser
            180

<210> SEQ ID NO 156
<211> LENGTH: 354
<212> TYPE: PRT
<213> ORGANISM: Streptomyces globisporus
<220> FEATURE:
<223> OTHER INFORMATION: orf(-5)

<400> SEQUENCE: 156

Met Thr Ile Ala Thr Glu Pro Ile Gly Ser Leu Pro Arg Ser Ala Thr
  1               5                  10                  15

Leu Leu His Ala Leu Ala Ala His Ala Gln Gly Thr Leu Asp Ala Thr
                 20                  25                  30

Asp Leu Ala Lys Gln Gln Glu Gln Ala Val Ala Asp Thr Leu Thr Arg
             35                  40                  45

Leu Glu Arg Val Gly Ser Pro Val Leu Val Asp Gly Glu Gln Ser Lys
         50                  55                  60

Pro Ser Phe Ala Thr Tyr Pro Val Thr Gly Leu Asp Thr Leu Ser Pro
 65                  70                  75                  80

Asp Gly Ala Val Ile Pro Phe Ala Asp Gly His Thr Arg Gln Leu Pro
                 85                  90                  95

Ser Ile Thr Gln Gly Pro Phe Arg Tyr Gln Val Arg Ala Glu Thr Tyr
                100                 105                 110

Leu Arg Ala Ala Arg Gln Leu Thr Asp Arg Pro Leu Lys Gln Ala Val
            115                 120                 125

Ile Ala Pro Ser Ala Leu Ser Leu Leu Tyr Pro Ala Thr Pro Ile Glu
130                 135                 140

Gly Tyr Pro Arg Glu Gln Phe Leu Arg Asp Leu Ala Asp Glu Ala Glu
145                 150                 155                 160

Ala Asp Ile Arg Gly Cys Leu Asp Ala Gly Ala His Val Val Gln Leu
                165                 170                 175

Asp Phe Thr Glu Gly Arg Leu Ser Leu Lys Leu Asp Pro Ser Gly Gly
            180                 185                 190

Val Leu Asp Asp Phe Ile Ala Leu Asn Asn Glu Val Leu Gly Arg Phe
        195                 200                 205

Ser Ala Glu Glu Thr Ala Arg Ile Gly Val His Thr Cys Pro Gly Gly
    210                 215                 220

Asp Gln Asp Ser Thr His Ser Leu Asp Ile Asp Tyr Ala Glu Leu Leu
225                 230                 235                 240

Pro Lys Leu Phe Gln Leu Lys Ala Gly Asn Phe Tyr Leu Glu Leu Ala
                245                 250                 255

Gly Glu Ala Asp Pro Glu Arg Val Leu Ser Ile Val Arg Asp His Leu
            260                 265                 270
```

```
Pro Pro Ala Ala Arg Val Phe Leu Gly Val Thr Asp Pro Ile Asp Pro
            275                 280                 285

Val Val Glu Thr Pro Glu Gln Val Arg Asp Arg Ile Leu Leu Ala Ala
        290                 295                 300

Arg Tyr Ile Pro Val Glu Gln Leu Gly Thr Cys Asp Asp Cys Gly Phe
305                 310                 315                 320

Ser Pro Phe Ala Asp Asp Thr Ser Thr Thr Arg Asp Leu Ala Phe Ala
                325                 330                 335

Lys Ile Glu Ala Arg Val Arg Gly Thr Ala Leu Ala Glu Val Leu
            340                 345                 350

Gly Leu

<210> SEQ ID NO 157
<211> LENGTH: 128
<212> TYPE: PRT
<213> ORGANISM: Streptomyces globisporus
<220> FEATURE:
<223> OTHER INFORMATION: orf(-4)

<400> SEQUENCE: 157

Met Ser Ser Leu Leu Thr Asp Ser Asp Leu Val His Glu Ala Lys Val
1               5                   10                  15

Val Trp Leu Glu Asp Pro Glu Gly Leu Asp Tyr Val Arg Gln Ala Leu
            20                  25                  30

Asp Lys Thr Pro Arg Arg Lys Asn Lys Pro Arg Tyr Ala Arg Asp Gly
        35                  40                  45

Arg Met Ile Gly Tyr Ile Glu Leu Gly Ala Asp Ala Glu Ala Asp Pro
    50                  55                  60

Asp Ser Gly Leu Tyr Arg Arg Val Phe Phe Leu Leu Pro His Asp
65                  70                  75                  80

Arg Asp Ser Asp Pro Glu Gly Val Tyr Arg Gln Gly Ala Pro Gly Glu
                85                  90                  95

Ala Val Asp Pro Arg Thr Ile Glu Pro Asn Arg Val Gly Glu Lys Thr
            100                 105                 110

Pro Arg Ser Gln Leu Gly Thr Ser Ser Thr Val Ala Ala Thr Gly Ser
        115                 120                 125

<210> SEQ ID NO 158
<211> LENGTH: 509
<212> TYPE: PRT
<213> ORGANISM: Streptomyces globisporus
<220> FEATURE:
<223> OTHER INFORMATION: orf(-3)

<400> SEQUENCE: 158

Met Ser Ser Ser Ala Glu Gly Pro Arg Phe Asp Ala Thr Ala Ala Ala
1               5                   10                  15

Gln Gln Met Leu Ala Leu Glu Thr Thr Pro Ala Pro Ala Pro Leu Leu
            20                  25                  30

Pro Val Gln Ala Ala Pro Glu Ala Pro Val Ala Ala Thr Ala Trp Glu
        35                  40                  45

Ala Gly Glu Ile Pro Ala Ser Leu Thr Asp Arg Gly Asn Ala Lys Leu
    50                  55                  60

Phe Val Arg Leu Tyr Arg Asp Gln Phe Arg His Val Glu Gly Leu Gly
65                  70                  75                  80

Trp Tyr Ser Trp Asp Gly Tyr Arg Trp Lys Arg Ala Gly Gly Glu Lys
                85                  90                  95
```

-continued

```
Ala Ala Leu Trp Ala Ala Gly Glu Met Ala Glu Met Pro Gly Ser
            100                 105                 110
Asp Pro Arg Gly Leu Phe Thr Asp Arg Glu Leu His His His Lys Arg
            115                 120                 125
Arg Thr Leu Ser Thr Thr Gly Met Lys Ala Leu Leu Thr Gln Ala Lys
            130                 135                 140
Ala Ser Pro Asp Leu Ser Leu Asp Pro Asp Thr Leu Asp Gly Asp Pro
145                 150                 155                 160
Tyr Ala Leu Cys Thr Pro Asp Gly Val Val Asp Leu Arg Asn Gly Arg
                165                 170                 175
Met Arg Lys Pro Asp Pro Thr Arg Asp Phe His Ser Arg Ala Thr Ser
            180                 185                 190
Ala Ser Pro Gln Asp Ile Pro Thr Pro Arg Trp His Arg Phe Leu Glu
            195                 200                 205
Asp Thr Phe Gly Ser Asp Ala Glu Gly Arg Glu Met Ile Asp Phe Leu
            210                 215                 220
His Leu Leu Leu Gly Tyr Ser Ile Thr Gly Asp Val Gly Ala Gln Val
225                 230                 235                 240
Leu Pro Phe Leu His Gly Gln Gly Lys Asn Gly Lys Ser Val Leu Leu
                245                 250                 255
Asp Val Met Ile Gln Ile Leu Gly Asp Tyr Ala Asp Ala Ala Pro Pro
            260                 265                 270
Gly Phe Leu Met Asp Arg Gly Ala Tyr Ser Glu His Ser Thr Glu Leu
            275                 280                 285
Thr Glu Leu His Gly Arg Arg Leu Ile Val Cys Ser Glu Leu Lys Pro
            290                 295                 300
Asn Asp Arg Phe Asp Glu Ala Arg Val Arg Leu Leu Thr Gly Gly Asp
305                 310                 315                 320
Lys Ile Lys Ala Arg Arg Met Arg Gln Asp Tyr Phe Ser Phe Thr Pro
                325                 330                 335
Thr His Lys Leu Trp Leu Leu Gly Asn His Arg Pro Glu Val Ser Thr
            340                 345                 350
Gly Gly Phe Ala Phe Trp Arg Arg Ile Arg Leu Leu Pro Phe Glu Arg
            355                 360                 365
Ile Val Pro Asp Glu Arg Lys Ile Asp Asn Leu Ala Val Glu Leu Val
            370                 375                 380
Gln Asp Glu Gly Pro Gly Ile Leu His Trp Leu Thr Glu Gly Ala Arg
385                 390                 395                 400
Arg Tyr Leu Ala Thr Arg Asp Thr Leu Ala Gly Pro Asp Arg Val Arg
                405                 410                 415
Ile Ala Thr Ser Ala Tyr Ala Asn Thr Glu Asp His Ile Gly Arg Phe
            420                 425                 430
Leu Ala Glu Cys Cys Leu His Asp Pro Glu Asn Ser Glu Leu Arg Val
            435                 440                 445
Glu Gln Gly Leu Leu Tyr Thr Ser Tyr Ser Thr Trp Cys Ala His Ser
            450                 455                 460
Glu Gly Ile Arg Pro Gly Thr Ala Arg Ala Phe Ala Thr Arg Val Arg
465                 470                 475                 480
Gln Glu Val Gly Leu Ala Ser Pro Ala Asp Met Ile Lys Ser Asn Gly
                485                 490                 495
Arg Lys Phe Tyr Pro Asn Leu Ala Leu Ala Ala Asp Glu
            500                 505
```

```
<210> SEQ ID NO 159
<211> LENGTH: 498
<212> TYPE: PRT
<213> ORGANISM: Streptomyces globisporus
<220> FEATURE:
<223> OTHER INFORMATION: orf(-2)

<400> SEQUENCE: 159
```

| | | | | | | | | | | | | | | |
|---|---|---|---|---|---|---|---|---|---|---|---|---|---|---|
|Met|Arg|Ala|Leu|Pro|Gly|Ser|Gly|Gly|Leu|Arg|Met|Ala|Gly|Asp|Ala|
|1| | | |5| | | | |10| | | | |15|

| | | | | | | | | | | | | |
|---|---|---|---|---|---|---|---|---|---|---|---|---|
|Pro|Thr|Ala|Ala|Gly|Asn|Arg|Arg|Cys|Pro|Pro|Thr|Pro|Ile|Gln|Arg|
| | | |20| | | | |25| | | | |30| |

Pro Leu Ile Leu Arg Arg Gln Thr Leu Gln Ala Pro Glu Ala Lys Asn
             35                  40                  45

Gly Arg Ser Pro Glu Gln Pro Gln Glu Glu Arg Ile Val Leu Asp Val
 50                      55                      60

Trp Leu Ala Asn Tyr Pro Phe Pro Thr Tyr Asp Gly Arg Asp Phe Leu
 65                  70                  75                  80

Ala Pro Leu Arg Glu Arg Ala Ala Glu Phe Glu Arg Ala His Pro Arg
                 85                  90                  95

Tyr Arg Val Asp Ile Asn Gly His Asp Phe Trp Thr Ile Pro Glu Lys
            100                 105                 110

Val Ala Arg Ala Thr Ala Glu Gly Arg Pro His Ile Ala Gly Tyr
            115                 120                 125

Tyr Ala Thr Asp Ser Gln Leu Ala Arg Asp Ala Arg Arg Pro Asp Gly
        130                 135                 140

Lys Pro Val Phe Thr Ser Val Glu Ala Ala Leu Ala Gly Arg Thr Glu
145                 150                 155                 160

Ile Leu Gly His Pro Val Val Glu Asp Leu Asp Pro Val Val Arg
                165                 170                 175

Asp Ser Tyr Ser Phe Gly Gly Glu Leu Val Ser Leu Pro Leu Thr Val
            180                 185                 190

Thr Thr Met Leu Cys Tyr Ala Asn Ser Ser Leu Leu Ala Arg Ala Gly
        195                 200                 205

Val Pro Glu Leu Pro Arg Thr Trp Asp Glu Val Glu Ala Ala Cys Gln
210                 215                 220

Ala Val Ala Ser Val Asp Gly Gly Pro Gly His Gly Ile Thr Trp Ala
225                 230                 235                 240

Asn Asp Gly Trp Val Phe Gln Gln Ala Val Ala Leu Gln Asn Gly Val
                245                 250                 255

Leu Thr Asp Gln Asp Asn Gly Arg Ser Gly Ser Ala Thr Thr Val Asp
            260                 265                 270

Val Thr Ser Asp Glu Met Leu Asp Trp Val Arg Trp Thr His Leu
        275                 280                 285

His Glu Arg Gly His Tyr Leu Tyr Thr Gly Gly Pro Ser Asp Trp Gly
        290                 295                 300

Gly Ala Phe Glu Ala Phe Val Gln Gln Lys Val Ala Phe Thr Phe Asp
305                 310                 315                 320

Ser Ser Lys Ala Ala Arg Glu Leu Ile Gln Ala Gly Ala Gln Ala Gly
                325                 330                 335

Phe Glu Val Ala Val Phe Pro Leu Pro Arg Asn Ala Lys Ala Pro Val
            340                 345                 350

Ala Gly Gln Pro Val Ser Gly Asp Ser Leu Trp Leu Ala Ala Gly Leu
        355                 360                 365

-continued

```
Asp Glu Thr Thr Gln Asp Gly Leu Leu Ala Leu Thr Gln Tyr Leu Ile
    370                 375                 380

Ser Pro Ala Asn Ala Ala Asp Trp His Arg Thr Asn Gly Phe Val Pro
385                 390                 395                 400

Val Thr Gly Ala Ala Gly Glu Leu Leu Glu Ala Thr Gly Trp Phe Asp
                405                 410                 415

Arg Arg Pro Gln Gln Arg Val Ala Gly Glu Gln Leu Lys Ala Ser Asp
            420                 425                 430

Arg Ser Pro Ala Ala Leu Gly Ala Leu Leu Gly Asp Phe Ala Ala Val
        435                 440                 445

Asn Glu Val Ile Thr Ala Ala Met Asp Asp Val Leu Arg Ser Gly Ala
    450                 455                 460

Asp Pro Ala Lys Ala Phe Ala Glu Ala Gly Val Ala Ala Gln Gln Leu
465                 470                 475                 480

Leu Asp Ala Tyr Asn Ala Arg Asn Arg Ser Gly Ser Gly Thr Pro Ser
                485                 490                 495

Ala Val
```

<210> SEQ ID NO 160
<211> LENGTH: 775
<212> TYPE: PRT
<213> ORGANISM: Streptomyces globisporus
<220> FEATURE:
<223> OTHER INFORMATION: orf(-1)

<400> SEQUENCE: 160

```
Met Ser Val Thr Asp Pro Thr Ala Gly Ala Gly Lys Thr Ser Gly Pro
  1               5                  10                  15

Gly Asp Gly Ile Arg Ile Ala Gly Ala Arg Ile His Asn Leu Lys Asp
                20                  25                  30

Val Ser Leu Thr Ile Pro Arg Asn Gln Ile Thr Val Phe Thr Gly Val
            35                  40                  45

Ser Gly Ser Gly Lys Ser Ser Ile Val Phe Asp Thr Val Ala Val Glu
        50                  55                  60

Ala Gln Arg Gln Leu Asn Ser Thr Phe Ser Trp Tyr Ile Arg Asn Gln
 65                  70                  75                  80

Leu Pro Lys Tyr Glu Arg Pro Gln Ala Glu Ala Ile Glu Asn Leu Thr
                 85                  90                  95

Thr Pro Val Ile Val Asp Gln Lys Pro Val Gly Gly Asn Ala Arg Ser
            100                 105                 110

Thr Val Gly Thr Met Thr Asp Val Gln Pro Met Ile Arg Ala Leu Phe
        115                 120                 125

Ala Arg Phe Gly Thr Thr Lys Asp Asp Gly Pro Ser Ser Leu Gly Val
    130                 135                 140

Ser Ala Phe Ser Phe Asn Asp Pro Gln Gly Met Cys Pro Asp Cys Asp
145                 150                 155                 160

Gly Leu Gly Gln Ser Ile Ala Leu Asp Leu Asp Lys Met Leu Asp Arg
                165                 170                 175

Ser Lys Ser Leu Asp Asp Gly Ala Val Leu Phe Pro Glu Tyr Lys Val
            180                 185                 190

Gly Ser Pro Asp Trp Gln Ile Trp Ala Lys Ser Gly Arg Leu Asp Pro
        195                 200                 205

Ala Lys Pro Ile Ala Glu Tyr Ser Ala Glu Glu Leu Asp Thr Leu Leu
    210                 215                 220

Arg Gly Thr Gly Gly Lys Val Thr Leu Lys Thr Lys Ser Thr Glu Phe
```

```
            225                 230                 235                 240
Gln Thr Asn Tyr Glu Gly Leu Ala Asp Arg Phe Glu Arg Leu Asn Leu
                245                 250                 255
Lys Arg Asp Leu Ser Ala Leu Ser Asp Arg Lys Arg Glu Val Ile Glu
            260                 265                 270
Arg Phe Val Thr Asp Gly Val Cys Pro Ser Cys Arg Gly Ala Arg Leu
        275                 280                 285
Asn Ala Ala Ala Leu Asp Val Arg Ile Asp Gly Lys Asn Ile Ala Asp
    290                 295                 300
Tyr Ser Ser Met Glu Val Arg Asp Leu Thr Glu Val Leu Ala Gly Val
305                 310                 315                 320
Thr Glu Pro Ala Ala Pro Leu Ala Lys Ala Ala Arg Thr Ala Leu
                325                 330                 335
Glu Arg Ile Val Ser Ile Gly Leu Gly Tyr Leu Thr Leu Asp Arg Pro
                340                 345                 350
Thr Ala Asp Leu Ser Gly Gly Glu Gly Gln Arg Leu Lys Met Val Arg
            355                 360                 365
His Leu Gly Ser Gly Leu Ala Gly Leu Thr Tyr Ile Phe Asp Glu Pro
    370                 375                 380
Ser Ile Gly Leu His Pro Arg Asp Val Gly Arg Leu Asn Asp Leu Leu
385                 390                 395                 400
Arg Ala Leu Arg Asp Lys Gly Asn Thr Val Leu Val Glu His Asp
                405                 410                 415
Pro Asp Val Ile Glu Ile Ala Asp His Ile Val Asp Val Gly Pro Gly
                420                 425                 430
Ala Gly Val His Gly Gly Glu Ile Val Phe Glu Gly Ser Phe Ala Lys
            435                 440                 445
Leu Arg Lys Ala Lys Thr Arg Thr Gly Glu Ala Leu Arg Arg Gly Ala
    450                 455                 460
Arg Val Lys Glu Glu Val Arg Pro Pro Thr Gly Glu Leu Thr Val Glu
465                 470                 475                 480
Asn Ala Asp Leu His Asn Leu Lys Gln Val Ser Val Ala Val Pro Thr
                485                 490                 495
Gly Val Leu Thr Ala Val Thr Gly Val Ala Gly Ser Gly Lys Ser Ser
            500                 505                 510
Leu Ile Ser Gly Ala Phe Met Glu Ala His Pro Asp Ala Val Phe Val
        515                 520                 525
Asp Gln Ser Ala Ile Ala Ala Ser Ser Arg Ser Thr Pro Val Ser Tyr
    530                 535                 540
Leu Gly Leu Met Asp Pro Leu Arg Lys Leu Phe Ala Lys Glu Thr Gly
545                 550                 555                 560
Ala Asn Ala Ser Leu Phe Ser Phe Asn Ser Lys Gly Ser Cys Glu Glu
                565                 570                 575
Cys Gln Gly Arg Gly Val Ile Ile Thr Glu Leu Ala Phe Met Asp Pro
            580                 585                 590
Val Thr Thr His Cys Gly Val Cys Glu Gly Arg Arg Phe Lys Pro Glu
        595                 600                 605
Val Leu Glu His Gln Leu Arg Gly Lys Ser Ile Ala Asp Val Leu Glu
    610                 615                 620
Leu Pro Ala Asp Glu Ala Val Glu Phe Phe Thr Glu Lys Ala Leu Leu
625                 630                 635                 640
Pro Lys Leu Arg Ala Leu Val Asp Val Gly Leu Gly Tyr Leu Ser Leu
                645                 650                 655
```

```
Gly Gln Pro Leu Ser Ser Leu Ser Gly Gly Glu Leu Gln Arg Ile Lys
            660                 665                 670

Leu Ala Asp Gln Leu His Arg Thr Gly Thr Val Tyr Val Leu Asp Glu
            675                 680                 685

Pro Thr Thr Gly Leu His Met Ser Asp Val Asp Thr Leu Leu Lys Leu
            690                 695                 700

Leu Asp Gly Leu Val Glu Ala Gly Asn Thr Val Val Ile Glu His
705                 710                 715                 720

Asn Leu Asp Val Val Gln Gln Ala Asp Trp Ile Ile Asp Leu Gly Pro
            725                 730                 735

Asp Gly Gly Arg Glu Gly Gly Glu Ile Val Phe Thr Gly Thr Pro Lys
            740                 745                 750

Asp Leu Leu Ala Ala Asp Ser Ser Leu Thr Gly Glu Tyr Leu Arg Arg
            755                 760                 765

His Leu Lys Ala Gln Ala Gly
            770                 775

<210> SEQ ID NO 161
<211> LENGTH: 455
<212> TYPE: PRT
<213> ORGANISM: Streptomyces globisporus
<220> FEATURE:
<223> OTHER INFORMATION: orf0

<400> SEQUENCE: 161

Val Ala Val Leu Ala Ala Thr Ser Pro Leu Gly Gly Glu Pro Leu Thr
  1               5                  10                  15

Val Phe Leu Leu Gln Val Gly Leu Leu Ala Cys Ala Tyr Gly Leu
             20                  25                  30

Gly Arg Leu Gly Thr Arg Ile Gly Leu Pro Pro Leu Val Gly Glu Leu
             35                  40                  45

Thr Ala Gly Val Leu Leu Gly Pro Thr Leu Leu Gly Gln Ile Ser Pro
     50                  55                  60

Gly Leu Ser Gly Arg Leu Phe Pro Glu Asp Ile Ser Gln Ala His Leu
 65                  70                  75                  80

Leu Asp Ala Phe Cys Gln Phe Gly Val Leu Leu Val Ala Ile Ala
             85                  90                  95

Gly Ala Gln Phe Asp Pro Arg Ile Leu Arg Lys Arg Gly Gly Leu Ala
            100                 105                 110

Ala Arg Val Ser Leu Ala Gly Leu Leu Ile Pro Leu Gly Leu Gly Ile
            115                 120                 125

Ala Thr Gly Tyr Leu Val Pro Ala Ser Leu Leu Ala Asp Ser Gly Glu
    130                 135                 140

Arg Gly Val Phe Ala Leu Phe Leu Gly Val Ala Met Cys Val Thr Ala
145                 150                 155                 160

Leu Pro Val Ile Ala Lys Thr Leu Ala Asp Leu Asn Leu Thr His Arg
            165                 170                 175

Asn Val Gly Gln Leu Leu Ile Ala Ala Val Phe Asp Asp Ala Val
            180                 185                 190

Gly Trp Leu Leu Leu Ala Leu Val Thr Ala Leu Ala Ser Gly Ala Ala
            195                 200                 205

Gly Gly Pro Val Val Leu Thr Thr Met Ala Trp Thr Thr Val Phe Val
    210                 215                 220

Ala Ala Ala Cys Ala Val Gly Gly Pro Ile Gly Arg Arg Leu Ser Arg
225                 230                 235                 240
```

```
Thr Gly Asp Ser Arg Val Pro Val Ser Ala Val Thr Val Gly Val Ala
                245                 250                 255

Val Val Val Leu Tyr Gly Ala Leu Thr Ala Ala Gly Met Glu Ala
            260                 265                 270

Leu Phe Gly Ala Phe Val Ala Gly Ala Thr Leu Leu Arg His Ile Ala
        275                 280                 285

Pro Val Arg Leu Ala Pro Leu Arg Thr Leu Val Met Ala Val Phe Ala
    290                 295                 300

Pro Val Phe Leu Gly Ser Val Gly Leu Arg Met Asp Leu Thr Ala Leu
305                 310                 315                 320

Ala Glu Pro Ser Val Leu Leu Thr Gly Leu Gly Val Leu Leu Val Ala
                325                 330                 335

Thr Phe Gly Lys Phe Ala Gly Ala Tyr Val Ala Ala Arg Ser Gly Gly
            340                 345                 350

Met Ser Arg Tyr Glu Gly Leu Ala Leu Gly Ala Gly Met Asn Ser Arg
        355                 360                 365

Gly Met Ile Glu Val Val Ile Ala Leu Val Gly Leu Arg Ile Gly Val
    370                 375                 380

Leu Asp Thr Val Thr Phe Thr Ile Ile Val Leu Val Ala Leu Ile Thr
385                 390                 395                 400

Ser Val Thr Ala Pro Pro Ile Leu Arg Trp Ala Ser Ser Arg Ile Val
                405                 410                 415

Leu Glu Glu Asp Glu Thr Glu Arg Gly Asp Arg Leu Ala Gly Trp Asn
            420                 425                 430

Thr Glu Pro Ala Leu Ser Gly Gly Pro Ala Pro Lys Ser Ala Arg Glu
        435                 440                 445

Glu Lys Thr Pro Asp Thr Ser
    450                 455

<210> SEQ ID NO 162
<211> LENGTH: 494
<212> TYPE: PRT
<213> ORGANISM: Streptomyces globisporus
<220> FEATURE:
<223> OTHER INFORMATION: orf11

<400> SEQUENCE: 162

Met Asp Val Ser Ala Gln Tyr Asp Val Ile Val Val Gly Gly Gly Pro
1               5                   10                  15

Ala Gly Ser Thr Val Ser Thr Leu Val Arg Lys Arg Gly His Arg Val
            20                  25                  30

Leu Gln Leu Glu Lys Glu Thr Phe Pro Arg Tyr Gln Ile Gly Glu Ser
        35                  40                  45

Leu Leu Pro Ser Thr Val His Gly Ile Ala His Leu Leu Gly Val Ser
    50                  55                  60

Asp Glu Leu Lys Lys Ala Ala Phe Thr Ile Lys His Gly Gly Thr Phe
65                  70                  75                  80

Lys Trp Gly Ala Asn Pro Glu Pro Trp Thr Phe Asp Phe Ala Val Ser
                85                  90                  95

Arg Arg Met Pro Gly Ala Thr Gly Tyr Ala Tyr Gln Val Glu Arg Met
            100                 105                 110

Lys Phe Asp Gln Ile Leu Leu Asp Asn Ala Arg Arg His Gly Val Glu
        115                 120                 125

Val Arg Glu Asn Ser Asp Val Leu Asp Val Leu Lys Ala Glu Asp Gly
    130                 135                 140
```

```
Arg Val Arg Gly Val Arg Tyr Arg Asp Ser Glu Gly Arg Glu His Glu
145                 150                 155                 160

Val Gly Ser Arg Phe Val Val Asp Ala Ser Gly Asn Thr Gly Gly Leu
            165                 170                 175

Tyr Lys Lys Ser Gly Ala Lys Arg Glu Tyr Ser Pro Phe Phe Arg Asn
            180                 185                 190

Leu Ala Leu Phe Gly Tyr Phe Asn Gly Gly Lys Arg Leu Pro Lys Pro
            195                 200                 205

Asn Ser Gly Asn Ile Phe Thr Cys Thr Phe Glu His Gly Trp Phe Trp
210                 215                 220

Tyr Ile Pro Leu Ser Pro Glu Leu Thr Ser Val Gly Ala Val Val Asn
225                 230                 235                 240

Arg Asp Ser Ala Ser Leu Val Gln Gly Asp Pro Glu Lys Ala Met Glu
            245                 250                 255

Ser Phe Ile Ala Ala Cys Pro Leu Ile Ala Glu Lys Leu Ser Glu Ala
            260                 265                 270

Thr Arg Val Thr Glu Gly Pro Tyr Gly Glu Leu Arg Val Arg Lys Asp
            275                 280                 285

Trp Ser Tyr Ser Asn Thr Lys Phe Trp Ala Pro Gly Met Ala Leu Val
290                 295                 300

Gly Asp Ala Ala Cys Phe Val Asp Pro Val Phe Ser Ser Gly Val His
305                 310                 315                 320

Leu Ala Thr Tyr Ser Gly Leu Leu Ala Ala Arg Ser Leu Asn Ser Cys
            325                 330                 335

Leu Asp Gly Ser Val Asp Glu Thr Ser Ala Phe Glu Glu Phe Glu Ala
            340                 345                 350

Arg Tyr Arg Leu Glu Tyr Gly Arg Phe Tyr Glu Phe Leu Val Gly Phe
            355                 360                 365

Tyr Asp Met His His Ser Glu Asp Ser Tyr Phe Trp Gln Ala Arg Lys
370                 375                 380

Ile Ser Asn Thr Ala Asp Ser Asp Leu Gln Ser Phe Val Glu Leu Ile
385                 390                 395                 400

Gly Gly Val Ser Ser Asp Glu Phe Ala Asp Thr Ala Arg Ala Arg Gln
            405                 410                 415

Arg Phe Ser Glu Ala Ser Asp Glu Met Ala Gly Met Thr His Thr Ala
            420                 425                 430

Ala Gly Asp Ala Asp Gly Pro His Gly Ala Val Pro Gly Lys Val Val
            435                 440                 445

Gly Arg Leu Met Glu Gln Ser Ala Ala Leu Gln Ala Arg Ala Leu Leu
450                 455                 460

Gly Asp Glu Ala Gly Ala Glu Arg Pro Val Arg Gln Gly Gly Leu Ala
465                 470                 475                 480

Ala Ser Thr Asp Gly Leu Gly Trp Val Pro Gly Ala Arg Ser
            485                 490
```

<210> SEQ ID NO 163
<211> LENGTH: 355
<212> TYPE: PRT
<213> ORGANISM: Streptomyces globisporus
<220> FEATURE:
<223> OTHER INFORMATION: orf10

<400> SEQUENCE: 163

```
Met Lys Ala Leu Val Leu Ser Gly Gly Ser Gly Thr Arg Leu Arg Pro
1               5                   10                  15
```

```
Ile Ser Tyr Ala Met Pro Lys Gln Leu Val Pro Ile Ala Gly Lys Pro
         20                  25                  30

Val Leu Glu Tyr Val Leu Asp Asn Ile Arg Asn Leu Asp Ile Lys Glu
         35                  40                  45

Val Ala Ile Val Gly Asp Trp Ala Gln Glu Ile Glu Ala Met
     50                  55                  60

Gly Asp Gly Ser Arg Phe Gly Leu Arg Leu Thr Tyr Ile Arg Gln Glu
 65              70                  75                      80

Gln Pro Leu Gly Ile Ala His Cys Val Lys Leu Ala Arg Asp Phe Leu
             85                  90                      95

Asp Glu Asp Asp Phe Val Leu Tyr Leu Gly Asp Ile Met Leu Asp Gly
             100                 105                 110

Asp Leu Ser Ala Gln Ala Gly His Phe Leu His Thr Arg Pro Ala Ala
             115                 120                 125

Arg Ile Val Val Arg Gln Val Pro Asp Pro Arg Ala Phe Gly Val Ile
         130                 135                 140

Glu Leu Asp Gly Glu Gly Arg Val Leu Arg Leu Val Glu Lys Pro Arg
145                 150                 155                 160

Glu Pro Arg Ser Asp Leu Ala Ala Val Gly Val Tyr Phe Phe Thr Ala
             165                 170                 175

Asp Val His Arg Ala Val Asp Ala Ile Ser Pro Ser Arg Arg Gly Glu
             180                 185                 190

Leu Glu Ile Thr Asp Ala Ile Gln Trp Leu Leu Glu Gln Gly Leu Pro
             195                 200                 205

Val Glu Ala Gly Arg Tyr Thr Asp Tyr Trp Lys Asp Thr Gly Arg Val
         210                 215                 220

Glu Asp Val Val Glu Cys Asn Arg Arg Met Leu Gly Arg Leu Ala Leu
225                 230                 235                 240

Gln Val Ser Gly Glu Val Asp Pro Glu Ser Glu Leu Val Gly Ala Val
             245                 250                 255

Val Val Glu Glu Gly Ala Arg Val Thr Arg Ser Arg Val Val Gly Pro
             260                 265                 270

Ala Val Ile Gly Ala Gly Thr Val Glu Asp Ser Gln Ile Gly Pro
             275                 280                 285

Tyr Ala Ser Ile Gly Arg Arg Cys Thr Val Arg Ala Ser Arg Leu Ser
         290                 295                 300

Asp Ser Ile Val Leu Asp Asp Ala Ser Ile Leu Ala Val Ser Gly Leu
305                 310                 315                 320

His Gly Ser Leu Ile Gly Arg Gly Ala Arg Ile Ala Pro Gly Ala Arg
             325                 330                 335

Gly Glu Ala Arg His Arg Leu Val Val Gly Asp His Val Gln Ile Glu
             340                 345                 350

Ile Ala Ala
         355

<210> SEQ ID NO 164
<211> LENGTH: 143
<212> TYPE: PRT
<213> ORGANISM: Streptomyces globisporus
<220> FEATURE:
<223> OTHER INFORMATION: orf9

<400> SEQUENCE: 164

Met Ser Leu Arg His Met Ser Arg Arg Ala Ser Arg Phe Gly Val Val
 1               5                  10                  15
```

```
Ala Val Ala Ser Ile Gly Leu Ala Ala Ala Gln Ser Val Ala Phe
            20                  25                  30

Ala Ala Pro Ala Phe Ser Val Ser Pro Ala Ser Gly Leu Ser Asp Gly
        35                  40                  45

Gln Ser Val Ser Val Ser Val Ser Gly Ala Ala Ala Gly Glu Thr Tyr
 50                  55                  60

Tyr Ile Ala Gln Cys Ala Pro Val Gly Gln Asp Ala Cys Asn Pro
 65                  70                  75                  80

Ala Thr Ala Thr Ser Phe Thr Thr Asp Ala Ser Gly Ala Ala Ser Phe
                    85                  90                  95

Ser Phe Val Val Arg Lys Ser Tyr Thr Gly Ser Thr Pro Glu Gly Thr
                100                 105                 110

Pro Val Gly Ser Val Asp Cys Ala Thr Ala Ala Cys Asn Leu Gly Ala
            115                 120                 125

Gly Asn Ser Gly Leu Asp Leu Gly His Val Ala Leu Thr Phe Gly
130                 135                 140
```

<210> SEQ ID NO 165
<211> LENGTH: 410
<212> TYPE: PRT
<213> ORGANISM: Streptomyces globisporus
<220> FEATURE:
<223> OTHER INFORMATION: orf8

<400> SEQUENCE: 165

```
Met Ser Gly Gly Pro Val Arg Leu Asp Ser Leu Pro Thr Pro Tyr Phe
 1               5                  10                  15

Ser Glu Pro Leu His Val Gly Arg Pro Asn Val Gly Ser Arg Asp Arg
            20                  25                  30

Leu Met Glu Arg Ile Asp Gly Ala Leu Glu Arg Leu Trp Phe Thr Asn
        35                  40                  45

Asp Gly Pro Leu Val Arg Glu Phe Glu Ala Arg Val Ala Glu Leu Thr
 50                  55                  60

Gln Val Arg His Cys Val Ala Val Ser Asn Ala Thr Thr Gly Ile Gln
 65                  70                  75                  80

Val Ala Ala Lys Ala Leu Gly Ile Gly Pro Gly Asp Glu Val Ile Val
                    85                  90                  95

Pro Ser Phe Thr Trp Val Ala Thr Ala His Ala Leu Asp Trp Ile Gly
                100                 105                 110

Ala Val Pro Val Phe Cys Glu Leu Asp Glu Glu Thr Gly Thr Ala Asp
            115                 120                 125

Val Ala His Val Glu Arg Leu Ile Gly Pro Arg Thr Arg Ala Ile Leu
130                 135                 140

Asp Val His Val Phe Gly Arg Pro Ala Arg Ile Asp Glu Leu Thr Lys
145                 150                 155                 160

Leu Ala Ala Glu His Gly Leu His Leu Leu Phe Asp Ala Ala His Ala
                    165                 170                 175

Phe Gly Cys Thr Tyr Arg Ser Lys Pro Ile Gly Gly Phe Gly Thr Ala
                180                 185                 190

Glu Ile Phe Ser Phe Gln Ala Thr Lys Phe Val Asn Ser Phe Glu Gly
            195                 200                 205

Gly Ala Ile Val Thr Asp Asp Ala Leu Ala Asp Arg Leu Arg Ala
210                 215                 220

Met Arg His Gln Gly Leu Asn Ala Ala His Glu Ile Thr Gly Ser Gly
225                 230                 235                 240
```

```
Thr Val Ala Arg Met His Glu Ile Ser Ala Ala Met Gly Leu Thr Ser
                245                 250                 255

Leu Glu Ser Ala Asp His Phe Thr Ala Ile Asn Arg Arg Asn Tyr Arg
            260                 265                 270

Leu Tyr Glu Gln Tyr Leu Asp Gly Leu Pro Gly Val Arg Val Arg Pro
        275                 280                 285

Gln Asp Pro Asn Glu Leu Ser Asn Cys Gln Tyr Val Ile Glu Val
    290                 295                 300

Asp Ala Val Arg Ala Gly Leu His Arg Asp Glu Leu Gln Ala Val Leu
305                 310                 315                 320

Gln Arg His Asn Val Leu Ala Arg Ala Tyr Phe Ser Pro Gly Cys His
                325                 330                 335

Ser Cys Glu Pro Tyr Arg Ser Asp Leu Ala Arg His Ala Pro Asp Pro
            340                 345                 350

Leu Pro Lys Val Glu Ala Leu Thr Glu Arg Val Leu Ser Leu Pro Thr
        355                 360                 365

Gly Thr Ala Val Gly Pro Glu Glu Val Arg Gly Val Cys Arg Ile Leu
    370                 375                 380

Arg Ala Ala Val Asp Gly Ser Ala Val Pro Glu Ile His Glu Ser Thr
385                 390                 395                 400

Glu Gly Asp Ala Gly Gly Arg Pro Ala Arg
                405                 410

<210> SEQ ID NO 166
<211> LENGTH: 20
<212> TYPE: PRT
<213> ORGANISM: Streptomyces globisporus
<220> FEATURE:
<223> OTHER INFORMATION: splice variant a

<400> SEQUENCE: 166

Asp Ala Pro Gly Arg Arg Ser Cys Arg Ala His Ala Asp Glu Glu Ala
  1               5                  10                  15

Gly Ala Val Gly
            20

<210> SEQ ID NO 167
<211> LENGTH: 20
<212> TYPE: PRT
<213> ORGANISM: Streptomyces globisporus
<220> FEATURE:
<223> OTHER INFORMATION: splice variant b

<400> SEQUENCE: 167

Thr His Arg Ala Ala Ala His Ala Val Arg Thr Pro Thr Lys Arg Pro
  1               5                  10                  15

Gly Leu Leu Gly
            20

<210> SEQ ID NO 168
<211> LENGTH: 20
<212> TYPE: PRT
<213> ORGANISM: Streptomyces globisporus
<220> FEATURE:
<223> OTHER INFORMATION: splice variant c

<400> SEQUENCE: 168

Arg Thr Gly Pro Pro Leu Met Pro Cys Ala Arg Arg Arg Gly Arg
  1               5                  10                  15
```

-continued

Gly Cys Trp Ala
           20

<210> SEQ ID NO 169
<211> LENGTH: 244
<212> TYPE: PRT
<213> ORGANISM: Streptomyces globisporus
<220> FEATURE:
<223> OTHER INFORMATION: orf7

<400> SEQUENCE: 169

Met Glu Tyr Gly Pro Glu His Ala Lys Phe Tyr Asp Leu Val Phe Arg
 1               5                  10                  15

Ser Arg Gly Lys Asp Phe Asp Leu Glu Ala Arg Gly Leu Thr Glu Leu
            20                  25                  30

Ile Leu Ala Ala Arg Pro Asp Ala Val Ser Leu Leu Asp Val Ala Cys
        35                  40                  45

Gly Thr Gly Ala His Leu Glu Thr Leu Ala Thr Leu Phe Gly His Val
    50                  55                  60

Glu Gly Leu Glu Tyr Ala Pro Ala Met Leu Glu Gln Ala Ala Gly Arg
65                  70                  75                  80

Leu Pro Gly Val Pro Leu His Ala Gly Asp Met Arg Ser Phe Asp Leu
                85                  90                  95

Gly Arg Thr Phe Asp Ala Ile Thr Cys Met Gly Asn Ala Leu Gly Glu
            100                 105                 110

Met Gly Ser Val Thr Glu Leu Lys Ala Ala Val Ser Ala Met Ala His
        115                 120                 125

His Leu Asn Pro Gly Gly Val Leu Val Ala Glu Pro Trp Tyr Phe Pro
    130                 135                 140

Glu Asn Phe Leu Asp Gly His Val Gly Gly His Leu His Gln Glu Glu
145                 150                 155                 160

Gly Arg Val Ile Thr Arg Met Thr His Ser Val Arg Gln Gly Asp Lys
                165                 170                 175

Ser Arg Leu Glu Val Arg Phe Arg Val Ala Asp Ala Ser Gly Phe Arg
            180                 185                 190

Glu Phe Ser Glu Val Leu Thr Ser Ser Leu Phe Thr Arg Glu Gln Tyr
        195                 200                 205

Thr Asp Ala Phe Glu Ser Val Gly Leu Ser Val Arg Phe Val Pro Gly
    210                 215                 220

Phe Arg Leu Ala Asp Gly Arg Pro Asn Ser Pro Gly Leu Phe Val Gly
225                 230                 235                 240

Val Arg Thr Ala

<210> SEQ ID NO 170
<211> LENGTH: 423
<212> TYPE: PRT
<213> ORGANISM: Streptomyces globisporus
<220> FEATURE:
<223> OTHER INFORMATION: orf6

<400> SEQUENCE: 170

Met Leu Glu Lys Cys Arg Arg Asp Glu Thr Cys Arg Val Cys Gly Ala
 1               5                  10                  15

Asp Asp Trp Thr Glu Val Ile Ser Phe Gly Ser Leu Pro Leu Ala Asn
            20                  25                  30

Gly Phe Val Asp Pro Ala Asp Ala Asp Glu Ala Gln Asp Val Phe Pro
        35                  40                  45

-continued

Leu Asp Val Ile Val Cys Arg Ser Cys Arg Leu Met Thr Leu Arg His
    50                  55                  60

Val Val Asp Pro Gly Thr Leu Phe Lys His Tyr Val Tyr Val Ser Ser
65                  70                  75                  80

Asp Ser Asp Gln Ile Arg Glu His Met Ala His Ile Val Gly Leu Ala
                85                  90                  95

Thr Arg Arg Ala Ser Leu Ala Ser Gly Asp Leu Val Val Glu Leu Gly
            100                 105                 110

Ser Asn Val Gly Thr Gln Leu Ala Met Phe Arg Ala Ala Gly Met Arg
        115                 120                 125

Val Ala Gly Val Asp Pro Ala Ala Asn Leu Ala Glu Ile Ala Asn Ala
    130                 135                 140

Arg Gly Ile Pro Thr Asp Pro Asp Phe Phe Gly Pro Glu Pro Ala Gly
145                 150                 155                 160

Arg Ile Ala Leu Glu Gln Gly Arg Ala Lys Ala Val Ile Gly Arg Gln
                165                 170                 175

Cys Phe Ala His Ile Asp Asp Val His Arg Ile Leu Asp Gly Val Asp
            180                 185                 190

Ala Val Leu Asp Asp Gly Val Leu Val Ile Glu Val Pro Tyr Leu
        195                 200                 205

Leu Asn Leu Leu Asp Glu Asn Gln Phe Asp Thr Ile Tyr His Glu His
    210                 215                 220

Leu Ser Tyr Phe Ser Leu His Thr Leu Arg His Leu Phe Gly Ala His
225                 230                 235                 240

Gly Leu Arg Ile Ile Asp Val Glu Arg Val Ala Val His Gly Gly Ser
                245                 250                 255

Ile Ala Val Val Ala Ala Arg Glu Ser Ala Ala Arg Val Pro Glu Pro
            260                 265                 270

Ser Val Ala Ala Leu Leu Gly Leu Glu Glu Glu Arg Gly Leu Leu Thr
        275                 280                 285

Asp Ala Pro Tyr Arg Ala Phe Ala Glu Arg Val Thr Arg Val Thr Glu
290                 295                 300

Ala Ile Arg Thr Leu Val Arg Gly Leu Ala Ala Asp Gly His Arg Val
305                 310                 315                 320

Ala Gly Tyr Gly Ala Pro Ser Lys Gly Thr Gln Leu Leu Met Ala Cys
                325                 330                 335

Gly Leu Thr Asp Gln Asp Ile Thr Val Cys Gly Asp Thr Thr Ser Leu
            340                 345                 350

Lys His Gly Lys Leu Leu Pro Gly Asn Arg Ile Pro Val Leu Pro Pro
        355                 360                 365

Glu Glu Val Ala Ala Thr Glu Pro Asp Tyr Tyr Leu Leu Leu Ala Trp
370                 375                 380

Asn Tyr Thr Asp Glu Val Val Arg Lys Glu Arg Arg Phe Leu Glu Ala
385                 390                 395                 400

Gly Gly Lys Phe Ile Val Pro Ile Pro Glu Pro Arg Ile Ile Ser Ala
                405                 410                 415

Gln Ser Ala Lys Glu Leu Val
            420

<210> SEQ ID NO 171
<211> LENGTH: 386
<212> TYPE: PRT
<213> ORGANISM: Streptomyces globisporus
<220> FEATURE:
<223> OTHER INFORMATION: orf17

```
<400> SEQUENCE: 171

Met Arg Pro Phe Arg Ile Glu Ile Asp Pro Val Arg His Ser Thr Thr
 1               5                  10                  15
Leu Thr Arg Arg Ile Asp Ala Thr Arg Trp Pro Ser Glu Ile Pro Gly
             20                  25                  30
Ser Gly Trp Asp Arg Gly Val Pro Leu Ser Tyr Leu Lys Glu Leu Thr
         35                  40                  45
Asp His Trp Arg His Gly Tyr Asp Trp Arg Ala Ala Glu Ala Glu Leu
     50                  55                  60
Asn Ala Phe Pro Gln Phe Val Thr Thr Ile Asp Gly Ala Asp Val His
 65                  70                  75                  80
Phe Leu His Val Arg Ser Pro Glu Pro Asp Ala Ile Pro Leu Ile Leu
                 85                  90                  95
Thr His Gly Trp Pro Gly Ser Val Ala Glu Phe Leu Asp Val Ile Gly
             100                 105                 110
Pro Leu Ser Asp Pro Arg Ala His Gly Gly Asp Pro Ala Asp Ala Phe
         115                 120                 125
His Val Val Pro Ser Met Pro Gly Tyr Gly Phe Ser Gly Pro Thr
     130                 135                 140
Ala Glu Pro Gly Trp Asp Val Arg Arg Ile Ala Arg Ala Trp Ala Glu
145                 150                 155                 160
Leu Met Asn Arg Leu Gly Tyr Glu Arg Tyr Val Ala Gln Gly Gly Asp
                165                 170                 175
Trp Gly Lys Val Val Ser Leu Glu Leu Gly Leu Ala Asp Pro Glu His
            180                 185                 190
Val Ala Gly Val His Leu Asn Met Leu Val Thr Phe Pro Pro Gln Asp
        195                 200                 205
Ala Pro Glu Ala Ile Gly Arg Leu Asp Glu Ser Asp Leu Gly Lys Leu
210                 215                 220
Ala His Ser Gly Glu Phe Ala Asp Thr Gly Ile Gly Trp Gln Arg Ile
225                 230                 235                 240
Gln Ala Thr Arg Pro Gln Thr Leu Ala Tyr Gly Leu Thr Asp Ser Pro
                245                 250                 255
Val Gly Gln Leu Ala Trp Ile Leu Asp Lys Phe Gln Glu Trp Ser Gly
            260                 265                 270
Gly Lys Asn Val Glu Glu Ala Ile Ser Arg Asp Arg Leu Leu Thr His
        275                 280                 285
Val Met Ile Tyr Trp Leu Thr Ala Thr Ala Gly Ser Ser Ala Gln Leu
    290                 295                 300
Tyr Tyr Glu Ser Ala Arg Gly Met Ala Asp Phe Ala Arg Thr Trp Gly
305                 310                 315                 320
Gly Pro Trp Pro Leu Thr Ala Pro Val Gly Val Ala Val Phe Pro Asp
                325                 330                 335
Asp Ala Thr Arg Pro Ile Arg Ser Phe Ala Glu Gly Ile Leu Pro Thr
            340                 345                 350
Leu Thr Arg Trp Thr Glu Phe Asp Arg Gly Gly His Phe Ala Ala Met
        355                 360                 365
Glu Gln Pro Gln Leu Leu Ile Glu Asp Val Arg Ala Phe Thr Arg Pro
    370                 375                 380
Leu Arg
385
```

<210> SEQ ID NO 172
<211> LENGTH: 220
<212> TYPE: PRT
<213> ORGANISM: Streptomyces globisporus
<220> FEATURE:
<223> OTHER INFORMATION: orf16

<400> SEQUENCE: 172

```
Met Ser Leu Trp Ser Pro Asp Gly Ser Gly Ala Gly Thr Glu Ala Pro
 1               5                  10                  15

Arg Val Leu Val Val Asp Ala Phe Asp Ser Phe Val Asp Ile Leu Arg
            20                  25                  30

Gln Tyr Leu Met Ser Ala Gly Ala Glu Pro Val Met Val Arg Ser His
        35                  40                  45

Leu Met Thr Pro Asp Glu Met Gly Leu Met Arg Pro Asp Ala Val Leu
    50                  55                  60

Leu Gly Pro Gly Pro Gly His Pro Asp Thr Ser Gly His Val Glu Ile
65                  70                  75                  80

Val Gln Ala Phe Ala Gly Arg Val Pro Leu Leu Gly Val Cys Leu Gly
                85                  90                  95

His Gln Ala Val Ala Arg Ala Tyr Gly Ala Ala Thr Val Pro Ala Arg
            100                 105                 110

His Leu Met His Gly Lys Thr Ser Arg Ile Thr His Asp Gly Arg Gly
        115                 120                 125

Val Phe Thr Gly Leu Pro Ala Gly Phe Phe Ala Thr Arg Tyr His Ser
    130                 135                 140

Leu Ile Val Pro Glu Gly Thr Val Pro Pro Ser Leu Glu Val Thr Gly
145                 150                 155                 160

Arg Ser Thr Asp Asp Gly Tyr Val Met Gly Leu Arg His Arg Ser Leu
                165                 170                 175

Pro Val Glu Ser Val Gln Phe His Pro Glu Ser Phe Arg Thr Glu His
            180                 185                 190

Gly Met Pro Met Ile Arg Asn Phe Leu Ser Ser Val Arg Ser Phe Ser
        195                 200                 205

Ala Arg Glu Gly Ala Ala Ala Pro Ala Glu Pro Ala
    210                 215                 220
```

<210> SEQ ID NO 173
<211> LENGTH: 493
<212> TYPE: PRT
<213> ORGANISM: Streptomyces globisporus
<220> FEATURE:
<223> OTHER INFORMATION: orf15

<400> SEQUENCE: 173

```
Met Thr Asp Gln Cys Val Val Ser Ala Pro Val Arg Val Arg Thr Arg
 1               5                  10                  15

Arg Leu Asp Val Lys Glu Thr Gly Ala Leu Pro Ala Tyr Arg Ala Leu
            20                  25                  30

Ala Glu His Phe Gly Pro Asp Glu Val Tyr Leu Leu Glu Ser Ala Ala
        35                  40                  45

Gly Pro Ala Arg Asp Arg Arg His Gln Phe Val Gly Phe Gly Ala Leu
    50                  55                  60

Leu Ser Leu Ser Val Thr Asp Arg Val Val Arg Val Glu Gly Val Pro
65                  70                  75                  80

Ala Leu Arg Gly Leu Leu Leu Glu Arg Ala Gly Ala Leu Leu Glu Asp
                85                  90                  95
```

```
Gly Pro Gln Gly Leu Arg Leu Arg Thr Ala Gly Gly Leu Trp Pro Leu
            100                 105                 110

Leu Arg Ala Met Arg Asp Met Phe Asp Ala Glu Gly Ser Ala Ser Gly
        115                 120                 125

Phe Arg Phe Gly Phe Leu Gly Phe Phe Gly Tyr Asp Thr Ala Arg Tyr
    130                 135                 140

Ile Glu Asp Leu Pro His Leu Ile Glu Asn Arg Pro Gly Leu Pro Asp
145                 150                 155                 160

Val Arg Met Val Leu His Arg Gly Ser Val Val Thr Asp Leu Ala Thr
                165                 170                 175

Gly Arg Cys Glu Leu Leu Leu His Glu Ser Pro Tyr Trp Pro Gly Leu
            180                 185                 190

Ala Pro Glu Thr Val Thr Gly Leu Leu Ala Asp Val Glu Gln Ala Trp
        195                 200                 205

Pro Asp Pro Ser Ala Asp Gly Phe Pro Ala Ser Ala Val Thr Asp Asp
    210                 215                 220

Ser Ala Pro Glu Val Phe Ala Asn Asp Val Glu Arg Cys Leu Lys His
225                 230                 235                 240

Ile Ala Val Gly Asp Ile Tyr Gln Val Gln Ile Gly His Glu Leu Ser
                245                 250                 255

Ile Arg Ser Thr Ala Asp Pro Ala Asp Val Tyr Gln Arg Leu Arg Gly
            260                 265                 270

Arg Asn Ala Ser Pro Tyr Met Tyr Leu Ala Gly Ile Asp Gly His Arg
        275                 280                 285

Leu Ile Gly Ala Ser Pro Glu Leu Phe Val Arg Ile Glu Asp Gly Glu
    290                 295                 300

Val Thr Met Arg Pro Ile Ala Gly Thr Val Pro Arg Ser Gly Ala Asp
305                 310                 315                 320

Gly Gly Ile Ala Ala Gly Val Arg Leu Arg Ser Asp Pro Lys Glu Ile
                325                 330                 335

Ala Glu His Thr Met Leu Val Asp Leu Cys Arg Asn Asp Ile Gly Arg
            340                 345                 350

Ile Ala Arg Pro Asn Thr Leu Asp Val Pro Asp Gln Leu Asp Val Glu
        355                 360                 365

Gly Tyr Ser His Val Leu His Leu Val Ser Thr Val Val Gly Arg Ala
    370                 375                 380

Arg Val Asp Thr Asp Ala Phe Asp Thr Ile Ala Ala Leu Phe Pro Ala
385                 390                 395                 400

Gly Thr Met Thr Gly Ala Pro Lys Ile Arg Ala Met Glu Ile Ile Glu
                405                 410                 415

Ser Val Glu Arg Ser Arg Arg Gly Leu Tyr Ala Gly Ala Leu Gly Leu
            420                 425                 430

Leu Asp Val Gly Gly Tyr Thr Asn Leu Ala Leu Cys Ile Arg Thr Leu
        435                 440                 445

Phe His His Glu Gly Val Tyr Arg Thr Arg Ala Ser Ala Gly Ile Val
    450                 455                 460

Ala Asp Ser Glu Pro Gly Ala Glu Trp Thr Glu Thr Leu Ala Lys Met
465                 470                 475                 480

Ser Ala Thr His Trp Ala Val Thr Gly Glu Glu Leu Leu
                485                 490

<210> SEQ ID NO 174
<211> LENGTH: 484
<212> TYPE: PRT
```

<213> ORGANISM: Streptomyces globisporus
<220> FEATURE:
<223> OTHER INFORMATION: orf14

<400> SEQUENCE: 174

```
Met Arg Asp Gly Arg Arg Pro Gly Pro Gly Gly Thr Gly Pro Leu Asp
  1               5                  10                  15

Pro Asp Ala Asp Ser Glu Phe Trp Ser Ala Tyr Gly Gln Val Ser Asp
             20                  25                  30

Ala Phe Tyr Arg Gly Glu Leu Thr Ala Ala Asp Arg Glu Arg Trp Glu
         35                  40                  45

Gly Glu Arg Leu Thr Ala Val Leu Arg His Val Thr Arg Arg Ser Pro
 50                  55                  60

Phe Tyr Arg Arg His Leu Ala Gly Val Asp Val Glu Ala Val Thr Pro
 65                  70                  75                  80

Ala Asn Leu Ala Asp Leu Pro Phe Thr Thr Lys Asp Asp Leu Arg Arg
             85                  90                  95

Glu Met His Asp Val Leu Ser Gly Pro Leu His Glu Ala Arg Ile Tyr
            100                 105                 110

Tyr Glu Thr Thr Gly Thr Thr Gly Ala Ala Thr Pro Cys Pro Arg Gly
        115                 120                 125

Glu Lys Asp Ile Ala Thr Ser Asn Ile Ala Val Arg Glu Ser Trp Arg
130                 135                 140

Arg Met Leu Glu Ala Arg Phe Gly Gly Arg Met Pro Val Val Gly Leu
145                 150                 155                 160

Met Gly Pro Ser Glu Leu Tyr Ala Phe Gly Asp Val Phe Thr Ala Val
                165                 170                 175

Ala Ala Glu Leu Gly Ala Cys His Val Lys Ile Trp Pro Glu Ser Pro
            180                 185                 190

Arg Val Gly Phe Arg Lys Ala Leu Arg Leu Ile Glu Glu Leu Glu Val
        195                 200                 205

Glu Val Val Val Cys Ala Pro Ala Leu Cys Leu Ser Leu Ala Lys Ala
210                 215                 220

Ala Leu His Tyr Gly Tyr Asp Leu Ala Arg Leu Pro Val Lys Leu Phe
225                 230                 235                 240

Leu Thr Leu Gly Glu Ile Cys Thr Pro Gln Phe Ala Asp Asn Val Ala
                245                 250                 255

Thr Leu Trp Pro Gln Ala Val Val Arg Pro Thr Leu Tyr Gly Ser Gln
            260                 265                 270

Glu Ala Leu Cys Ile Ala Thr Gly Ala Asp Thr Gly Ala Leu His Leu
        275                 280                 285

Ala Gln Pro Asn Tyr Leu Thr Glu Leu Val Glu Pro Asp Thr Gly Ala
290                 295                 300

Val Val Gly Asp Thr Gly Glu Gly Leu Val Leu Thr Met Leu Val
305                 310                 315                 320

Asp Gly Ile Lys Pro Leu Ile Arg Tyr Arg Thr Gly Asp Leu Val Arg
                325                 330                 335

Ile Leu Pro Ala Gly Pro Gly Glu Pro Leu Gly Pro Arg Ile Gln
            340                 345                 350

Val Ile Gly Arg Val Ala Asp Arg Ile Pro Leu Gly Asp Val Thr Leu
        355                 360                 365

Gln Pro Ala Glu Leu Glu Ala Ala Ile Leu Asp Gly Val Gly Gly Cys
370                 375                 380

Leu Gly Tyr Gln Val Val Ile Asp Arg Gln Asp Asp Gly Ser Asp Ala
```

```
                385                 390                 395                 400
Val Thr Val Arg Met Asp Leu Leu Ala Gly Ala Glu Gly Glu Arg Gln
                    405                 410                 415
Gly Ile Gly Glu Ala Val Ala Ala Arg Leu Arg Glu Arg Thr Gly Ala
                420                 425                 430
His Ala Gly Ile Val Val Asp Thr Asp Leu Asp Pro Val Thr His Thr
                435                 440                 445
Gly Ser Phe Val Ser Trp Lys Ala Ala Arg Val Val Asp Asn Arg Ser
            450                 455                 460
Gly Pro Asp Arg Ala Val Leu Thr Ala Arg Gln Val Ala His Arg Tyr
465                 470                 475                 480
Ala Ile Thr Thr

<210> SEQ ID NO 175
<211> LENGTH: 223
<212> TYPE: PRT
<213> ORGANISM: Streptomyces globisporus
<220> FEATURE:
<223> OTHER INFORMATION: orf21

<400> SEQUENCE: 175

Met Ser Ala Gln Leu Lys Ile Leu Ala Ile Asn Gly Ser Glu Arg Asp
  1               5                  10                  15
Gly Asn Thr Ala Asp Val Leu Arg His Ala Ala Arg Val Ala Glu Asn
                 20                  25                  30
Arg Gly Val Asp Phe Glu Ala Val Asp Leu Arg Ser Ile Arg Met Glu
             35                  40                  45
Arg Cys Gly Pro Cys Gly Asp Cys Asn Asp Arg Pro Val Ala Cys Thr
         50                  55                  60
Leu Ala Asp Gly Val Pro Glu Val Val Ala Lys Met Val Ala Ala Asp
 65                  70                  75                  80
Gly Ile Ile Phe Ala Ala Pro Val His Phe Gly Thr Ala Ser Leu
                 85                  90                  95
Met Gln Thr Phe Ile Glu Arg Ala Gly Val Gly Tyr Leu Arg Phe Asp
                100                 105                 110
Arg Pro Leu Ser Asn Lys Val Ala Gly Ile Ile Ser Val Ala Arg Arg
            115                 120                 125
Tyr Ser Ala Gly Glu Val Trp Ala Gln Leu Thr Val Asn Ala Leu Leu
        130                 135                 140
Asn Arg Met Ile Leu Val Gly Ser Gly Phe Pro Ala Thr Val His Ala
145                 150                 155                 160
Leu His Arg Gly Asp Ala Leu Lys Asp Glu Glu Gly Leu Thr Asn Val
                165                 170                 175
Ser Arg Leu Val Glu Arg Met Thr Asp Met Ile Glu Leu Leu Asp Glu
            180                 185                 190
His Arg Arg Leu Thr Gly Arg Ser Asp Val Leu Ala Ser Asn Glu Val
        195                 200                 205
Asn Glu Arg Val Gly Leu Ala Leu Asn Glu Leu Gln Ala Gln Pro
    210                 215                 220

<210> SEQ ID NO 176
<211> LENGTH: 378
<212> TYPE: PRT
<213> ORGANISM: Streptomyces globisporus
<220> FEATURE:
<223> OTHER INFORMATION: orf13
```

<400> SEQUENCE: 176

```
Met Pro Ser Pro Phe Phe Ala Leu Ser Gly Met Met Leu Tyr Lys Pro
 1               5                  10                  15

Tyr Ala Arg Val Thr Ile Ser Gly Thr Lys Arg Pro Ala Thr Gly Arg
             20                  25                  30

Phe Leu Lys Arg Arg Ala Leu Arg Ile Leu Pro Ala Tyr Tyr Leu Leu
         35                  40                  45

Leu Val Phe Ala Ile Pro Gly Tyr Asn Trp Phe Glu Ile Asp Ser Val
     50                  55                  60

Ser Asp Val Leu Arg Pro Val Leu Leu Met His Phe Tyr Leu Pro Glu
 65                  70                  75                  80

Gly Gln Pro Met His Gly Ile Glu Pro Thr Trp Thr Val Pro Ala Glu
                 85                  90                  95

Phe Thr Phe Tyr Leu Ala Leu Pro Leu Ile Ala Trp Ile Gly His Arg
            100                 105                 110

Leu Ala Arg Gly Gly Ser Thr Pro Gly Gln Lys Ala Arg Arg Leu Leu
        115                 120                 125

Leu Pro Leu Ala Ala Leu Glu Val Met Ala Ile Gly Trp Val Thr Tyr
    130                 135                 140

Thr Asn Leu Pro Ser Thr Gly Ala Thr Met Gln Trp Tyr Trp Pro Pro
145                 150                 155                 160

Tyr Tyr Ala Gly Cys Phe Ala Ala Gly Met Ala Leu Ala Ile Tyr Ser
                165                 170                 175

Ala Tyr Ala Glu Ala Thr Pro Gly Thr Pro Gly Phe Tyr Arg Phe Val
            180                 185                 190

Ile Arg Arg Pro Leu Ile Cys Trp Val Pro Leu Ile Pro Leu Tyr Leu
        195                 200                 205

Leu Tyr Ala Thr Lys Pro Ile Gly Ile Pro Gly Met Gly Asp Asn Ala
    210                 215                 220

Ala Leu Ala Gln Glu Leu Val Asp His Phe Ile Leu Thr Ser Phe Thr
225                 230                 235                 240

Leu Leu Leu Leu Ala Pro Met Thr Val Pro Gly Ala Glu Ser Arg Phe
                245                 250                 255

Ser Asp Ala Leu Phe Thr Ser Lys Pro Ile Leu Phe Leu Gly Gln Ile
            260                 265                 270

Ser Leu Gly Val Tyr Leu Trp His Glu Ile Val Ile Asn Leu Trp Leu
        275                 280                 285

Arg Asn Gly Ser Ile Phe Gly Lys Ser Pro Val Pro Thr Pro Glu Phe
    290                 295                 300

Arg Gly Asp Met Gly Phe Trp Glu Leu Phe Leu Phe Thr Ile Ser Ile
305                 310                 315                 320

Ser Val Val Leu Ala Thr Ile Ser Phe Tyr Leu Val Glu Lys Pro Leu
                325                 330                 335

Ile Arg Phe Gly Glu Arg Gly Pro Pro Arg Gly Leu Pro Pro
            340                 345                 350

Ala Pro Ala Glu Pro Ala Leu Arg Leu Pro Asp Gln Arg Arg Pro Asp
        355                 360                 365

Ser Ser Pro Glu Pro Thr Ala Glu Arg Thr
    370                 375
```

<210> SEQ ID NO 177
<211> LENGTH: 192
<212> TYPE: PRT
<213> ORGANISM: Streptomyces globisporus

```
<220> FEATURE:
<223> OTHER INFORMATION: orf12

<400> SEQUENCE: 177

Met Lys Pro Ile Gly Ile Ser Gly Ala Trp Thr Glu Glu Lys Gln Val
  1               5                  10                  15

Phe Arg Asp Glu Arg Gly Ser Phe Arg Glu Trp Phe Gln Gly Glu Pro
                 20                  25                  30

Phe Arg Arg Thr Val Gly His Ser Phe Asp Leu Arg Gln Ala Asn Cys
             35                  40                  45

Ala Ile Ser Ser His Gly Val Leu Arg Gly Ile His Phe Ala Gly Gly
     50                  55                  60

Val Pro Gly Gln Ala Lys Tyr Phe Ser Cys Leu Arg Gly Ser Val Phe
 65                  70                  75                  80

Gly Ala Val Val Asp Ile Arg Val Gly Ser Pro Thr Phe Gly Gly Trp
                 85                  90                  95

Arg Thr Val Glu Leu Gly Glu Glu Asn Gly Arg Ala Leu Tyr Val Ser
            100                 105                 110

Ala Gly Leu Gly Phe Gly Phe Leu Thr Leu Ser Asp Glu Ala Val Ile
        115                 120                 125

Val Tyr Leu Cys Ser Ala Ala Tyr Asp Pro Arg Leu Glu His Gly Leu
130                 135                 140

Asn Pro Leu Asp Pro Glu Val Gly Ile Ala Trp Pro Pro Glu Ile Thr
145                 150                 155                 160

Pro Ile Leu Ser Glu Arg Asp Ser Ser Ala Pro Gly Leu Ala Glu Ala
                165                 170                 175

Gly Arg Arg Gly Trp Leu Pro Ser His Ser Gly Arg Asn Lys Ser Ser
            180                 185                 190

<210> SEQ ID NO 178
<211> LENGTH: 451
<212> TYPE: PRT
<213> ORGANISM: Streptomyces globisporus
<220> FEATURE:
<223> OTHER INFORMATION: orf20

<400> SEQUENCE: 178

Met Thr Lys His Ala Arg Asp Arg Ala Val Val Leu Gly Ala Gly Met
  1               5                  10                  15

Ala Gly Leu Leu Ala Ala Arg Val Leu Ser Glu Thr Tyr Lys Glu Val
                 20                  25                  30

Leu Val Ile Asp Arg Asp Arg Leu Gly Gly Thr Glu Gln Arg Arg Gly
             35                  40                  45

Val Pro His Gly Arg His Ala His Ala Leu Leu Ala Lys Gly Gln Gln
     50                  55                  60

Ile Leu Asn Glu Leu Phe Pro Gly Leu Asp Thr Glu Leu Thr Ser Ala
 65                  70                  75                  80

Gly Ile Pro Ala Gly Asp Ile Ala Gly Asn Leu Arg Trp Tyr Phe Asn
                 85                  90                  95

Gly Arg Arg Leu Gln Pro Phe Asp Thr Gly Leu Ile Ser Val Ser Ala
            100                 105                 110

Thr Arg Pro Glu Leu Glu Ser His Val Arg Ala Arg Val Ala Ala Leu
        115                 120                 125

Pro Gln Val Lys Ile Met Asp Gly Cys Val Ile Arg Gly Leu Thr Ala
130                 135                 140

Ser Ala Asp Arg Ser Arg Val Thr Gly Val Glu Val Val Asp Glu Ser
```

145              150              155              160
Gly Thr Asp Thr Pro Thr Arg Leu Glu Ala Asp Leu Val Val Asp Val
                165              170              175

Thr Gly Arg Gly Ser Arg Thr Pro Ala Trp Leu Glu Glu Phe Gly Tyr
            180              185              190

Glu Arg Pro Ala Glu Asp Arg Phe Lys Ile Asp Leu Ala Tyr Thr Thr
        195              200              205

Arg His Phe Lys Leu Lys Glu Asp Pro Tyr Gly Thr Asp Leu Ser Ile
    210              215              220

Asn Pro Val Ala Ser Pro Ser Asn Pro Arg Gly Ala Phe Phe Pro Arg
225              230              235              240

Leu Ala Asp Gly Ser Ser Gln Leu Ser Leu Thr Gly Ile Leu Gly Asp
                245              250              255

His Pro Pro Thr Asp Asp Glu Gly Phe Leu Ala Phe Ala Lys Ser Leu
            260              265              270

Ala Ala Pro Glu Ile Tyr Arg Ala Val Arg Asp Ala Glu Pro Leu Asp
        275              280              285

Glu Pro Val Thr Phe Arg Phe Pro Ala Ser Val Arg Arg Tyr Glu
    290              295              300

Arg Leu Arg Arg Phe Pro Gly Gly Phe Leu Val Met Gly Asp Gly Val
305              310              315              320

Cys Ser Phe Asn Pro Val Tyr Gly Gln Gly Met Thr Val Ala Ala Leu
                325              330              335

Glu Ala Val Ala Leu Arg Asp His Leu Arg Asp Ala Pro Asp Pro Asp
            340              345              350

Ala Leu Arg Phe Phe Arg Arg Ile Ser Thr Val Ile Asp Val Pro Trp
        355              360              365

Asp Ile Ala Ala Gly Ala Asp Leu Asn Phe Pro Gly Val Glu Gly Pro
    370              375              380

Arg Thr Met Lys Val Lys Met Ala Asn Ala Tyr Met Ala Arg Leu His
385              390              395              400

Ala Ala Ala Ala Val Asp Gly Ala Val Thr Gly Ala Phe Phe Arg Val
                405              410              415

Ala Gly Leu Val Asp Pro Pro Gln Ala Leu Met Arg Pro Ser Leu Ala
            420              425              430

Leu Arg Val Met Arg Asn Ser Ser Ala Lys Pro Ser Val Pro Ser Gly
        435              440              445

Ala Ala Val
    450

<210> SEQ ID NO 179
<211> LENGTH: 459
<212> TYPE: PRT
<213> ORGANISM: Streptomyces globisporus
<220> FEATURE:
<223> OTHER INFORMATION: orf19

<400> SEQUENCE: 179

Met Arg Val Met Ile Thr Val Phe Pro Ala Arg Ala His Phe Leu Pro
 1               5                  10                  15

Leu Val Pro Tyr Ala Trp Ala Leu Gln Ser Ala Gly His Glu Val Cys
            20                  25                  30

Val Val Ala Pro Pro Gly Tyr Pro Thr Gly Val Ala Asp Pro Asp Phe
        35                  40                  45

His Glu Ala Val Thr Ala Ala Gly Leu Lys Ser Val Thr Cys Gly Gln

-continued

```
                50                  55                  60
Pro Gln Pro Leu Ala Val His Asp Arg Asp Pro Gly Tyr Ala Ala
 65                  70                  75                  80

Met Leu Pro Thr Ala Ala Glu Ser Glu Arg Tyr Val Ala Ala Leu Gly
                 85                  90                  95

Ile Ser Glu Lys Glu Arg Pro Thr Trp Asp Val Phe Tyr His Phe Thr
                100                 105                 110

Leu Leu Ala Ile Arg Asp Tyr His Pro Arg Pro Arg Gln Asp Val
                115                 120                 125

Asp Gln Val Ile Glu Phe Ala Arg Ile Trp Gln Pro Asp Leu Val Leu
130                 135                 140

Trp Asp Ala Trp Phe Pro Ser Gly Ala Ile Ala Ala Arg Val Ser Gly
145                 150                 155                 160

Ala Ala His Ala Arg Val Leu Val Ala Pro Asp Tyr Thr Gly Trp Val
                165                 170                 175

Thr Glu Arg Phe Ala Ala Ala Gly Pro Ala Ala Gly Ala Asp Leu Leu
                180                 185                 190

Ala Glu Thr Met Arg Pro Leu Ala Glu Arg Tyr Gly Val Glu Val Asp
                195                 200                 205

Asp Asp Leu Leu Leu Gly Gln Trp Thr Val Asn Pro Phe Pro Ala Pro
210                 215                 220

Met Asn Pro Pro Thr Arg Leu Thr Asn Val Pro Val Arg Tyr Val Pro
225                 230                 235                 240

Tyr Thr Gly Ala Ser Val Met Pro Ala Trp Leu Tyr Ala Arg Pro Ser
                245                 250                 255

Arg Pro Arg Val Ala Leu Ser Leu Gly Val Ser Ala Arg Ala Phe Leu
                260                 265                 270

Lys Gly Asp Trp Gly Arg Thr Ala Lys Leu Leu Glu Ala Val Ala Glu
                275                 280                 285

Leu Asp Ile Glu Val Ile Ala Thr Leu Asn Asp Asn Gln Leu Ala Glu
                290                 295                 300

Ser Gly Pro Leu Pro Asp Asn Val His Thr Leu Asp Tyr Val Pro Leu
305                 310                 315                 320

Asp Gln Leu Leu Pro Thr Cys Ser Ala Val Ile His His Gly Ser Thr
                325                 330                 335

Gly Thr Phe Ala Ala Ala Ser Ala Ala Gly Leu Pro Gln Val Val Cys
                340                 345                 350

Asp Thr Asp Glu Pro Leu Leu Leu Phe Gly Asp Thr Pro Asp Gly
                355                 360                 365

Ile Ala Trp Asp Phe Thr Cys Gln Lys Gln Leu Thr Ala Thr Leu Thr
370                 375                 380

Ser Arg Val Val Thr Asp Tyr Gly Ala Gly Val Arg Val Asp His Gln
385                 390                 395                 400

Lys Gln Ser Ala Gly Gln Ile Arg Glu Gln Leu Arg Arg Val Leu Thr
                405                 410                 415

Glu Pro Ser Phe Arg Glu Gly Ala Arg Arg Ile Arg Glu Asp Arg Asn
                420                 425                 430

Ser Ala Pro Ser Pro Val Glu Leu Val Ser Leu Leu Val Glu Leu Thr
                435                 440                 445

Lys Arg His Arg Arg Asp Lys Glu Ala Asp Arg
450                 455
```

<210> SEQ ID NO 180

```
<211> LENGTH: 332
<212> TYPE: PRT
<213> ORGANISM: Streptomyces globisporus
<220> FEATURE:
<223> OTHER INFORMATION: orf1

<400> SEQUENCE: 180

Met Arg Met Leu Val Thr Gly Ala Gly Phe Ile Gly Ser Gln Phe
 1               5                  10                  15

Val Arg Ala Thr Leu His Gly Glu Leu Pro Gly Ser Glu Asp Ala Arg
                20                  25                  30

Val Thr Val Leu Asp Lys Leu Thr Tyr Ser Gly Asn Pro Ala Asn Leu
            35                  40                  45

Thr Ser Val Ala Ala His Pro Arg Tyr Thr Phe Val Gln Gly Asp Thr
     50                  55                  60

Val Asp Pro Arg Val Val Asp Glu Val Val Ala Gly His Asp Val Ile
 65                  70                  75                  80

Val His Phe Ala Ala Glu Ser His Val Asp Arg Ser Ile Asp Thr Ala
                 85                  90                  95

Thr Arg Phe Val Thr Thr Asn Val Leu Gly Thr Gln Thr Leu Leu Glu
                100                 105                 110

Ala Ala Leu Arg His Gly Val Gly Arg Phe Val His Val Ser Thr Asp
            115                 120                 125

Glu Val Tyr Gly Ser Ile Ala Ser Gly Ser Trp Thr Glu Asp Thr Pro
    130                 135                 140

Leu Ala Pro Asn Val Pro Tyr Ala Ala Ser Lys Ala Gly Ser Asp Leu
145                 150                 155                 160

Met Ala Leu Ala Trp His Arg Thr Arg Gly Leu Asp Val Val Thr
                165                 170                 175

Arg Cys Thr Asn Asn Tyr Gly Pro Tyr Gln Tyr Pro Glu Lys Val Ile
                180                 185                 190

Pro Leu Phe Val Thr Asn Ile Leu Asp Gly Leu Arg Val Pro Leu Tyr
                195                 200                 205

Gly Asp Gly Ala His Arg Arg Asp Trp Leu His Val Ser Asp His Cys
    210                 215                 220

Arg Ala Ile Gln Met Val Met Asn Ser Gly Arg Ala Gly Glu Val Tyr
225                 230                 235                 240

His Ile Gly Gly Gly Thr Glu Leu Ser Asn Glu Leu Thr Gly Leu
                245                 250                 255

Leu Leu Thr Ala Cys Gly Thr Asp Trp Ser Cys Val Asp Arg Val Ala
            260                 265                 270

Asp Arg Gln Gly His Asp Arg Arg Tyr Ser Leu Asp Ile Thr Lys Ile
            275                 280                 285

Arg Gln Glu Leu Gly Tyr Glu Pro Leu Val Ala Phe Glu Asp Gly Leu
    290                 295                 300

Ala Ala Thr Val Lys Trp Tyr His Glu Asn Arg Ser Trp Trp Gln Pro
305                 310                 315                 320

Leu Lys Glu Ala Ala Gly Leu Leu Asp Ala Val Gly
                325                 330

<210> SEQ ID NO 181
<211> LENGTH: 521
<212> TYPE: PRT
<213> ORGANISM: Streptomyces globisporus
<220> FEATURE:
<223> OTHER INFORMATION: orf2
```

-continued

```
<400> SEQUENCE: 181

Met Thr Ala Val Lys Glu Pro Thr Ser Arg Ala Gly Arg Arg Glu Trp
 1               5                  10                  15

Ile Ala Leu Val Val Leu Ser Leu Pro Thr Met Leu Leu Met Leu Asp
                20                  25                  30

Ile Asn Val Leu Met Leu Ala Leu Pro Gln Leu Ser Glu Asp Leu Gly
            35                  40                  45

Ala Ser Ser Thr Gln Gln Leu Trp Ile Thr Asp Ile Tyr Gly Phe Ala
        50                  55                  60

Ile Ala Gly Phe Leu Val Thr Met Gly Thr Leu Gly Asp Arg Ile Gly
 65                  70                  75                  80

Arg Arg Arg Leu Leu Leu Gly Gly Ala Ala Val Phe Ala Val Val Ser
                85                  90                  95

Val Val Ala Ala Phe Ser Asp Ser Ala Ala Met Leu Val Val Ser Arg
                100                 105                 110

Ala Val Leu Gly Val Ala Gly Ala Thr Val Met Pro Ser Thr Leu Ala
            115                 120                 125

Leu Ile Ser Asn Met Phe Glu Asp Pro Lys Glu Arg Gly Thr Ala Ile
        130                 135                 140

Ala Met Trp Ala Ser Ala Met Met Ala Gly Val Ala Leu Gly Pro Ala
145                 150                 155                 160

Val Gly Gly Leu Val Leu Ala Ala Phe Trp Trp Gly Ser Val Phe Leu
                165                 170                 175

Ile Ala Val Pro Val Met Leu Leu Val Val Thr Gly Pro Val Leu
                180                 185                 190

Leu Thr Glu Ser Arg Asp Pro Asp Ala Gly Arg Leu Asp Leu Leu Ser
            195                 200                 205

Ala Gly Leu Ser Leu Ala Thr Val Leu Pro Val Ile Tyr Gly Leu Lys
        210                 215                 220

Glu Leu Ala Arg Thr Gly Trp Asp Pro Leu Ala Ala Gly Ala Val Val
225                 230                 235                 240

Leu Gly Val Ile Phe Gly Ala Leu Phe Val Gln Arg Gln Arg Arg Leu
                245                 250                 255

Ala Asp Pro Met Leu Asp Leu Gly Leu Phe Ala Asp Arg Thr Leu Arg
                260                 265                 270

Ala Gly Leu Thr Val Ser Leu Val Asn Ala Val Ile Met Gly Gly Thr
            275                 280                 285

Gly Leu Met Val Ala Leu Tyr Leu Gln Thr Ile Ala Gly His Ser Pro
        290                 295                 300

Leu Ala Ala Gly Leu Trp Leu Leu Ile Pro Ala Cys Met Leu Val Val
305                 310                 315                 320

Gly Val Gln Leu Ser Asn Leu Leu Ala Gln Arg Met Pro Pro Ser Arg
                325                 330                 335

Val Leu Leu Gly Gly Leu Leu Ile Ala Ala Val Gly Gln Leu Leu Ile
            340                 345                 350

Thr Gln Val Asp Thr Glu Asp Thr Ala Leu Leu Ile Ala Ala Thr Thr
        355                 360                 365

Leu Ile Tyr Phe Gly Ala Ser Pro Val Gly Pro Ile Thr Thr Gly Ala
    370                 375                 380

Ile Met Gly Ala Ala Pro Pro Glu Lys Ala Gly Ala Ala Ser Ser Leu
385                 390                 395                 400

Ser Ala Thr Gly Gly Glu Phe Gly Val Ala Leu Gly Ile Ala Gly Leu
                405                 410                 415
```

```
Gly Ser Leu Gly Thr Val Val Tyr Ser Ala Gly Val Glu Val Pro Asp
            420                 425                 430

Ala Ala Gly Pro Ala Asp Ala Asp Ala Ala Gln Glu Ser Ile Ala Gly
            435                 440                 445

Ala Leu His Thr Ala Gly Gln Leu Ala Pro Gly Ser Ala Asp Ala Leu
            450                 455                 460

Leu Asp Ser Ala Arg Ala Ala Phe Thr Ser Gly Val Gln Ser Val Ala
465                 470                 475                 480

Ala Val Cys Ala Val Phe Ser Leu Ala Leu Ala Val Leu Ile Gly Thr
                485                 490                 495

Arg Leu Arg Asp Ile Ser Ala Met Asp His Gly His Gly Glu Glu Pro
            500                 505                 510

Ala Glu Asn Asp Ala Gln Pro Ala Thr
            515                 520

<210> SEQ ID NO 182
<211> LENGTH: 436
<212> TYPE: PRT
<213> ORGANISM: Streptomyces globisporus
<220> FEATURE:
<223> OTHER INFORMATION: orf3

<400> SEQUENCE: 182

Met Glu Tyr Trp Asn Ser Thr Ala Glu Thr Met Pro Arg Gln Glu Leu
 1               5                  10                  15

Glu Gln Trp Lys Trp Arg Arg Leu Gln Ala Ala Met Asp His Ala Arg
             20                  25                  30

Arg Leu Ser Pro Phe Trp Arg Glu Arg Leu Pro Glu Asn Ile Thr Ser
         35                  40                  45

Met Ala Asp Tyr Ala Ala Arg Val Pro Leu Leu Arg Lys Ala Asp Leu
     50                  55                  60

Leu Ala Ala Glu Ala Ala Ser Pro Pro Tyr Gly Thr Trp Pro Ser Leu
 65                  70                  75                  80

Asp Pro Ala Leu Gly Val Arg His His Gln Thr Ser Gly Thr Ser Gly
                 85                  90                  95

Asn Pro Pro Ile Arg Thr Phe Asp Thr Glu Arg Asp Trp Ala Trp Cys
            100                 105                 110

Val Asp Thr Phe Cys Thr Ala Leu His Ser Met Gly Val Arg Pro His
        115                 120                 125

His Lys Gly Leu Val Ala Phe Gly Tyr Gly Leu Phe Ala Gly Phe Trp
    130                 135                 140

Gly Met His Tyr Gly Leu Glu Arg Met Gly Ala Thr Val Ile Pro Ala
145                 150                 155                 160

Gly Gly Leu Asp Ser Arg Ser Arg Val Arg Leu Val Asp Tyr Gln
                165                 170                 175

Ile Glu Val Leu Gly Leu Thr Pro Ser Tyr Ala Met Arg Leu Ile Glu
            180                 185                 190

Thr Ala Arg Glu Met Gly Ile Asp Leu Ala Arg Glu Ala Asn Val Gln
        195                 200                 205

Ile Ile Leu Ala Gly Ala Glu Pro Arg Ser Ala Phe Thr Thr Arg Thr
    210                 215                 220

Ile Glu Glu Ala Phe Gly Ala Arg Val Phe Asn Ala Ala Gly Thr Thr
225                 230                 235                 240

Glu Phe Gly Gly Val Phe Met Phe Glu Cys Thr Ala Arg Arg Glu Ala
                245                 250                 255
```

-continued

```
Cys His Ile Ile Glu Pro Ser Cys Ile Glu Glu Val Leu Asp Pro Val
            260                 265                 270

Thr Glu Gln Pro Val Gly Tyr Gly Glu Glu Val Arg Val Thr Thr
        275                 280                 285

Gly Leu Asn Arg Glu Gly Met Gln Leu Phe Arg His Trp Thr Glu Asp
    290                 295                 300

Val Val Val Lys Arg Pro His Thr Glu Cys Gly Cys Gly Arg Thr Trp
305                 310                 315                 320

Asp Phe Tyr Asp Gly Ile Leu Arg Val Asp Asp Met Arg Lys
                325                 330                 335

Ile Arg Gly Val Ser Ile Thr Pro Val Met Ile Glu Asp Val Leu Arg
            340                 345                 350

Gly Phe Asp Glu Val Asn Glu Phe His Ser Ser Ile Arg Thr Val Arg
        355                 360                 365

Gly Leu Asp Thr Ile His Val Lys Val Glu Ala Gly Asp Ile Ser Gly
    370                 375                 380

Glu Ala Glu Ser Leu Cys Gly Arg Ile Thr Glu Glu Phe Lys Arg
385                 390                 395                 400

Glu Ile Gly Ile Arg Pro Gln Val Glu Leu Thr Pro Ala Gly Ser Leu
                405                 410                 415

Pro Arg Ser Lys Trp Lys Ala Arg Leu His Asp Glu Arg Glu Leu
            420                 425                 430

Ala Pro Gln Ala
        435
```

<210> SEQ ID NO 183
<211> LENGTH: 527
<212> TYPE: PRT
<213> ORGANISM: Streptomyces globisporus
<220> FEATURE:
<223> OTHER INFORMATION: orf4

<400> SEQUENCE: 183

```
Met Pro His Gly Ala Glu Arg Glu Ala Ser Pro Ala Glu Glu Ser Ala
1               5                   10                  15

Gly Thr Arg Pro Leu Thr Gly Glu Glu Tyr Leu Glu Ser Leu Arg Asp
            20                  25                  30

Ala Arg Glu Val Tyr Leu Asp Gly Ser Arg Val Lys Asp Val Thr Ala
        35                  40                  45

His Pro Ala Phe His Asn Pro Ala Arg Met Thr Ala Arg Leu Tyr Asp
    50                  55                  60

Ser Leu His Asp Pro Ala Gln Lys Ala Val Leu Thr Ala Pro Thr Asp
65                  70                  75                  80

Ala Gly Asp Gly Phe Thr His Arg Phe Phe Thr Ala Pro Arg Ser Val
                85                  90                  95

Asp Asp Leu Val Lys Asp Gln Ala Ala Ile Ala Ser Trp Ala Arg Lys
            100                 105                 110

Ser Tyr Gly Trp Met Gly Arg Ser Pro Asp Tyr Lys Ala Ser Phe Leu
        115                 120                 125

Gly Thr Leu Gly Ala Asn Ala Asp Phe Tyr Glu Pro Phe Ala Asp Asn
    130                 135                 140

Ala Arg Arg Trp Tyr Arg Glu Ser Gln Glu Lys Val Leu Tyr Trp Asn
145                 150                 155                 160

His Ala Phe Leu His Pro Pro Val Asp Arg Ser Leu Pro Ala Asp Glu
                165                 170                 175
```

```
Val Gly Asp Val Phe Ile His Val Glu Arg Glu Thr Asp Ala Gly Leu
            180                 185                 190
Val Val Ser Gly Ala Lys Val Val Ala Thr Gly Ser Ala Leu Thr His
        195                 200                 205
Ala Ala Phe Ile Ser His Trp Gly Leu Pro Ile Lys Asp Arg Lys Phe
        210                 215                 220
Ala Leu Val Ala Thr Val Pro Met Asp Ala Asp Gly Leu Lys Val Ile
225                 230                 235                 240
Cys Arg Pro Ser Tyr Ser Ala Asn Ala Ala Thr Thr Gly Ser Pro Phe
                245                 250                 255
Asp Asn Pro Leu Ser Ser Arg Leu Asp Glu Asn Asp Ala Ile Leu Val
            260                 265                 270
Leu Asp Gln Val Leu Ile Pro Trp Glu Asn Val Phe Val Tyr Gly Asn
        275                 280                 285
Leu Gly Lys Val His Leu Leu Ala Gly Gln Ser Gly Met Ile Glu Arg
        290                 295                 300
Ala Thr Phe His Gly Cys Thr Arg Leu Ala Val Lys Leu Glu Phe Ile
305                 310                 315                 320
Ala Gly Leu Leu Ala Lys Ala Leu Asp Ile Thr Gly Ala Lys Asp Phe
                325                 330                 335
Arg Gly Val Gln Thr Arg Leu Gly Glu Val Leu Ala Trp Arg Asn Leu
            340                 345                 350
Phe Trp Ser Leu Ser Asp Ala Ala Arg Asn Pro Val Pro Trp Lys
        355                 360                 365
Asn Gly Thr Leu Leu Pro Asn Pro Gln Ala Gly Met Ala Tyr Arg Trp
        370                 375                 380
Phe Met Gln Ile Gly Tyr Pro Arg Val Leu Glu Ile Val Gln Gln Asp
385                 390                 395                 400
Val Ala Ser Gly Leu Met Tyr Val Asn Ser Ser Thr Glu Asp Phe Arg
                405                 410                 415
Asn Pro Glu Thr Gly Pro Tyr Leu Glu Lys Tyr Leu Arg Gly Ser Asp
            420                 425                 430
Gly Ala Gly Ala Val Glu Arg Val Lys Val Met Lys Leu Leu Trp Asp
        435                 440                 445
Ala Val Gly Ser Asp Phe Gly Gly Arg His Glu Leu Tyr Glu Arg Asn
        450                 455                 460
Tyr Ser Gly Asn His Glu Asn Thr Arg Ile Glu Leu Leu Ser Gln
465                 470                 475                 480
Thr Ala Ser Gly Lys Leu Asp Ser Tyr Met Asp Phe Ala Gln Ala Cys
                485                 490                 495
Met Asp Glu Tyr Asp Leu Asp Gly Trp Thr Ala Pro Asp Leu Glu Ser
            500                 505                 510
Phe His Ala Met Arg Ser Ala Ser Arg Asp Leu Leu Gly Gly Leu
        515                 520                 525

<210> SEQ ID NO 184
<211> LENGTH: 278
<212> TYPE: PRT
<213> ORGANISM: Streptomyces globisporus
<220> FEATURE:
<223> OTHER INFORMATION: orf22

<400> SEQUENCE: 184

Met Ser Ser Thr Arg Glu Lys Ala Ala Lys Val Glu Ser Thr Thr Val
1               5                   10                  15
```

-continued

Ser Ala Asp Gly Thr Thr Ala Ile Phe Asp Lys Ser Gly Glu Gly Pro
            20                  25                  30

Ala Val Ile Leu Val Ala Ser Ala Leu Ala Asp Arg Ser Asp Ala Lys
        35                  40                  45

Lys Leu Ala Gly Leu Leu Ala Glu His Phe Thr Val Val Asn Tyr Asp
    50                  55                  60

Arg Arg Gly Arg Gly Ala Ser Ala Asp Gly Pro Ala Tyr Ala Val Glu
65                  70                  75                  80

Arg Glu Ile Glu Asp Ile Ala Ala Leu Ile Asp Gln Val Gly Gly Ser
                85                  90                  95

Ala Ser Leu Phe Gly Ser Ser Gly Ala Val Leu Ala Leu Arg Ala
            100                 105                 110

Ala Ala Ala Gly Leu Lys Val Asn Lys Leu Ala Val Tyr Glu Pro Pro
            115                 120                 125

Phe Ser Val Thr Ser Asp Gly Phe Gly Pro Pro Ala Gly Phe Gly Gly
        130                 135                 140

Gln Ile Asp Ser Leu Leu Ala Glu Asp Arg Arg Ser Asp Ala Val Lys
145                 150                 155                 160

Ala Phe Met Val Lys Ala Gln Gly Met Pro Ser Phe Met Val Gly Ala
                165                 170                 175

Met Arg Leu Met Pro Gly Val Trp Ser Asn Leu Lys Gly Leu Ala Asn
            180                 185                 190

Thr Leu Pro Tyr Asp Ile Ala Val Met Gly Asp Thr Gln Gln Gly Lys
        195                 200                 205

Pro Leu Pro Ala Glu Pro Trp Ser Ala Ala Ser Ala Pro Thr Leu Val
    210                 215                 220

Leu Thr Gly Ser Lys Ser Pro Asp Gly Phe Gln Arg Ala Ala Lys Glu
225                 230                 235                 240

Leu Thr Gly Val Leu Pro Asp Ala Ser His Arg Thr Leu Asn Gly Leu
                245                 250                 255

Asn His Gly Ala Val Ala Met Ala Pro Lys Lys Leu Ala Pro Glu Leu
            260                 265                 270

Ile Gly Phe Leu Arg Gly
        275

<210> SEQ ID NO 185
<211> LENGTH: 140
<212> TYPE: PRT
<213> ORGANISM: Streptomyces globisporus
<220> FEATURE:
<223> OTHER INFORMATION: orf18

<400> SEQUENCE: 185

Met Thr Ser Thr Asp Ser Thr Thr Ser Ala Pro Asp Ala Ala Leu Ala
1               5                   10                  15

Ala Val Ala Ala Leu Pro Ala Arg Ile Val Ala Ala Trp Ala Asp His
            20                  25                  30

Asp Ala Asp Arg Phe Ala Asp Val Phe Ala Glu Asp Gly Thr Met Ile
        35                  40                  45

Leu Pro Gly Leu Phe Arg Lys Gly Arg Glu Asn Ile Arg Thr His Met
    50                  55                  60

Ala Ala Ala Phe Ala Gly Pro Tyr Lys Gly Thr Arg Val Ile Gly Ser
65                  70                  75                  80

Pro Ile Asp Ala Arg Leu Leu Gly Asp Gly Ile Ala Leu Leu Ile Thr
                85                  90                  95

```
Glu Gly Gly Ile Leu Ala Pro Gly Thr Glu Ala Ser Gly Asp Gly
            100                 105                 110

Ala Val Arg Ala Ser Trp Leu Ala Val Glu Gln Asp Gly Gln Trp Arg
            115                 120                 125

Leu Ala Ala Tyr Gln Asn Ser Pro Arg Gly Asn Asp
    130                 135                 140

<210> SEQ ID NO 186
<211> LENGTH: 441
<212> TYPE: PRT
<213> ORGANISM: Streptomyces globisporus
<220> FEATURE:
<223> OTHER INFORMATION: orf5

<400> SEQUENCE: 186

Met Pro Ala Val Asn Gly Ser Val Gln Ser Gly Gln Ser His Arg Arg
  1               5                  10                  15

Ser Val Val Ala Thr Val Val Gly Asn Phe Val Glu Ser Phe Asp Trp
             20                  25                  30

Leu Ala Tyr Gly Leu Phe Ala Pro Leu Phe Ala Gln Phe Phe Pro
         35                  40                  45

Ser Ser Asn Gln Phe Thr Ser Leu Leu Gly Ala Phe Ala Val Phe Gly
 50                  55                  60

Thr Gly Met Leu Phe Arg Pro Ile Gly Gly Val Leu Leu Gly Arg Leu
 65                  70                  75                  80

Ala Asp Arg Arg Gly Arg Arg Pro Ala Leu Met Leu Ala Ile Gly Leu
                 85                  90                  95

Met Thr Gly Gly Ser Thr Leu Ile Ala Val Val Pro Thr Tyr Glu His
             100                 105                 110

Ile Gly Ile Leu Ala Pro Leu Leu Leu Leu Ala Arg Leu Ala Gln
             115                 120                 125

Gly Val Ser Ser Gly Gly Glu Trp Thr Ala Ala Thr Tyr Leu Met
    130                 135                 140

Glu Ile Ala Pro Lys Asn Arg Arg Cys Leu Tyr Ser Ser Leu Phe Ser
145                 150                 155                 160

Val Thr Thr Met Ala Gly Pro Phe Val Ala Ser Leu Leu Gly Ala Gly
                 165                 170                 175

Leu Gly Val Trp Leu Gly Thr Ala Thr Met Glu Ala Trp Gly Trp Arg
             180                 185                 190

Val Pro Phe Leu Leu Gly Val Phe Gly Val Ile Leu Leu Phe Leu
             195                 200                 205

Arg Arg Arg Leu Thr Glu Thr Glu Val Phe Arg Arg Glu Val Arg Pro
    210                 215                 220

Arg Ala Arg Arg Gly Ser Leu Gly Gln Leu Ile Gly Ala His Arg Pro
225                 230                 235                 240

Gln Val Leu Leu Ala Val Met Leu Val Ala Gly Leu Gly Val Ile Gly
                 245                 250                 255

Gly Thr Trp Ser Thr Ala Val Pro Ala Met Gly His Arg Leu Ile Gly
             260                 265                 270

Ser Gln Thr Met Phe Trp Val Val Cys Val Thr Gly Ser Val Ile
         275                 280                 285

Leu Leu Gln Val Pro Ile Gly Leu Leu Ala Asp Arg Val Glu Pro Gly
    290                 295                 300

Arg Phe Leu Ile Val Ser Ser Val Phe Ala Ala Val Gly Ser Tyr
305                 310                 315                 320
```

```
Ala Tyr Leu Thr Val Gln Asp Ser Phe Ala Ser Leu Ala Phe Thr Tyr
            325                 330                 335

Ser Thr Gly Val Ile Phe Leu Gly Cys Val Thr Met Val Leu Pro Lys
            340                 345                 350

Met Leu Ser Arg Ile Phe Pro Pro Gln Ile Arg Gly Leu Gly Ile Gly
            355                 360                 365

Leu Pro His Ala Ser Thr Thr Ala Leu Leu Gly Ala Gly Pro Leu
            370                 375                 380

Leu Ala Ala Tyr Ser Asp Glu Arg Gly Ala Ser Gly Trp Phe Ile Ala
385                 390                 395                 400

Ala Val Met Ala Ala Val Leu Leu Ala Trp Pro Ala Thr Leu Trp Glu
            405                 410                 415

Arg Arg Leu Phe Arg Ala Arg Thr Ala Pro Gly Ser Glu Pro Val Pro
            420                 425                 430

Glu Ser Ala Val Ala Arg Pro Val Gly
            435                 440
```

<210> SEQ ID NO 187
<211> LENGTH: 459
<212> TYPE: PRT
<213> ORGANISM: Streptomyces globisporus
<220> FEATURE:
<223> OTHER INFORMATION: orf23

<400> SEQUENCE: 187

```
Met Thr Thr Ser Asp Thr Thr Asp Arg Ser Gln Asp Gly Val Pro Pro
1               5                   10                  15

Leu Ser Phe His Gln Glu Phe Leu Cys Met Phe Asp Ser Gly Asn Asp
            20                  25                  30

Gly Ala Asp Val Gly Pro Phe Gly Pro Met Tyr His Ile Val Gly Ala
            35                  40                  45

Trp Arg Leu Thr Gly Gly Ile Asp Glu Glu Thr Leu Arg Glu Ala Leu
            50                  55                  60

Gly Asp Val Val Arg His Glu Ala Leu Arg Thr Ser Leu Val Arg
65                  70                  75                  80

Glu Gly Gly Thr His Arg Pro Glu Ile Leu Pro Ala Gly Pro Ala Ala
            85                  90                  95

Leu Glu Val Arg Asp Leu Gly Asp Val Asp Glu Ser Glu Arg Val Arg
            100                 105                 110

Arg Gly Glu Glu Leu Leu Asn Glu Val Glu Ser Thr Gly Leu Ser Val
            115                 120                 125

Arg Glu Leu Pro Leu Leu Arg Ala Val Leu Gly Arg Phe Asp Gln Lys
            130                 135                 140

Asp Ala Val Leu Val Leu Ile Ala His His Thr Ala Ala Asp Ala Trp
145                 150                 155                 160

Ala Met His Val Ile Ala Arg Asp Leu Leu Asn Leu Tyr Ala Ala Arg
            165                 170                 175

Arg Gly Asn Pro Val Pro Pro Leu Pro Glu Pro Ala Gln His Ala Glu
            180                 185                 190

Phe Ala Arg Trp Glu Arg Glu Ala Ala Glu Pro Arg Val Ala Val
            195                 200                 205

Ser Lys Glu Phe Trp Arg Lys Arg Leu Gln Gly Ala Arg Ile Ile Gly
            210                 215                 220

Leu Glu Thr Asp Ile Pro Arg Ser Ala Gly Leu Pro Lys Gly Thr Ala
225                 230                 235                 240
```

```
Trp Gln Arg Phe Ala Val Arg Gly Glu Leu Ala Asp Ala Val Glu
                245                 250                 255

Phe Ser Arg Ala Ala Lys Cys Ser Pro Phe Met Thr Met Phe Ala Ala
                260                 265                 270

Tyr Gln Val Leu Leu His Arg Arg Thr Gly Glu Leu Asp Ile Thr Val
                275                 280                 285

Pro Thr Phe Ser Gly Gly Arg Asn Asn Ser Arg Phe Glu Asp Thr Val
                290                 295                 300

Gly Ser Phe Ile Asn Phe Leu Pro Leu Arg Thr Asp Leu Ser Gly Cys
305                 310                 315                 320

Ala Ser Phe Arg Glu Val Val Leu Arg Thr Arg Thr Cys Gly Glu
                325                 330                 335

Ala Phe Thr His Glu Leu Pro Phe Ser Arg Leu Ile Pro Glu Val Pro
                340                 345                 350

Glu Leu Met Ala Ser Ala Ala Ser Asp Asn His Gln Ile Ser Val Phe
                355                 360                 365

Gln Ala Val His Ala Pro Ala Ser Glu Gly Pro Glu Gln Ala Gly Asp
                370                 375                 380

Leu Thr Tyr Ser Lys Ile Trp Glu Arg Gln Leu Ser Gln Ala Glu Gly
385                 390                 395                 400

Ser Asp Ile Pro Asp Gly Val Leu Trp Ser Ile His Ile Asp Pro Ser
                405                 410                 415

Gly Ser Met Ala Gly Ser Leu Gly Tyr Asn Thr Asn Arg Phe Lys Asp
                420                 425                 430

Glu Thr Met Ala Ala Phe Leu Ala Asp Tyr Leu Asp Val Leu Glu Asn
                435                 440                 445

Ala Val Ala Arg Pro Asp Ala Pro Phe Thr Ser
    450                 455
```

<210> SEQ ID NO 188
<211> LENGTH: 93
<212> TYPE: PRT
<213> ORGANISM: Streptomyces globisporus
<220> FEATURE:
<223> OTHER INFORMATION: orf26

<400> SEQUENCE: 188

```
Met Ser Thr Val Ser Asp Thr Ala Ala Gly Ser Ser Leu Glu Glu Lys
1               5                   10                  15

Val Thr Arg Ile Trp Thr Gly Val Leu Gly Thr Ser Gly Glu Glu Gly
                20                  25                  30

Ala Thr Phe Ile Glu Leu Gly Gly Gln Ser Val Ser Ala Val Arg Ile
                35                  40                  45

Ala Thr Arg Ile Gln Glu Glu Leu Asp Ile Trp Val Asp Ile Gly Val
        50                  55                  60

Leu Phe Asp Asp Pro Asp Leu Pro Thr Phe Ile Ala Ala Val Val Arg
65                  70                  75                  80

Thr Ala Asp Ala Ala Gly Gly Glu Gly Ser Gly Thr Gln
                85                  90
```

<210> SEQ ID NO 189
<211> LENGTH: 499
<212> TYPE: PRT
<213> ORGANISM: Streptomyces globisporus
<220> FEATURE:
<223> OTHER INFORMATION: orf24

<400> SEQUENCE: 189

Met Ala Leu Thr Gln Val Glu Thr Glu Ile Val Pro Val Ser Val Asp
1               5                   10                  15

Gly Glu Thr Leu Thr Val Glu Ala Val Arg Val Ala Glu Glu Arg
            20                  25                  30

Ala Thr Val Asp Val Pro Ala Glu Ser Ala Lys Ala Gln Lys Ser Arg
        35                  40                  45

Glu Ile Phe Glu Gly Ile Ala Glu Gln Asn Ile Pro Ile Ala Glu Asp
    50                  55                  60

Glu Ala Arg Ala Ile Val Ala Ala Arg Leu Asn Thr Leu Ala Lys Gly
65                  70                  75                  80

His Ser Ala Val Arg Pro Ile Ile Leu Glu Arg Leu Ala Gln Tyr Leu
                85                  90                  95

Asn Glu Gly Ile Thr Pro Ala Ile Pro Glu Ile Gly Ser Leu Gly Ala
            100                 105                 110

Ser Gly Asp Leu Ala Pro Leu Ser His Val Ala Ser Thr Leu Ile Gly
        115                 120                 125

Glu Gly Tyr Val Leu Arg Asp Gly Arg Pro Val Glu Thr Ala Gln Val
    130                 135                 140

Leu Ala Glu Arg Gly Ile Glu Pro Leu Glu Leu Arg Phe Lys Glu Gly
145                 150                 155                 160

Leu Ala Leu Ile Asn Gly Thr Ser Gly Met Thr Gly Leu Gly Ser Leu
                165                 170                 175

Val Val Gly Arg Ala Leu Glu Gln Ala Gln Gln Ala Glu Ile Val Thr
            180                 185                 190

Ala Leu Leu Ile Glu Ala Val Arg Gly Ser Thr Ser Pro Phe Leu Ala
        195                 200                 205

Glu Gly His Asp Ile Ala Arg Pro His Glu Gly Gln Ile Asp Thr Ala
    210                 215                 220

Ala Asn Met Arg Ala Leu Met Arg Gly Ser Gly Leu Thr Val Glu His
225                 230                 235                 240

Ala Asp Leu Arg Arg Glu Leu Gln Lys Asp Lys Glu Ala Gly Lys Asp
                245                 250                 255

Val Gln Arg Ser Glu Ile Tyr Leu Gln Lys Ala Tyr Ser Leu Arg Ala
            260                 265                 270

Ile Pro Gln Val Val Gly Ala Val Arg Asp Thr Leu Tyr His Ala Arg
        275                 280                 285

His Lys Leu Arg Ile Glu Leu Asn Ser Ala Asn Asp Asn Pro Leu Phe
    290                 295                 300

Phe Glu Gly Lys Glu Ile Phe His Gly Ala Asn Phe His Gly Gln Pro
305                 310                 315                 320

Ile Ala Phe Ala Met Asp Phe Val Thr Ile Ala Leu Thr Gln Leu Gly
                325                 330                 335

Val Leu Ala Glu Arg Gln Ile Asn Arg Val Leu Asn Arg His Leu Ser
            340                 345                 350

Tyr Gly Leu Pro Glu Phe Leu Val Ser Gly Asp Pro Gly Leu His Ser
        355                 360                 365

Gly Phe Ala Gly Ala Gln Tyr Pro Ala Thr Ala Leu Val Ala Glu Asn
    370                 375                 380

Arg Thr Ile Gly Pro Ala Ser Thr Gln Ser Val Pro Ser Asn Gly Asp
385                 390                 395                 400

Asn Gln Asp Val Val Ser Met Gly Leu Ile Ser Ala Arg Asn Ala Arg
                405                 410                 415

```
Arg Val Leu Ser Asn Asn Lys Ile Leu Ala Val Glu Tyr Leu Ala
            420                 425                 430

Ala Ala Gln Ala Val Asp Ile Ser Gly Arg Phe Asp Gly Leu Ser Pro
        435                 440                 445

Ala Ala Lys Ala Thr Tyr Glu Ala Val Arg Arg Leu Val Pro Thr Leu
        450                 455                 460

Gly Val Asp Arg Tyr Met Ala Asp Ile Glu Leu Val Ala Asp Ala
465                 470                 475                 480

Leu Ser Arg Gly Glu Phe Leu Arg Ala Ile Ala Arg Glu Thr Asp Ile
            485                 490                 495

Gln Leu Arg

<210> SEQ ID NO 190
<211> LENGTH: 519
<212> TYPE: PRT
<213> ORGANISM: Streptomyces globisporus
<220> FEATURE:
<223> OTHER INFORMATION: orf25

<400> SEQUENCE: 190

Met Thr Arg Pro Val His Ala Ser Val Arg Arg His Ala Glu His Asp
 1               5                  10                  15

Gly Val Ala Val Ser Phe Gly Gly Thr Arg Thr Ser Tyr Ala Glu Leu
            20                  25                  30

Thr Ala Glu Leu Thr Ala Asp Ala Ala Arg Val Ala Ser Ala Leu Thr
        35                  40                  45

Ala Ala Gly Ala Gly His Gly Ser Pro Val Ala Val Arg Met Gln Pro
    50                  55                  60

Gly Ala Arg Arg Ile Ala Val Leu Leu Gly Val Leu Glu Ala Gly Ala
65                  70                  75                  80

His Leu Ala Trp Phe Ala Pro Asp Gly Ala Gly Glu Arg His Arg Ser
                85                  90                  95

Met Leu Ser Asp Leu Arg Pro Ala Cys Leu Val Leu Asp Gly Asp Pro
            100                 105                 110

Gln Glu Asp Pro Leu Ala Leu Trp Tyr Ala Gly Glu Pro Gly Ala Thr
        115                 120                 125

Leu Leu Asp Ala Ser Ser Val Leu Gly Pro Arg Pro Ala Ala Gly Pro
    130                 135                 140

Asp Ala Thr Thr Ala Ala Gly Pro Gly Leu Ala Asp Leu Ala Tyr Val
145                 150                 155                 160

Ala Phe Thr Ser Gly Ser Thr Gly Arg Pro Lys Gly Ile Ala Gln Ser
                165                 170                 175

His Ala Ala Leu Gly Gln Phe Ala Gly Trp Met Gly Glu Arg Phe Ala
            180                 185                 190

Met Gly Pro Gly Ala Arg Val Ala Gln Trp Val Ser Pro Glu His Asp
        195                 200                 205

Pro Ala Leu Ala Glu Val Phe Ala Thr Leu Val Ala Gly Gly Thr Leu
    210                 215                 220

Cys Pro Val Pro Glu Arg Val Arg Val Asn Pro Asp Lys Leu Val Pro
225                 230                 235                 240

Trp Leu Val Gln Glu Arg Ile Thr His Leu Gln Thr Val Pro Ser Phe
                245                 250                 255

Ala Arg Asp Leu Leu Gly Val Ile Thr Ala Ser Asp Pro Gly Asp Arg
            260                 265                 270
```

```
Pro Gly Thr Leu Gly His Leu Leu Met Gly Glu Ala Leu Pro Gly
        275                 280                 285

Glu Leu Val Asp Gly Leu Arg Ala Ala Leu Pro Arg Thr Arg Leu Ile
    290                 295                 300

Asn Leu Tyr Gly Pro Thr Glu Thr Ile Ala Ala Thr Trp His Glu Ile
305                 310                 315                 320

Thr Gly Pro Val Thr Gly Pro Ala Pro Ile Gly Tyr Pro Leu Pro Gly
                325                 330                 335

Arg Gln Val Leu Val Val Asp Ala Asp Arg Pro Ser Pro Ala Gly
        340                 345                 350

Val Thr Gly Glu Leu Val Ile Arg Ser Pro Tyr Val Thr Pro Gly Tyr
        355                 360                 365

Leu Ala Val Glu Gly Gly Pro Asp His Ser Ala Leu Phe Ala Pro Leu
    370                 375                 380

Ala Gly Leu Ala Pro Asp Gly Asp Arg Trp Tyr Arg Thr Gly Asp Leu
385                 390                 395                 400

Ala Arg Val Arg Phe Asp Gly Ala Leu Glu Phe Arg Gly Arg Lys Asp
                405                 410                 415

Phe Gln Val Lys Leu Phe Gly Asn Arg Leu Glu Leu Thr Glu Ile Glu
        420                 425                 430

Ala Ala Leu Asn Arg Asp Pro Ser Val Leu Glu Cys Ala Val Leu Pro
    435                 440                 445

His Val Asn Gly Gln Gly Leu Val Thr Arg Leu Ala Val Tyr Val Val
    450                 455                 460

Pro Gln Gly Glu Gly Arg Glu Asp Val Arg Ala Asp Ile Arg Ala Trp
465                 470                 475                 480

Arg Ser His Leu Arg Gly Gln Phe Gly Pro Leu Ala Leu Pro Ala Val
                485                 490                 495

Phe Thr Arg Leu Thr Ser Arg Leu Pro Arg Asn Ala Ala Gly Lys Val
        500                 505                 510

Asp Arg Ser Arg Leu Thr Arg
        515

<210> SEQ ID NO 191
<211> LENGTH: 692
<212> TYPE: PRT
<213> ORGANISM: Streptomyces globisporus
<220> FEATURE:
<223> OTHER INFORMATION: orf27

<400> SEQUENCE: 191

Val Pro Gly Asp Arg Arg Gly Lys Trp Leu Val Leu Ala Ala Trp Leu
1               5                   10                  15

Ile Ile Ala Met Ala Leu Gly Pro Leu Ala Gly Lys Leu Ala Asp Val
                20                  25                  30

Gln Asp Ser Ser Ala Asn Ala Phe Leu Pro Arg Ser Ser Glu Ser Ala
        35                  40                  45

Lys Leu Asn Lys Glu Leu Glu Lys Phe Arg Ala Asp Glu Leu Met Pro
    50                  55                  60

Ala Val Val Tyr Ser Ala Asp Gly Ser Leu Pro Ala Glu Gly Arg
65                  70                  75                  80

Ala Lys Ala Glu Lys Asp Ile Ala Ala Phe Gln Glu Leu Ala Ala Glu
                85                  90                  95

Gly Glu Lys Val Glu Ala Pro Leu Glu Ser Glu Asp Gly Gln Ala Leu
            100                 105                 110
```

-continued

```
Met Val Val Pro Leu Ile Ser Asp Ala Asp Ile Val Ala Thr Thr
        115                 120                 125
Lys Lys Val Arg Asp Val Ala Asp Ala Asn Ala Pro Pro Gly Val Ala
130                 135                 140
Ile Glu Val Gly Gly Pro Ala Gly Ser Thr Thr Asp Ala Ala Gly Ala
145                 150                 155                 160
Phe Glu Ser Leu Asp Ser Met Leu Met Met Val Thr Gly Leu Val Val
                165                 170                 175
Ala Ile Leu Leu Leu Ile Thr Tyr Arg Ser Pro Ile Leu Trp Leu Leu
                180                 185                 190
Pro Leu Leu Ser Val Gly Phe Ala Ser Val Leu Thr Gln Val Gly Thr
            195                 200                 205
Tyr Met Leu Ala Lys Tyr Ala Gly Leu Pro Val Asp Pro Gln Ser Ser
    210                 215                 220
Gly Val Leu Met Val Leu Val Phe Gly Val Gly Thr Asp Tyr Ala Leu
225                 230                 235                 240
Leu Leu Ile Ala Arg Tyr Arg Glu Glu Leu Arg Arg Glu Gln Asp Arg
                245                 250                 255
His Val Ala Met Lys Thr Ala Leu Arg Arg Ser Gly Pro Ala Ile Leu
                260                 265                 270
Ala Ser Ala Gly Thr Ile Ala Ile Gly Leu Val Cys Leu Val Leu Ala
            275                 280                 285
Asp Val Asn Ser Ser Arg Ser Met Gly Leu Val Gly Ala Ile Gly Val
    290                 295                 300
Val Cys Ala Leu Leu Ala Met Val Thr Ile Leu Pro Ala Leu Leu Val
305                 310                 315                 320
Ile Leu Gly Arg Trp Val Phe Trp Pro Phe Val Pro Arg Trp Thr Pro
                325                 330                 335
Glu Ser Ala Ala Ala Pro Glu Ala Pro Ala Ser His Ser Arg Trp Glu
                340                 345                 350
Arg Ile Gly Ser Val Thr Ala Ala Arg Pro Arg Arg Ala Trp Val Leu
            355                 360                 365
Ser Leu Ala Ala Thr Gly Leu Leu Ala Leu Ser Ser Leu Gly Leu Asp
    370                 375                 380
Met Gly Leu Thr Gln Ser Glu Leu Leu Gln Thr Lys Pro Glu Ser Val
385                 390                 395                 400
Val Ala Gln Glu Arg Ile Ser Ala His Tyr Pro Ser Gly Ser Ser Asp
                405                 410                 415
Pro Ala Thr Val Val Ala Pro Ser Ala Asp Val Ala Glu Val Arg Arg
                420                 425                 430
Ala Ala Glu Gly Thr Asp Gly Val Val Ser Val Gln Asp Gly Pro Thr
            435                 440                 445
Thr Pro Asp Gly Glu Leu Thr Met Leu Ser Val Leu Lys Asp Val
    450                 455                 460
Pro Asp Ser Ser Gly Ala Lys Asp Thr Ile Asp Ala Leu Arg Asp Asn
465                 470                 475                 480
Thr Asp Ala Leu Val Gly Gly Thr Thr Ala Gln Ser Leu Asp Thr Gln
                485                 490                 495
Arg Ala Ser Val Arg Asp Leu Trp Val Thr Val Pro Ala Val Leu Leu
                500                 505                 510
Val Val Leu Leu Val Leu Ile Trp Leu Leu Arg Ser Val Thr Gly Pro
            515                 520                 525
Leu Ile Met Leu Gly Thr Val Val Val Ser Phe Phe Ala Ala Leu Gly
```

-continued

```
            530                 535                 540
Ala Ser Asn Leu Leu Phe Glu Tyr Val Met Gly His Ala Gly Val Asp
545                 550                 555                 560

Trp Ser Val Pro Leu Leu Gly Phe Val Tyr Leu Val Ala Leu Gly Ile
                565                 570                 575

Asp Tyr Asn Ile Phe Leu Met His Arg Val Lys Glu Glu Val Ala Leu
                580                 585                 590

His Gly His Ala Lys Gly Val Leu Thr Gly Leu Thr Thr Thr Gly Gly
            595                 600                 605

Val Ile Thr Ser Ala Gly Val Val Leu Ala Ala Thr Phe Ala Val Ile
610                 615                 620

Ala Thr Leu Pro Leu Val Pro Met Ala Gln Met Gly Val Val Val Gly
625                 630                 635                 640

Leu Gly Ile Leu Leu Asp Thr Phe Leu Val Arg Thr Ile Leu Leu Pro
                645                 650                 655

Ala Leu Ala Leu Asp Leu Gly Pro Arg Phe Trp Trp Pro Gly Ala Leu
                660                 665                 670

Ser Lys Thr Ser Gly Gly Pro Ala Pro Val Arg Glu Asp Arg Thr Ser
            675                 680                 685

Gln Pro Val Gly
    690
```

<210> SEQ ID NO 192
<211> LENGTH: 334
<212> TYPE: PRT
<213> ORGANISM: Streptomyces globisporus
<220> FEATURE:
<223> OTHER INFORMATION: orf28

<400> SEQUENCE: 192

```
Val Leu Gly Asp Glu Asp Gly Lys Ala Ala Glu Leu Trp Ser Met Ala
 1               5                  10                  15

Asn Leu Gly Thr Pro Met Ala Val Arg Val Ala Ala Thr Leu Arg Ile
                20                  25                  30

Ala Asp His Ile Thr Ala Gly Ala His Thr Ala Gly Glu Ile Ala Glu
            35                  40                  45

Ala Ala Ala Val His Glu Glu Ser Leu Asp Arg Leu Leu Arg Tyr Leu
        50                  55                  60

Thr Val Arg Gly Leu Leu Asp Arg Asp Gly Leu Gly Arg Tyr Thr Leu
65                  70                  75                  80

Thr Pro Leu Gly Arg Pro Leu Cys Glu Asp His Pro Ala Gly Val Arg
                85                  90                  95

Ala Trp Phe Asp Met Glu Gly Ala Gly Arg Gly Glu Leu Ser Phe Val
                100                 105                 110

Asp Leu Leu His Ser Val Arg Thr Gly Lys Ala Ala Phe Pro Leu Arg
            115                 120                 125

Tyr Gly Arg Pro Phe Trp Glu Asp Leu Ala Glu Asp Pro Arg Arg Ala
        130                 135                 140

Glu Ser Phe Asn Arg Leu Leu Gly Gln Asp Val Ala Thr Arg Ala Pro
145                 150                 155                 160

Ala Val Val Ala Gly Phe Asp Trp Ala Ser Thr Gly His Val Ile Asp
                165                 170                 175

Leu Gly Gly Gly Asp Gly Ser Leu Leu Thr Ala Leu Leu Thr Ala Cys
            180                 185                 190

Pro Ser Leu Arg Gly Thr Val Leu Asp Leu Pro Glu Ala Val Gln Arg
```

```
                195                 200                 205
Ala Lys Glu Ser Phe Ala Val Ser Gly Leu Asp Asp Arg Ala Asn Ala
    210                 215                 220

Val Ala Gly Ser Phe Phe Asp Ala Leu Pro Ala Gly Ala Gly Ala Tyr
225                 230                 235                 240

Val Leu Ser Leu Val Leu His Asp Trp Asp Glu Ala Ser Val Ala
                245                 250                 255

Ile Leu Arg Arg Cys Ala Glu Ala Ala Gly Gln Thr Gly Ser Val Phe
            260                 265                 270

Val Ile Glu Ser Thr Gly Ser Ala Gly Asp Ala Pro His Thr Gly Met
        275                 280                 285

Asp Leu Arg Met Leu Cys Ile Tyr Gly Ala Lys Glu Arg Arg Val Glu
    290                 295                 300

Glu Phe Glu Glu Leu Ala Gly Arg Ala Gly Leu Arg Val Val Ala Val
305                 310                 315                 320

His Pro Ala Gly Pro Ser Ala Ile Ile Gln Met Ser Ala Val
                325                 330

<210> SEQ ID NO 193
<211> LENGTH: 418
<212> TYPE: PRT
<213> ORGANISM: Streptomyces globisporus
<220> FEATURE:
<223> OTHER INFORMATION: orf29

<400> SEQUENCE: 193

Met Ala Gly Leu Val Met Ser Pro Val Glu Ala Leu Asp Ala Leu Gly
  1               5                  10                  15

Thr Val Gln Gly Arg Gln Asp Pro Tyr Pro Phe Tyr Glu Ala Ile Arg
             20                  25                  30

Ala His Gly Gln Ala Val Pro Thr Lys Pro Gly Arg Phe Val Val Val
         35                  40                  45

Gly His Asp Ala Cys Asp Arg Ala Leu Arg Glu Pro Ala Leu Arg Val
     50                  55                  60

Gln Asp Ala Arg Ser Tyr Asp Val Val Phe Pro Ser Trp Arg Ser His
 65                  70                  75                  80

Ser Ser Val Arg Gly Phe Thr Ser Ser Met Leu Tyr Ser Asn Pro Pro
                 85                  90                  95

Asp His Gly Arg Leu Arg Gln Val Val Ser Phe Ala Phe Thr Pro Pro
            100                 105                 110

Lys Val Arg Arg Met His Gly Val Ile Glu Asp Met Thr Asp Arg Leu
        115                 120                 125

Leu Asp Arg Met Ala Arg Leu Gly Ser Gly Ser Pro Val Asp Leu
    130                 135                 140

Ile Ala Glu Phe Ala Ala Arg Leu Pro Val Ala Val Ile Ser Glu Met
145                 150                 155                 160

Ile Gly Phe Pro Ala Lys Asp Gln Val Trp Phe Arg Asp Met Ala Ser
                165                 170                 175

Arg Val Ala Val Ala Thr Asp Gly Phe Thr Asp Pro Gly Ala Leu Thr
            180                 185                 190

Gly Ala Asp Ala Ala Met Asp Glu Met Ser Ala Tyr Phe Asp Asp Leu
        195                 200                 205

Leu Asp Arg Arg Arg Arg Thr Pro Ala Asp Asp Leu Val Thr Leu Leu
    210                 215                 220

Ala Glu Ala His Asp Gly Ser Pro Gly Arg Leu Asp His Asp Glu Leu
```

```
                225                 230                 235                 240
Met Gly Thr Met Met Val Leu Leu Thr Ala Gly Phe Glu Thr Thr Ser
                    245                 250                 255

Phe Leu Ile Gly His Gly Ala Met Ile Ala Leu Glu Gln Arg Ala His
                260                 265                 270

Ala Ala Arg Leu Arg Ala Glu Pro Asp Phe Ala Asp Gly Tyr Val Glu
            275                 280                 285

Glu Ile Leu Arg Phe Glu Pro Pro Val His Val Thr Ser Arg Trp Ala
        290                 295                 300

Ala Glu Asp Leu Asp Leu Leu Gly Leu Ser Val Pro Ala Gly Ser Lys
305                 310                 315                 320

Leu Val Leu Ile Leu Ala Ala Ala Asn Arg Asp Pro Gly Arg Tyr Pro
                325                 330                 335

Glu Pro Gly Arg Phe Asp Pro Asp Arg Tyr Ala Pro Arg Pro Gly Gly
            340                 345                 350

Pro Glu Ala Thr Arg Pro Leu Ser Phe Gly Ala Gly His Phe Cys
        355                 360                 365

Leu Gly Ala Pro Leu Ala Arg Leu Glu Ala Arg Ile Ala Leu Pro Arg
    370                 375                 380

Leu Leu Arg Arg Phe Pro Asp Leu Ala Val Ser Glu Pro Val Tyr
385                 390                 395                 400

Arg Asp Arg Trp Val Val Arg Gly Leu Glu Thr Phe Pro Val Thr Leu
                405                 410                 415

Gly Ser

<210> SEQ ID NO 194
<211> LENGTH: 368
<212> TYPE: PRT
<213> ORGANISM: Streptomyces globisporus
<220> FEATURE:
<223> OTHER INFORMATION: orf30

<400> SEQUENCE: 194

Val Asp Gln Thr Ser Thr Pro Ala Arg Thr Glu Leu Val Glu Arg Ala
  1               5                  10                  15

Ser Lys Leu Arg Pro Leu Leu Gln Ser His Ala Ala Trp Thr Glu Glu
                 20                  25                  30

Asn Arg Arg Leu His Glu Glu Ser Val Glu Ala Met Ala Glu Ala Gly
             35                  40                  45

Ile Phe Arg Met Arg Val Pro Ala Arg Tyr Gly Gly Phe Glu Ser Asp
         50                  55                  60

Ala Arg Thr Leu Val Asp Val Ala Ala Glu Leu Ala Arg Gly Asp Gly
 65                  70                  75                  80

Ser Ala Ala Trp Thr Ala Ser Val Trp Trp Ile Pro Thr Trp Met Ala
                 85                  90                  95

Gly Leu Phe Pro Asp His Val Gln Asp Glu Val Phe Ser Arg Pro Asp
            100                 105                 110

Val Arg Val Ser Gly Thr Leu Ser Pro Gly Gly Met Ala Ala Pro Val
        115                 120                 125

Asp Gly Gly Val Val Asn Gly Lys Trp Gly Phe Ile Ser Gly Ala
    130                 135                 140

Trp His Ser His Trp Gln Val Leu Ile Ala Val Ser Pro Thr Pro Asp
145                 150                 155                 160

Gly Gly Met Gln Pro Val Met Ala Leu Val Pro Thr Asp Gln Leu Gln
                165                 170                 175
```

```
Ile Val Asp Asp Trp His Thr Ser Gly Leu Arg Gly Ser Gly Ser Val
            180                 185                 190

Ser Thr Ile Ala Ala Asp Val Phe Val Pro Gln Glu Arg Val Leu Pro
        195                 200                 205

Leu Gly Ala Val Leu Gln Gln Gln Tyr Ala Ser Glu Leu Asn Ala Gly
    210                 215                 220

Ser Pro Met Phe Arg Ala Pro Met Leu Ala Val Ala Ser Ala Ser Ser
225                 230                 235                 240

Val Gly Thr Met Thr Gly Leu Ala Ala Ala Gln Asp Val Phe Arg
                245                 250                 255

Gly Arg Leu Pro Gly Arg Lys Ile Thr Tyr Thr Glu Tyr Glu Glu Gln
            260                 265                 270

Gly Ser Ala Pro Ile Thr His Leu Gln Leu Gly Glu Ala Thr Leu Leu
            275                 280                 285

Ala Asp Glu Ala Arg Phe His Ala His Arg Leu Ala Asp Leu Val Asp
    290                 295                 300

Ser Lys Gly Ala Ser Gly Glu Ala Trp Thr Leu Glu Glu Arg Val Leu
305                 310                 315                 320

Cys Arg Gly Leu Leu Gly Arg Ala Cys Arg Leu Gly Lys Glu Ser Val
                325                 330                 335

Asp Ile Leu Ala Gln Ala Ser Gly Gly Ser Ser Ile Tyr Asn Asp Val
            340                 345                 350

Pro Ile Gln Arg Val Gln Arg Cys Pro Glu His His Ala Ala Pro Ala
            355                 360                 365

<210> SEQ ID NO 195
<211> LENGTH: 346
<212> TYPE: PRT
<213> ORGANISM: Streptomyces globisporus
<220> FEATURE:
<223> OTHER INFORMATION: orf31

<400> SEQUENCE: 195

Met Arg Pro Leu Val Arg Ala Val Leu Arg Gly Ser Leu Arg Gln Val
1               5                   10                  15

Arg Tyr Val Asp Val Val Ser Pro Arg Ala Arg Ser Leu Val Ala
            20                  25                  30

Arg Val Tyr Arg Glu Thr Glu Glu Gln Phe Gly Val Leu Ala Pro Pro
        35                  40                  45

Leu Ala Leu His Ser Pro Ala Ala Ser Leu Ala Ala Thr Trp Leu
    50                  55                  60

Met Leu Arg Glu Thr Leu Leu Val Asp Gly Arg Val Ser Arg Ala Val
65                  70                  75                  80

Lys Glu Thr Val Ala Thr Glu Val Ser Arg Ala Asn Asp Cys Pro Tyr
                85                  90                  95

Cys Val Gln Val His Gln Ala Val Leu Gly Thr Leu Pro Pro Asp Gly
                100                 105                 110

Gly Gln Ala Gly Leu Leu Arg Trp Val Arg Glu Ala Gly Arg Pro
        115                 120                 125

Gly Gly Gly Ala Val Gly Gly Arg Pro Leu Pro Phe Ser Gly Glu
    130                 135                 140

Gln Ala Pro Glu Leu Cys Gly Val Val Thr Phe His Tyr Ile Asn
145                 150                 155                 160

Arg Met Val Ser Leu Phe Leu Asp Asp Ser Pro Met Pro Thr Arg Thr
                165                 170                 175
```

-continued

Pro Thr Pro Leu Arg Gly Pro Ile Met Arg Thr Thr Ala Leu Ala Met
            180                 185                 190

Arg Pro Val Gly Pro Gly Leu Leu Thr Pro Gly Ala Ser Leu Gly Leu
        195                 200                 205

Leu Pro Pro Ala Pro Leu Pro Pro Gly Leu Glu Trp Ala Glu Gly Asn
210                 215                 220

Pro Phe Val Ala Gln Ala Leu Gly Arg Ala Val Ala Ala Val Asp Gln
225                 230                 235                 240

Gly Ala His Trp Val Pro Glu Pro Val Arg Glu Arg Leu Arg Thr Arg
                245                 250                 255

Leu Asp Thr Trp Asp Gly Ser Ala Pro Gly Leu Gly Arg Gly Trp Leu
            260                 265                 270

Asp Glu Ala Val Ser Gly Leu Pro Pro Gln Asp Val Pro Ala Ala Arg
        275                 280                 285

Leu Ala Leu Leu Thr Ala Phe Ala Pro Tyr Gln Val Leu Pro Asp Asp
    290                 295                 300

Val Glu Glu Phe Arg Arg Arg Pro Thr Asp Arg Glu Leu Val Glu
305                 310                 315                 320

Leu Thr Ser Tyr Ala Ala Leu Thr Thr Ala Val Arg Val Gly Arg Thr
                325                 330                 335

Leu Val Val Pro Asp Ala Ala Gly Pro Gly
            340                 345

<210> SEQ ID NO 196
<211> LENGTH: 306
<212> TYPE: PRT
<213> ORGANISM: Streptomyces globisporus
<220> FEATURE:
<223> OTHER INFORMATION: orf32

<400> SEQUENCE: 196

Met Arg Thr Arg Arg Arg Trp Ser Ala Ala Asp Val Pro Asp Arg Thr
1               5                   10                  15

Gly Thr Thr Ala Val Val Thr Gly Ala Ser Ser Gly Ile Gly Leu His
            20                  25                  30

Leu Ala Gln Glu Leu Ala Arg His Gly Ala His Val Val Leu Ala Val
        35                  40                  45

Arg Asp Pro Asp Arg Gly Val Ala Ala Ala Arg Ile Gln Ser Arg
    50                  55                  60

Val Pro Ser Ala Gln Leu Thr Val Arg Arg Leu Asp Leu Ser Arg Leu
65                  70                  75                  80

Ala Ser Val Arg Ala Gly Ala Glu Glu Leu Arg Asp Arg Phe Pro Arg
                85                  90                  95

Ile His Leu Leu Val Asn Asn Ala Gly Val Met Trp Thr Asp Arg Ala
            100                 105                 110

Arg Thr Pro Asp Gly His Glu Leu Gln Phe Ala Thr Asn His Leu Gly
        115                 120                 125

His Phe Ala Leu Thr Gly Leu Leu Leu Asp Ser Leu Arg Ala Ala Pro
    130                 135                 140

Gly Ala Arg Val Val Thr Ile Ser Ser Tyr Leu His Arg Leu Gly Arg
145                 150                 155                 160

Ile Asp Phe Ser Asp Leu His Gly Glu Arg Tyr Ser Arg Tyr Arg
                165                 170                 175

Ala Tyr Asn Gln Ser Lys Leu Ala Asn Leu Met Phe Ala Leu Glu Leu
            180                 185                 190

His His Arg Leu Ala Glu Ser Gly Ala Glu Leu Ala Ser Leu Ala Ala
            195                 200                 205

His Pro Gly Leu Thr Ala Thr Gly Leu Gly Arg Asp Phe Pro Ala Pro
            210                 215                 220

Val Arg Arg Leu Gly Ser Pro Leu Ala Pro Leu Phe Leu Gln Pro Ala
225                 230                 235                 240

Ala Ala Gly Met Leu Pro Gly Leu Arg Ala Thr Asp Pro Gly Ala
            245                 250                 255

Arg Gly Gly Glu Phe Tyr Gly Pro Leu Gly Val Thr Glu Thr Arg Gly
            260                 265                 270

Ala Pro Gly Leu Val Arg Pro Gly Ala Ala Val Asp Pro Arg Ala
            275                 280                 285

Arg Arg Arg Leu Trp Glu Glu Ser Glu His Leu Thr Gly Val Arg Leu
            290                 295                 300

Arg Pro
305

<210> SEQ ID NO 197
<211> LENGTH: 277
<212> TYPE: PRT
<213> ORGANISM: Streptomyces globisporus
<220> FEATURE:
<223> OTHER INFORMATION: orf33

<400> SEQUENCE: 197

Val Tyr Gln Pro Asp Cys Arg Pro Leu Val Lys Thr Glu Arg Arg Asp
1               5                   10                  15

Pro Ala Thr Ala Ser Gln Ser Ser Arg Val Cys Ser Pro Ser Val Gly
            20                  25                  30

Ala Ala Ser Met Ser Arg Thr Gly Ser Val Thr Pro Ser Ser Arg Leu
            35                  40                  45

Ile Leu Arg Thr Ser Arg Val Met Ser Arg Glu Ser Pro Pro Trp Ala
        50                  55                  60

Lys Lys Ser Ala Pro Ser Glu Gly Ser Gly Lys Pro Ser Arg Ser Pro
65                  70                  75                  80

Gln Pro Arg Thr Ser Thr Trp Arg Met Ser Pro Val Val Thr Thr Val
            85                  90                  95

Arg Arg Glu Pro Arg Arg Ala Glu Arg Ser Arg Glu Ala Cys Thr Ser
            100                 105                 110

Ala Thr Trp Ser Pro Arg Leu Arg Arg Asp Ser Ser Arg Ser Asp Thr
            115                 120                 125

Val Thr Pro Asn Leu Ser Val Ile Leu Arg Thr Ser Arg Val Ile Ser
            130                 135                 140

Ser Val Ser Pro Pro Arg Ala Lys Lys Ser Glu Cys Ser Val Arg Ser
145                 150                 155                 160

Glu Arg Pro Arg Ser Ser Leu His Ala Pro Thr Met Asn Ser Pro Thr
            165                 170                 175

Ser Pro Ser Arg Cys Ser Ser Pro Ser Gly Pro Phe Gly Ala Pro Asp
            180                 185                 190

Pro Ala Glu Arg Phe Arg Pro Glu Thr Ala Glu Arg Ser Leu Val Thr
            195                 200                 205

Phe Ala Thr Ser Arg Gly Met Cys Arg Leu His Arg Leu Pro Ala Thr
            210                 215                 220

Val Arg Glu His Met Leu His Gly Asn Thr Phe Pro Ser Arg Trp Gln
225                 230                 235                 240

```
Pro Ser Leu Pro Ser Thr His Cys Ser Trp Ala Arg Cys Val Gly Ile
                245                 250                 255

Arg Gly Pro Gln Val Cys Gln Ala Ala Arg Asp Arg His Thr Leu Trp
            260                 265                 270

His Asn Trp Asn Glu
        275

<210> SEQ ID NO 198
<211> LENGTH: 382
<212> TYPE: PRT
<213> ORGANISM: Streptomyces globisporus
<220> FEATURE:
<223> OTHER INFORMATION: orf34

<400> SEQUENCE: 198

Met Ser Thr Gly Tyr Leu Ser Arg Leu Glu Ser Gly Ala Arg Gln Pro
1               5                   10                  15

Ser Asp Arg Ala Val Ala His Leu Ala Gly Gln Leu Gly Ile Ser Pro
            20                  25                  30

Ser Glu Phe Glu Gly Ser Arg Ala Thr Ser Leu Ala Gln Ile Leu Ser
        35                  40                  45

Leu Ser Thr Ser Leu Glu Ser Asp Glu Thr Ser Glu Leu Leu Ala Glu
    50                  55                  60

Ala Val Arg Ser Ala His Gly Gln Asp Pro Met Leu Arg Trp Gln Ala
65                  70                  75                  80

Leu Trp Leu Leu Gly Gln Trp Lys Arg Arg His Gly Asp Ser Ala Gly
                85                  90                  95

Glu His Gly Tyr Leu Gln Arg Leu Val Thr Leu Ser Glu Glu Ile Gly
            100                 105                 110

Leu Ala Glu Leu Arg Ala Arg Ala Leu Thr Gln Phe Ala Arg Ser Leu
        115                 120                 125

Arg Val Leu Gly Glu Ile Val Pro Ala Val Glu Ala Ala Ala Ala Ala
    130                 135                 140

His Arg Leu Ala Val Asp His Ala Leu Ser Ser Gln Asp Arg Ala Ala
145                 150                 155                 160

Ser Leu Leu Val Leu Val Ser Val Glu Ala Glu Ala Gly Arg Met Pro
                165                 170                 175

Asp Ala Arg Arg His Ala Asp Glu Leu Thr Val Leu Val Arg Gly Arg
            180                 185                 190

Ser Asp Thr Leu Trp Ala Glu Ala Leu Trp Thr Ala Gly Ala Leu Lys
        195                 200                 205

Val Arg Gln Gly Glu Phe Ala Ala Ala Glu Val Leu Phe Gln Glu Ala
    210                 215                 220

Leu Asp Gly Phe Asp Ser Arg Glu Asn Leu Thr Ile Trp Leu Arg Leu
225                 230                 235                 240

Arg Ile Ala Met Ala Glu Leu His Leu Gln Lys Leu Pro Pro Glu Pro
                245                 250                 255

Asp Ala Ala Gln Leu Cys Ile Glu Ala Ala Glu Ala Leu Pro Phe
            260                 265                 270

Ala Arg Thr Ser Ala Leu Glu Gln Ser Leu Ala Ala Leu Arg Ala Arg
        275                 280                 285

Leu Ala Phe His Glu Gly Arg Phe Ala Asp Ala Arg Ala Leu Leu Glu
    290                 295                 300

Arg Leu Gly Arg Thr Glu Leu Arg Leu Pro Tyr Gln Ser Arg Ile Arg
305                 310                 315                 320
```

```
Leu Glu Val Leu Gly His Gln Leu Arg Ile Leu Ser Gly Glu Glu
            325                 330                 335

Glu Gly Leu Ala Gly Leu Gln Leu Leu Ala Glu Glu Ala Gln Glu Asn
            340                 345                 350

Ser Asn Ile Asn Leu Ala Ala Glu Ile Trp Arg Leu Ala Ala Glu Cys
            355                 360                 365

Leu Met Arg Ala Arg Gly Lys Val Arg Gly Ala Thr Gly Gly
370                 375                 380

<210> SEQ ID NO 199
<211> LENGTH: 284
<212> TYPE: PRT
<213> ORGANISM: Streptomyces globisporus
<220> FEATURE:
<223> OTHER INFORMATION: orf35

<400> SEQUENCE: 199

Met Phe Ser Pro Ala Ala Arg Arg Tyr Val Leu Ala Ser Asp Arg Ala
  1               5                  10                  15

Gly Phe Phe Glu Gln Ala Val Arg Leu Arg Ser Arg Gly Tyr Arg Val
                 20                  25                  30

Ser Ala Glu Phe Val Gly Pro Asp Gln Gly Ala Thr Asp Ala Leu His
             35                  40                  45

Ala Glu His Val Val Glu Glu His Leu Arg Leu Leu Asp Gln Glu Pro
         50                  55                  60

Ala Pro Asp Arg Ile Gly Val Asp Val Ser Arg Ile Gly Leu Ala His
 65                  70                  75                  80

Ser Ala Gln Thr Ala Leu Arg Asn Thr Gly Arg Leu Ala Ala Ala Ala
                 85                  90                  95

Ala Leu Arg Gly Ser Glu Val Val Leu Leu Met Glu Gly Ser Glu Asp
            100                 105                 110

Ile Asp Thr Val Leu Ala Val His Asp Ala Leu Val Asn Arg Tyr Asp
            115                 120                 125

Asn Val Gly Ile Thr Leu Gln Ala His Leu His Arg Thr Val Asp Asp
        130                 135                 140

Ala Met Ala Val Ala Gly Pro Gly Arg Thr Val Arg Leu Val Met Gly
145                 150                 155                 160

Ser Ser Ala Glu Pro Ala Gly Thr Ala Leu Ser Arg Gly Pro Ala Leu
                165                 170                 175

Glu Asp Arg Tyr Leu Asp Leu Ala Glu Leu Leu Val Asp Arg Gly Val
            180                 185                 190

Arg Leu Ser Leu Ala Thr Pro Asp Ala Glu Val Leu Ala Gly Ala Gln
        195                 200                 205

Glu Arg Gly Leu Leu Glu Arg Val Gln Asp Ile Glu Met Leu Tyr Gly
210                 215                 220

Val Arg Pro Glu Leu Leu Arg Arg His Arg Ala Ala Gly Arg Pro Cys
225                 230                 235                 240

Arg Ile His Ala Ala Tyr Gly Met Asn Trp Trp Leu Pro Leu Leu Arg
                245                 250                 255

Arg Leu Ala Asp Asn Pro Pro Met Val Leu Asn Ala Leu Ala Asp Ile
            260                 265                 270

Gly Arg Asp Arg Glu Pro Val Ala His Gln Ala Tyr
        275                 280

<210> SEQ ID NO 200
```

-continued

```
<211> LENGTH: 267
<212> TYPE: PRT
<213> ORGANISM: Streptomyces globisporus
<220> FEATURE:
<223> OTHER INFORMATION: orf36

<400> SEQUENCE: 200
```

Met Asn Ser Leu Asp Asp Val Leu Lys His Leu Ala Thr Asp Ile Glu
1               5                   10                  15

Glu Leu Ala Gln Leu Val Glu Lys Ile Asp Asp Glu Ala Trp Asn Thr
            20                  25                  30

Pro Thr Pro Ala Pro Gly Trp Thr Val Thr Asp Gln Ile Ala His Leu
        35                  40                  45

Thr Phe Val Phe Asn Leu Ala Arg Thr Ala Ala Ala Pro Glu Glu
    50                  55                  60

Phe Lys Ala Val Thr Ala Ala Ala Gly Asn Phe Asp Gly Ala Val
65                  70                  75                  80

Asn Ala Ala Leu Gln Gln Phe Lys Gly Phe Pro Pro Gln Glu Leu Leu
                85                  90                  95

Thr Arg Phe Arg Gly Met Gly Arg Ala Ser Val Glu Ala Leu Ala Ala
            100                 105                 110

Val Pro Ala Gly Gln Val Val Pro Trp Leu Val Asn Pro Leu Pro Pro
        115                 120                 125

Val Val Leu Gly Cys Ala Gly Ile Met Glu Val Phe Ala His Gly Gln
130                 135                 140

Asp Val Ala Asp Ala Leu Gly Val Arg Arg Thr Pro Thr Glu Arg Leu
145                 150                 155                 160

Arg Asn Ile Val Asp Phe Ala Trp Leu Thr Arg Asp Phe Gly Tyr Glu
                165                 170                 175

Ser His Gly Leu Thr Pro Pro Ala Ala Pro Phe Arg Phe Glu Leu Thr
            180                 185                 190

Ala Pro Ser Gly Glu Val Trp Thr Val Gly Pro Glu Asp Ala Thr Glu
        195                 200                 205

Thr Val Ser Gly Pro Ala His Asp Phe Cys Leu Leu Val Thr Arg Arg
    210                 215                 220

Arg His Arg Asp Asp Leu Ala Leu Thr Ala Ser Gly Gln Glu Ala Glu
225                 230                 235                 240

Lys Trp Leu Asp Ile Ala Gln Ala Tyr Arg Gly Pro Ala Gly Glu Gly
                245                 250                 255

Arg Arg Pro Gly Gln Phe Ala Ala Thr Gly Ser
            260                 265

```
<210> SEQ ID NO 201
<211> LENGTH: 156
<212> TYPE: PRT
<213> ORGANISM: Streptomyces globisporus
<220> FEATURE:
<223> OTHER INFORMATION: orf37

<400> SEQUENCE: 201
```

Met Thr Ala Thr Asn Pro Asp Tyr Phe Glu Leu Arg His Thr Val Gly
1               5                   10                  15

Phe Glu Glu Thr Asn Leu Val Gly Asn Val Tyr Tyr Val Asn Tyr Leu
            20                  25                  30

Arg Trp Gln Gly Arg Cys Arg Glu Leu Phe Leu Lys Glu Arg Ala Pro
        35                  40                  45

Ser Val Leu Ala Glu Val Gln Glu Asp Leu Lys Leu Phe Thr Leu Lys

```
                 50                  55                  60
Val Asp Cys Glu Phe Phe Ala Glu Ile Thr Ala Phe Asp Glu Leu Ser
 65                  70                  75                  80

Ile Arg Met Arg Leu Ser Glu Leu Arg Gln Thr Gln Leu Glu Phe Thr
                 85                  90                  95

Phe Asp Tyr Ile Lys Leu Gly Asp Asp Gly Glu Thr Leu Val Ala
                100                 105                 110

Arg Gly Arg Gln Arg Ile Ala Cys Met Arg Gly Pro Asn Thr Ala Thr
                115                 120                 125

Val Pro Thr Leu Ile Pro Glu Ala Leu Ala Ala Leu Ala Pro Tyr
130                 135                 140

Ser Asp Arg Ala Gly Ser Tyr Ala Gly Arg Ala Ala
145                 150                 155

<210> SEQ ID NO 202
<211> LENGTH: 551
<212> TYPE: PRT
<213> ORGANISM: Streptomyces globisporus
<220> FEATURE:
<223> OTHER INFORMATION: orf38

<400> SEQUENCE: 202

Met Ser Thr Thr Ala Glu Arg Thr Asp Val Leu Val Ile Gly Ser Gly
 1                   5                  10                  15

Phe Gly Gly Ala Ile Ala Ala Tyr His Leu Ala Ala Gly Gly Ala Asp
                 20                  25                  30

Val Thr Val Leu Glu Arg Gly Pro Trp Leu Glu Ser Lys Glu Phe Glu
                 35                  40                  45

His Asp Tyr Lys Leu Gly Ser Ser Tyr Thr Arg Ala Phe Asp Phe Thr
 50                  55                  60

Val Gly Asp Gly Met Ser Ile Leu Gly Gly Asn Cys Val Gly Gly Gly
 65                  70                  75                  80

Ser Val Val Tyr Phe Ala Ala Met Pro Arg Ala Pro Arg Phe Val Phe
                 85                  90                  95

Asp Arg Gln Gly Ser Ile Gly Arg Arg Met Trp Pro Gln Ala Val Ser
                100                 105                 110

Arg Glu Thr Leu Asp Pro Trp Tyr Asp Arg Val Glu Glu Ser Leu Ser
                115                 120                 125

Val Thr Arg Gln Asp Trp Asn Asp Val Ser Tyr Ala Gly Gly Leu Trp
130                 135                 140

Ala Ala Ala Cys Asn His Ala Gly Arg Thr Ala Asn Pro Leu Ala Val
145                 150                 155                 160

Ala Ile Asp Asn Thr Lys Cys Val Asn Cys Asn Trp Met Met Ala Gly
                165                 170                 175

Cys Arg Phe Glu Ala Lys Gln Ser Leu Leu Val Asn Tyr Leu Pro Ala
                180                 185                 190

Ala Ile Ala His Gly Ala Arg Ile Arg Pro Leu His Glu Val Gln His
                195                 200                 205

Leu Ser Arg Thr Pro Asp Gly Ser Tyr Arg Val His Tyr Asn Val Val
210                 215                 220

His Asp Asp Tyr Arg Leu Gln Ala Gly Ser Gly Val Ile Glu Ala
225                 230                 235                 240

Lys Ile Val Val Met Ala Ala Gly Ala Gly Ala Thr Pro Val Ile Leu
                245                 250                 255

Gln Arg Ser Glu Ala His Leu Gly Thr Met Pro Arg Ala Val Gly Arg
```

```
                    260                 265                 270
Tyr Phe Ser Gly Asn Gly Glu Arg Leu Asn Thr Ala Ile Ile Asp Glu
            275                 280                 285

Ala Lys Ala Ala Glu Leu Phe Gly Leu Asp Arg Gly Asp Gly Leu Ala
290                 295                 300

Tyr Ala Ala Asn Gln Ile Gly Lys Gly Pro Thr Val Ala Ser Trp Asp
305                 310                 315                 320

Arg Leu Asp Gly Ser Leu Pro Glu Tyr Ser Arg Tyr Ser Leu Glu Gln
                325                 330                 335

Leu Tyr Phe Pro Pro Gly Leu Gly Thr Ile Leu Ala Gln Val Pro Gly
            340                 345                 350

Ala Thr Gly Pro Ser Trp Phe Gly Lys Glu Lys Lys Glu Ile Leu Lys
            355                 360                 365

Gln Trp Thr Ser Trp Leu Thr Ile Phe Thr Met Ile Glu Asp Asp Asn
            370                 375                 380

Glu Gly Val Phe Gly Pro Pro Ala Thr Gly Asn Ala His Arg Ile
385                 390                 395                 400

Ser Gln Gln Met Leu Gly Arg Gly Asn Leu Arg Tyr Asp Pro Thr Lys
                405                 410                 415

Asn Thr Leu Gly Ala Trp Ala Ala Ser Asp Ala Glu Val Lys Glu Ile
            420                 425                 430

Leu Glu Lys Asp Gly Leu Ala Lys Val Met Pro Trp Thr Asn Asp Leu
            435                 440                 445

Val Gly Ala Tyr Thr Val His Pro Leu Ser Ser Cys Arg Met Gly Asp
            450                 455                 460

Asp Pro His Thr Ser Ala Leu Asp Asp Ser Asn Glu Leu Arg Asp His
465                 470                 475                 480

Pro Gly Ile Phe Val Thr Asp Gly Ser Ser Val Pro Gly Ala Leu Thr
                485                 490                 495

Val Asn Pro Ala Met Thr Ile Ala Ala Leu Ala Glu Arg Ala Met Pro
            500                 505                 510

Gly Ile Val Arg Ala Ala Gln Ser Arg Gly Ile Ser Val Thr Tyr Gly
            515                 520                 525

Ala Pro Ala Pro Asp Gly Ser Thr Ser Gly Arg Glu Arg Val Leu Pro
530                 535                 540

Leu Leu Pro Ser Ala Arg Gly
545                 550

<210> SEQ ID NO 203
<211> LENGTH: 176
<212> TYPE: PRT
<213> ORGANISM: Streptomyces globisporus
<220> FEATURE:
<223> OTHER INFORMATION: orf39

<400> SEQUENCE: 203

Met Thr Leu Glu Ala Tyr Ala Asp Thr Ile Val Pro Gly Gln Lys Arg
  1               5                  10                  15

Phe Ala Asp Asp Arg Ala Ile Ala Gly Val Ser Thr Gly Gly Ala
                 20                  25                  30

Val Gln Ala Gly Ala Leu Glu Leu Leu Gln Trp Asp Ala Thr Gly Ile
             35                  40                  45

His Glu Gly Leu Asp Asp Leu Val Arg Leu Val Asn Glu His Ala Leu
         50                  55                  60

Ala Tyr Ala Ala Glu Arg Arg Leu Ala Pro Asp Pro Thr Val Pro Pro
```

```
            65                  70                  75                  80
Phe Val Ala Leu Asp Tyr Pro Asp Arg Ala Leu Ile Gln Arg Leu
                85                  90                  95

Thr Thr Pro Gly His Pro Glu Lys Glu Phe Trp Val Leu Ser Leu
            100                 105                 110

Phe Cys Asn Met Ala Phe Asp Ser Ala His Leu Asn Thr Ala Gln
            115                 120                 125

Ala Met Glu Asp Gly His Pro Gly Leu Glu Ala Met Gly Leu Ser Met
        130                 135                 140

Pro Asp Ala Asp Gly Leu Trp Arg Phe Lys Asp Tyr Ser Tyr Gly Arg
145                 150                 155                 160

Glu Phe Ala Arg Leu His Pro Asp Thr Thr Ser Thr Gly Ser Pro Ala
                165                 170                 175

<210> SEQ ID NO 204
<211> LENGTH: 359
<212> TYPE: PRT
<213> ORGANISM: Streptomyces globisporus
<220> FEATURE:
<223> OTHER INFORMATION: orf40

<400> SEQUENCE: 204

Val Lys Ser Asp Ser Ala Gln Arg Ala Val Glu Arg Ser Arg Arg Val
  1               5                  10                  15

Val Arg Ile Asp Glu Leu Ile Pro Ala Asp Ser Pro Arg Leu Asn Gly
                20                  25                  30

Ile Asp Arg Ser His Val Gln Arg Leu Ala Thr Val Tyr Ala Ser Leu
            35                  40                  45

Pro Pro Val Leu Val His Arg Pro Thr Met Arg Val Val Asp Gly Met
    50                  55                  60

His Arg Ile Gly Ala Ala Arg Leu Lys Gly Leu Asp Thr Val Glu Val
 65                  70                  75                  80

Thr Phe Phe Glu Gly Ala Glu Gln Val Phe Leu Arg Ser Val Ala
                85                  90                  95

Ala Asn Ile Thr Asn Gly Leu Pro Leu Ser Val Ala Asp Arg Lys Thr
            100                 105                 110

Ala Ala Ala Arg Ile Leu Ala Ser His Pro Thr Leu Ser Asp Arg Ala
        115                 120                 125

Val Ala Ala His Val Gly Leu Asp Ala Lys Thr Val Ala Gly Val Arg
    130                 135                 140

Thr Cys Ser Ala Ala Gly Ser Pro Leu Leu Asn Met Arg Thr Gly Ala
145                 150                 155                 160

Asp Gly Arg Val His Pro Leu Asp Arg Thr Ala Glu Arg Leu His Ala
                165                 170                 175

Ala Ala Leu Leu Thr Gln Asp Pro Gly Leu Pro Leu Arg Ser Val Val
            180                 185                 190

Glu Gln Thr Gly Leu Ser Leu Gly Thr Ala His Asp Val Arg Arg Arg
        195                 200                 205

Leu Leu Arg Gly Glu Asp Pro Val Pro Gln Asn Arg Gln Ser Ala Met
    210                 215                 220

Leu Glu Pro Gly Leu Ala Pro Gln Lys Lys Ala Thr Ala Lys Pro Pro
225                 230                 235                 240

Val Gly Pro Ala Ala Arg Pro Val Pro Lys Val Pro Ala Val Ala
                245                 250                 255

Gly Arg Pro Pro Val Ser Pro Arg Ser Arg Ala Pro Leu Glu Ala Leu
```

```
                         260                 265                 270
Arg Lys Leu Ser Asn Asp Pro Ser Leu Arg His Ser Asp Gln Gly Arg
        275                 280                 285
Glu Leu Met Arg Trp Leu His Asn Arg Phe Val Val Asp Glu Ala Trp
    290                 295                 300
Arg Arg Arg Ala Asp Ala Val Pro Ala His Cys Val Asp Ser Met Ala
305                 310                 315                 320
Glu Leu Ala Gln His Cys Ser Asp Ala Trp His Arg Phe Ala Glu Glu
                325                 330                 335
Met Val Arg Arg Arg His Ser Ala Ala Ala Asp Gly Ser Gly Leu Arg
            340                 345                 350
Thr Thr Gln Pro Thr Arg Arg
        355

<210> SEQ ID NO 205
<211> LENGTH: 284
<212> TYPE: PRT
<213> ORGANISM: Streptomyces globisporus
<220> FEATURE:
<223> OTHER INFORMATION: orf41

<400> SEQUENCE: 205

Val Thr Thr Asn Thr Ile Glu Asp Ala Val Arg Arg Val Val Glu Tyr
  1               5                  10                  15
Met His Val Asn Leu Gly Gln Asn Leu Thr Ile Asp Asp Met Ala Arg
             20                  25                  30
Thr Ala Met Phe Ser Lys Phe His Phe Thr Arg Ile Phe Arg Glu Val
         35                  40                  45
Thr Gly Thr Ser Pro Gly Arg Phe Leu Ser Ala Leu Arg Ile Gln Glu
     50                  55                  60
Ala Lys Arg Leu Leu Val His Thr Ala Leu Ser Val Ala Asp Ile Ser
 65                  70                  75                  80
Ser Gln Val Gly Tyr Ser Ser Val Gly Thr Phe Ser Ser Arg Phe Lys
                 85                  90                  95
Ala Cys Val Gly Leu Ser Pro Ser Ala Tyr Arg Asp Phe Gly Gly Val
            100                 105                 110
Gln Pro Gly Phe Pro Ser Ala Ala Ala Arg Leu Thr Pro Thr Ala His
        115                 120                 125
Asn Pro Ser Val Arg Gly Arg Ile His Ser Ala Pro Gly Asp Arg Pro
    130                 135                 140
Gly Arg Ile Phe Val Gly Leu Phe Pro Gly Arg Met Arg Gln Gly Arg
145                 150                 155                 160
Pro Ala Arg Trp Thr Val Met Glu Ser Pro Gly Ala Phe Glu Leu Arg
                165                 170                 175
Asp Val Pro Val Gly Thr Trp His Ile Leu Val His Ser Phe Pro Ala
            180                 185                 190
Gly His Arg Pro His Gln Leu Asp Ser Glu Pro Leu Leu Gly His
        195                 200                 205
Ser Gly Pro Leu Val Val His Pro Gly Ala Leu Leu Arg Pro Ala Asp
    210                 215                 220
Ile Leu Leu Arg Ala Val Asp Ala Leu Asp Pro Val Leu Leu Ala
225                 230                 235                 240
His Phe Ala Leu Glu Ser Arg Leu Thr Ser Pro Tyr Ser Pro Ser Ser
                245                 250                 255
Val Ala Leu Arg Ala Ser Ala Gly Arg Ala Trp Val Arg Gln Pro Pro
```

```
-continued
                    260                 265                 270
Gly Val Arg Arg Arg Tyr Ala Asp Arg Asp Arg Gly
            275                 280

<210> SEQ ID NO 206
<211> LENGTH: 125
<212> TYPE: PRT
<213> ORGANISM: Streptomyces globisporus
<220> FEATURE:
<223> OTHER INFORMATION: orf42

<400> SEQUENCE: 206

Gly Ile Leu Pro Arg Val Ala Gln Gln Arg Asp Val Val Gly Gly Tyr
 1               5                  10                  15

Thr Val Ser Ala Gly Ser Asp Val Leu Val Cys Pro Tyr Ile Met His
            20                  25                  30

Arg His Pro Gly Leu Trp Glu Asp Pro Glu Arg Phe Asp Pro Glu Arg
        35                  40                  45

Phe Glu Pro Arg Gln Thr Ala Asp Arg Pro Arg Tyr Ala Tyr Ile Pro
    50                  55                  60

Phe Gly Ala Gly Pro Arg Phe Cys Val Gly Ser Asn Leu Gly Met Met
65                  70                  75                  80

Glu Ala Val Phe Val Thr Ala Leu Val Thr Arg Asp Leu Asp Leu Arg
                85                  90                  95

Thr Val Ala Gly His Arg Ala Val Ala Glu Pro Met Leu Ser Leu Arg
            100                 105                 110

Met Arg Gly Gly Leu Pro Met Thr Val Ser Thr Ala Arg
        115                 120                 125

<210> SEQ ID NO 207
<211> LENGTH: 6
<212> TYPE: PRT
<213> ORGANISM: Artificial Sequence
<220> FEATURE:
<223> OTHER INFORMATION: Description of Artificial Sequence: 6-His tag

<400> SEQUENCE: 207

His His His His His His
 1               5
```

GENE CLUSTER FOR PRODUCTION OF THE ENEDIYNE ANTITUMOR ANTIBIOTIC C-1027

CROSS-REFERENCE TO RELATED APPLICATIONS

This application claims benefit of and priority to U.S. application Ser. No. 09/478,188, filed on Jan. 5, 2000, which claims benefit under 35 U.S.C. §119 of provisional application U.S. application Ser. No. 60/115,434, filed on Jan. 6, 1999, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was supported in part by a grant from the Cancer Research Coordinating Committee, University of California, the National Institutes of Health grant CA78747, and the Searle Scholars Program/The Chicago Community Trust. The Government of the United States of America may have certain rights in this invention.

FIELD OF THE INVENTION

This invention relates to the field of enediyne antibiotics. In particular this invention elucidates the gene cluster controlling the biosynthesis of the C-1027 enediyne.

BACKGROUND OF THE INVENTION

The enediyne antibiotics are currently the focus of intense research activity in the fields of chemistry, biology, and medical sciences, because of their unique molecular architecture, biological activities, and modes of actions (Doyle and Borders (1995) *Enediyne antibiotics as antitumor agents*. Marcel-Dekker, New York, Thorson et al. (1999) *Bioorg. Chem.*, 27: 172–188). Since the unveiling of the structure of neocarzinostatin chromophore (Edo et al. (1985) *Tetrahedron Lett.* 26: 331–340) in 1985, the enediyne family has grown steadily. Thus far, there have been three basic groups within the enediyne antibiotic family: (a) the calicheamicin/esperamicin type, which includes the calicheamicins, the esperamicins, and namenamicin, (b) the dynemicin type, and (c) the chromoprotein type, consisting of an apoprotein and an unstable enediyne chromophore. The latter group includes neocarzinostatin, kedarcidin, C-1027 (FIG. 1), and maduropeptin, whose enediyne chromophore structures have been established, as well as several others whose enediyne chromophore structures are yet to be determined due to their instability (Thorson et al. (1999) *Bioorg. Chem.*, 27: 172–188). N1999A2, in contrast to the other chromoproteins, exists as an enediyne chromophore alone despite the fact that its structure is very similar to the other chromoprotein chromophore (Ando et al.(1998) *Tetra. Letts.*, 39: 6495–6480).

As a family, the enediyne antibiotics are the most potent, highly active antitumor agents ever discovered. Some members are 1000 times more potent than adriamycin, one of the most effective, clinically used antitumor antibiotics (Zhen et al. (1989) *J. Antibiot.* 42: 1294–1298). All members of this family contain a unit consisting of two acetylenic groups conjugated to a double bond or incipient double bond within a nine or ten-membered ring; i.e., the enediyne core as exemplified by C-1027 in FIG. 1. As the consequence of this structural feature, these compounds share a common mechanism of action: the enediyne core undergoes an electronic rearrangement to form a transient benzenoid diradical, which is positioned in the minor groove of DNA so as to damage DNA by abstracting hydrogen atoms from deoxyriboses on both strands (FIG. 1). Reaction of the resulting deoxyribose carbon-centered radicals with molecular oxygen initiates a process that results in both single-strand and double-strand DNA cleavages (Doyle and Borders (1995) *Enediyne antibiotics as antitumor agents*. Marcel-Dekker, New York; Ikemoton et al. (1995) *Proc. Natl. Acad. Sci. USA* 92:10506–10510; Myers et al. (1997) *J. Am. Chem. Soc.* 119: 2965–2972; Stassinopoulos et al. (1996) *Science* 272: 1943–1946; Thorson et al. (1999) *Bioorg. Chem.*, 27: 172–188; Xu et al. (1997) *J. Am. Chem. Soc.* 119: 1133–1134). This novel mechanism of DNA damage has important implications for their application as potent cancer chemotherapeutic agents (Doyle and Borders (1995) supra.; Sievers et al. (1999) *Blood* 93: 3678–3684).

As an alternative to making structural analogs of microbial metabolites by chemical synthesis, manipulations of genes governing secondary metabolism offer a promising alternative allowing preparation of these compounds biosynthetically (Cane et al. (1998) *Science* 282: 63–68; Hutchinson and Fujii. (1995) *Ann. Rev. Microbiol.* 49: 201–38; Katz and Donadio (1993) *Ann. Rev. Microbiol.* 47: 875–912). The success of the latter approach depends critically on the availability of novel genetic systems and on genes encoding novel enzyme activities. The enediynes offer a distinct opportunity to study the biosynthesis of their unique molecular scaffolds and the mechanism of self-resistance to extremely cytotoxic natural products. Elucidation of these aspects provides access to rational engineering of enediyne biosynthesis for novel drug leads and makes it possible to construct enediyne overproducing strains by de-regulating the biosynthetic machinery. In addition, elucidation of an enediyne gene cluster contributes to the general field of combinatorial biosynthesis by expanding the repertoire of novel polyketide synthase (PKS) and deoxysugar biosynthesis genes as well as other genes uniquely associated with enediyne biosynthesis, leading to the making of novel enediynes via combinatorial biosynthesis.

SUMMARY OF THE INVENTION

This invention provides nucleic acid sequences and characterization of the gene cluster responsible for the biosynthesis of the enediyne C-1027 (produced by *Streptomyces globisporus*). In particular structural and functional characterization is provided for the open reading frames (ORFs) comprising this gene cluster. Thus, in one embodiment, this invention provides an isolated nucleic acid comprising a nucleic acid selected from the group consisting of a nucleic acid encoding any of C-1027 open reading frames (ORFs) −7 through 60, excluding ORF 9 (cagA), a nucleic acid encoding a polypeptide encoded by any of C-1027 open reading frames (ORFs) −7 through 60, excluding ORF 9 (cagA); and a nucleic acid amplified by polymerase chain reaction (PCR) using primer pairs that amplify any of C-1027 open reading frames (ORFs) −7 through 60, excluding ORF 9 (cagA). In certain embodiments, preferred nucleic acids comprise a nucleic acid encoding at least one, preferably at least two and more preferably at least three or more open reading frames between orf(−3) and orf54. In one embodiment, preferred nucleic acids comprise a nucleic acid encoding at least two (more preferably at least three or more)

open reading frames (ORFs) selected from the group consisting of ORF–1 through ORF 60 or sgcR3, excluding ORF 9 (cagA).

In another embodiment this invention provides an isolated nucleic acid comprising a nucleic acid that specifically hybridizes under stringent conditions to an open reading frame (ORF) of the C-1027 biosynthesis gene cluster, excluding ORF 9 (cagA), and can substitute for the ORF to which it specifically hybridizes to direct the synthesis of an enediyne. In certain embodiments this also includes nucleic acids that would stringently hybridizes indicated above, but for, the degeneracy of the nucleic acid code. In other words, if silent mutations could be made in the subject sequence so that it hybridizes to he indicated sequence(s) under stringent conditions, it would be included in certain embodiments. Particularly preferred nucleic acids comprises a nucleic acid that specifically hybridizes under stringent conditions to a nucleic acid selected from the group consisting of orf(–7), orf(–6), orf(–5), orf(–4), orf(–3), orf(–2), orf(–1), orf0, orf1, orf2, orf3, orf4, orf5, orf6, orf7, orf8, orf10, orf11, orf12, orf13, orf14, orf15, orf16, orf17, orf18, orf19, orf20, orf21, orf22, orf23, orf24, orf25, orf26, orf27, orf28, orf29, orf30, orf31, orf32, orf33, orf34, orf35, orf36, orf37, orf38, orf39, orf40, orf41, orf42, orf43, orf44, orf45, orf46, orf47, orf48, orf49, orf50, orf51, orf52, orf53, orf54, orf55, orf56, orf57, orf58, orf59, and orf60. Particularly preferred isolated nucleic acid comprises a nucleic acid selected from the group consisting of orf(–7), orf(–6), orf(–5), orf(–4), orf(–3), orf(–2), orf(–1), orf0, orf1, orf2, orf3, orf4, orf5, orf6, orf7, orf8, orf10, orf11, orf12, orf13, orf14, orf15, orf16, orf17, orf18, orf19, orf20, orf21, orf22, orf23, orf24, orf25, orf26, orf27, orf28, orf29, orf30, orf31, orf32, orf33, orf34, orf35, orf36, orf37, orf38, orf39, orf40, orf41, orf42, orf43, orf44, orf45, orf46, orf47, orf48, orf49, orf50, orf51, orf52, orf53, orf54, orf55, orf56, orf57, orf58, orf59, and orf60. The nucleic acid may comprises a nucleic acid that is a single nucleotide polymorphism (SNP) of a nucleic acid selected from the group consisting of orf(–7), orf(–6), orf(–5), orf(–4), orf(–3), orf(–2), orf(–1), orf0, orf1, orf2, orf3, orf4, orf5, orf6, orf7, orf8, orf10, orf11, orf12, orf13, orf14, orf15, orf16, orf17, orf18, orf19, orf20, orf21, orf22, orf23, orf24, orf25, orf26, orf27, orf28, orf29, orf30, orf31, orf32, orf33, orf34, orf35, orf36, orf37, orf38, orf39, orf40, orf41, orf42, orf43, orf44, orf45, orf46, orf47, orf48, orf49, orf50, orf51, orf52, orf53, orf54, orf55, orf56, orf57, orf58, orf59, and orf60.

This invention also provides an isolated gene cluster comprising open reading frames encoding polypeptides sufficient to direct the assembly of a C-1027 enediyne or a C-1027 enediyne analogue. The gene cluster may be present in a cell, more preferably in a bacterial cell (e.g. *Actinomycetes, Actinoplanetes, Actinomadura, Micromonospora,* or *Streptomycetes*). Particular preferred bacterial cells include, but are not limited to *Streptomyces globisporus, Streptomyces lividans, Streptomyces coelicolor, Micromonospora echinospora* spp. *calichenisis, Actinomadura verrucosospora, Micromonospora chersina, Streptomyces carzinostaticus,* and *Actinomycete* L585-6. The gene cluster may contain one or more open reading frames is operatively linked to a heterologous promoter (e.g. a constitutive or an inducible promoter).

This invention also provides for an polypeptide encoded by any one or more of the nucleic acids described herein.

Also provided are host cell(s) (e.g. eukaryotic cells or bacterial cells as described herein) transformed with one or more of the expression vectors described herein. Preferred host cells are transformed with an exogenous nucleic acid comprising a gene cluster encoding polypeptides sufficient to direct the assembly of a C-1027 enediyne or a C-1027 enediyne analogue. In certain embodiments, heterologous nucleic acid may comprise only a portion of the gene cluster, but the cell will still be able to express an enediyne.

This invention also provides methods of chemically modifying a biological molecule. The methods involve contacting a biological molecule that is a substrate for a polypeptide encoded by a C-1027 biosynthesis gene cluster open reading frame, with a polypeptide encoded by a C-1027 biosynthesis gene cluster open reading frame whereby the polypeptide chemically modifies the biological molecule. In one preferred embodiment, the polypeptide is an enzyme selected from the group consisting of a hydroxylase, a homocysteine synthase, a dNDP-glucose dehydrogenase, a citrate carrier protein, a C-methyl transferase, an N-methyl transferase, an aminotransferase, a CagA apoprotein, an NDP-glucose synthase, an epimerase, an acyl transferase, a coenzyme F390 synthase, and epoxidase hydrolase, an anthranilate synthase, a glycosyl transferase, a monooxygenase, a type II condensation protein, an aminomutase, a type II adenylation protein, an O-methyl transferase, a P-450 hydroxylase, an oxidoreductase, and a proline oxidase. In a preferred embodiment the method involves contacting the biological molecule with at least two (preferably at least three or more) different polypeptides encoded by C-1027 biosynthesis gene cluster open reading frames. The contacting may be in a host cell (e.g. a eukaryotic cell or a bacterial cell) or the contacting can be ex vivo. The biological molecule can be an endogenous metabolite produced by said host cell or an exogenous supplied metabolite. In preferred embodiments, the host cell is a bacterial cell or eukaryotic cell (e.g., a mammalian cell, a yeast cell, a plant cell, a fungal cell, an insect cell, etc.). In certain preferred embodiments, the host cell synthesizes sugars and glycosylates the biological molecule. In other preferred embodiments, the host cell synthesizes deoxysugars. The method can further involve contacting the biological molecule with a polyketide synthase or a non-ribosomal polypeptide synthetase. The contacting can be in a cell (e.g., a bacterial cell) or ex vivo. In one preferred embodiment the method comprises contacting the biological molecule with at substantially all of the polypeptides encoded by C-1027 biosynthesis gene cluster open reading frames and said method produces an enediyne or enediyne analogue. In another preferred embodiment, the biological molecule is a fatty acid and the biological molecule is contacted with a C-1027 orf polypeptide selected from the group consisting of an epoxide hydrase, a monooxygenase, an iron-sulfer flavoprotein, a p-450 hydroxylase, an oxidoreductase, and a proline oxidase. In certain embodiments, the biological molecule is a fatty acid and said biological molecule is contacted with a plurality of C-1027 orf polypeptides comprising an epoxide hydrase, a monooxygenase, an iron-sulfer flavoprotein, a p-450 hydroxylase, an oxidoreductase, and a proline oxidase. In one especially preferred embodiment, the biological molecule is contacted with polypeptides encoded by ORF17, ORF20, ORF21, ORF29, ORF30, ORF32, ORF35, and ORF38. In another especially preferred embodiment, the biological molecule is contacted with polypeptides encoded by ORF 15, ORF 16, ORF 28, ORF3, ORF 14, and ORF 13, and, in certain embodiments, ORF 4 and ORF 3 as well.

In certain embodiments, the method may comprise contacting a sugar with one or more C-1027 open reading frame polypeptides selected from the group consisting of a dNDP-glucose synthase, a dNDP glucose dehydratase, an epimerase, an aminotransferase, a C-methyltransferase, an N-methyltransferase, and a glycosyl transferase. Particularly preferred variant of this method comprise contacting a dNDP-glucose with a plurality of C-1027 open reading frame polypeptides comprising a dNDP-glucose synthase, a dNDP glucose dehydratase, an epimerase, an aminotransferase, a C-methyltransferase, an N-methyltransferase, and a glycosyl transferase.

In certain other embodiments, the method comprises contacting an amino acid with one or one or more C-1027 open reading frame polypeptides selected from the group consisting of a hydroxylase, an aminomutase, a type II NRPS condensation enzyme, a type II NRPS adenylation enzyme, and a type II peptidyl carrier protein. These methods may involve contacting an amino acid with a plurality of C-1027 open reading frame polypeptides comprising a hydroxylase, a halogenase, an aminomutase, a type II NRPS condensation enzyme, a type II NRPS adenylation enzyme, and a type II peptidyl carrier protein. In particularly preferred embodiments, the amino acid is a tyrosine.

This invention also provides a method of synthesizing a chromaprotein type enediyne core, said method comprising contacting a fatty acid with one or more C-1027 orf polypeptides selected from the group consisting of an epoxide hydrase, a monooxygenase, an iron-sulfer flavoprotein, a p-450 hydroxylase, an oxidoreductase, and a proline oxidase. In preferred embodiments, the fatty acid may be contacted with a plurality of C-1027 orf polypeptides comprising an epoxide hydrase, a monooxygenase, an iron-sulfer flavoprotein, a p-450 hydroxylase, an oxidoreductase, and a proline oxidase. In particularly preferred embodiments, the fatty acid is contacted with polypeptides encoded by ORF17, ORF20, ORF21, ORF29, ORF30, ORF32, ORF35, and ORF38.

In still yet another embodiment, this invention provides a method of synthesizing a deoxysugar. This method involves contacting a sugar with one or more C-1027 open reading frame polypeptides selected from the group consisting of a dNDP-glucose synthase, a dNDP glucose dehydratase, an epimerase, an aminotransferase, a C-methyltransferase, an N-methyltransferase, and a glycosyl transferase. In preferred embodiments, this method involves contacting a dNDP-glucose with a plurality of C-1027 open reading frame polypeptides comprising a dNDP-glucose synthase, a dNDP glucose dehydratase, an epimerase, an aminotransferase, a C-methyltransferase, an N-methyltransferase, and a glycosyl transferase. In particularly preferred embodiments, the dNDP-glucose is contacted with polypeptides encoded by orf17, orf20, orf21, orf29, orf30, orf32, orf35, and orf38.

This invention also provides methods of synthesizing a beta amino acid by contacting an amino acid with one or one or more C-1027 open reading frame polypeptides selected from the group consisting of a hydroxylase, an aminomutase, a type II NRPS condensation enzyme, a type II NRPS adenylation enzyme, and a type II peptidyl carrier protein. The method preferably comprises contacting an amino acid with a plurality of C-1027 open reading frame polypeptides comprising a hydroxylase, a halogenase, an aminomutase, a type II NRPS condensation enzyme, a type II NRPS adenylation enzyme, and a type II peptidyl carrier protein. Particularly preferred embodiments comprise contacting the amino acid (e.g. tyrosine) with polypeptides encoded by ORF 4, ORF11, ORF24, ORF23, ORF25, and ORF26.

Also provided are methods of synthesizing an enediyne or an enediyne analogue. These methods involve culturing a cell (e.g. a eukaryotic cell or a bacterium) comprising a recombinantly modified C-1027 gene cluster under conditions whereby said cell expresses said enediyne or enediyne analogue; and recovering the enediyne or enediyne analogue. In preferred embodiments, the gene cluster is present in a bacterium (e.g., *Actinomycetes, Actinoplanetes, Actinomadura, Micromonospora*, or *Streptomycetes*). Particularly preferred bacteria include, but are not limited to *Streptomyces globisporus, Streptomyces lividans, Streptomyces coelicolor, Micromonospora echinospora* spp. *calichenisis, Actinomadura verrucosospora, Micromonospora chersina, Streptomyces carzinostaticus*, and *Actinomycete* L585-6. In another preferred embodiment, the gene cluster is present in a eukaryotic cell (e.g. a mammalian cell, a yeast cell, a plant cell, a fungal cell, an insect cell, etc.). The host cell can be one that synthesizes sugars and glycosylates the enediyne or enediyne analogue. The host can be one that synthesizes deoxysugars.

This invention also provides a method of making a cell (e.g., a bacterial or eukaryotic cell) resistant to an enediyne or an enediyne metabolite. This method involves expressing in the cell one or more isolated C-1027 open reading frame nucleic acids that encode a protein selected from the group consisting of a CagA apoprotein, a SgcB transmembrane efflux protein, a transmembrane transport protein, a Na+/H+ transporter, an ABC transport, a glycerol phosphate tranporter, and a UvrA-like protein. In preferred embodiments, the isolated C-1027 open reading frame nucleic acids are selected from the group consisting of orf 9, orf2, orf 27, orf 0, orf 1 c-terminus, orf 2, and orf 1 N-terminus. Certain embodiments exclude cagA (orf 9).

In one embodiment, this invention specifically excludes one or more of open reading frames −7 through 42. In particular, in one embodiment this invention excludes cagA (orf9), and/or sgcA (orf1), and/or sgcB (orf2).

DEFINITIONS

The terms "C-1027 open reading frame", and "C-1027 ORF" refer to an open reading frame in the C-1027 biosynthesis gene cluster as isolated from *Streptomyces globisporus*. The term also embraces the same open reading frames as present in other enediyne-synthesizing organisms (e.g. other strains and/or species of *Streptomyces, Actinomyces*, and the like). The term encompasses allelic variants and single nucleotide polymorphisms (SNPs). In certain instances the C-1027 ORF is used synonymously with the polypeptide encoded by the C-1027 ORF and may include conservative substitutions in that polypeptide. The particular usage will be clear from context.

The terms "isolated" "purified" or "biologically pure" refer to material which is substantially or essentially free from components which normally accompany it as found in its native state. With respect to nucleic acids and/or polypeptides the term can refer to nucleic acids or polypeptides that are no longer flanked by the sequences typically flanking them in nature.

The terms "polypeptide", "peptide" and "protein"0 are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49:1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111 :2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

A "coding sequence" or a sequence which "encodes" a particular polypeptide (e.g. a PKS, an NRPS, etc.), is a nucleic acid sequence which is ultimately transcribed and/or translated into that polypeptide in vitro and/or in vivo when placed under the control of appropriate regulatory sequences. In certain embodiments, the boundaries of the coding sequence are determined by a start codon at the 5' (amino) terminus and a translation stop codon at the 3' (carboxy) terminus. A coding sequence can include, but is not limited to, cDNA from procaryotic or eucaryotic mRNA, genomic DNA sequences from procaryotic or eucaryotic DNA, and even synthetic DNA sequences. In preferred embodiments, a transcription termination sequence will usually be located 3' to the coding sequence.

Expression "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Recombination" refers to the reassortment of sections of DNA or RNA sequences between two DNA or RNA molecules. "Homologous recombination" occurs between two DNA molecules which hybridize by virtue of homologous or complementary nucleotide sequences present in each DNA molecule.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes part I chapter 2 Overview of principles of hybridization and the strategy of nucleic acid probe assays*, Elsevier, N.Y., Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) *Molecular Cloning—A Laboratory Manual* (2nd ed.) Vol. 1–3, Cold Spring Harbor Laboratory, Cold Spring Harbor Press, NY, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Expression vectors are defined herein as nucleic acid sequences that are direct the transcription of cloned copies of genes/cDNAs and/or the translation of their mRNAs in an appropriate host. Such vectors can be used to express genes or cDNAs in a variety of hosts such as bacteria, bluegreen algae, plant cells, insect cells and animal cells. Expression vectors include, but are not limited to, cloning vectors, modified cloning vectors, specifically designed plasmids or viruses. Specifically designed vectors allow the shuttling of DNA between hosts, such as bacteria-yeast or bacteria-animal cells. An appropriately constructed expression vector preferably contains: an origin of replication for autonomous replication in a host cell, a selectable marker, optionally one or more restriction enzyme sites, optionally one or more constitutive or inducible promoters. In preferred embodiments, an expression vector is a replicable DNA construct in which a DNA sequence encoding a one or more PKS and/or NRPS domains and/or modules is operably linked to suitable control sequences capable of effecting the expression of the products of these synthase and/or synthetases in a suitable host. Control sequences include a transcriptional promoter, an optional operator sequence to control transcription and sequences which control the termination of transcription and translation, and so forth.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The "group consisting of orf(−7) through orf(60)" refers to the group consisting of orf(−7), orf(−6), orf(−5), orf(−4), orf(−3), orf(−2), orf(−1), orf0, orf1, orf2, orf3, orf4, orf5, orf6, orf7, orf8, orf10, orf11, orf12, orf13, orf14, orf15, orf16, orf17, orf18, orf19, orf20, orf21, orf22, orf23, orf24, orf25, orf26, orf27, orf28, orf27, orf28, orf30, orf31, orf32, orf33, orf34, orf35, orf36, orf37, orf37, orf38, orf39, orf40, orf41, orf42, orf43, orf44, orf45, orf46, orf47, orf48, orf49, orf50, orf51, orf52, orf53, orf54, orf55, orf56, orf57, orf58, orf59, and orf60, as identified in Tables II and III. In certain embodiments ORF 9 (cagA) is excluded.

A "biological molecule that is a substrate for a polypeptide encoded by a enediyne (e.g., C-1027) biosynthesis gene" refers to a molecule that is chemically modified by one or more polypeptides encoded by open reading frame(s) of the C-1027 biosynthesis gene cluster. The "substrate" may be a native molecule that typically participates in the biosynthesis of an enediyne, or can be any other molecule that can be similarly acted upon by the polypeptide.

A "polymorphism" is a variation in the DNA sequence of some members of a species. A polymorphism is thus said to be "allelic," in that, due to the existence of the polymorphism, some members of a species may have the unmutated sequence (i.e. the original "allele") whereas other members may have a mutated sequence (i.e. the variant or mutant "allele"). In the simplest case, only one mutated sequence may exist, and the polymorphism is said to be diallelic. In the case of diallelic diploid organisms, three genotypes are possible. They can be homozygous for one allele, homozygous for the other allele or heterozygous. In the case of diallelic haploid organisms, they can have one allele or the other, thus only two genotypes are possible. The occurrence of alternative mutations can give rise to trialleleic, etc. polymorphisms. An allele may be referred to by the nucleotide(s) that comprise the mutation.

"Single nucleotide polymorphism" or "SNPs are defined by their characteristic attributes. A central attribute of such a polymorphism is that it contains a polymorphic site, "X," most preferably occupied by a single nucleotide, which is the site of the polymorphism's variation (Goelet and Knapp U.S. patent application Ser. No. 08/145,145). Methods of identifying SNPs are well known to those of skill in the art (see, e.g., U.S. Pat. No. 5,952,174).

Abbreviations used herein include LB, Luria-Bertani; NGDH, dNDP-glucose 4,6-dehydratase; nt, nucleotide; ORF, open reading frame; PCR, polymerase chain reaction; PEG, polyethyleneglycol; PKS, polyketide synthase; RBS, ribosomal binding site; Apr, apramycin; R, resistant; Th, thiostrepton; WT, wild-type; and TS, temperature sensitive

BRIEF DESCRIPTION OF THE DRAWINGS

FIG. 5A shows a restriction map of the 75-kb sgc gene cluster from S. globisporus as represented by three cosmid clones. FIG. 5B illustrates the genetic organization of the sgcA, sgcB, and cagA genes, showing that they are clustered in the sgc gene cluster. Probe 1, the 0.55-kb dNDP-glucose 4,6-dehydratase gene fragment from pBS1002. Probe 2, the 0.73-kb cagA fragment from pBS1003. A, ApaI; B, BamHI; E, EcoRI; K, KpnI, S, SacII; Sp, SphI. FIG. 5C shows the genetic organization of the C-1027 biosynthesis gene cluster.

FIG. 6 shows the DNA and deduced amino acid sequences of the 3.0-kb BamHI fragment from pBS1007 (SEQ ID NQ:217), showing the sgcA (amino acid seQuence: SEQ ID NO:218) and sgcB (amino acid sequence: SEQ ID NO:219) genes. Possible RBSs are boxed. The presumed translational start and stop sites are in boldface. Restriction enzyme sites of interest are underlined. The amino acids, according to which the degenerated PCR primer were designed for amplifying the dNDP-glucose 4,6-dehydratase gene from S. globisporus, are underlined.

FIG. 7 shows the amino acid sequence alignment of SgcA (SEQ ID NO:220) with three other dNDP-glucose 4,6-dehydratases. Gdh, TDP-glucose 4,6-dehydratase of S. erythraea (AAA68211, SEQ ID NO:221); MtmE, TDP-glucose 4,6-dehydratase in the mithramycin pathway of S. argillaceus (CAA71847, SEQ ID NO:222); IA2, TDP-glucose 4,6-dehydratase in the tylosin pathway of S. fradiae (549054, SEQ ID NO:223). Given in parentheses are protein accession numbers. The αβα fold with the NAD$^+$-binding motif of GxGxxG (SEQ ID NO:225) is boxed. Consensus sequence is SEQ ID NO:224.

FIGS. 8A and 8B show disruption of sgcA by single crossover homologous recombination. FIG. 8A shows construction of sgcA disruption mutant and restriction maps of the wild-type *S. globisporus* C-1027 and *S. globisporus* SB1001 mutant strains showing predicted fragment sizes upon BamHI digestion. FIGS. 8B and 8C show a Southern analysis of *S. globisporus* C-1027 (lane 1) and *S. globisporus* SB1001 (lanes 2, 3, and 4, three individual isolates) genomic DNA, digested with BamHI, using (FIG. 8B) pOJ260 vector or (FIG. 8C) the 0.75-kb SacII/KpnI fragment of sgcA from pBS1012 as a probe, respectively. B, BamHI; K, KpnI; S, SacII.

FIGS. 9A, 9B, 9B, and 9D illustrate the determination of C-1027 production in various *S. globisporus* strains by assaying their antibacterial activity against *M. luteus*. FIG. 9A:1, *S. globisporus*C-1027; 2,3, and 4, *S. globisporus* SB1001 (three individual isolates); 5, *S. globisporus* AF67; 6, *S. globisporus* AF40. FIG. 9B: 1, *S. globisporus* C-1027; 2, *S. globisporus* SB1001 (pWHM3); 3 and 4, *S. globisporus* SB1001 (pBS1015) (two individual isolates). Both *S. globisporus* SB1001 (pWHM3) and *S. globisporus* SB1001 (pBS1015) were grown in the presence of 5 µg/mL thiostrepton. FIG. 9C: 1, *S. globisporus*C-1027; 2, *S. globisporus* SB1001 (pBS1015); 3. *S. globisporus* SB1001; 4. *S. globisporus* SB1001 (pWHM3); 5. *S. globisporus* AF40; 6. *S. globisporus* AF44. All *S. globisporus* strains were grown in the absence of thiostrepton. FIG. 9D: 1. *S. globisporus* (pKC1139); 2. *S. globisporus* (pBS1018).

FIG. 12 shows that the upstream boundary has been determined to be between orf(-3) and sgcB1 (designated B1 in FIG. 12), and the downstream boundary has been determined to be between sgcR3 (designated R3 in FIG. 12) and orf54.

FIG. 13A: Comparison between the SgcE PKS catalyzing the nine-membered enediyne core in C-1027 biosynthesis and the CalD8 PKS catalyzing the ten-membered enediyne core in calicheamicin biosynthesis. aa, amino acid; KS, ketoacyl synthase; AT, acyltransferase; ACP, acyl carrier protein; KR, ketoreductase; DH, dehydratase; TD, COOH-terminal domain. FIG. 13B shows a proposal of rthe C-1027 core biosynthesis by the SgcE PKS and other accessory proteins.

(FIG. 14B deoxy amino sugar, (FIG. 14C) β-amino acid, and (FIG. 14D) benzoxazolinate.

DETAILED DESCRIPTION

This invention provides a complete gene cluster regulating the biosynthesis of C-1027, the most potent member of the enediyne antitumor antibiotic family. C-1027 is produced by *Streptomyces globisporus* C-1027 and consists of an apoprotein (encoded by the cagA gene) and a nonpeptidic chromophore. The C-1027 chromophore could be viewed as being derived biosynthetically from a benzoxazolinate, a deoxyamino hexose, a β-amino acid, and an enediyne core. Adopting a strategy to clone the C-1027 biosynthesis gene cluster by mapping a putative dNDP-glucose 4,6-dehydratase (NGDH) gene to cagA, we localized 75 kb contiguous DNA from *S. globisporus* encoding a complete C-1027 gene cluster.

Initial sequencing of the cloned gene cluster revealed two genes, sgcA and sgcB, that encode an NGDH enzyme and a transmembrane efflux protein, respectively, and confirmed that the cagA gene resides approximately 14 kb upstream of the sgcA,B locus. The involvement of the cloned gene cluster in C-1027 biosynthesis was demonstrated by disrupting the sgcA gene to generate C-1027-nonproducing mutants and by complementing the sgcA mutants in vivo to restore C-1027 production.

Figure 10:
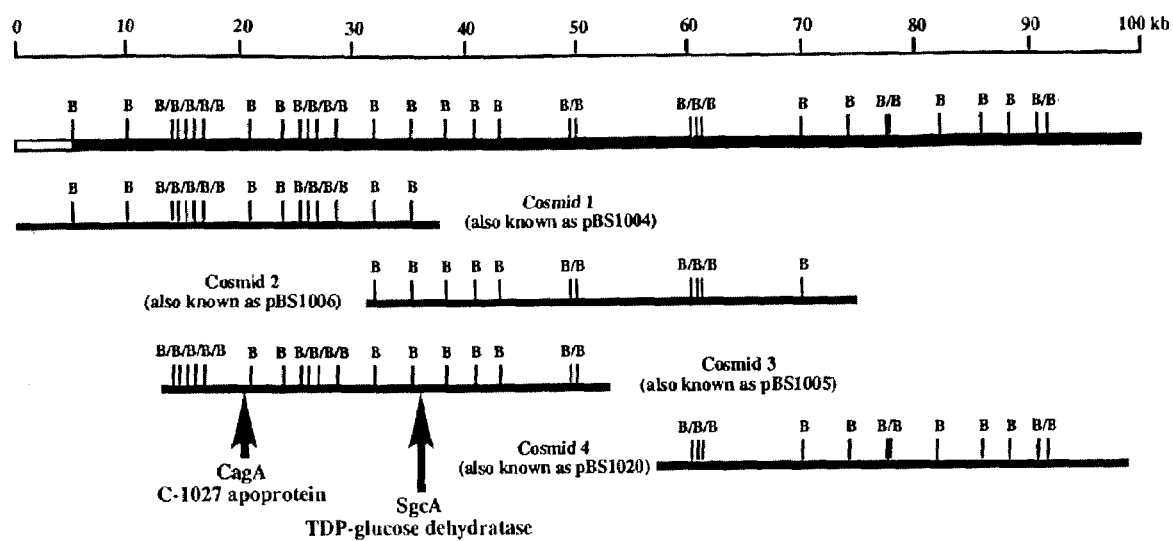
FIG. 10 shows a restriction map of the 100-kb DNA region from *S. globisporus* as represented by four overlapping cosmid clones (B, BamHI).
Figure 11:
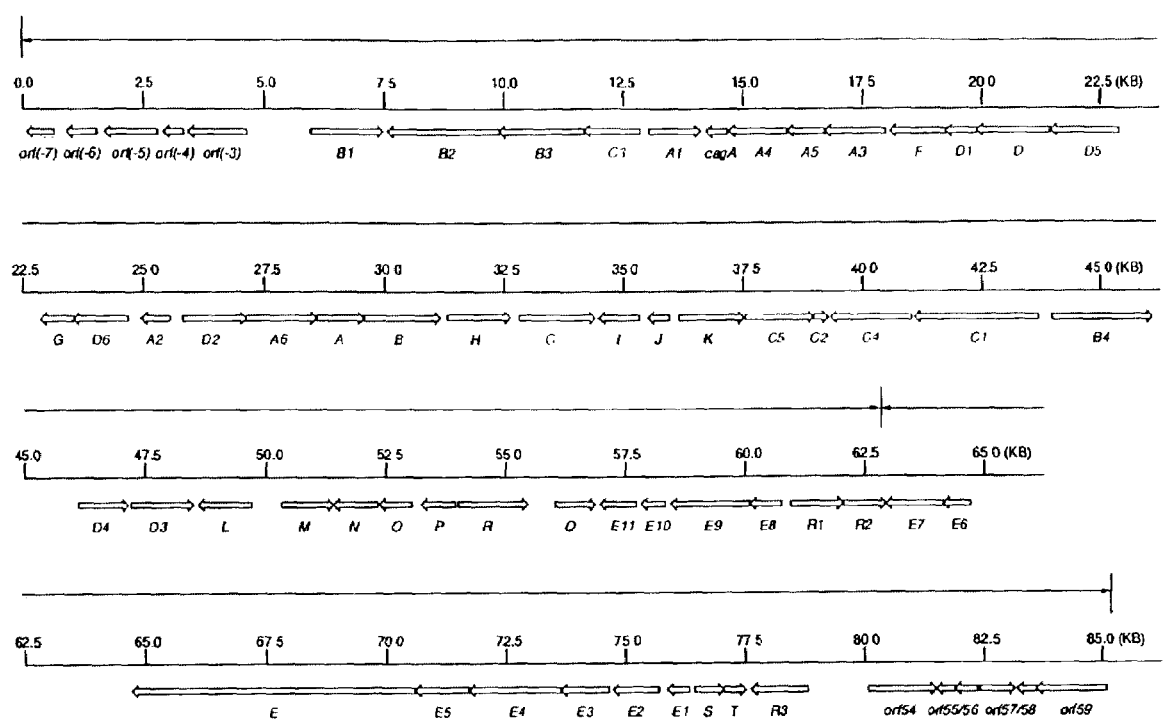
FIG. 11 illustrates the genetic organization of the C-1027 biosynthesis gene cluster form *S. globisporus*.

Subsequent DNA sequence analysis provided the complete enediyne C-1027 gene cluster sequence (SEQ ID NOs: 1 and 2) revealing open reading frames (orf) from orf(-7) to sgcR2 and sgcE7 (partial) (FIG. 10 and FIG. 11). All of the open reading frames (orfs) have been given gene names as shown in Tables I1 and III. Open reading frame 33 is now assigned to two genes (sgcO and sgcP) as illustrated in Table III.

The C-1027 gene biosynthesis gene cluster is extended to 85,168 bp by the addition of cosmid 4 as illustrated in FIG. 10 which encodes sgcE7, sgcR3, and orf54 to orf59 (FIG. 11 and Sequence Listing). Putative functions for these genes have been assigned according to sequence homology with proteins with confirmed or predicted functions in the database and are summarized in Tables II and III.

Figure 12:
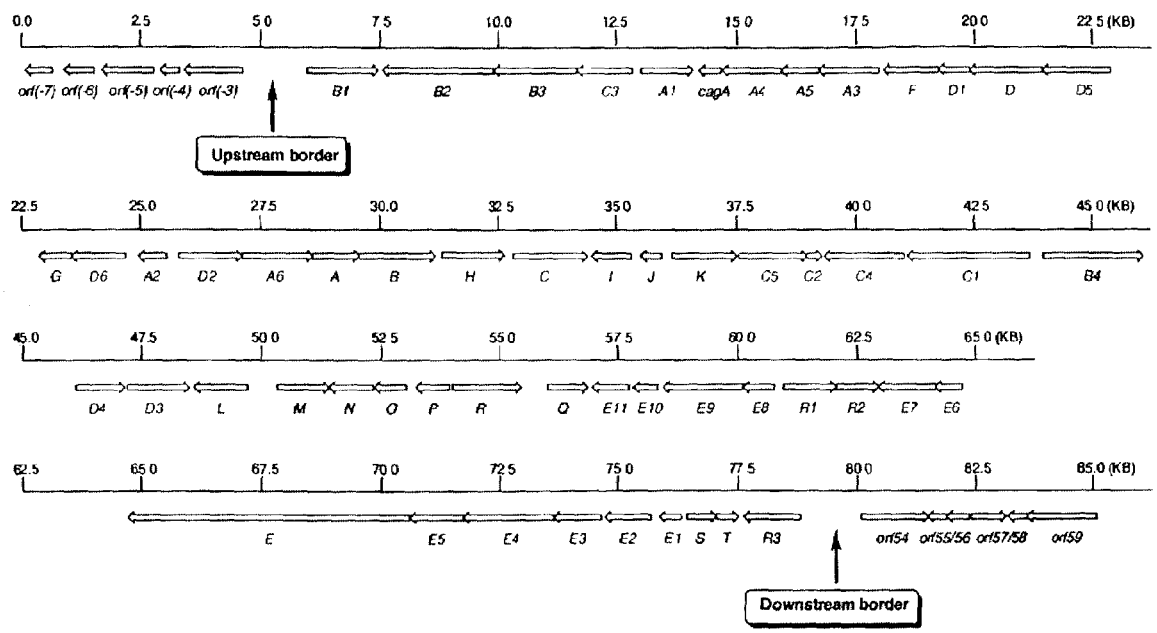
FIG. 12 illustrates the organization of the C-1027 biosynthesis gene cluster and determination of its upstream and downstream boundaries.

The boundary of the C-1027 biosynthesis gene cluster has been established by insertional gene disruption to generate *S. globisporus* mutants, followed by fermentation of these mutants to examine their ability for C-1027 production. As summarized in FIG. 12, the upstream and downstream boundaries of the C-1027 biosynthesis gene cluster have been assigned to be between orf(−3) and sgcB1 and sgcR3 and orf54, respectively (FIG. 12).

To determine the upstream boundary, orf(−5), orf(−3), sgcB1, sgcB2, sgcC3, sgcA3, and sgcA5 were disrupted, respectively to generate the corresponding *S. globisporus* mutant strains. These mutant strains were cultured under standard conditions for C-1027 production with the *S. globisporus* wild type strain as a positive control. C-1027 production was analyzed by HPLC. As summarized in FIG. 4, disrupting orf(−5), orf(−3), sgcB1, or sgcB2, respectively, had no effect on C-1027 production and the corresponding *S. globisporus* mutant strains produced C-1027 as the *S. globisporus* wild type strain.

In contrast, disrupting sgcC3, sgcA3, or sgcA5 yielded *S. globisporus* mutant strains whose ability to produce C-1027 was completely abolished. Therefore, genes upstream of sgcB2 are not essential for C-1027 production and hence are not a part of the C-1027 biosynthesis gene cluster, while sgcC3, sgcA3, and sgcA5 are essential for C-1027 production and hence, must be within the C-1027 gene cluster. These results defined the upstream boundary of the C-1027 biosynthesis gene cluster to be between orf(−3) and sgcB1. We prefer to include sgcB1 and sgcB2 as part of the C-1027 gene cluster, although their gene disruption mutants can produce C-1027 normally. Since sgcB1 and sgcB2 encode putative C-1027 resistance proteins, we reasoned that inactivation of them may have little effect on C-1027 production because of multiple C-1027 resistance mechanisms within the C-1027 gene cluster.

To determine the downstream boundary, sgcE7, sgcE, sgcE2, sgcR3, and orf54 were disrupted, respectively, to generate the corresponding *S. globisporus* mutant strains. These mutant strains were similarly cultured under the standard conditions for C-1027 production with the *S. globisporus* wild type strain as positive control. C-1027 production was analyzed by HPLC.

As summarized in Table I, disrupting sgcE7, sgcE, sgcE2, or sgcR3 abolished C-1027 production completely, while disrupting orf54 had no effect on C-1027 production. Therefore, genes upstream of sgcR3 were essential for C-1027 production and hence ar within the C-1027 biosynthesis gene cluster, while genes downstream of orf54 are not essential for C-1027 production and hence are not a part of the C-1027 gene cluster. These results therefore defined the downstream boundary of the C-1027 biosynthesis gene cluster to be between sgcR3 and orf54.

Three types of polyketide synthases (PKSs) are known for polyketide biosynthesis in bacteria: type I and type II systems, both of which use acyl carrier protein (ACP) to activate substrates as described herein channel the growing intermediates for aliphatic and aromatic polyketides, respectively, and the type III system that has no apparent amino acid sequence similarity to the former and acts directly on acyl CoAs, largely for monocyclic aromatic polyketides. The enediyne cores bear no structural resemblance to any of the polyketides studied to date, failing to predict what type of PKS may be responsible for their biosynthesis. In fact, a controversy remained as to whether the enediyne cores are assembled via a de novo polyketide biosynthesis, or by degradation from a fatty acid precursor, although feeding experiments with 13C-labeled precursors for neocarzinostatin, dynemicin, and esperamicin unambiguously established that the enediyne cores were all derived from minimally eight head-to-tail acetate units.

TABLE I

The production of C-1027 by *S. globisporus* wild type and mutant strains as determined by HPLC analysis. The mutant strains were isolated by insertional gene disruption of the targeted genes. *S. globisporus* wild type and mutant strains were grown under standard conditions for C-1027 production. Holo-C-1027 chromoprotein complex was isolated from the fermentation broth by (NH4)2SO4 precipitation. The C-1027 chromophore was extracted from the holo-chromoprotein complex with ethyl acetate. HPLC analysis was carried out on a Prodigy ODS-2 column (5 μ, 150 × 4.6 mm, Phenomenex, Torrance, CA), eluted isocratically with 20 mM potassium phosphate (pH 6.86)/CH3CN (50:50, v/v) at a flow rate of 1.0 ml/min and UV detection at 350 nm.

| Strain | C-10277 (% yield) |
|---|---|
| Wild-type | 100 |
| orf(−5) mutant | 100 |
| orf(−3) mutant | 100 |
| sgcB1 mutant | 100 |
| sgcB2 mutant | 100 |
| sgcC3 mutant | 0 |
| sgcA5 mutant | 0 |
| sgcA3 mutant | 0 |
| sgcE7 mutant | 0 |
| sgcE mutant | 0 |
| sgcE2 mutant | 0 |
| sgcR3 mutant | 0 |
| orf54 mutant | 100 |

Figure 13A:
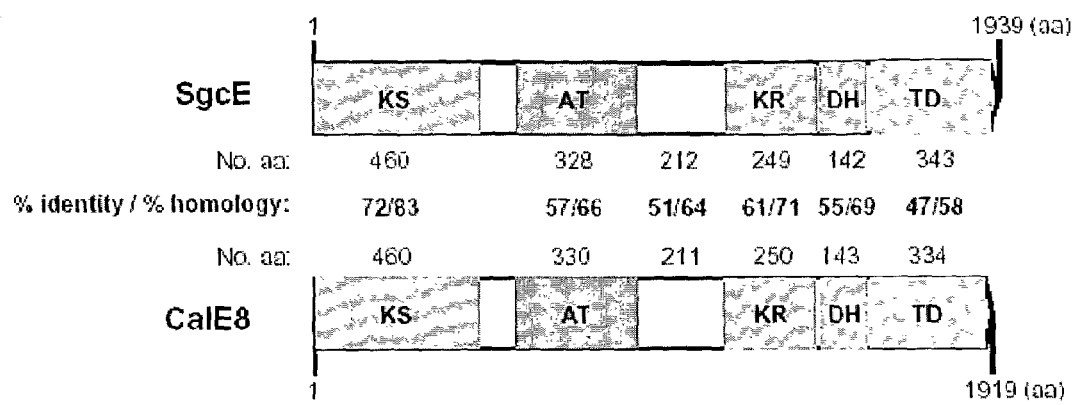
FIGS. 13A and 13B illustrate enediyne core structure and biosynthesis.
Figure 13B:
Figure 14A:
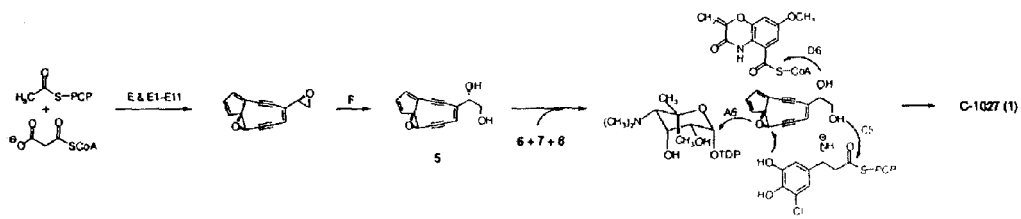
FIGS. 14A–14D illustrate biosynthetic pathways for (FIG. 14A) enediyne core and a convergent assembly strategy for the C-1027 chromophore.
Figure 15:
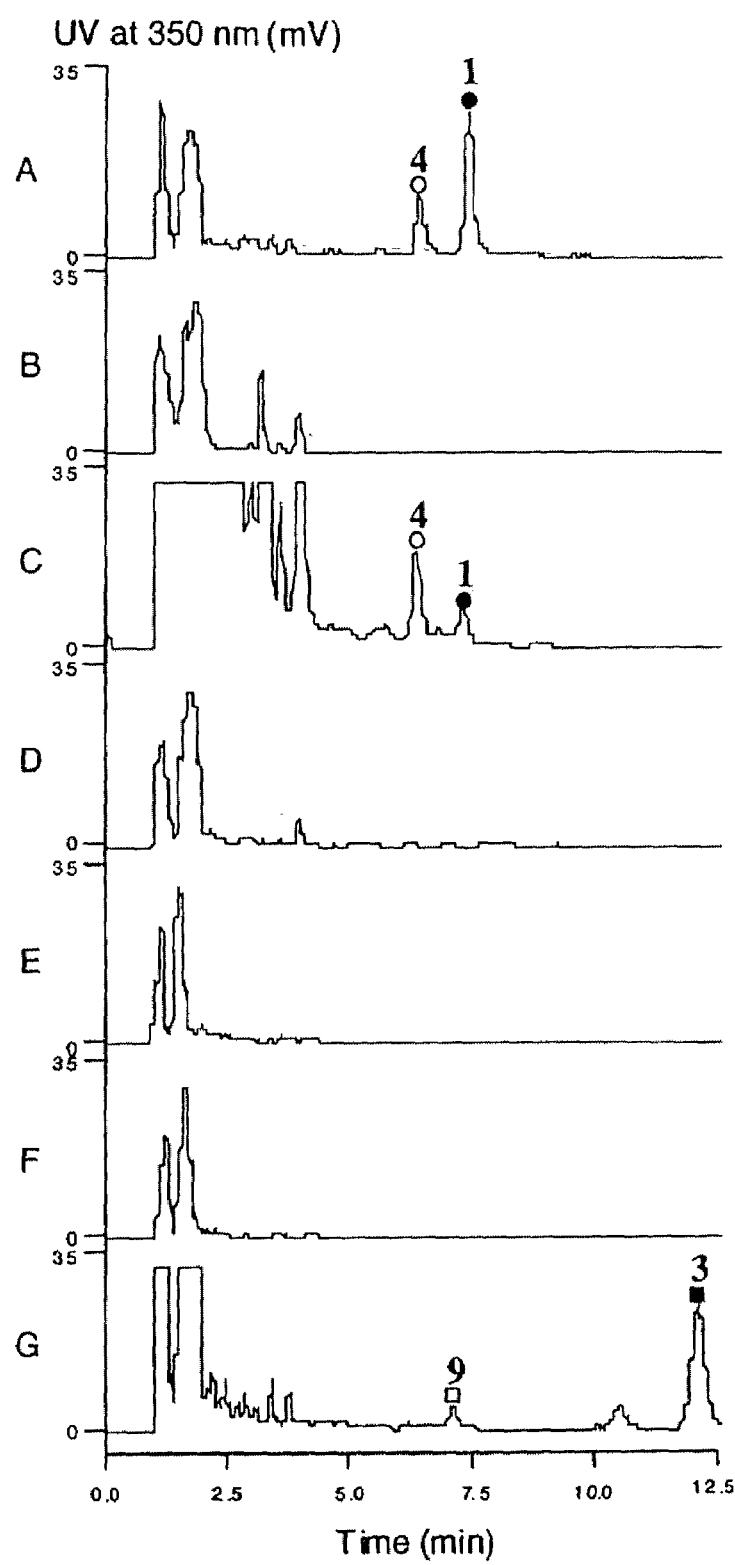
FIG. 15 panels A–G show HPLC analysis of the C-1027 chromophores isolated from *S. globisporus* strains: (Panel A) wild-type, (Panel B) sgcE replacement mutant SB1005, (Panel C) SB1005 complemented by pBS1019 that overexpresses sgcE, (Panel D) sgcA disruption mutant SB1001, (Panel E) sgcC1 disruption mutant SB1003, (Panel F) sgcD6 disruption mutant SB1004, (G) sgcC disruption mutant SB1006. Structures for 1, 3, 4, 9 are shown in FIG. 18.

Strikingly, of the genes identified within the C-1027 cluster, there is only one, sgcE, that encodes a PKS. SgcE contains six domains—the ketoacyl synthase (KS), acyltransferase (AT), ketoreductase (KR), and dehydratase (DH) ACPs, and a domain at the COOH-terminus (TD) that, unique only to enediyne PKSs, shows not sequence homology to any other proteins (FIG. 13). SgcE can be envisaged catalyzing the assembly of a nascent linear polyunsaturated intermediate from acetyl and malonyl CoAs in an iterative process, which, upon action of other enzyme activities, is subsequently desaturated to furnish the two yne groups and cyclized to afford the enediyne core (FIG. 14A). An enzyme that catalyzes the formation of an acetylenic bond from a C—C double bond has been reported from the plant *Crepis alpine* and characterized as acetylenase that is a non-heme diiron protein. While no such homolog was found within the C-1027 cluster, close comparison of the C-1027 gene cluster with that for neocarzinostatin, another rnine-membered enediyne antibiotic revealed a group of orfs(sgcE1 to sgcE11), in addition to sgcE, that are highly conserved. SgcE6, SgcE7, and SgcE9 resemble various oxidoreductases, SgcE1, SgcE2, SgcE3, SgcE4, SgcE5, SgcE8, or SgcE11 show no sequence homology, or homology only to proteins of unknown functions, and sgcE10 is highly homologous to a family of thioesterases. These enzymes, together with the SgcF epoxide hydrolase, serve as candidates for processing the nascent linear polyunsaturated intermediate into an enediyne intermediate such as 5 (FIGS. 13B and 14A). To experimentally test this hypothesis, the sgcE domain was replaced with the erythromycin resistance gene, ermE. The Resultant *S. globisporus* SB1005 mutant strain completely lost its ability to produce 1 (FIG. 15, panel B), and this phenotype can be complemented by introduction of pBS1019, in which the expression of sgcE is under the control of the constitutive ermE* promoter, into SB1005, restoring 1 production to the level comparable to the wild-type organism (FIG. 15, panel C). These findings unambiguously established that C-1027 enediyne core biosynthesis proceeds via a polyketide pathway.

TABLE II

Summary of the C-1027 gene cluster open reading frames (−7 to 26), primers for ORF amplification, and proposed functions

| ORF # gene name | Relative position in SEQ ID NO: 1 Size | Primers | Function | Seq ID No. |
|---|---|---|---|---|
| orf(−7) orf(−7) | 658–11 648 bp | Fwd: ATG GGC ATG ACG GGT Rev: CTA GAG GAT CCC GGG | very weak homology to putative hydroxylase | 3 4 |
| orf(−6) orf(−6) | 1478–930 549 bp | Fwd: ATG CCG CGG ATT CCC Rev: TCA GCT GTC GAT GTC | Viral infectivity potentiator protein | 5 6 |
| orf(−5) orf(−5) | 2713–1649 1065 bp | Fwd: ATG ACC ATC GCC ACT Rev: TCA GAG GCC GAG CAC | N-truncated Methionine synthase (likely psuedogene) | 7 8 |
| orf(−4) orf(−4) | 3238–2851 387 bp | Fwd: ATG AGC TCG CTA CTG Rev: CTA GGA GCC GGT CGC | Viral transcription factor | 9 10 |
| orf(−3) orf(−3) | 4971–3442 1530 bp | Fwd: ATG AGC AGC AGC GCC Rev: TCA TTC GTC GGC TGC | Viral Homolog possibly primase | 11 12 |
| orf(−2) sgcB1 | 5982–7478 3027 bp | Fwd: GTG AGG GCT CTG CCG Rev: TCA GAC GGC GGA GGG | Glycerol-Phosphate ABC Transporter (SnoX drug resistance) | 13 14 |
| orf(−1) sgcB2 | 9900–7573 2328 bp | Fwd: GTG AGC GTC ACC GAC Rev: TCA ACC CGC CCT GCG | UvrA-like drug resistance pump | 15 16 |
| orf0 sgcB3 | 11349–9982 1368 bp | Fwd: ATG AGG ATG CTG GTG Rev: GTG GCT GTG CTC GCA | Na$^+$/H$^+$ efflux pump | 17 18 |
| orf1 sgcA | 28590–29588 999 bp | Fwd: ATG AGG ATG CTG GTG Rev: TCA GCC GAC GGC GTC | dNTP-glucose dehydratase | 19 20 |
| orf2 sgcB | 29632–31197 1566 bp | Fwd: GTG ACA GCA GTC AAG Rev: TCA TGT GGC CGG TTG | Transmembrane efflux protein | 21 22 |
| orf3 sgcH | 31280–32590 1311 bp | Fwd: GTG GAG TAC TGG AAC Rev: TCA GGC CTG AGG GGC | Coenzyme F390 synthase phenylacetyl-CoA ligase | 23 24 |
| orf4 sgcC | 32809–34392 1584 bp | Fwd: GTG CCC CAC GGT GCA Rev: CTA CAG CCC TCC GAG | phenol hydroxylase chlorophenol-4-mono-oxygenase | 25 26 |
| orf5 sgcK | 35274–34458 | Fwd: ATG TCT TCA ACC CGT Rev: TCA GCC GCG CAG GAA | citrate transport protein | 27 28 |
| orf6 sgcA3 | 17924–16653 1272 bp | Fwd: ATG CTG GAG AAA TGC Rev: TCA GAC GAG CTC CTT | C-methyl transferase hydroxylase | 29 30 |
| orf7 sgcA5 | 16653–15919 735 bp | Fwd: ATG GAG TAC GGC CCC Rev: TCA TGC CCT GCG CAC | N-methyltransferase | 31 32 |
| orf8 sgcA4 | 15922–14690 1233 bp | Fwd: ATG AGC GGC GGC CCG Rev: TCA CCT CGC CGG ACG | Aminotransferase | 33 34 |
| orf9 cagA | 14643–14212 432 bp | Fwd: ATG TCG TTA CGT CAC Rev: TCA GCC GAA GGT CAG | CagA | 35 36 |
| orf10 sgcA1 | 13012–14079 1068 bp | Fwd: ATG AAG GCA CTT GTA Rev: TCA GGC CGC CAT CTC | dNTP-glucose synthase | 37 38 |
| orf11 sgcC3 | 12835–11351 1485 bp | Fwd: GTG GAC GTG TCA CGC Rev: TCA GGA CCG CGC ACC | Hydroxylase, Halogenase | 39 40 |
| orf12 sgcA2 | 25564–24986 579 bp | Fwd: ATG AAG CCG ATC CGG Rev: TCAGGA CGA CTT GTT | dNTP-4-keto-6-deoxyglucose 3,5-epimerase | 41 42 |
| orf13 sgcD6 | 24702–23566 1137 bp | Fwd: ATG CCT TCC CCC TTC Rev: TCA GGT GCG CTC GGC | 3-O-acyltransferase | 43 44 |
| orf14 sgcD5 | 22878–21424 1455 bp | Fwd: GTG AGA GAC GGC CGG Rev: TCA CGT GGT GAT GGC | Coenzyme F-390 Synthase Phenylacetyl CoA Ligase | 45 46 |

TABLE II-continued

Summary of the C-1027 gene cluster open reading frames (-7 to 26), primers for ORF amplification, and proposed functions

| ORF # gene name | Relative position in SEQ ID NO: 1 Size | Primers | Function | Seq ID No. |
|---|---|---|---|---|
| orf15 sgcD | 21407–19926 1482 bp | Fwd: ATG ACC GAC CAG TGC<br>Rev: TCA CAG CAA CTC CTC | Anthranilate Synthase I | 47<br>48 |
| orf16 sgcD1 | 19929–19267 663 bp | Fwd: GTG AGC TTG TGG TCT<br>Rev: TCA GGC CGG TTC GGC | Anthranilate Synthase II | 49<br>50 |
| orf17 sgcF | 19191–18031 1161 bp | Fwd: GTG CGT CCC TTC CGT<br>Rev: TCA GCG GAG CGG ACG | epoxide hydrolase | 51<br>52 |
| orf18 sgcJ | 35938–35516 423 bp | Fwd: ATG CCA GCA CCG ACT<br>Rev: TCA GTC GTT GCC GCG | Unknown | 53<br>54 |
| orf19 sgcA6 | 27214–28593 1380 bp | Fwd: ATG CGG GTG ATG ATC<br>Rev: TCA TCG GTC CGC CTC | glycosyl transferase | 55<br>56 |
| orf20 sgcD2 | 25815–27170 1356 bp | Fwd: ATG ACC AAG CAC GCC<br>Rev: TCA TAC GGC GGC GCC | squalene monooxygenase | 57<br>58 |
| orf21 sgcG | 23546–22875 672 bp | Fwd: GTG AGC GCA CAA CTC<br>Rev: TCA CGG CTG TGC CTG | hypothetical Fe-S flavoprotein | 59<br>60 |
| orf22 sgc1 | 35274–34458 816 bp | Fwd: ATG TCT TCA ACC CGT<br>Rev: TCA GCC GCG CAG GAA | haloacetate dehalogenase hydrolase | 61<br>62 |
| orf23 sgcC5 | 37559–38938 1380 bp | Fwd: ATG ACG ACG TCC GAC<br>Rev: TCA GGA GGT GAA GGG | peptide synthetase | 63<br>64 |
| orf24 sgcC4 | 40986–39367 1620 bp | Fwd: ATG GCA TTG ACT CAA<br>Rev: TCA GCG CAG CTG GAT | Histidine Ammonia lyase | 65<br>66 |
| orf25 sgcC1 | 42611–41052 1560 bp | Fwd: ATG ACG CGG CCG GTG<br>Rev: TCA GCG GGT GAG CCG | Type II adenylation protein | 67<br>68 |
| orf26 sgcC2 | 38983–39264 282 bp | Fwd: GTG TCC ACC CTT TCC<br>Rev: TCA CTG CGT TCC GGA | Type II peptidyl carrier protein | 69<br>70 |

TABLE III

C-1027 gene cluster open reading frames (27 to 60), primers for ORF amplification, and proposed functions

| ORF | Relative Position in SEQ ID NO: 1 Size (bp) | Primers | Function | SEQ ID NO. |
|---|---|---|---|---|
| orf27 sgcB4 | 43945–46023 | Fwd: GTG TGC CCG GTG ACA GAC<br>Rev: TCA GCC CAC GGG CTG GGA | Antibiotic Transporter | 71<br>72 |
| orf28 sgcD4 | 46167–47171 | Fwd: GTG TTG GGC GAT GAG GAC<br>Rev: TCA GAC CGC GGA CAT CTG | O-methyltransferase | 73<br>74 |
| orf29 sgcD3 | 47227–48485 | Fwd: ATG GCC GGC CTG GTC ATG<br>Rev: TCA GGA CCC GAG GGT CAC | p450 hydroxylase | 75<br>76 |
| orf30 sgcL | 48610–49714 | Fwd: GTG GAC CAG ACG TCT ACG<br>Rev: TCA TGC AGG TGC AGC GTG | Oxidoreductase | 77<br>78 |
| orf31 sgcM | 50350–51390 | Fwd: ATG AGG CCG CTC GTT CGG<br>Rev: TCA TCC CGG CCC GGC GGC | Unknown Protein | 79<br>80 |
| orf32 sgcN | 51420–52341 | Fwd: ATG AGA ACG CGG CGA CGC<br>Rev: TCA CGG CCG GAG GCG TAC | Oxidoreductase | 81<br>82 |
| orf33 sgcO | 52366–53013 | Fwd: ATG TGC TCC CGT ACC<br>Rev: TCA GCC GGA CTG TCG | Unknown protein | 83<br>84 |
| orf33 | 53246–53926 | Fwd: ATG GCC CTT CAC CCG | Type II ACP/PCP | 85 |

TABLE III-continued

C-1027 gene cluster open reading frames (27 to 60), primers for ORF amplification, and proposed functions

| ORF | Relative Position in SEQ ID NO: 1 Size (bp) | Primers | Function | SEQ ID NO. |
|---|---|---|---|---|
| sgcP | | Rev: TCA GCC GGC CTG GGC | | 86 |
| orf34 sgcR | 54230–55379 | Fwd: ATG TCT ACG GGC TAT CTC Rev: TCA GCC CCC GGT GGC GCC | Unknown Protein | 87 88 |
| orf35 sgcQ | 56027–56881 | Fwd: ATG TTC TCC CCC GCC GCC Rev: TCA GTA CGC CTG GTG GGC | Oxidase Dehydrogenase | 89 90 |
| orf36 sgcE11 | 56928–57730 | Fwd: ATG AAT TCG CTC GAC GAC Rev: TCA GCT CCC GGT CGC CGC | Unknown Protein | 91 92 |
| orf37 sgcE10 | 57834–58304 | Fwd: ATG ACC GCG ACG AAT CCT Rev: CTA GGC GGC GCG TCC CGC | Regulatory | 93 94 |
| orf38 sgcE9 | 58440–60091 | Fwd: ATG AGC ACC ACG GCC GAG Rev: TCA GCC GCG CGC CGA CGG | Oxidoreductase | 95 96 |
| orf39 sgcE8 | 60092–60622 | Fwd: ATO ACC CTG GAG GCC TAC Rev: TCA TGC GGG GCT CCC GGT | Regulatory | 97 98 |
| orf40 sgcR1 | 60940–62020 | Fwd: GTG AAA ACT GAC TCT CCC Rev: TCA ACG GCG AGT TGG CTG | Regulatory | 99 100 |
| orf41 sgcR2 | 62045–62899 855 bp | Fwd: GTG ACC ACG AAC ACC ATC Rev: TCA CCC GCG ATC TCG ATC | Regulatory | 101 102 |
| orf42 sgcE7 | 64136–62787 1350 bp | Fwd: (partial ORF) Rev: TCA CCT CGC CGT ACT CAC | p450 hydroxylase | 103 104 |
| orf45 sgcE6 | 64681–64133 549 bp | Fwd: ATC ATC CCG ATC ATC Rev: TCA TGC CGC CCT TCC | Oxidoreductase | 105 106 |
| orf46 sgcE | 70581–64762 5820 bp | Fwd: ATG AGC CGC ATA GCC Rev: TCA CGC GCG GGC GCT | Type I polyketide synthase | 107 108 |
| orf47 sgcE5 | 71708–70578 1131 bp | Fwd: GTG ACC GTG CCC GGT Rev: TCA TAC AGG CAC CGT | Unknown | 109 110 |
| orf48o sgcE4 | 73633–71705 1929 bp | Fwd: ATG GCG GAG AGT TTC Rev: TCA CTT CTC CTT CAC | Unknown | 111 112 |
| orf49 sgcE3 | 74616–73630 987 bp | Fwd: GTG CCC CGG GCC TTT Rev: TCA TGC GAC GGC GCC | Unknown | 113 114 |
| orf50 sgcE2 | 75693–74712 982 bp | Fwd: GTG GCA TCG GTA CCG Rev: TCA GGG GTA TGT GAG | Unknown | 115 116 |
| orf51 sgcE1 | 76321–75878 444 bp | Fwd: ATG CTG CCA CGG ACG Rev: TCA GCG CGT CCG GCG | Unknown | 117 118 |
| orf52 sgcS | 76426–77031 606 bp | Fwd: GTG ATG ACC CAC TGC Rev: TCA GGC CTT CGG GGC | Unknown | 119 120 |
| orf53 sgcT | 77036–77497 462 bp | Fwd: GTG ACG ACG AGC GGC Rev: TCA GCT CCC CGC CGG | Unknown | 121 122 |
| orf54 sgcR3 | 78774–77587 1188 bp | Fwd: ATC GCG GCA CAC GAC Rev: TCA GCT CCC CTC CTG | Regulatory protein | 123 124 |
| orf55 sgc54 | 80065–81489 1425 bp | Fwd: GTG GAC GAG GCC GGC Rev: TCA CCC GGA TGT CGT | Orf(−3) homolog | 125 126 |
| orf56 sgc55 | 81860–81447 414 bp | Fwd: GTG AGT GCT CTG ATC Rev: TCA CCG CGG AAC GGA | Orf(−4) homolog | 127 128 |
| orf57 sgc56 | 82356–81886 471 bp | Fwd: GTG CCG CTT CTA CGC Rev: CTA CTG GAC ACT GTG | Unknown | 129 130 |
| orf58 sgc57 | 82413–83096 684 bp | Fwd: ATG CCG CAC AGG ACC Rev: TCA GCC GGT GAG AGC | Unknown | 131 132 |

TABLE III-continued

C-1027 gene cluster open reading frames (27 to 60), primers for ORF amplification, and proposed functions

| ORF | Relative Position in SEQ ID NO: 1 Size (bp) | Primers | Function | SEQ ID NO. |
|---|---|---|---|---|
| orf59 | 83518–83120 | Fwd: GTG AGT GCT CTG ATC | Orf(-4) homolog | 133 |
| sgc58 | 399 bp | Rev: TCA CCC CGG CAC AGG | | 134 |
| orf60 | 85050–83515 | Fwd: ATC ACC CCC GGA GGC | Orf(-3) homolog | 135 |
| sgc59 | 1536 bp | Rev: TCA CTC CGC CTC CTC | | 136 |

Figure 14B:
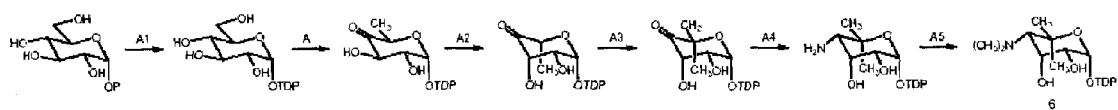

The availability of the gene cluster has set the stage to investigate the molecular basis of rC-1027 biosynthesis and to engineer novel enediyne compounds by manipulating C-1027 biosynthesis genes. Thus, the seven deoxy aminosugar biosyntheisi genes encode a TDP-glucose synthetase (SgcA1), a TDP-glucose 4,6dehydratase (SgcA), a TDP-4-keto-6-deoxyglucose epimerase (SgcA2), a C-methyl transferase (SgcA3), and amino transferase (SgcA4), an N-methyl transferase (SgcA5), and a glycosyl transferase (SgcA6). Together they are in an exact agreement with the enzyme functions that would be required for the biosynthesis of 6 from glucose-1-phosphate (FIG. 14B) and the attachment of 6 to 5 (FIG. 14A).

Figure 14C:
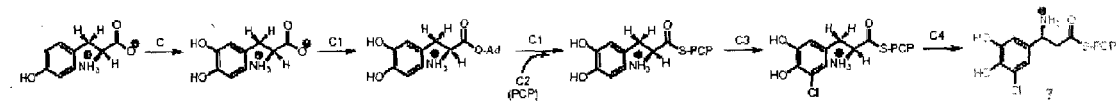

This hypothesis was validated experimentally by inactivating sgcA, and the resultant S. globisporus SB1001 mutant strain completely loses its ability to produce 1 (FIG. 15, panel D). The six β-amino acid biosynthesis genes encode a phenol hydroxylase (SgcC), a nonribosomal peptide synthetase halogenase (SgcC3), and aminomutase (SgcC4), and an NRPS condensation enzyme (SgcC5). These enzyme functions agree well with the proposed biosynthetic pathway for 7 from tyrosine (FIG. 14C), which is apparently activated as aminoacyl-S-PCP for its attachment to 5 by SgcC5 (FIG. 14A). Although the precise timing of each reaction in the pathways remains unknown, i.e., the substrate for any of these reactions could be a free amino acid or aminoacyl-S-PCT, sequence analysis of SgcC1 suggests that it activates an α-amino acid. Indeed inactivation of sgcC1 resulted in the isolation of the S. globisporus SB1003 mutant strain that completely lost its ability to produce 1 (FIG. 15, panel E).

Figure 14D:
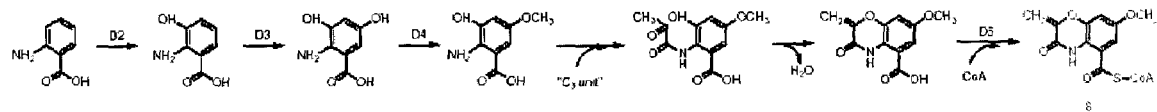

The seven benzoxazolinate biosynthesis genes encode the anthranilate synthase I and II subunits (SgcD and SGCD1), a monooxygenase (SgcD2), a p-450 hydroxylase (SgcD3), and O-methyltransferase (SgcD4), an coenzyme A (CoA) ligase (SgcD5), and an acyltransferase (SgcD6). These enzyme functions support the hypothesis that the biosynthesis of 8 starts from anthranilate, a commonly available intermediate from the shikimate pathway (FIG. 14D). The co-localization of SgcD and SgcD1 along with the rest of the C-1027 production genes assures the availability of anthranilate for secondary metabolite biosynthesis. Although it remains unclear what the origin of the C3 unit is and how it is fused to the anthranilate intermediate to form the morpholinone moiety of 8, the latter is apparently activated as acyl-S-CoA for its attachment to 5 by SgcD6 (FIG. 14A). We inactivated sgcD6 to test this hypothesis, and the resultant S. globisporus SB1004 mutant strain completely lost its ability to produce 1 (FIG. 15, panel F). The fact that the biosynthetic building blocks are activated as aminoacy-S-ACP, acyl-S-CoA, and nucleotide diphosphosugar, and attached to the enediyne core by an NRPS condensation enzyme, an acyltransferase, and a glycosyl transferase, respectively, highlights natures efficiency and versatility in synthesizing complex molecules.

Figure 16:
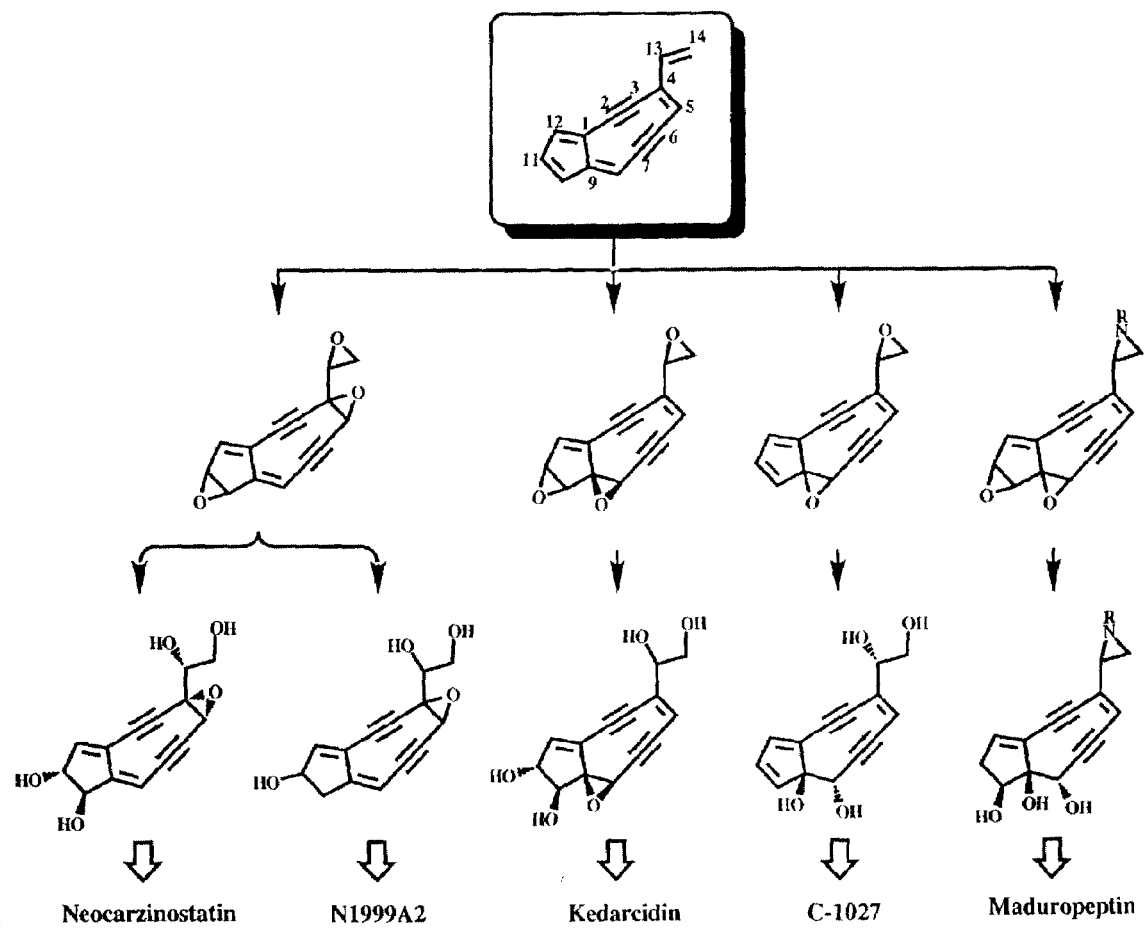
FIG. 16 illustrates C-1027 biosynthesis in *S. globisporus* as a model for the biosynthesis of the chromoprotein family of enediyne antibiotics. Variation of the C-1027 enediyne core biosynthetic pathway leads to all members of this family known to date.

The data presented herein unambiguously establish a convergent pathway for C-1027 biosynthesis, the enediyne core of which proceeds via a polyketide pathway (FIG. 14). Given the similar enediyne core structure, C-1027 biosynthesis can be viewed as a model for the biosynthesis of the chromoprotein family of all enediyne antibiotics known to date. Variation of the C-1027 enediyne core polyketide biosynthetic pathway can lead to the other members of this family (FIG. 16).

The C-1027 open reading frames, encode polypeptides exhibiting a wide variety of enzymatic activities (e.g., epoxide hydrase, monooxygenase, oxidoreductase, P-450 hydroxylase, etc.). The isolated C-1027 gene cluster can be used to synthesize C-1027 enediyne antibiotics and/or analogues thereof. The C-1027 gene cluster can also be modified and/or augmented to increase C-1027 and/or C-1027 analogue production.

Figure 17:
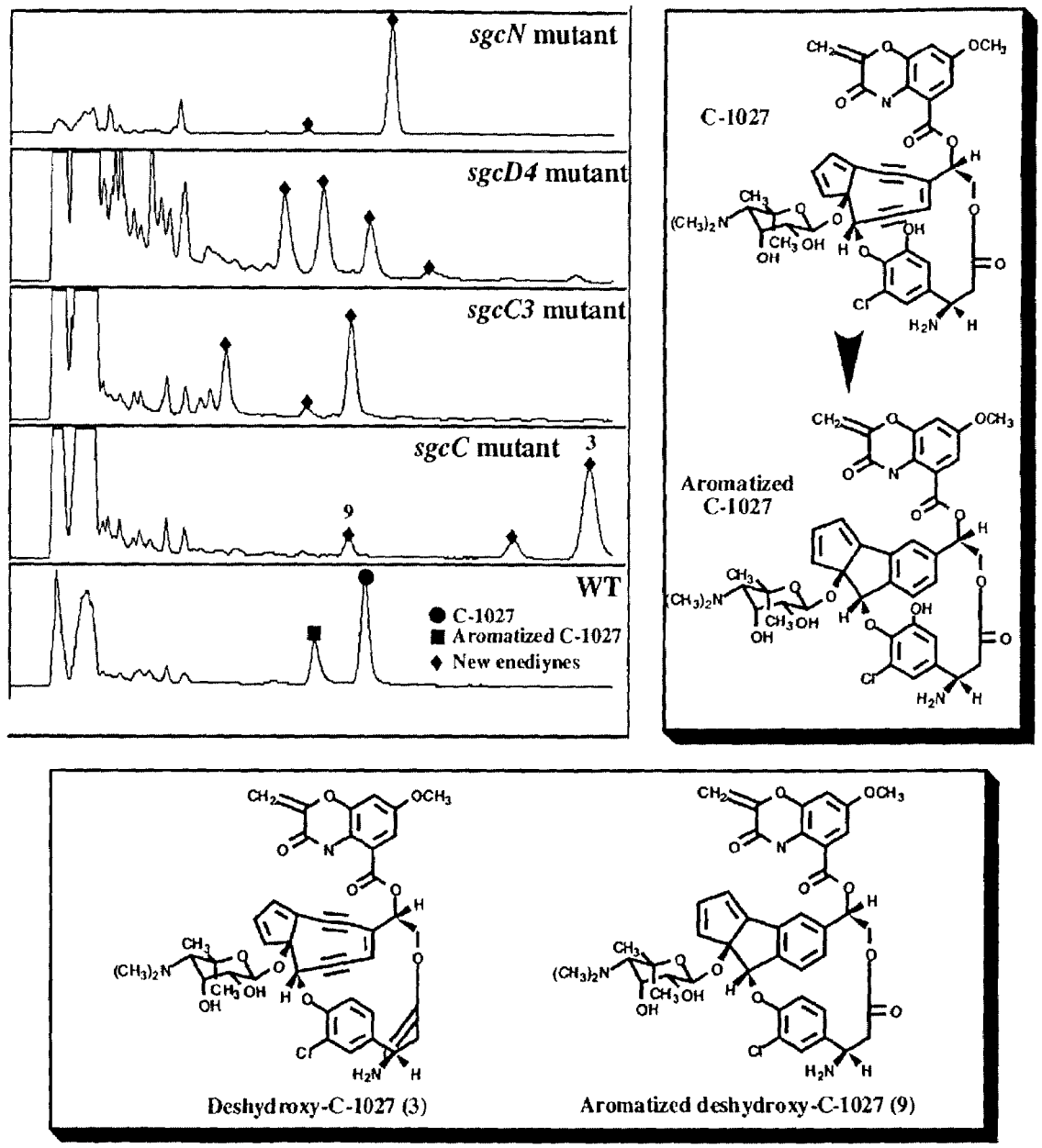
FIG. 17 illustrates a demonstration of the production of novel C-1027 analogs by engineering the C-1027 biosynthetic pathway in *S globisporus*. Mutant strain generation, C-1027 and its novel analog isolation and HPCL conditions are described herein. The new peaks, detected from the mutant strains exhibited a different retention time than C-1027 and its aromatized product as observed from the wild type strain are examples of novel C-1027 analogs. The structures of deshydroxy-C-1027 (3) and its aromatized product (9) have been confirmed by electrospray ionization-mass spectrometry analysis.

We inactivated several genes within the C-1027 gene cluster (sgcN, sgcD4, sgcC3, and sgcC) to demonstrate the production of novel enediyne metabolites by manipulating genes governing the C-1027 biosynthesis. A shown in FIG. 17, several novel enediynes have already been produced by S. globisporus mutant strains, demonstrating the feasibility of the production of novel enediyne compounds by rational engineering of C-1027 biosynthesis. For example, inactivation of sgcC resulted in the isolation of the S. globisporus SB1006 mutant strain. The latter strain produces a chromoprotein that is biologically active as judged by bioassay against M luteus, but is distinct from 1 upon HPLC analysis (FIG. 15m, panel A vs 15, panel G and FIG. 17). The new compounds were isolated and subjected to ESI-MS analysis: 3 exhibited a $(M+H)^+$ ion at m/z=830 consistent with the molecular formula of $C_{43},H_{42},N_3O_{12}Cl$, and 9 showed a $(M+H)^+$ ion at m/z=830, consistent with the molecular formula of $C_{43}H_{44}N_3O_{12}Cl$. By comparison with 1, the new compounds were deduced to be deshydroxy-C-1027 (3) and its aromatized product (9), as would be predicted according to FIG. 14C. Intriguingly, 3 is at lest 5-fold more stable than 1 at 25° C. in respect to undergoing the Bergman cyclization, a property that could be potentially explored in developing C-1027 into a clinically useful drug.

Alternatively, various components of the C-1027 gene cluster can be used to synthesize and/or chemically modify a wide variety of metabolites. Thus, for example, ORF 6 (C-methyltransferase) can be used to methylate a carbon, while ORF 12, an epimerase, can be used to change the conformation of a sugar. The ORFs can be combined in their native configuration or in modified configurations to synthesize a wide variety of biomolecules/metabolites. Thus, for example, various combinations of C-1027 open reading frames can be used to synthesize an enediyne core, to synthesize a deoxy sugar, to synthesize a β-amino acid, to make a benzoxazolinate, etc (see, e.g., FIGS. 2, 3, and 4).

The native C-1027 gene cluster ORFs can be re-ordered, modified, and combined with other biosynthetic units (e.g. polyketide synthases (PKSs) or catalytic domains thereof and/or non-ribosomal polypeptide synthetases (NRPSs) or catalytic domains thereof) to produce a wide variety of molecules. Large chemical libraries can be produced and then screened for a desired activity.

The C-1027 gene cluster also includes a number of drug resistance genes (see, e.g., Table IV) that confer resistance to C-1027 and/or metabolites involved in C-1027 biosynthesis thereby permitting the cell to complete the enediyne biosynthesis. These resistance genes can be used to confer enediyne resistance on a cell lacking such resistance or to augment the enediyne resistance of a cell that does tolerate enediynes. Such cells can be used to produce high levels of enediynes and/or enediyne metabolites, and/or enediyne analogues.

TABLE IV

C-1027 cluster drug resistance genes.

| ORF | Protein | Mechanism |
| --- | --- | --- |
| orf9: | CagA apoprotein | Drug sequestering |
| orf2: | SgcB transmembrane efflux protein | Drug exporting |
| orf27 | Transmembrane transport protein | Drug exporting |
| orf0 | $Na^+/H^+$ transporter | Drug exporting |
| orf(−1) | ABC transport (C-terminus) | Drug exporting |
| orf(−2) | Glycerol phosphate transporter | Drug exporting |
| orf(−1) | UvrA-like protein (N-terminus) | DNA repairing |

I. Isolation, Preparation, and Expression of C-1027 Nucleic Acids.

The C-1027 gene cluster nucleic acids can be isolated, optionally modified, and inserted into a host cell to create and/or modify a metabolic (biosynthetic) pathway and thereby enable that host cell to synthesize and/or modify various metabolites. Alternatively the C-1027 gene cluster nucleic acids can be expressed in the host cell and the encoded C-1027 polypeptide(s) recovered for use as chemical reagents, e.g. in the ex vivo synthesis and/or chemical modification of various metabolites. Either application typically entails insertion of one or more nucleic acids encoding one or more isolated and/or modified C-1027 enediyne open reading frames in a suitable host cell. The nucleic acid(s) are typically in an expression vector, a construct containing control elements suitable to direct expression of the C-1027 polypeptides. The expressed C-1027 polypeptides in the host cell then act as components of a metabolic/biosynthetic pathway (in which case the synthetic product of the pathway is typically recovered) or the C-1027 polypeptides themselves are recovered. Using the sequence information provided herein, cloning and expression of C-1027 nucleic acids can be accomplished using routine and well known methods.

A) C-1027 Nucleic Acids.

The nucleic acids comprising the C-1027 gene cluster are identified in Tables II and III and are listed in the sequence listing provided herein. In particular, Tables II and III identify genes and functions of open reading frames (ORFs) in the C-1027 enediyne biosynthesis gene cluster and identifies primers suitable for the amplification/isolation of any one or more of the C-1027 open reading frames. Of course, using the sequence information provided herein, other primers suitable for amplification/isolation of one or more C-1027 open reading frames can be determined according to standard methods well known to those of skill in the art (e.g. using Vector NTI Suite™, InforMax, Gaithersberg, Md., USA).

Typically, such amplifications will utilize the DNA or RNA of an organism containing the requisite genes (e.g. *Streptomyces globisporus*) as a template. Typical amplification conditions include the following PCR temperature program: initial denaturing at 94° C. for 5 min, 24–36 cycles of 45 sec at 94° C., 1 min at 60° C., 2 min at 72° C., followed by additional 7 min at 72° C. One of skill will appreciate that optimization of such a protocol, e.g. to improve yield, etc. is routine (see, e.g., U.S. Pat. No. 4,683,202; Innis (1990) *PCR Protocols A Guide to Methods and Applications* Academic Press Inc. San Diego, Calif., etc). In addition, primer may be designed to introduce restriction sites and so facilitate cloning of the amplified sequence into a vector.

In one embodiment, this invention provides nucleic acids for the recombinant expression of an enediyne (e.g. a C-1027 enediyne or an analogue thereof). Such nucleic acids include isolated gene cluster(s) comprising open reading frames encoding polypeptides sufficient to direct the assembly of the enediyne. In other embodiments of this invention, the C-1027 open reading frames may be unchanged, but the control elements (e.g. promoters, enhancers, etc.) may be modified. In still other embodiments, the nucleic acids may encode selected components (e.g. one or more C-1027 or modified C-1027 open reading frames) and/or may optionally contain other heterologous biosynthetic elements including, but not limited to polyketide synthase (PKS) and/or non-ribosomal polypeptide synthetase (NRPS) modules or enzymatic domains.

Such variations may be introduced by design, for example to modify a known molecule in a specific way, e.g. by replacing a single substituent of the enediyne with another, thereby creating a derivative enediyne molecule of predicted structure. Alternatively, variations can be made randomly, for example by making a library of molecular variants of a known enediyne by systematically or haphazardly replacing one or open reading frames in the biosynthetic pathway. Production of alternative/modified enediyne, and hybrid enediyne PKSs and/or NRPSs and hybrid systems is described below.

Using the information provided herein other approaches to cloning the desired sequences will be apparent to those of skill in the art. For example, the enediyne, and/or optionally PKS and/or NRPS modules or enzymatic domains of interest can be obtained from an organism that expresses such, using recombinant methods, such as by screening cDNA or genomic libraries, derived from cells expressing the gene, or by deriving the gene from a vector known to include the same. The gene can then be isolated and combined with other desired biosynthetic elements using standard techniques. If the gene in question is already present in a suitable expression vector, it can be combined in situ with, e.g., other PKS subunits, as desired. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence can be assembled from overlapping oligonucleotides prepared by standard methods and assembled into a complete coding sequence (see, e.g., Edge (1981) *Nature*

292:756; Nambair et al. (1984) *Science* 223: 1299; Jay et al. (1984) *J. Biol. Chem.* 259:6311). In addition, it is noted that custom gene synthesis is commercially available (see, e.g. Operon Technologies, Alameda, Calif.).

Examples of such techniques and instructions sufficient to direct persons of skill through many cloning exercises are found in Berger and Kimmel (1989) *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY; Ausubel (19 1994) *Current Protocols in Molecular Biology*, Current Protocols, a joint venture between Greene Publishing Associates, Inc. and John Wiley & Sons, Inc., U.S. Pat. No. 5,017,478; and European Patent No. 0,246,864.

B) Expression of f C-1027 Open Reading Frames.

The choice of expression vector depends on the sequence(s) that are to be expressed. Any transducible cloning vector can be used as a cloning vector for the nucleic acid constructs of this invention. However, where large clusters are to be expressed, it phagemids, cosmids, P1s, YACs, BACs, PACs, HACs or similar cloning vectors be used for cloning the nucleotide sequences into the host cell. Phagemids, cosmids, and BACs, for example, are advantageous vectors due to the ability to insert and stably propagate therein larger fragments of DNA than in M13 phage and lambda phage, respectively. Phagemids which will find use in this method generally include hybrids between plasmids and filamentous phage cloning vehicles. Cosmids which will find use in this method generally include lambda phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., supra). The utility of employing such vectors having different marker genes may be exploited to facilitate a determination of successful transduction.

In preferred embodiments of this invention, vectors are used to introduce C-1027 biosynthesis genes or gene clusters into host (e.g. Streptomyces) cells. Numerous vectors for use in particular host cells are well known to those of skill in the art. For example described in Malpartida and Hopwook, (1984) *Nature,* 309:462–464; Kao et al., (1994), *Science,* 265: 509–512; and Hopwood et al., (1987) *Methods Enzymol.,* 153:116–166 all describe vectors for use in various Streptomyces hosts.

In one preferred embodiment, *Streptomyces* vectors are used that include sequences that allow their introduction and maintenance in *E. coli*. Such Streptomyces/*E. coli* shuttle vectors have been described (see, for example, Vara et al., (1989) *J. Bacteriol.,* 171:5872–5881; Guilfoile & Hutchinson (1991) *Proc. Natl. Acad. Sci. USA,* 88: 8553–8557.)

The wildtype and/or modified C-1027 enediyne open reading frame(s) of this invention, can be inserted into one or more expression vectors, using methods known to those of skill in the art. Expression vectors will include control sequences operably linked to the desired open reading frame. Suitable expression systems for use with the present invention include systems that function in eucaryotic and/or prokaryotic host cells. However, as explained above, prokaryotic systems are preferred, and in particular, systems compatible with *Streptomyces* spp. are of particular interest. Control elements for use in such systems include promoters, optionally containing operator sequences, and ribosome binding sites. Particularly useful promoters include control sequences derived from enediyne, and/or PKS, and/or NRPS gene clusters. Other promoters (e.g. ermE* as illustrated in Example 1) are also suitable. Other bacterial promoters, such as those derived from sugar metabolizing enzymes, such as galactose, lactose (lac) and maltose, will also find use in the present constructs. Additional examples include promoter sequences derived from biosynthetic enzymes such as tryptophan (trp), the beta-lactamase (bla) promoter system, bacteriophage lambda PL, and T5. In addition, synthetic promoters, such as the tac promoter (U.S. Pat. No. 4,551,433), which do not occur in nature also function in bacterial host cells. In *Streptomyces*, numerous promoters have been described including constitutive promoters, such as ErmE and TcmG (Shen and Hutchinson, (1994) *J. Biol. Chem.* 269: 30726–30733), as well as controllable promoters such as actI and actIII (Pleper et al., (1995) *Nature*, vol. 378: 263–266; Pieper et al., (1995) *J. Am. Chem. Soc.,* 117: 11373–11374; and Wiesmann et al., (1995) *Chem. & Biol.* 2: 583–589).

Other regulatory sequences may also be desirable which allow for regulation of expression of the enediyne open reading frame(s) relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The various enediyne cluster open reading frames, and/or PKS, and/or NRPS clusters or subunits of interest can be cloned into one or more recombinant vectors as individual cassettes, with separate control elements, or under the control of, e.g., a single promoter. The various open reading frames can include flanking restriction sites to allow for the easy deletion and insertion of other open reading frames so that hybrid synthetic pathways can be generated. The design of such unique restriction sites is known to those of skill in the art and can be accomplished using the techniques described above, such as site-directed mutagenesis and PCR.

Methods of cloning and expressing large nucleic acids such as gene clusters, including PKS- or NRPS-encoding gene clusters, in cells including *Streptomyces* are well known to those of skill in the art (see, e.g., Stutzman-Engwall and Hutchinson (1989) *Proc. Natl. Acad. Sci. USA,* 86: 3135–3139; Motamedi and Hutchinson (1987) *Proc. Natl. Acad. Sci. USA,* 84: 4445–4449; Grim et al. (1994) *Gene,* 151: 1–10; Kao et al. (1994) *Science,* 265: 509–512; and Hopwood et al. (1987) *Meth. Enzymol.,* 153: 116–166). In some examples, nucleic acid sequences of well over 100 kb have been introduced into cells, including prokaryotic cells, using vector-based methods (see, for example, Osoegawa et al., (1998) *Genomics,* 52: 1–8; Woon et al., (1998) *Genomics,* 50: 306–316; Huang et al., (1996) *Nucl. Acids Res.,* 24: 4202–4209). In addition, the cloning and expression of C-1027 enediyne is illustrated in Example 1.

C) Host Cells.

The vectors described above can be used to express various protein components of the enediyne, and/or enediyne shunt metabolites, and/or other modified metabolites for subsequent isolation and/or to provide a biological synthesis of one or more desired biomolecules (e.g. C-1027 and/or a C-1027 analogue, etc.). Where one or more proteins of the enediyne biosynthetic gene cluster are expressed (e.g. overexpressed) for subsequent isolation and/or characterization, the proteins are expressed in any prokaryotic or eukaryotic cell suitable for protein expression. In one preferred embodiment, the proteins are expressed in *E. coli*.

Host cells for the recombinant production of the subject enediynes, enediyne metabolites, shunt metabolites, etc. can be derived from any organism with the capability of harboring a recombinant enediyne gene cluster and/or subset thereof. Thus, the host cells of the present invention can be derived from either prokaryotic or eucaryotic organisms. Preferred host cells are those of species or strains (e.g. bacterial strains) that naturally express enediynes. Such host cells include, but are not limited to *Actinomycetes, Actinoplanetes*, and *Streptomycetes, Actinomadura, Micromonospra*, and the like. Particularly preferred host cells include, but are not limited to *Streptomyces globisporus, Streptomyces lividans, Streptomyces coelicolor, Micromonospora echinospora* spp. *calichenisis, Actinomadura verrucosospora, Micromonospora chersina, Streptomyces carzinostaticus*, and *Actinomycete* L585-6. Other suitable host cells include, but are not limited to *S. verticillis S. ambofaciens, S. avermitilis, S. azureus, S. cinnamonensis, S. coelicolor, S. curacoi, S. erythraeus, S. fradiae, S. galilaeus, S. glaucescens, S. hygroscopicus, S. lividans, S. parvulus, S. peucetius, S. rimosus, S. roseofulvus, S. thermotolerans*, and *S. violaceoruber* (see, e.g., Hopwood and Sherman (1990) *Ann. Rev. Genet.* 24: 37–66; O'Hagan (1991) *The Polyketide Metabolites*, Ellis Horwood Limited, etc.).

In certain embodiments, a eukaryotic host cell is preferred (e.g. where certain glycosylation patterns are desired). Suitable eukaryotic host cells are well known to those of skill in the art. Such eukaryotic cells include, but are not limited to yeast cells, insect cells, plant cells, fungal cells, and various mammalian cells (e.g. COS, CHO HeLa cells lines and various myeloma cell lines).

D) Recovery of the Expression Product

Recovery of the expression product (e.g., enediyne, enediyne analogue, enediyne biosynthetic pathway polypeptide, etc.) is accomplished according to standard methods well known to those of skill in the art. Thus, for example where enediyne biosynthetic gene cluster proteins are to be expressed and isolated, the proteins can be expressed with a convenient tag to facilitate isolation (e.g. a His6) tag. Other standard protein purification techniques are suitable and well known to those of skill in the art (see, e.g., (Quadri et al. (1998) *Biochemistry* 37: 1585–1595; Nakano et al. (1992) *Mol. Gen. Genet.* 232: 313–321, etc.).

Similarly where components (e.g. enediyne biosynthetic cluster orfs) are used to synthesize and/or modify various biomolecules (e.g. enediynes, enediyne analogues, shunt metabolites, etc.) the desired product and/or shunt metabolite(s) are isolated according to standard methods well know to those of skill in the art (see, e.g., Carreras and Khosla (1998) *Biochemistry* 37: 2084–2088, Deutscher (1990) *Methods in Enzymology Volume* 182: *Guide to Protein Purification*, M. Deutscher, ed. etc.).

II. Use of C-1027 Open Reading Frames in Directed Biosynthesis.

Elements (e.g. open reading frames) of the C-1027 biosynthetic gene cluster and/or variants thereof can be used in a wide variety of "directed" biosynthetic processes (i.e. where the process is designed to modify and/or synthesize one or more particular preselected metabolite(s)). Essentially the entire C-1027 gene cluster can be used to synthesize a C-1027 enediyne and/or a C-1027 enediyne analogue. Individual C-1027 cluster open reading frames can be used to perform chemically modifications on particular substrates and/or to synthesize various metabolites. Thus, for example, ORF 6 (C-methyltransferase can be used to methylate a carbon), while ORF 7 (N-methyltransferase) can be used to methylate a nitrogen. ORF 12, and epimerase, can be used to change the conformation of a sugar, and ORF 8 (an amino transferase) can be used to aminate a suitable substrate. Similarly, combinations of C-1027 open reading frames can be used to direct the synthesis of various metabolites (e.g. β-amino acids, deoxysugars, benzoxazolinates, and the like). These examples, are merely illustrative. One of skill in the art, utilizing the information provided here, can perform literally countless chemical modifications and/or syntheses using either "native" enediyne biosynthesis metabolites as the substrate molecule, or other molecules capable of acting as substrates for the particular enzymes in question. Other substrates can be identified by routine screening. Methods of screening enzymes for specific activity against particular substrates are well known to those of skill in the art.

The biosyntheses can be performed in vivo, e.g. by providing a host cell comprising the desired C-1027 gene cluster open reading frames and/or in vivo, e.g., by providing the polypeptides encoded by the C-1027 gene cluster ORFs and the appropriate substrates and/or cofactors.

A) Synthesis of Enediynes and Enediyne Analogues.

In one embodiment, this invention provides for the synthesis of C-1027 enediynes and/or C-1027 analogues or derivatives. In a preferred embodiment, this is accomplished by providing a cell comprising a C-1027 gene cluster and culturing the cell under conditions whereby the desired enediyne or enediyne analogue is synthesized. The cell can be a cell that does not normally synthesize an enediyne and the entire gene cluster can be transfected into the cell. Alternatively, a cell that typically synthesizes enediynes can be utilized and all or part of the C-1027 gene cluster can be introduced into the cell.

Enediyne derivatives/analogues can be produced by varying the order of, or kind of, gene cluster subunits present in the cell, and/or by changing the host cell (e.g. to a eukaryotic cell that glycosylates the biosynthetic product), and/or by providing altered metabolites (e.g. adding exogenous aglycones to a host that carries a gene cassette of the deoxysugar biosynthesis and glycosylation genes for the production of glycosylated metabolites), etc.

In certain embodiments, the host cell need not be transfected with an entire C-1027 gene cluster. Rather, various components of a C-1027 gene cluster can be altered within a cell already harboring a C-1027 cluster. By varying or adding various biosynthetic open reading frames, C-1027 enediyne variants can be produced.

The use of standard techniques of molecular biology (gene disruption, gene replacement, gene supplement) can be used to modulate and/or otherwise alter enediyne and/or other metabolite (e.g. shunt metabolite) production in an organism that naturally synthesizes an enediyne (e.g. *S. globisporus*) or an organism that is modified to synthesize an enediyne.

In addition, or alternatively, control sequences that alter the expression of various open reading frames can be introduced that alter the amount and/or timing of enediyne production. Thus, for example, by placing particular C-1027 open reading frames under control of a constitutive promoter (erinE*) C-1027 production was increased by as much as 4-fold (see, e.g. Table V and Example 1).

TABLE V

Alteration of C-1027 production by engineering the C-1027 biosynthesis gene cluster.

| Strain | Yield (%) |
|---|---|
| WT | 100 |
| WT/pKC1139 | 100 |
| WT/ermE*/ORF2 | >150 |
| WT/ORF 9 | >100 |
| WT/ermE*/ORF 9 | <10 |
| WT/ORF 10, 11 | >100 |
| WT/ermE*/ORF 10, 11 | >100 |
| WT/ORF 9, 10, 11 | >400 |

ORF 2: transmembrane eflux protein;
ORF 9: CagA apoprotein;
ORF 10: TDP-glucose synthase;
ORF 11: Hydroxylase/halogenase Where enediyne analogues are synthesized, it will often prove desirable to assay them for biological activity. Such assays are well know to those of skill in the art. One such assay is illustrated in Example 1. Briefly, this example depicts an assay of antibacterial activity against *M. luteus* as described by Hu et al. (1988) *J. Antibiot.* 41: 1575–1579). Other suitable assays for enediyne activity will be known to those of skill in the art.

B) Use of C-1027 Open Reading Frames to Synthesize an Enediyne Core.

Figure 4:
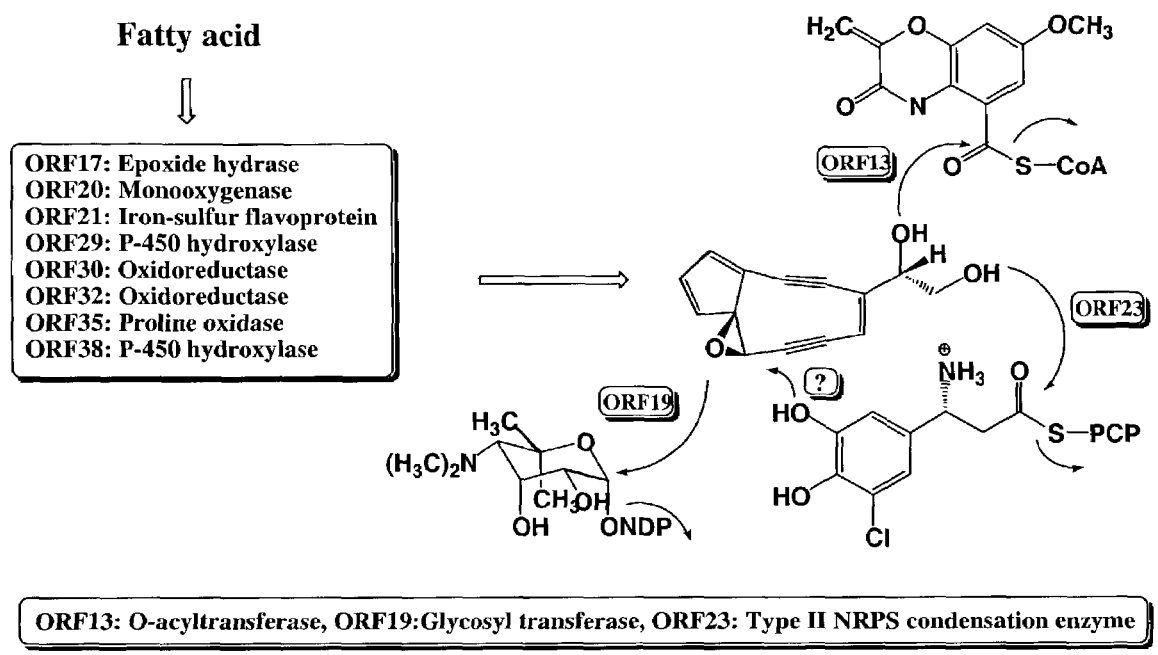
FIG. 4 illustrates the synthesis of the enediyne core and final assembly of the C-1027 enediyne.

The C-1027 open reading frames described herein, or variants thereof, can be used to synthesize an enediyne core, e.g., from a fatty acid precursor. One such synthetic pathway is illustrated in FIG. 4. This reaction scheme utilizes ORF 17 (epoxide hydrase), ORF 20 (monooxygenase), ORF 21 (iron-sulfur flavoprotein), ORF 29 (P-450 hydroxylase, ORF 30 (oxidoreductase), ORF 32 (oxidoreductase), ORF 35 (proline oxidase), and ORF 38 (P-450 hydroxylase) to synthesize anenediyne core.

This synthetic pathway, is not considered limiting, but merely illustrative. Using this as a model, one of ordinary skill in the art can design numerous other synthetic schemes to produce enediyne cores and/or core variants.

C) Use of C-1027 Open Reading Frames to Synthesize Deoxy Sugars.

The biosynthesis of various deoxy sugars (e.g., deoxyhexoses) typically share a common key intermediate—4-keto-6-deoxyglucose nucleoside diphosphate or its analogs, whose formation from glucose nucleoside diphosphate is catalyzed by the NGDH enzyme, an $NAD^+$-dependent oxidoreductase (Liu and Thorson (1994) *Ann. Rev. Microbiol.* 48: 223–256; Piepersberg (1997) pp. 81–163. In *Biotechnology of antibiotics,* 2nd ed. W. R. Strohl (ed). Marcel Dekker, New York.). Similarly, the C-1027 gene cluster includes an NAGDH enzyme which can be exploited to synthesize a variety of deoxy sugars.

Figure 2:
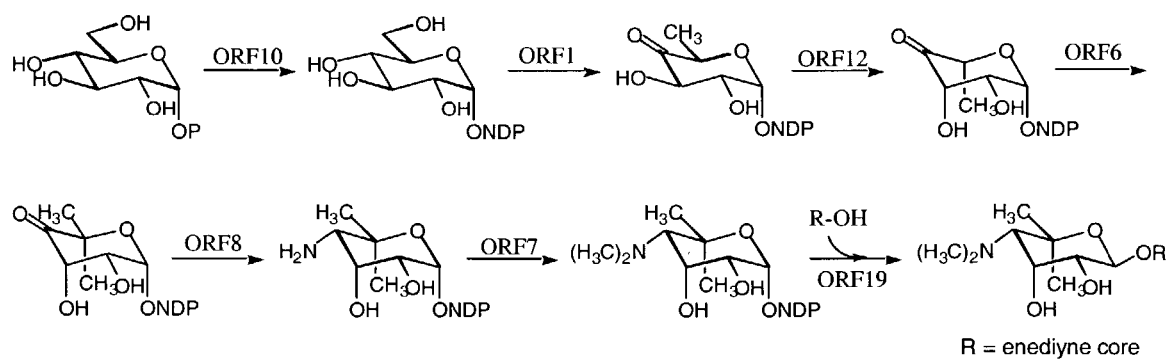
FIG. 2 illustrates a scheme using C-1027 open reading frame polypeptides for the synthesis of deoxysugars.

One illustrative synthetic pathway is shown in FIG. 2. This biosynthetic scheme utilizes ORF 10 (dNDP-glucose synthase), ORF 1 (dNDP-glucose dehydratase), ORF 12 (epimerase), ORF 8 (aminotransferase), ORF 6 (C-methyltransferase), ORF 7 (N-methyltransferase) and ORF 19 (glycosyl transferase).

This synthetic pathway, is not considered limiting, but merely illustrative. Using this as a model, one of ordinary skill in the art can design numerous other synthetic schemes to produce various deoxy sugars.

D) Use of C-1027 Open Reading Frames to Synthesize β-Amino Acids.

Figure 3A:
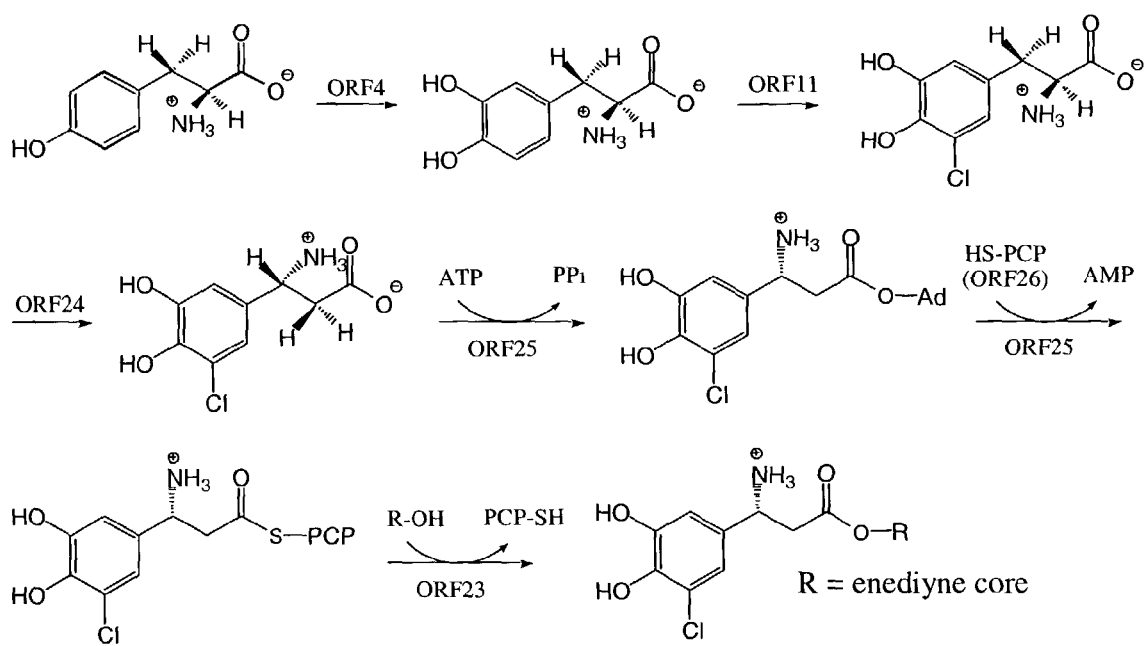
FIG. 3A illustrates a scheme using C-1027 open reading frame polypeptides for the synthesis of a β-amino acid.

In still another embodiment, C-1027 biosynthetic polypeptides can be used in the biosynthesis of β-amino acids. One illustrative synthetic pathway is shown in FIG. 3A. This biosynthetic scheme utilizes ORF 4 (hydroxylase), ORF 11 (hydroxylase/halogenase), ORF 24 (aminomutase), ORF 23 (type II NRPS condensation enzyme), ORF 25 (type II NRPS adenylation enzyme), and ORF 26 (type II peptidyl carrier protein).

Again, this synthetic pathway, is not considered limiting, but merely illustrative. Using this as a model, one of ordinary skill in the art can design numerous other synthetic schemes to produce other beta amino acids.

E) Use of C-1027 Open Reading Frames to Synthesize Benzoxazolinates.

Figure 3B:
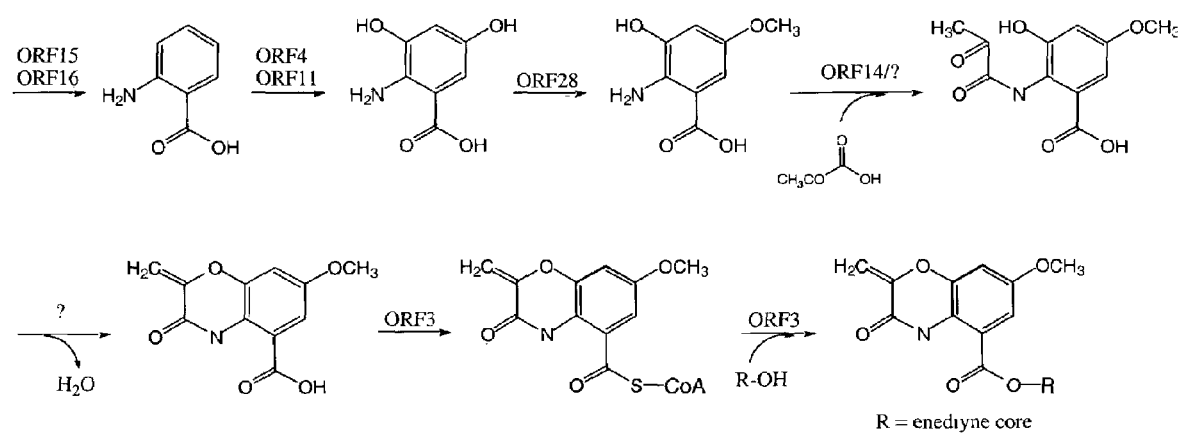
FIG. 3B illustrates a scheme using C-1027 open reading frame polypeptides for the synthesis of a benzoxazolinate.

The C-1027 open reading frames can also be used to synthesize a benzoxazolinate. One illustrative synthetic pathway is shown in FIG. 3B. This biosynthetic scheme utilizes ORF 15 (anthranilate synthase I, ORF 16 (anthranilate synthase II), ORF 4 (phenol hydroxylase/chlorophenol-4-monooxygenase), ORF 11 (Hydroxylase/Halogenase), ORF 28 (O-methylferase), ORF 3 (coenzyme F390 synthetase, ORF 14 (coenzyme F390 synthetase), and ORF 13 (O-acyltransferase). Again, this synthetic pathway, is not considered limiting, but merely illustrative. Using this as a model, one of ordinary skill in the art can design numerous other synthetic schemes to produce other beta amino acids.

III. Generation of Chemical Diversity.

In addition to the directed modification and/or biosynthesis of various metabolites as described above, the C-1027 biosynthetic gene cluster open reading frames can be utilized, by themselves or in combination with other biosynthetic subunits (e.g. NRPS and/or PKS modules and/or enzymatic domains of other PKS and/or NRPS systems) to produce a wide variety of compounds including, but not limited to various enediyne or enediyne derivatives, various polyketides, polypeptides, polyketide/polypeptide hybrids, various thiazoles, various sugars, various methylated polypeptides/polyketides, and the like.

As with the directed production of various metabolites described above, such compounds can be produced, in vivo or in vitro, by catalytic biosynthesis, e.g., using large, enediyne cluster units and/or modular PKSs, NRPSs, and hybrid PKS/NRPS systems. In a preferred embodiment large combinatorial libraries of cells harboring various megasynthetases can be produced by the random or directed modification of particular pathways and then selected for the production of a molecule or molecules of interest. It will be appreciated that, in certain embodiments, such libraries of megasynthetases/modified pathways, can be used to generate large, complex combinatorial libraries of compounds which themselves can be screened for a desired activity.

Such combinatorial libraries can be created by the deliberate modification/variation of selected biosynthetic pathways and/or by random/haphazard modification of such pathways.

A) Directed Engineering of Novel Synthetic Pathways.

In numerous embodiments of this invention, novel polyketides, polypeptides, and combinations thereof are created by modifying the entediyne gene cluster ORFs and/or known PKSs, and/or NRPSs so as to introduce variations into metabolites synthesized by the enzymes. Such variations may be introduced by design, for example to modify a known molecule in a specific way, e.g. by replacing a single monomeric unit within a polymer with another, thereby creating a derivative molecule of predicted structure. Such variations can also be made by adding one or more modules or enzymatic domains to a known PKS or NRPS or enediyne cluster, or by removing one or more module from a known PKS or NRPS.

Using any of these methods, it is possible to introduce PKS domains, NRPS domains, and entediyne domains into a megasynthetase. Mutations can be made to the native enediyne, and/or NRPS, and/or PKS subunit sequences and such mutants used in place of the native sequence, so long as the mutants are able to function with other subunits (domains) in the synthetic pathway. Such mutations can be made to the native sequences using conventional techniques such as by preparing synthetic oligonucleotides including the mutations and inserting the mutated sequence into the gene encoding a NRPS and/or PKS subunit using restriction endonuclease digestion. (see, e.g., Kunkel, (1985) *Proc. Natl. Acad. Sci. USA* 82: 448; Geisselsoder et al. (1987) *BioTechniques* 5: 786). Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located (Zoller and Smith (1983) *Meth, Enzymol.* 100: 468). Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations (see, e.g., Dalbie-McFarland et al. (1982) *Proc. Natl. Acad. Sci USA* 79:6409). PCR mutagenesis will also find use for effecting the desired mutations.

B) Random Modification of Enedivne Pathways.

In another embodiment, variations can be made randomly, for example by making a library of molecular variants (e.g. of a known enediyne) by randomly mutating one or more elements of the subject gene cluster or by randomly replacing one or more open reading frames in a gene cluster with one or more of alternative open reading frames.

The various open reading frames can be combined into a single multi-modular enzyme, thereby dramatically increasing the number of possible combinations obtained using these methods. These combinations can be made using standard recombinant or nucleic acid amplification methods, for example by shuffling nucleic acid sequences encoding various modules or enzymatic domains to create novel arrangements of the sequences, analogous to DNA shuffling methods described in Crameri et al. (1998) *Nature* 391: 288–291, and in U.S. Pat. Nos. 5,605,793 and in 5,837,458. In addition, novel combinations can be made in vitro, for example by combinatorial synthetic methods. Novel molecules or molecule libraries, can be screened for any specific activity using standard methods.

Random mutagenesis of the nucleotide sequences obtained as described above can be accomplished by several different techniques known in the art, such as by altering sequences within restriction endonuclease sites, inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

Large populations of random enzyme variants can be constructed in vivo using "recombination-enhanced mutagenesis." This method employs two or more pools of, for example, $10^{\neq}$ mutants each of the wild-type encoding nucleotide sequence that are generated using any convenient mutagenesis technique, described more fully above, and then inserted into cloning vectors.

C) Incorporation and/or Modification of Non-C-1027 Cluster Elements.

In either the directed or random approaches, nucleic acids encoding novel combinations of gene cluster ORFs are introduced into a cell. In one embodiment, nucleic acids encoding one or more enediyne synthetic cluster ORFS and/or PKS and/or NRPS domains are introduced into a cell so as to replace one or more domains of an endogenous gene cluster within a cell. Endogenous gene replacement can be accomplished using standard methods, such as homologous recombination. Nucleic acids encoding an entire enediyne, enediyne ORF, PKS, NRPS, or combination thereof can also be introduced into a cell so as to enable the cell to produce the novel enzyme, and, consequently, synthesize the novel polymer. In a preferred embodiment, such nucleic acids are introduced into the cell optionally along with a number of additional genes, together called a 'gene cluster,' that influence the expression of the genes, survival of the expressing cells, etc. In a particularly preferred embodiment, such cells do not have any other enediyne and/or PKS- and/or NRPS-encoding genes or gene clusters, thereby allowing the straightforward isolation of the molecule(s) synthesized by the genes introduced into the cell.

Furthermore, the recombinant vector(s) can include genes from a single enediyne and/or PKS and/or NRPS gene cluster, or may comprise hybrid replacement PKS gene clusters with, e.g., a gene for one cluster replaced by the corresponding gene from another gene cluster. For example, it has been found that ACPs are readily interchangeable among different synthases without an effect on product structure. Furthermore, a given KR can recognize and reduce polyketide chains of different chain lengths. Accordingly, these genes are freely interchangeable in the constructs described herein. Thus, the replacement clusters of the present invention can be derived from any combination of PKS and/or NRPS gene sets that ultimately function to produce an identifiable polyketide.

Examples of hybrid replacement clusters include, but are not limited to, clusters with genes derived from two or more of the act gene cluster, the whiE gene cluster, frenolicin (fren), granaticin (gra), tetracenomycin (tcm), 6-methylsalicylic acid (6-msas), oxytetracycline (otc), tetracycline (tet), erythromycin (ery), griseusin (gris), nanaomycin, medermycin, daunorubicin, tylosin, carbomycin, spiramycin, avermectin, monensin, nonactin, curamycin, rifamycin and candicidin synthase gene clusters, among others. (For a discussion of various PKSs, see, e.g., Hopwood and Sherman (1990) *Ann. Rev. Genet.* 24: 37–66; O'Hagan (1991) The Polyketide Metabolites, Ellis Horwood Limited.

A number of hybrid gene clusters have been constructed, having components derived from the act, fren, tcm, gris and gra gene clusters (see, e.g., U.S. Pat. No. 5,712,146). Other hybrid gene clusters, as described above, can easily be produced and screened using the disclosure herein, for the production of identifiable polyketides, polypeptides or polyketide/polypeptide hybrids.

Host cells (e.g. *Streptomyces*) can be transformed with one or more vectors, collectively encoding a functional PKS/NRPS set, or a cocktail comprising a random assortment of enediyne ORFs and/or PKS and/or NRPS genes, modules, active sites, or portions thereof. The vector(s) can include native or hybrid combinations of enediyne ORFs, and/or PKS and/or NRPS subunits or cocktail components, or mutants thereof. As explained above, the gene cluster need not correspond to the complete native gene cluster but need only encode the necessary enediyne ORFs and/or PKS and/or NRPS components to catalyze the production of the desired product(s).

IV. Variation of Starter and/or Extender Units, and/or Host Cells.

In addition to varying the nucleic acids comprising the subject gene cluster, variations in the products produced by the gene cluster(s) can be obtained by varying the the host cell, the starter units and/or the extender units. Thus, for example different fatty acids can be utilized in the enediyne synthetic pathway resulting in different enediyne variants. Similarly different intermediate metabolites can be provided (e.g. endogenously produced by the host cell, or produced by an introduced herterologous construct, and/or supplied from an exogenous source (e.g. the culture media)). Similarly, varying the host cell can vary the resulting product(s). For example, a gene cassette carrying the enediyne biosynthesis genes can be introduced into a deoxysugar-synthesizing host for the production of glycosylated enediyne metabolites.

V. Use of C-1027 Resistance Genes.

The antibiotic C-1027 and metabolites present in C-1027 biosynthesis are highly potent cytotoxins. Accordingly the biosynthesis of C-1027 is facilitated by the presence of one or more antibiotic (e.g. enediyne) resistance genes. Without being bound to a particular theory, it is believed that CagA and SgcB function cooperatively to provide resistance. It is believed that the C-1027 chromophore is first sequestered by binding to the preaproprotein CagA (ORF 9) to form a complex, which is then transported out of the cell by the efflux pump SgcB (ORF 2) and processed by removing the leader peptide to yield the chromoprotein. Other genes that appear to mediate resistance in the C-1027 biosynthesis gene cluster include a transmembrane transport protein (ORF 27), a $Na^+/H^+$ transporter (ORF 0), an ABC transporter (ORF −1, C-terminus), a glycerol phosphate transporter (ORF −2), and a UvrA-like protein (ORF −1, N-terminus) (see, e.g., Table III).

These ORFs and/or the polypeptides encoded by these ORFs can be utilized alone, or in combination with one or more other C-1027 ORFs to confer resistance to enediyne or enediyne metabolites on a cell. This is useful in a wide variety of contexts. For example, to increase production of enediynes. For example, it is believed that C-1027 resistance could be a limiting factor at the onset of C-1027 production. Provision of an extra copy of the plasmid-born sgcB, and overexpression of sgcB under the control of the constitutive ermE* promoter resulted in increase of C-1027 production (see example 1).

In a therapeutic context, it is sometimes desirable to confer resistance on certain vulnerable cells. Thus, for example, where an enediyne is used as a chemotherapeutic, transfection of vulnerable, but healthy cells (e.g. liver cells remote from the tumor site, stem cells, etc.) with vector(s) expressing the resistance gene(s) permits administration of the enediyne at a higher dosage with fewer adverse effects to the organism. Such approaches have been taken using the multi-drug resistance gene (MDR1) expressing p-glycoprotein.

In another embodiment vectors are provided containing one or more resistance genes of this invention under control of a constitutive and/or inducible promoter thereby providing a "ready-made" expression system suitable for the expression of an enediyne or enediyne metabolite at high concentration.

It is also noted that the resistance genes are expected to confer resistance to compounds other than enediynes. The resistance genes are expected to confer resistance to essentially any cytotoxic compound that can act as a substrate for the resistance gene(s) of this invention.

VI. Kits.

In still another embodiment, this invention provides kits for practice of the methods described herein. In one preferred embodiment, the kits comprise one or more containers containing nucleic acids encoding one or more of the C-1027 biosynthesis gene cluster open reading frames. Certain kits may comprise vectors encoding the sgc gene cluster orfs and/or cells containing such vectors. The kits may optionally include any reagents and/or apparatus to facilitate practice of the methods described herein. Such reagents include, but are not limited to buffers, labels, labeled antibodies, bioreactors, cells, etc.

In addition, the kits may include instructional materials containing directions (i.e., protocols) for the practice of the methods of this invention. Preferred instructional materials provide protocols utilizing the kit contents for creating or modifying C-1027 gene cluster and/or for synthesizing or modifying a molecule using one or more sgc gene cluster ORFs. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Figure 1:
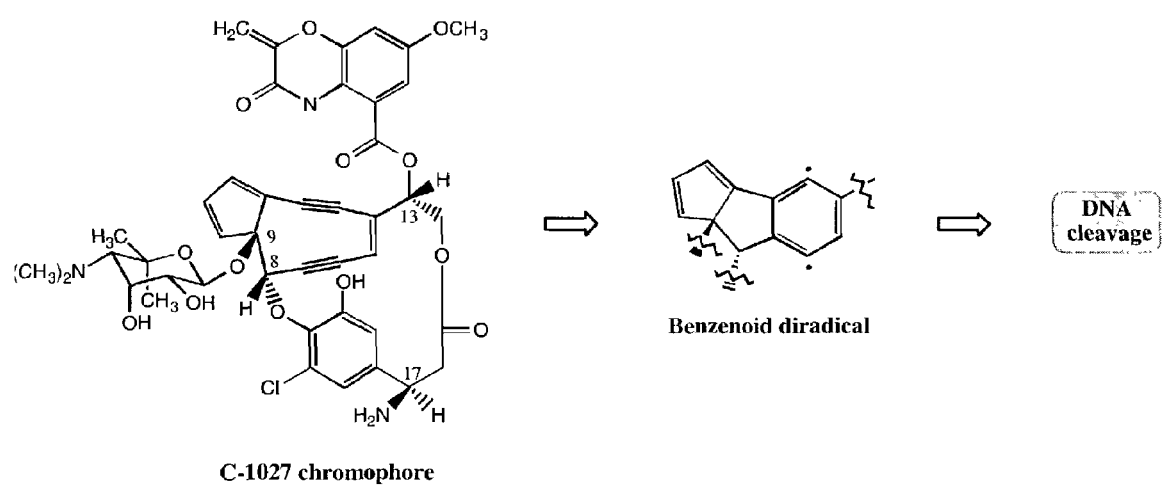
FIG. 1 illustrates the structures of C-1027 chromophore and the benzenoid diradical intermediate proposed to initiate DNA cleavage.

EXAMPLES

The following examples are offered to illustrate, but not to limit the claimed invention.

Example 1

Genes for Production of the Enediyne Antitumor Antibiotic C-1027 in *Streptomyces globisporus* are Clustered with the cagA Gene that Encodes the C-1027 Apoprotein We have been studying the biosynthesis of C-1027 in *Streptomyces globisporus* C-1027 as a model for the enediyne family of antitumor antibiotics (Thorson et al. (1999) *Bioorg. Chem.,* 27: 172–188). C-1027 consists of a non-peptidic chromophore and an apoprotein, CagA [also called C-1027AG (Otani et al. (1991) *Agri. Biol. Chem.* 55: 407–417)]. The C-1027 chromophore is extremely unstable in the protein-free state, the structure of which was initially deduced from an inactive but more stable degradation product (Minami et al. (1993) *Tetrahedron Lett.* 34: 2633–2636)

and subsequently confirmed by spectroscopic analysis of the natural product (Yoshida et al. (1993) Tetrahedron Lett. 34: 2637–2640) (FIG. 1). While the absolute stereochemistry of the deoxysugar moiety was established by total synthesis (Iida et al. (1993) Tetrahedron Lett. 34: 4079–4082), the 8S, 9S, 13S and 17R configuration of the C-1027 chromophore were based only on computer modeling (Okuno et al. (1994) J. Med. Chem. 37: 2266–2273). Although no biosynthetic study has been carried out specifically on C-1027, the polyketide origin of the enediyne cores has been implicated by feeding experiments with $^{13}$C-labeled acetate for the neocarzinostatin chromophore A (Hensens et al. (1989) J. Am. Chem. Soc. 111: 3295–3299), dynemicin (Tokiwa et al. (1992) J. Am. Chem. Soc. 114: 4107–4110), and esperamicin (Lam et al. (1993) J. Am. Chem. Soc. 115: 12340–12345); and deoxysugar biosynthesis has been well characterized in actinomycetes (Liu and Thorson (1994) Ann. Rev. Microbiol. 48: 223–256; Piepersberg (1997) pp. 81–163. In Biotechnology of antibiotics, 2nd ed. W. R. Strohl (ed). Marcel Dekker, New York). Given the structural similarity of C-1027 to the other enediyne cores and to deoxysugars found in other secondary metabolites, we decided to clone either a PKS or a deoxysugar biosynthesis gene as the first step of identifying the C-1027 gene cluster from S. globisporus.

Furthermore, the CagA apoprotein of C-1027 has been isolated, its amino acid sequence has been determined, and the corresponding cagA gene has been cloned and sequenced (Otani et al. (1991) Agri. Biol. Chem. 55: 407–417; Sakata et al. (1992) Biosci. Biotech. Biochem. 56: 1592–1595). Since genes encoding secondary metabolite production in actinomycetes have invariably been found to be clustered in one region of the microbial chromosome (Hopwood (1997) Chem. Rev. 97: 2465–2497), we further reasoned that mapping the cagA gene with either a putative PKS gene, a deoxysugar biosynthesis gene, or both to the same region of the S. globisporus chromosome should be viewed as strong evidence supporting the proposition that the cloned genes constitute the C-1027 biosynthesis gene cluster.

We report here the cloning and sequencing of two genes, sgcA (Streptomyces globisporus C-1027) and sgcB, that encode a dNDP-glucose 4,6-dehydratase (NGDH) and a transmembrane efflux protein, respectively. The sgcA,B locus is indeed clustered with the cagA gene, leading to the localization of a 75-kb gene cluster from S. globisporus. The involvement of the cloned gene cluster in C-1027 biosynthesis was demonstrated by disrupting the sgcA gene to generate C-1027-nonproducing mutants and by complementing the sgcA mutants in vivo to restore C-1027 production. Our results, together with similar effort in the Thorson laboratory on the calicheamicin gene cluster (Thorson et al. (1999) Bioorg. Chem., 27: 172–188), represent the first cloning of a gene cluster for enediyne antitumor antibiotic biosynthesis.

Materials and Methods.

Bacterial Strains and Plasmids.

Escherichia coli DH5α was used as a general host for routine subcloning (Sambrook et al. (1989) Molecular cloning, a laboratory manual. Cold Spring Harbor Laboratory, Cold Spring Harbor, N.Y.). E. coli XL 1-Blue MR (Stratagene, La Jolla, Calif.) was used as the transduction host for cosmid library construction. E. coli S17-1 was used as the donor host for E. coli-S. globisporus conjugation (Mazodier et al. (1989) J. Bacteriol. 171: 3583–3585). Micrococcus luteus ATCC9431 was used as the testing organism to assay the antibacterial activity of C-1027 (Hu et al. (1988) J. Antibiot. 41: 1575–1579). The pGEM-3zf, -5zf, and -7zf and pGEM-T vectors were from Promega (Madison, Wis.). S. globisporus strains and other plasmids in this study are listed in Table VI.

TABLE VI

Strains and plasmids.

| Strain or plasmid | Relevant Characteristics |
|---|---|
| S. globisporus | |
| C-1027 | Wild-type (Hu et al. (1988) J. Antibiot. 41: 1575–1579) |
| AF40 | Mutant resulted from acriflavine treatment of S. globisporus C-1027, C-1027-nonproducing (Mao et al. (1997) Chinese J. Biotechnol. 13: 195–199) |
| AF44 | Mutant resulted from acriflavine treatment of S. globisporus C-1027, C-1027-nonproducing (Mao et al., supra) |
| AF67 | Mutant resulted from acriflavine treatment of S. globisporus C-1027, C-1027-nonproducing (Mao et al., supra) |
| SB1001 | sgcA-disrupted mutant resulted from integration of pBS1012 into S. globisporus C-1027 Apr$^R$, C-1027-nonproducing |
| SB1002 | sgcA-disrupted mutant resulted from integration of pBS1013 into S. globisporus C-1027 Apr$^R$, C-1027-nonproducing |
| Plasmids: | |
| pOJ446 | E. coli-Streptomyces shuttle cosmid, Apr$^R$ (Bierman et al. (1992) Gene, 116: 43– |
| pOJ260 | E. coli vector, non-replicating in Streptomyces, Apr$^R$ (Bierman et al. supra) |
| pKC1139 | E. coli-Streptomyces shuttle vector, rep$^{TS}$, Apr$^R$ (Bierman et al. supra) |
| pWHM3 | E. coli-Streptomyces shuttle vector, Th$^R$ (Vara et al. (1989) J. Bacteriol. 171: 5872–5881) |
| pWHM79 | ermE* promoter in pGEM-3zf (Shen and Hutchinson (1996) Proc. Natl. Acad. Sci. USA 93: 6600–6604) |
| pBS1001 | 0.75-kb PCR product amplified from S. globisporus with type I PKS primers in pGEM-T |

TABLE VI-continued

Strains and plasmids.

| Strain or plasmid | Relevant Characteristics |
| --- | --- |
| pBS1002 | 0.55-kb PCR product amplified from S. globisporus with NGDH gene primers in pGEM-T |
| pBS1003 | 0.73-kb PCR product amplified from pBS1005 with cagA primers in pGEM-T |
| pBS1004 | pOJ446 S. globisporus genomic library cosmid |
| pBS1005 | pOJ446 S. globisporus genomic library cosmid |
| pBS1006 | pOJ446 S. globisporus genomic library cosmid |
| pBS1007 | 3.0-kb BamHI fragment from pBS1005 in pGEM-3zf, sgcA, sgcB |
| pBS1008 | 4.0-kb BamHI fragment from pBS1005 in pGEM-3zf, cagA |
| pBS1009 | 1.0-kb KpnI truncated fragment of sgcA from pBS1007 in pGEM-3zf |
| pBS1010 | 0.75-kb SacII/SphI internal fragment of sgcA from pBS1009 in pGEM-5zf |
| pBS1011 | 0.75-kb SacI/SphI internal fragment of sgcA from pBS1010 in pGEM-3zf |
| pBS1012 | 0.75-kb EcoRI/HindIII internal fragment of sgcA from pBS1010 in pOJ260 |
| pBS1013 | 0.75-kb EcoRI/HindIII internal fragment of sgcA from pBS1010 in pKC1139 |
| pBS1014 | 2.0-kb EcoRI/SphI fragment from pBS1007 in the SmaI/SphI sites of pWHM79, ermE*, sgcA |
| pBS1015 | 2.5-kb EcoRI/HindIII fragment from pBS1014 in pWHM3, ermE*, sgcA |
| pBS1016 | Self-ligation of the 5.2-kb KpnI fragment from pBS1007 |
| pBS1017 | 0.45-kb EcoRI/SacI fragment from pWHM79 in EcoRI/SacI sites of pBS1016, ermE*, sgcB |
| pBS1018 | 2.5-kb EcoRI/HindIII fragment from pBS1017 in pKC1139, ermE*, sgcB |

Biochemicals and Chemicals.

Ampicillin, apramycin, nalidixic acid, and thiostrepton were from Sigma (St. Louis, Mo.). Unless specified otherwise, restriction enzymes and other molecular biology reagents were from standard commercial sources.

Media and Culture Conditions.

E. coli strains carrying plasmids were grown in Luria-Bertani (LB) medium and were selected with appropriate antibiotics. S. globisporus strains were grown on ISP-4 (Difco Laboratories, Detroit, Mich.) or R2YE at 28° C. for sporulation and in TSB (Hopwood et al. (1985) Genetic manipulation of Streptomyces: a laboratory manual. John Innes Foundation, Norwich, UK) supplemented with 5 mM $MgCl_2$ and 0.5% glycine at 28° C., 250 rpm for isolation of genomic DNA. For transformation, S. globisporus strains were grown in YEME (Hopwood et al., supra.) for preparation of protoplasts and on R2YE for protoplast regeneration. For conjugation, both the E. coli S17–1 donors and the S. globisporus recipients (upon germination in TSB) were prepared in LB, and donors/recipients were grown on either ISP-4 medium with 0.05% yeast extract and 0.1% tryptone or AS-1 medium (Baltz (1980) Dev. Ind. Microbiol. 21: 43–54; Bierman et al. (1992) Gene 116: 43–69) at 30° C. for isolation of exconjugants.

For C-1027 production, S. globisporus strains were grown either on R2YE or ISP-4 agar medium at 28° C. or in liquid medium by a two-stage fermentation. For liquid culture, the seed inoculum was prepared by inoculating 50 mL medium (consisting of 2% glycerol, 2% dextrin, 1% fish meal, 0.5% peptone, 0.2% $(NH_4)_2SO_4$, and 0.2% $CaCO_3$, pH 7.0) with an aliquot of spore suspension, incubating at 28° C., 250 rpm for two days. To a fresh 50 mL of the same medium was then added the seed culture (5%), and incubation continued at 28° C., 250 rpm for three to six days (Hu et al. (1988) J. Antibiot. 41: 1575–1579). The fermentation supernatants were harvested by centrifugation (Eppendorf 5415C, 4° C., 10 min, 14,000 rpm) on day 3, 4 and 5, and assayed for their antibacterial activity against M. luteus (Hu et al. (1988) J. Antibiot., 41: 1575–1579).

DNA Isolation and Manipulation.

Plasmid preparation and DNA extraction were carried out by using commercial kits (Qiagen, Santa Clarita, Calif.). Total S. globisporus DNA was isolated according to literature protocols (Hopwood et al. (1985) Genetic manipulation of Streptomyces: a laboratory manual. John Innes Foundation, Norwich, UK; Rao et al. (1987) Methods Enzymol. 153: 166–198). Restriction endonuclease digestion and ligation followed standard methods (Sambrook et al. (1989) Molecular cloning, a laboratory manual. Cold Spring Harbor Laboratory, Cold Spring Harbor, N.Y.). For Southern analysis, digoxigenin labeling of DNA probes, hybridization, and detection were performed according to the protocols provided by the manufacturer (Boehringer Mannheim Biochemicals, Indianapolis, Ind.).

DNA Sequencing.

Automated DNA sequencing was carried out on an ABI Prism 377 DNA Sequencer using the ABI Prism dye terminator cycle sequencing ready reaction kit and AmpliTaq DNA polymerase FS (Perkin-Elmer/ABI, Foster City, Calif.). Sequencing service was provided by either the DBS Automated DNA Sequencing Facility, UC Davis, or Davis Sequencing Inc. (Davis, Calif.). Data were analyzed by ABI Prism Sequencing 2.1.1 software and the Genetics Computer Group program (Madison, Wis.).

Polymerase Chain Reaction (PCR).

Primers were synthesized at the Protein Structure Laboratory, UC Davis. PCR was carried out on a Gene Amp PCR System 2400 (Perkin-Elmer/ABI) with Taq polymerase and buffer from Promega. A typical PCR mixture consisted of 5 ng of S. globisporus genomic or plasmid DNA as template, 25 pmoles of each primers, 25 µM dNTP, 5% DMSO, 2 units of Taq polymerase, 1× buffer, with or without 20% glycerol in a final volume of 50 µL. The PCR temperature program was as follows: initial denaturing at 94° C. for 5 min, 24–36 cycles of 45 sec at 94° C., 1 min at 60° C., 2 min at 72° C., followed by additional 7 min at 72° C.

For type II PKS, the following two pairs of degenerate primers were used—5'-AGC TCC ATC AAG TCS ATG RTC GG-3' (forward, SEQ ID NO:137), 5'-CC GGT GTT SAC SGC GTA GAA CCA GGC G-3' (reverse, SEQ ID NO:138) and 5'-GAC ACV GCN TGY TCB TCV-3' (forward, SEQ ID NO: 139), 5'-RTG SGC RTT VGT NCC RCT-3' (SEQ ID NO: 140) (B, C+G+T; N, A+C+G+T; R, A+G; S, C+G; V, A+C+G; Y, C+T) (reverse) (Seow et al. (1997) *J. Bacteriol.*, 179: 7360–7368). No product was amplified under all conditions tested. For type I PKS, the following pair of degenerate primers were used—5'-GCS TCC CGS GAC CTG GGC TTC GAC TC-3' (forward, SEQ ID NO: 141), 5'-AG SGA SGA SGA GCA GGC GGT STC SAC-3' (S, G+C) (reverse, SEQ ID NO: 142) (Kakavas et al. (1997) *J. Bacteriol.*, 179: 7515–7522). A distinctive product with the predicted size of 0.75 kb was amplified in the presence of 20% glycerol and cloned into pGEM-T according to the protocol provided by the manufacturer (Promega) to yield pBS1001.

For NGDH, the following pair of degenerate primers were used—5'-CS GGS GSS GCS GGS TTC ATC GG-3' (forward, SEQ ID NO: 143)/5'-GG GWR CTG GYR SGG SCC GTA GTT G-3' (R, A+G; S, C+G; W, A+T; Y, C+T) (reverse, SEQ ID NO: 144) (Decker, et al. (1996) *FEMS Lett.*, 141: 195–201). A distinctive product with the predicted size of 0.55 kb was amplified and cloned into pGEM-T to yield pBS1002.

For cagA, the following pair of primers, flanking its coding region, were used—5'-AG GTG GAG GCG CTC ACC GAG-3' (forward, SEQ ID NO: 145)/5'-G GGC GTC AGG CCG TAA GAA G-3' (reverse, SEQ ID NO: 146) (Sakata et al. (1992) *Biosci. Biotechnol. Biochem.*, 56: 159201595). A distinctive product with the predicted size of 0.73 kb was amplified from pBS1005 and cloned into pGEM-T to yield pBS1003.

Genomic Library Construction and Screening.

*S. globisporus* genomic DNA was partially digested with MboI to yield a smear around 60 kb, as monitored by electrophoresis on a 0.3% agarose gel. This sample was dephosphorylated upon treatment with shrimp alkaline phosphatase and ligated into the *E. coli*-*Streptomyces* shuttle vector pOJ446 (Bierman et al. (1992) *Gene* 116: 43–69) that was prepared by digestion with HpaI, shrimp alkaline phosphatase treatment, and additional digestion with BamHI. The resulting ligation mixture was packaged with the Gigapack II XL two-component packaging extract (Stratagene). The package mixture was transduced into *E. coli* XL 1-Blue MR. The transduced cells were spread onto LB plates containing apramycin (100 µg/mL) and incubated at 37° C. overnight. The titer of the primary library was approximately 6,000 colony-forming units per µg of DNA. Restriction enzyme analysis of twelve randomly selected cosmids confirmed that the average size of inserts was about 35 to 45 kb (Rao et al. (1987) *Meth. Enzymol.*, 153: 166–198).

Figure 5A:
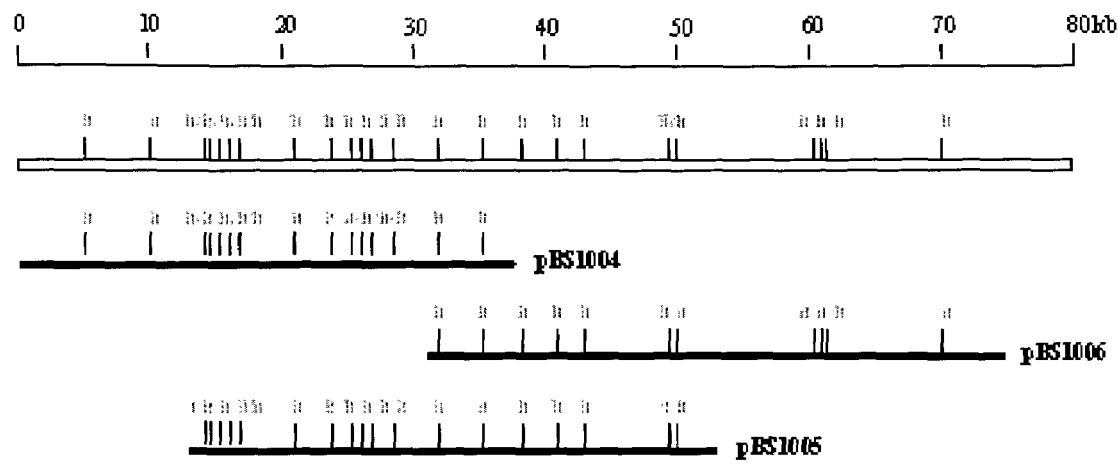
FIGS. 5A, 5B, and 5C illustrate the organization of the C-1027 enediyne biosynthetic gene cluster.
Figure 5B:
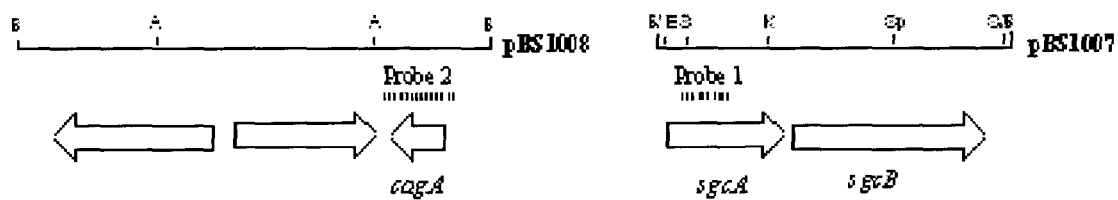

To screen the genomic library, colonies from five LB plates containing apramycin (100 µg/mL, with approximately 2,000 colonies per plate) were transferred to nylon transfer membranes (Micro Separations, Inc., Westborough, Mass.) and screened by colony hybridization with the PCR-amplified 0.55-kb NGDH fragment from pBS1002 as a probe. The positive cosmid clones were re-screened by PCR with primers for NGDH and confirmed by Southern hybridization (Sambrook et al., supra.). Further restriction enzyme mapping and chromosomal walking of these overlapping cosmids led to the genetic localization of the 75-kb sgc gene cluster, as represented by pBS1004, pBS1005, and pBS1006 (FIG. 5A). A 3.0-kb BamHI fragment from pBS1005 that hybridized to the NGDH probe was cloned into the same sites of pGEM-3zf to yield pBS1007. Similarly, a 4.0-kb BamHI fragment from pBS1005 that hybridizes to the PCR-amplified 0.73-kb cagA probe from pBS1003 was cloned into the same sites of pGEM-3zf to yield pBS1008 (FIG. 5B).

Generation of sgcA Mutants by Insert-directed Homologous Recombination in *S. globisporus*.

A 1.0-kb KpnI fragment from pBS1007, containing the C-terminal truncated sgcA, was subcloned into pGEM-3zf to yield pBS1009. An internal fragment of sgcA was moved sequentially as a 0.75-kb SacII/SphI fragment from pBS1009 into the same sites of pGEM-5zf to yield pBS1010 and as a 0.75-kb SacI/SphI fragment from pBS1010 into the same sites of pGEM-3zf to yield pBS1011. The latter plasmid was digested with EcoRI and HindIII, and the resulting 0.75-kb EcoRI/HindIII fragment was cloned into the same sites of pOJ260 and pKC1139 (Bierman et al. (1992) *Gene*, 116: 43–69) to yield pBS1012 and pBS1013, respectively.

Introduction of pBS1012 and pBS1013 into *S. globisporus* was carried out by either polyethyleneglycol (PEG)-mediated protoplast transformation (Hopwood et al. (1985) *Genetic manipulation of Streptomyces: a laboratory manual.* John Innes Foundation, Norwich, UK) or *E. coli*-*S. globisporus* conjugation (Bierman et al. (1992) *Gene* 116: 43–69; Matsushima and Baltz (1996) *Microbiology* 142: 261–267; Matsushima et al. (1994) *Gene* 146: 39–45), methods for both of which were developed recently in our laboratory. In brief, for transformation, pBS1012 and pBS1013 were propagated in *E. coli* ET12567 (MacNeil et al. (1992) *Gene* 111: 61–68), and the resulting double strand plasmid DNA was denatured by alkaline treatment (Ho and Chater (1997) *J. Bacteriol.* 179: 122–127). The latter DNA (5 µL) and 200 µL of 25% PEG 1000 in P buffer (Hopwood et al. supra) were sequentially added to 50 µL of *S. globisporus* protoplasts ($10^9$) in P buffer. The resulting suspension was mixed immediately and spread on R2YE plates. After incubation at 28° C. for 16 to 20 hrs, the plates were overlaid with soft R2YE (0.7% agar) containing apramycin (100 µg/mL, final concentration); incubation continued until colonies appeared (in 5 to 7 days). For conjugation, *E. coli* S17-1(pBS1012) or *E. coli* S17-1 (pBS1013) was grown to an $OD_{600}$ of 0.3 to 0.4. Cells from a 20-mL culture were pelleted by centrifugation, washed in LB, and resuspended in 2 mL of LB as the *E. coli* donors. *S. globisporus* spores ($10^3$ to $10^9$) were washed, resuspended in TSB, and incubated at 50° C. for 10 min to activate germination. After additional incubation at 37° C. for 2 to 5 hrs, the spores were pelleted and resuspended in LB as the *S. globisporus* recipients. The donors (100 µL) and recipients (100 µL) were mixed and spread equally onto two modified ISP-4 or AS-1 plates supplemented freshly with 10 mM $MgCl_2$ (see Media and culture conditions). The plates were incubated at 28° C. for 16 to 22 hrs. After removal of most of the *E. coli* S17-1 donors by washing the surface with sterile water, the plates were overlaid with 3 mL of soft LB (0.7% agar) containing nalidixic acid (50 µg/mL, final concentration) and apramycin (100 µg/mL, final concentration) and incubated at 28° C. until exconjugants appeared (in approximately 5 days).

Unlike pBS1012, which is a *Streptomyces* non-replicating plasmid, pBS1013 bears a temperature-sensitive *Streptomyces* replication origin (Bierman et al. (1992) *Gene* 116: 43–69; Muth et al. (1989) *Mol. Gen. Genet.* 219: 341–348) that is unable to replicate at temperatures above 34° C. (Table IV), while the *S. globisporus* wild-type strain grows normally up to 37° C. Thus, spores of *S. globisporus* (pBS1013), from either the transformants or the exconjugants, were spread onto R2YE plates containing apramycin (100 µg/mL). The plates were incubated directly at 37° C., and mutants, resulting from single crossover homologous recombination between pBS1013 and the *S. globisporus* chromosome, were readily obtained in 7 to 10 days. Alternatively, the plates were first incubated at 28° C. for 2 days until pinpoint-size colonies became visible and then shifted to 37° C. to continue incubation. Mutants resulting from single crossover homologous recombination grew out of the original pinpoint-size colonies as easily distinguishable sectors in 7 to 10 days.

Construction of the sgcA and sgcB Expression Plasmids.

pBS1007 was digested with EcoRI, and made blunt-ended by treatment with the Klenow fragment of DNA polymerase I. Upon additional digestion with SphI, the resulting 2.0-kb blunt-ended SphI fragment containing the intact sgcA gene was cloned into the SmaI/SphI sites of pWHM79 (Shen et al. (1996) *Proc. Natl. Acad. Sci., USA,* 93: 6600–6604) to yield pBS1014. The latter was digested with EcoRI and HindIII, and the resulting 2.5-kb EcoRI/HindIII fragment was cloned into the same sites of pWHM3 (Vara et al. (1989) *J. Bacteriol.* 171: 5872–5881) to yield pBS1015, in which the expression of sgcA is under the control of the ermE* promoter (Bibb et al. (1994) *Mol. Microbiol.* 14: 533–545).

Alternatively, pBS1007 was digested with KpnI, removing most of the sgcA gene, and the 5.2-kb KpnI fragment was recovered and self-ligated to yield pBS1016. The ermE* promoter was subcloned from pWHM79 (Shen et al. (1996) *Proc. Natl. Acad. Sci., USA,* 93: 6600–6604) as a 0.45-kb EcoRI/SacI fragment and cloned into the same sites of pBS1016 to yield pBS1017. The latter was digested with EcoRI and HindIII, and the resulting 2.5-kb EcoRI/HindIII fragment was cloned into the same sites of pKC1139 to yield pBS1018, in which the expression of sgcB is under the control of the ermE* promoter.

Determination of C-1027 Production.

The production of C-1027 was detected by assaying its antibacterial activity against *M. luteus* (Hu et al. (1988) *J. Antibiot.* 41: 1575–1579). From liquid culture, fermentation supernant (180 µL) was added to stainless steel cylinders placed on LB plates pre-seeded with overnight *M. luteus* culture (0.01% vol/vol). From solid culture, a small square block (0.5×0.5×0.5 cm$^3$) of agar from either R2YE or ISP-4 medium was directly placed on *M. luteus*-seeded LB plates. The plates were incubated at 37° C. for 24 hrs, and C-1027 production was estimated by measuring the size of inhibition zones.

Nucleotide Sequence Accession Number.

The nucleotide sequence reported here has been deposited in the GenBank database with the accession number AF201913.

Results.

No Polyketide Synthase Gene was Amplified by PCR from *S. globisporus.*

On the assumption that the C-1027 enediyne core is of polyketide origin, the PCR approach was adopted to screen *S. globisporus* for any putative PKS genes, although it is far from certain a priori if the biosynthesis of the enediyne core invokes a PKS and, if so, whether the enediyne PKS will exhibit a type I or type II structural organization. PCR methods for cloning either type I or type II PKS genes have been developed, and these methods have proven to be very effective in cloning PKS genes from various polyketide-producing actinomycetes (Kakavas et al. (1997) *J. Bacteriol.* 179: 7515–7522; Seow et al. (1997) *J. Bacteriol.* 179: 7360–7368). While no distinctive product was amplified under all conditions examined with both pairs of primers designed for type II PKS, a single product with the expected size of 0.75 kb was readily amplified by PCR from *S. globisporus* with primers designed for type I PKS, which was subsequently cloned (pBS1001). Intriguingly, sequence analysis of six randomly selected pBS1001 clones yielded an identical product—indicative of a specific PCR amplification—the deduced amino acid sequence of which, however, showed no homology to known PKSs (data not shown), excluding the possibility of using PKS as a probe to identify the sgc biosynthesis gene cluster.

Cloning of a Putative NGDH Gene by PCR from *S. globisporus.*

The biosynthesis of various deoxyhexoses share a common key intermediate—4-keto-6-deoxyglucose nucleoside diphosphate and its analogs—whose formation from glucose nucleoside diphosphate is catalyzed by the NGDH enzyme, an NAD$^+$-dependent oxidoreductase (Liu and Thorson (1994) *Ann. Rev. Microbiol.* 48: 223–256; Piepersberg (1997) pp. 81–163. In *Biotechnology of antibiotics,* 2nd ed. W. R. Strohl (ed). Marcel Dekker, New York). The PCR method was adopted to clone the putative NGDH gene from *S. globisporus* with primers designed according to the homologous regions of various NGDH enzymes from actinomycetes (Decker et al. (1996) *FEMS Lett.* 141: 195–201), resulting in the amplification of a single product with the expected size of 0.55 kb (pBS1002). Sequence analysis of pBS1002 confirmed its identity as a part of a putative NGDH gene.

To clone the complete NGDH gene, an *S. globisporus* genomic library, constructed in the *E. coli-Streptomyces* shuttle vector pOJ446 (Bierman et al. (1992) *Gene* 116: 43–69; Rao et al. (1987) *Methods Enzymol.* 153: 166–198), was analyzed by Southern hybridization with the PCR-amplified 0.55-kb fragment from pBS1002 as a probe. Of the 10,000 colonies screened, 36 positive colonies were identified, 9 of which were confirmed by PCR to harbor the DGDH gene. Restriction enzyme mapping showed that all of them contained a single 3.0-kb BamHI fragment hybridizing to the NGDH probe. Additional chromosomal walking from this locus eventually led to the localization of the 75-kb sgc gene cluster, covered by 18 overlapping cosmids as represented by pBS1004, pBS1005, and pBS1006 (FIG. 5A). The 3.0-kb BamHI fragment was subcloned (pBS1007) (FIG. 5B), and its nucleotide (nt) sequence was determined.

Analysis of the DNA Sequences of the sgcA and sgcB Genes.

Figure 6A:
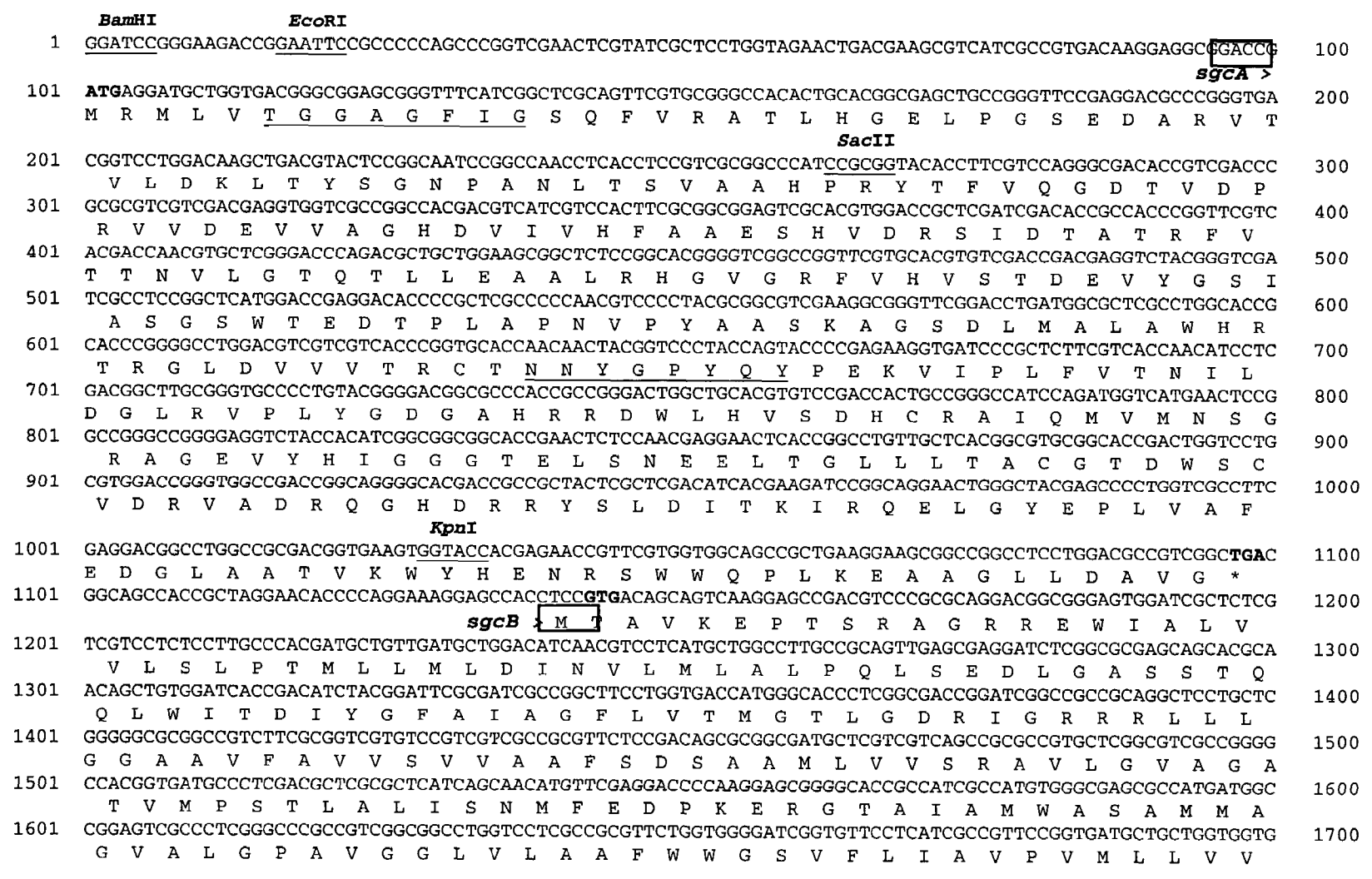

Two complete open reading frames (ORFs) (sgcA and sgcB) were identified within the 3.0-kb BamHI fragment of pBS1007, the 3,035-nt sequence of which is shown in FIG. 6. The sgcA gene most likely begins with an ATG at nt 101, preceded by a probable ribosome biding site (RBS), GGAGG, and ends with a TGA stop codon at nt 1099. SgcA should therefore encode a 332-amino acid protein with a molecular weight of 36,341 and an isoelectric point of 6.01. A Gapped-BLAST search showed that the deduced sgcA gene product is highly homologous to various putative and known NGDH enzymes from antibiotic-producing actinomycetes, including Gdh from the erythromycin biosynthesis gene cluster in *Saccharopolyspora erythraea* (64% identity and 70% similarity) (Linton et al. (1995) *Gene* 153: 33–40), MtmE from the mithramycin biosynthesis gene cluster in *Streptomyces argillaceus* (64% identity and 68% similarity) (Lombo et al. (1997) *J. Bacteriol.* 179: 3354–3357), and TylA2 from the tylosin biosynthesis gene cluster in *Streptomyces fradiae* (62% identity and 68% similarity) (Merson-Davies and Cundliffe (1994) *Mol. Microbiol.* 13: 349–355) (FIG. 7). A conserved sequence of 14 amino acid residues close to the N-termini can be easily identified in these proteins, which has been described as a βαβ fold with an $NAD^+$-binding motif, GxGxxG (SEQ ID NO:225), (FIG. 7, boxed), consistent with their biochemical role in deoxyhexose biosynthesis (Liu and Thorson (1994) *Ann. Rev. Microbiol.* 48: 223–256; Piepersberg (1997) pp. 81–163. In *Biotechnology of antibiotics,* 2nd ed. W. R. Strohi (ed). Marcel Dekker, New York). The function of Gdh and MtmE as TDP-glucose 4,6-dehydratases, requiring $NAD^+$ as a cofactor, has been confirmed by an enzyme assay following expression of the gdh (Linton et al. (1995) *Gene* 153: 33–40) and mtmE gene (Lombo et al. (1997) *J. Bacteriol.* 179: 3354–3357) in *E. coli*, respectively, and by purification of the Gdh protein from *Sacc. erythraea* (Vara et al. (1989) *J. Bacteriol.* 171: 5872–5881). From these data, it is reasonable to suggest that sgcA encodes the NGDH enzyme required for the biosynthesis of the 4,6-dideoxy-4-dimethylamino-5-methylrhamnose moiety of the C-1027 chromophore.

Transcribed in the same direction as sgcA, the sgcB gene is located 43 nt downstream of sgcA. It should begin with a GTG at nt 1143, preceded by a probable RBS, AGGAG, and end with a TGA at nt 2708 (FIG. 6). Correspondingly, sgcB should therefore encode a 521-amino acid protein with a molecular weight of 52,952 and an isoelectric point of 4.64. Database comparison of the deduced sgcB product revealed that SgcB is closely related to a family of membrane efflux pumps, such as LfrA from *Mycobacterium smegmatis* (43% identity and 50% similarity, protein accession number AAC43550) (Takiff et al. (1996) *Proc. Natl. Acad. Sci. USA* 93: 362–366), OrfA from *Streptomyces cinnamomeus* (42% identity and 47% similarity, protein accession number AAB71209) (Sommer et al. (1997) *Appl. Environ. Microbiol.* 63: 3553–3560), and RifP from the rifamycin biosynthesis gene cluster in *Amycolatopsis mediterranei* (35% identity and 44% similarity, protein accession number AAC01725) Augus et al. (1998) *Chem. Biol.* 5: 69–79). These proteins are membrane-localized transporters involved in the transport of antibiotics (conferring resistance), sugars, and other substances. While direct evidence is lacking for RifP conferring rifamycin resistance in *A. mediterranei* by transporting it out of the cells (August et al. (1998) *Chem. Biol.,* 5: 68–79), it has been proven that LfrA employs the transmembrane proton gradient in an antiporter mode to drive the efflux of intracellular antibiotics, resulting in fluoroquinolone resistance in *M. smegmatis* (Takiff et al. (1996) *Proc. Natl. Acad. Sci. USA* 93: 362–366). On the basis of the high degree of amino acid sequence conservation, an equivalent role could be proposed for SgcB, conferring resistance by exporting C-1027 from *S. globisporus*.

The cagA Gene is Clustered with the sgcA and sgcB Locus.

Figure 5C:
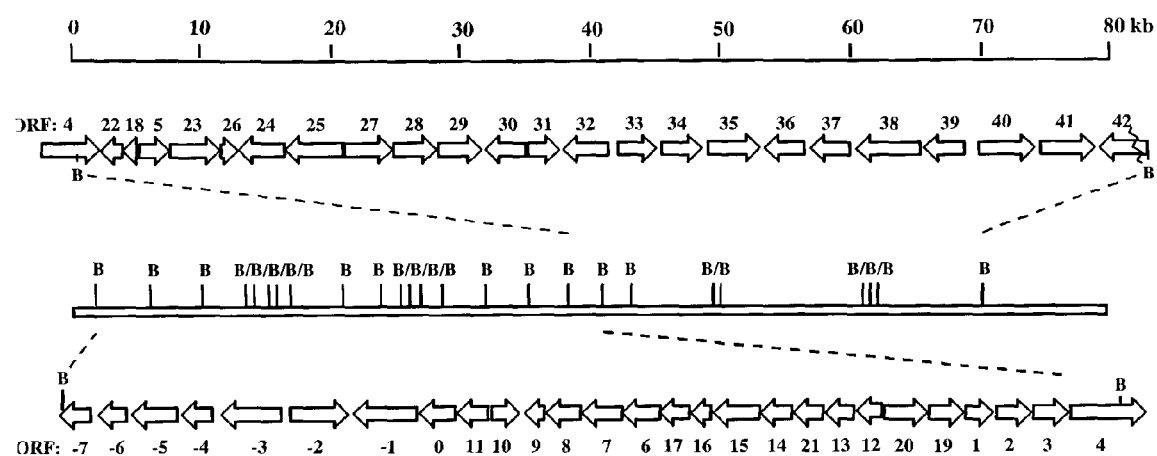

To determine if cagA is clustered with the sgcA and sgcB locus, PCR primers were designed according to the flanking regions of cagA (Sakata et al. (1992) *Biosci. Biotech. Biochem.* 56: 1592–1595). A single product with the predicted size of 0.73 kb was indeed amplified from several of the overlapping cosmids (which cover the 75-kb sgc cluster), including pBS1004 and pBS1005, the identity of which as cagA was confirmed by sequencing. Restriction enzyme mapping and Southern hybridization analysis localized cagA to a single 4.0-kb BamHI fragment that is approximately 14 kb upstream of the sgcA,B locus (FIG. 5B). The 4.0-kb BamHI fragment was subcloned (pBS1008), and its nt sequence was determined, revealing the cagA gene along with two additional ORFs (data not shown) (FIG. 5). As reported earlier, cagA encodes a 142-amino acid protein that is processed by cleavage of a 32-amino acid lead peptide to yield the mature CagA apoprotein (Sakata et al. (1992) *Biosci. Biotech. Biochem.* 56: 1592–1595).

Disruption of the sgcA Gene in *S. globisporus*.

Figure 8A:
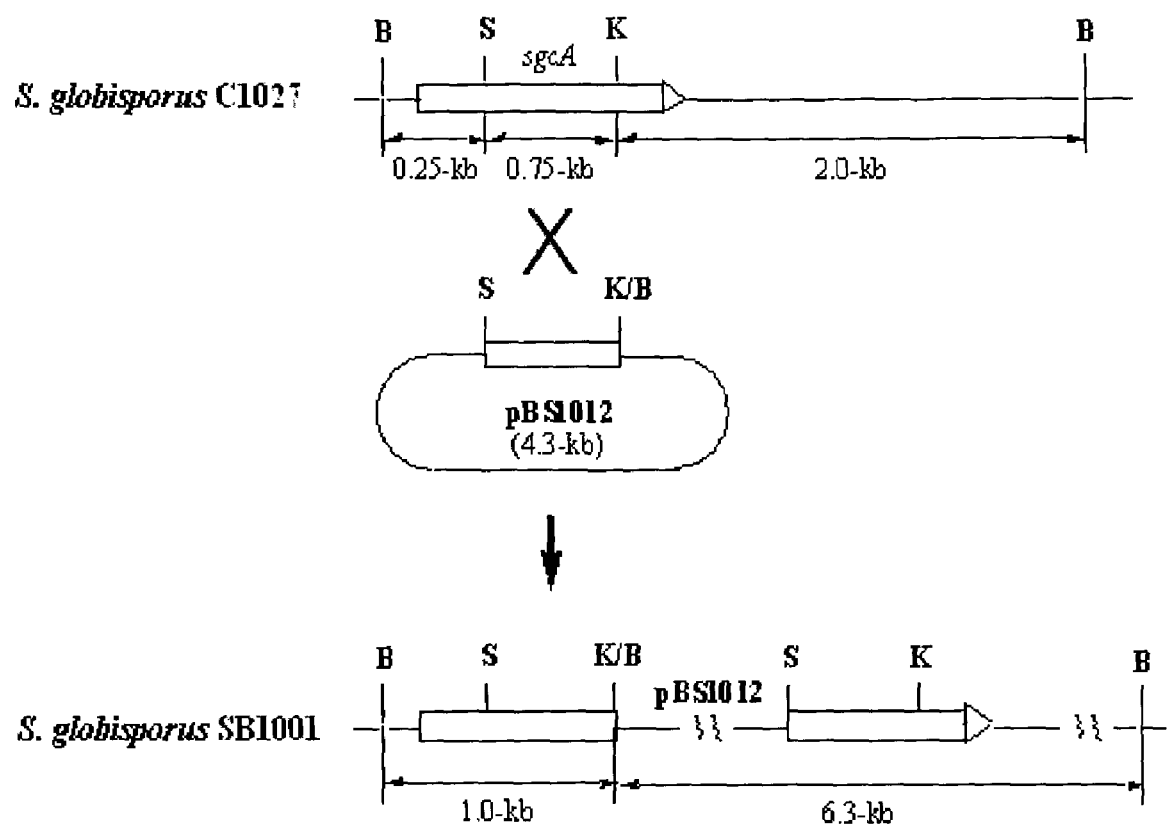

To examine if the cloned sgc cluster encodes C-1027 biosynthesis, sgcA was insertionally disrupted by a single crossover homologous recombination event to generate C-1027-nonproducing mutant strains (FIG. 8A). Two plasmids were used—pBS1012 (a pOJ260 derivative) and pBS1013 (a pKC1139 derivative), each of which contain a 0.75-kb internal fragment from sgcA (Table IV). After introduction of pBS1012 into *S. globisporus* either by PEG-mediated protoplast transformation or *E. coli-S. globisporus* conjugation, transformants or exconjugants that were resistant to apramycin were isolated in all cases. Since pBS1012 is derived from the *Streptomyces* non-replicating plasmid of pOJ260, these isolates must have resulted from integration of pBS1012 into the *S. globisporus* chromosome by homologous recombination. Plasmid pBS1013 was similarly introduced into *S. globisporus*. However, since pBS1013 is derived from pKC1139 that carries the temperature-sensitive Streptomyces replication origin from pSG5 and can replicate normally at 28° C. (Muth et al. (1989) *Mol. Gen. Genet.* 219: 341–348), these isolates were subjected to incubation at the non-permissive temperature of 37° C. to eliminate free plasmids from the host cells. As expected, normal growth stopped except for the recombinants that continue to grow at 37° C., indicative of integration of pBS1013 into *S. globisporus* by homologous recombination. The apramycin-resistant *S. globisporus* SB1001 and *S. globisporus* SB1002 strains were chosen as representatives of mutant strains with disrupted sgcA gene resulted from integration of pBS1012 and pBS1013, respectively.

To confirm that targeted sgcA disruption has occurred by a single crossover homologous recombination event, Southern analysis of the DNA from the mutant strains was performed as exemplified for *S. globisporus* SB1001 with either pOJ260 or the 0.75-kb SacII/KpnI internal fragment of sgcA from pBS1010 as a probe. As shown in FIG. 8B, a distinctive band of the predicted size of 6.3 kb was detected with the pOJ260 vector as a probe in all mutant strains (lanes 2, 3, and 4); this band was absent from the wild-type strain (lane 1). Complementarily, when using the 0.75-kb SacII/KpnI internal fragment of sgcA as a probe (FIG. 8C), the 3.0-kb band in the wild-type strain (lane 1) was split into two fragments with the size of 6.3 kb and 1.0 kb in the mutant strains (lanes 2, 3, and 4), as would be expected for disruption of sgcA by a single crossover homologous recombination event.

*S. globisporus* SB1001 and *S. globisporus* SB1002 are C-1027-Nonproducing Mutants.

No apparent difference in growth characteristics and morphologies between the wild-type *S. globisporus* and mutant *S. globisporus* SB1001 and *S. globisporus* SB1002 strains was observed. While C-1027 production in the wild-type *S. globisporus* strain could be detected on day 3, peaked on day 5, and continued for a few more days, as judged by assaying the antibacterial activity of the culture supernant against *M. luteus* (Hu et al. (1988) *J. Antibiot.* 41: 1575–1579), C-1027 production is completely abolished in the sgcA mutant strains *S. globisporus* SB1001 and *S. globisporus* SB1002 (FIG. 9A). The latter phenotype was identical to that of the AF40, AF44, and AF67 mutants, C-1027-nonproducing *S. globisporus* strains that have been characterized previously (FIGS. 9A and 9C) (Mao, et al. (1997) *Chinese J. Biotechnol.* 13: 195–199).

In vivo Complementation of *S. globisporus* SB1001.

The ability of the wild-type sgcA gene to complement the disrupted sgcA gene was tested in the *S. globisporus* SB1001 strain. The construction of pBS1015, in which the expression of sgcA is under the control of the constitutive ermE* promoter, was described in Materials and Methods. Both the pBS1015 construct and the pWHM3 vector as a control were introduced by transformation into the *S. globisporus* SB1001 mutant strains. Culture supernants from each transformant were bioassayed against *M. luteus* for C-1027 production. pBS1015 restored C-1027 production to *S. globisporus* SB1001 to the wild-type level; no C-1027 production was detected in the control in which pWHM3 was introduced into *S. globisporus* SB1001 (FIGS. 9B and 9C). A significant reduction of C-1027 production was observed when *S. globisporus* SB1001(pBS1015) was cultured under identical conditions but without thiostrepton (FIG. 9B vs. 6C), indicative that pBS1015 may be unstable in *S. globisporus* SB1001 in the absence of antibiotic selection pressure.

Expression of sgcB in *S. globisporus*.

The effect of sgcB on C-1027 production was tested in the wild-type *S. globisporus* strain. The construction of pBS1018, in which the expression of sgcB is under the control of the constitutive ermE* promoter, was described in Materials and Methods. pBS1018 and the pKC1139 vector as a control were each introduced by conjugation into *S. globisporus*. Culture supernants from each exconjugant were harvested on days 3, 4, and 5, and assayed for C-1027 production by determining the antibacterial activity against *M. luteus*. While no apparent difference for C-1027 production was observed between the *S. globisporus* and *S. globisporus* (pKC1139) strains, a significant increase in C-1027 production (150±25%) was evident in the early stage of *S. globisporus* (pBS1018) fermentation (FIG. 9D, day 3). However, such effect on C-1027 production leveled off as the fermentation proceeded and became insignificant when the culture reached the late stationary phase of fermentation (FIG. 9D, day 4 and 5).

Discussion.

Our inability to clone the putative enediyne PKS gene by PCR, with degenerate primers designed according to the highly conserved amino acid sequences of either type I or type II PKSs, or by DNA hybridization, with homologous type I or type II PKS as probes (data not shown), was unexpected, since feeding experiments by incorporation of [1-$^{13}$C]- and [1,2-$^{13}$C]acetate into the enediyne cores of esperamicin (Lam et al. (1993) *J. Am. Chem. Soc.* 115: 12340–12345), dynemicin (Tokiwa et al. (1992) *J. Am. Chem. Soc.* 114: 4107–4110), and neocarzinostatin (Hensens et al. (1989) *J. Am. Chem. Soc.* 111: 3295–3299) supported their polyketide origin. Although the enediyne cores are structurally distinct from either the reduced or aromatic polyketides, the biosynthesis of which is well characterized by type I or type II PKS, respectively, it could be imagined that an enediyne PKS catalyzes the biosynthesis of a polyunsaturated linear heptaketide intermediate that is subsequently cyclized into the enediyne core structure (Hu et al. (1994) *Mol. Microbiol.* 14: 163–172; Spaink et al. (1991) *Nature* 354: 125–130; Thorson et al. (1999) *Bioorg. Chem.*, 27: 172–188). Alternatively, Hensens and co-workers proposed a fatty acid origin for the enediyne core that was also consistent with the isotope labeling results. These authors suggested oleate as a precursor that is shortened by loss of carbons from both ends and is desaturated via the oleate-crepenynate pathway to furnish the enediyne core (Hensens et al. (1989) *J. Am. Chem. Soc.* 111: 3295–3299). The latter pathway resembles polyacetylene biosynthesis in higher plants and fungi and requires an acetylene forming enzyme—a plant gene encoding such an enzyme was identified recently (Lee et al. (1998) *Science* 280: 915–918). Our DNA sequence analysis of approximately 60 kb of the sgc gene cluster, fails to reveal any gene that resembles PKS.

Although little is known about the resistance mechanism for the enediyne antibiotics in general, the apoproteins of the chromoprotein type of enediynes could be viewed as resistance elements that confer self-resistance to the producing organisms by drug sequestration (Thorson et al. (1999) *Bioorg. Chem.*, 27: 172–188). Such a resistance mechanism is in fact well established in antibiotic-producing actinomycetes, for example, BlmA, the bleomycin-binding protein from *Streptomyces verticillus* (Shen et al. (1999) *Bioorg. Chem.* 27: 155–171). Given the fact that antibiotic production genes have invariably been found to be clustered in one region of the microbial chromosome, consisting of structural, resistance, and regulatory genes, we adopted a strategy to clone the sgc gene cluster by mapping a putative C-1027 structural gene to the previously cloned cagA gene, considered as a resistance gene that encodes the C-1027 apoprotein.

We chose NGDH as the putative C-1027 structural gene on the basis of the 4,6-dideoxy-4-dimethylamino-5-methyl-rhamnose moiety of the C-1027 chromophore. It has been well established that all deoxyhexoses could be derived from the common intermediate of 4-keto-6-deoxyglucose nucleoside diphosphate, the biosynthesis of which from glucose nucleoside diphosphate is catalyzed by an NGDH enzyme. We cloned the NGDH gene from *S. globisporus* by PCR and used it as a probe to screen an *S. globisporus* genomic library, resulting in the isolation of the 75-kb sgc gene cluster. DNA sequence analysis of a 3.0-kb BamHI fragment of the sgc cluster confirmed the presence of the NGDH protein, encoded by sgcA, along with sgcB that encodes a transmembrane efflux protein (FIG. 6). The cagA gene indeed resides approximately 14 kb upstream of sgcA (FIG. 5); DNA sequence analysis of a 4.0-kb BamHI fragment confirmed the identity of cagA along with two additional ORFs (data not shown). These results underline once again the effectiveness of cloning natural product biosynthesis gene clusters by exploiting the clustering phenomenon between resistance and structural genes.

The involvement of the cloned gene cluster in C-1027 biosynthesis was demonstrated by disrupting the sgcA gene to generate *S. globisporus* mutants, the ability of which to produce C-1027 was completely abolished (FIG. 9A), and by complementing the sgcA mutants in vivo upon expression of sgcA in trans to restore C-1027 production (FIGS. 9B and 6C). These data unambiguously establish that sgcA is essential for C-1027 production, and thus support the conclusion that the cloned gene cluster encodes C-1027 biosynthesis. It should be pointed out that, although the sgcA mutants *S. globisporus* SB1001 and *S. globisporus* SB1002 were characterized as C-1027-nonproducing on the basis of the antibacterial assay alone (FIG. 9A), this phenotype was identical to that of the controls of the AF40, AF44, and AF67 mutants (FIGS. 9A and 9C). The latter strains were isolated previously upon randomly mutagenizing the wild-type *S. globisporus* strain with acriflavine and confirmed to be C-1027-nonproducing by both the antibacterial bioassay and an antitumor spermatogonial assay (Mao, et al. (1997) *Chinese J. Biotechnol.* 13: 195–199), providing strong support to the current study. Gene disruption and complementation in *S. globisporus* were made possible by the recently developed genetic system that allowed us to introduce plasmid DNA into *S. globisporus* via either PEG-mediated protoplast transformation (Hopwood et al. (1985) *Genetic manipulation of Streptomyces: a laboratory manual*. John Innes Foundation, Norwich, UK) or *E. coli-S. globisporus* conjugation (Bierman et al. (1992) *Gene* 116: 43–69; Matsushima and Baltz (1996) *Microbiology* 142: 261–267; Matsushima et al. (1994) *Gene* 146: 39–45) for analyzing the sgc biosynthesis gene cluster in vivo. Given the difficulties encountered with calicheamicin biosynthesis in *Micromonospora echinospora*, into which all attempts to introduce plasmid DNA have failed (Thorson et al. (1999) *Bioorg. Chem.*, 27: 172–188), the latter results underscore the importance of selecting C-1027 as a model system for enediyne biosynthesis so that many of the genetic tools developed in Streptomyces species can now be directly applied to the study of enediyne biosynthesis.

Finally, the function of sgcB was probed by examining C-1027 production, following expression of the gene in the wild-type *S. globisporus* strain. Database comparison of the deduced amino acid sequence clearly suggested SgcB as a transmembrane efflux protein, conferring resistance by exporting C-1027 out of the cell. Hence, in addition to CagA, SgcB could be viewed as the second resistance element identified for C-1027 biosynthesis. Multiple resistance genes have been identified in numerous antibiotic biosynthesis gene clusters (Hopwood (1997) *Chem. Rev.* 97: 2465–2497). It could be imagined that CagA and SgcB function cooperatively to provide resistance—the C-1027 chromophore is first sequestered by binding to the preproprotein CagA to form a complex, which is then transported out of the cell by the efflux pump SgcB and processed by removing the leader peptide to yield the chromoprotein, although we do not have any experimental data to substantiate this speculation. Since it is known that yields for antibiotic production could be profoundly altered by the introduction of extra copies of regulatory, resistance, or structural genes into wild-type organisms (Hutchinson (1994) *Bio/Technology* 12: 375–380), we tested the effect of overexpressing sgcB in *S. globisporus* on C-1027 production. While no apparent adverse effect on C-1027 production was observed upon introduction of the pKC1139 vector into *S. globisporus* (data not shown), a significant increase in C-1027 production (150±25%) was observed in the early stage of *S. globisporus* (pBS1017) fermentation (FIG. 9D, day 3), supporting the predicted function for SgcB in C-1027 biosynthesis. We propose that C-1027 resistance could be a limiting factor at the onset of C-1027 production, which is circumvented by the extra copy of the plasmid-born sgcB, and overexpression of sgcB under the control of the constitutive ermE* promoter results in increase of C-1027 production. However, as the *S. globisporus* (pBS1017) fermentation proceeds to its stationary phase, C-1027 resistance is no longer a limiting factor for overall C-1027 production, and the effect of extra copy of SgcB on C-1027 production consequently became insignificant (FIG. 9D, day 5).

In conclusion, genetic analysis of enediyne biosynthesis has heretofore met with little success in spite of considerable effort (Thorson et al. (1999) *Bioorg. Chem.*, 27: 172–188).

The localization of the sgc gene cluster and characterization of the sgcA and sgcB genes have now provided an excellent basis for genetic and biochemical investigations and/or modification of C-1027 biosynthesis, and gene disruption and overexpression in *S. globisporus* clearly demonstrated the potential to construct enediyne-overproducing strains and to produce novel enediynes that may have enhanced potency as novel anticancer drugs using combinatorial biosynthesis and targeted mutagenesis. We envisage that the results from C-1027 biosynthesis should facilitate the cloning and characterization of biosynthesis gene clusters of other enediyne antibiotics in *Streptomyces* as well as in other actinomycetes, and could have a great impact on the overall field of combinatorial biosynthesis.

Example 2

Biosynthesis of Enediyne Antitumor Antibiotic C-1027 by a Polyketide Synthase and Engineered Biosynthesis of a C-1027 Analog C-1027 is an extremely potent antitumor agent with a unique molecular architecture and mode of action. Cloning and characterization of the 85-kb C-1027 biosynthesis gene cluster from *Streptomyces globisporus* revealed (1) an iterative type I polyketide synthase (PKS) that is distinct from any bacterial PKSs known to date, (2) a general polyketide pathway for the biosynthesis of both the nine- and ten-membered enediyne antibiotics, and (3) a convergent biosynthetic strategy for the C-1027 chromophore from four building blocks. Manipulation of genes governing C-1027 biosynthesis allowed us to produce a new enediyne compound in a predicted manner.

Figure 18:
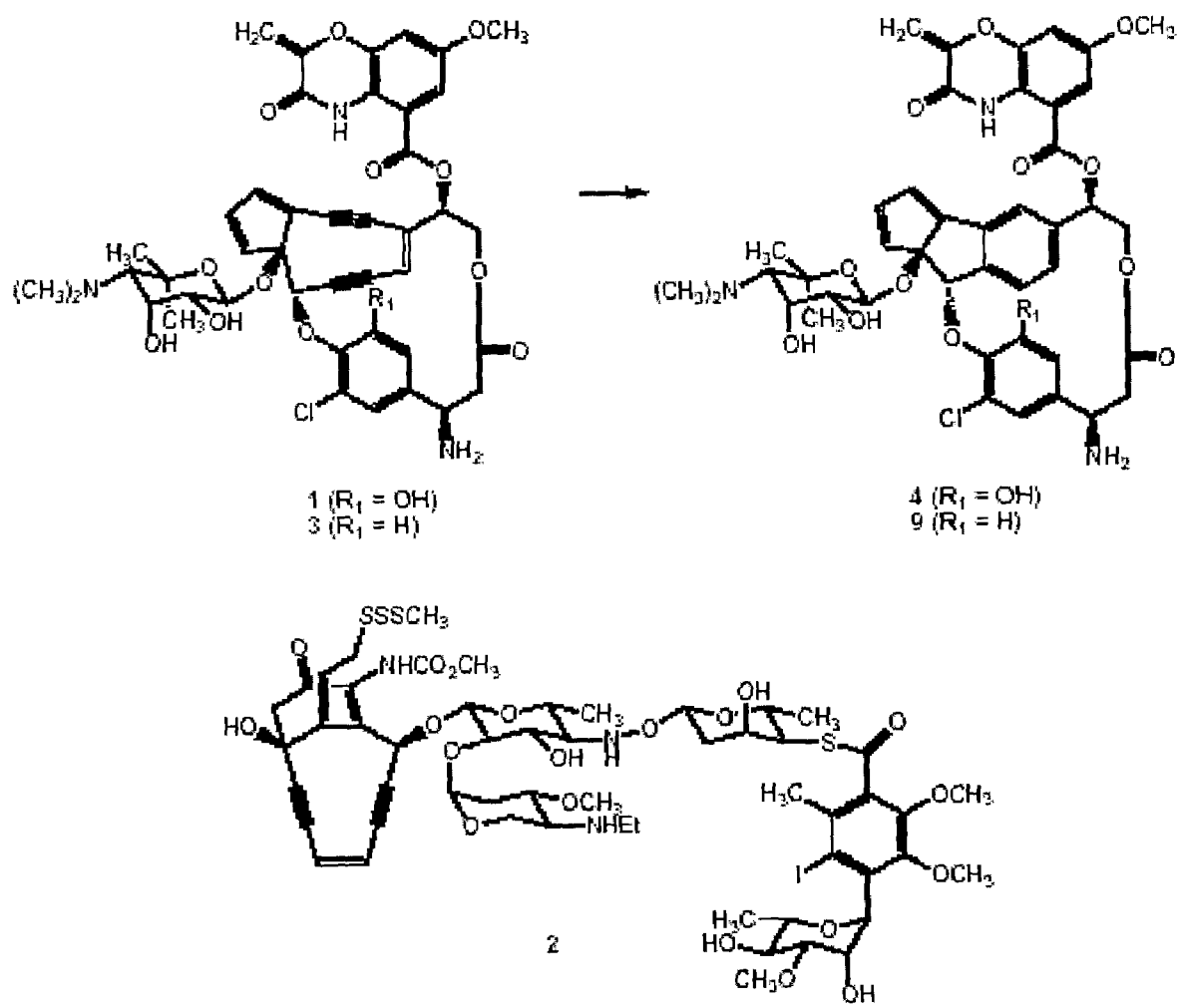
FIG. 18 shows the structures of the C-1027 (1) and deshydroxy-C-1027 (3) chromophores and their aromatized products (4 and 9), and calicheamicin (2).

C-1027 is a chromoprotein antibiotic produced by *Streptomyces globisporus* and composed of an apoprotein and the C-1027 chromophore (1) (Otani (1988) *J. Antibiot.* 41:1580). It belongs to the enediyne family of antibiotics, structurally characterized by a unit consisting of two acetylenic groups conjugated to a double bond or incipient double bond within a nine- or ten-membered ring, i.e., the enediyne core, as exemplified by 1 or calicheamicin $\gamma^I_1$ (2), respectively (FIG. 18). The enediyne antibiotics are extremely potent antitumor agents with a unique molecular architecture and mode of action (Nicolaou (1991) *Angew. Chem. Int. Ed. Engl.* 30: 1387; Xi and Goldberg (1999) Pp. 553–592 In: *Comprehensive Natural Products Chemistry*, Vol. 7, D. Barton, K. Nakanish, O. Meth-Cohn, Eds. (Elesvier, N.Y.; Brukner (2000) *Curr. Opinion Oncologic, Endocrine & Met. Invest. Drugs* 2: 344). Although the natural enediynes have seen limited use as clinical drugs mainly because of significant toxicity, various polymer-based delivery systems or enediyne-antibody conjugates have shown clinical promise and success in anticancer chemotherapy. For example, the poly(styrene-co-maleic acid)-conjugated neocarzinostatin has been used clinically against hepatoma in Japan since 1994 (Maeda and Konno (1997) Pp 227–267 In: *Neocarzinostatin: the Past, Present, and Future of an Anticancer Drug*, H. maeda, K. Edo, N. Ishida, Eds. (Speinger-Verlag, New York). A CD33 monclononal antibody (MAb)-calicheamicin conjugate was approved in U.S. in 2000 for acute myeloid leukemia patients (Sievers et al., (1999) *Blood* 93: 3678). Several MAb-C-1027 conjugates are under evaluation as promising anticancer drugs (Brukner (2000) *Curr. Opinion Oncologic, Endocrine & Met. Invest. Drugs* 2: 344). These successes have demonstrated that the enediynes can be developed into powerful drugs when their extremely potent cytotoxicity is harnessed and delivered directly onto the targeted tumor cells. A challenge is the synthesis of enediynes and their analogs for further mechanistic and clinical studies.

Complementary to making microbial metabolites and their structural analogs by chemical synthesis, genetic manipulations of genes governing secondary metabolism offer a promising alternative to preparing these structurally complex natural products biosynthetically (Cane et al. (1998) *Science* 282: 63; Du and Shen (2001) *Curr. Opinion Drug Discov. Develop.* 4: Staunton and Wilkinson (1998) *Top. Curr. Chem.* 195: 49; Shen (2000) *Top. Curr. Chem.* 209: 1). The success of the latter approach depends on the cloning and genetic and biochemical characterization of the biosynthetic pathways of the metabolites. Given the structural complexity and remarkable biological activity, the enediynes offer a distinct opportunity to decipher the genetic and biochemical basis for the biosynthesis of an unprecedented molecular scaffold and to explore ways to make novel antitumor agents by manipulating genes governing enediyne biosynthesis. Here we report the cloning, sequencing, and characterization of the complete C-1027 biosynthesis gene cluster from *S. globisporus*, revealing an iterative type I polyketide synthase (PKS) with unprecedented domain organization and a convergent biosynthetic strategy for 1 from four biosynthetic building blocks. Our results, in conjunction with the similar findings for 2, establish a new paradigm both in PKS structure and mechanism for the formation of both nine- and ten-membered enediyne antibiotics. Manipulation of genes governing C-1027 biosynthesis allowed us to engineer novel enediyne compounds as exemplified by deshydroxy-C-1027 (3).

We have reported the cloning and characterization of the sgcAB genes that encode a TDP-glucose 4,6-dehydratase and transmembrane efflux protein, respectively, and demonstrated that sgcAB are essential for C-1027 production in *S. globisporus* (see, e.g. U.S. Ser. No. 09/478,188 and Liu and Shen (2000) *Antimicrobiol. Agents Chemother.* 44: 382). Since antibiotic production genes commonly occur as a cluster in actinomycetes, we set out to identify the C-1027 biosynthesis gene cluster by chromosomal walking from the sgcAB locus. An 85-kb contiguous DNA from *S. globisporus* was sequenced and analyzed, revealing 67 open reading frames (orfs).

The C-1027 gene cluster was previously mapped to three overlapping cosmids, pBS1004, pBS1005, and pBS1006 (U.S. Ser. No. 09/478,188; Liu and Shen (2000) *Antimicrobiol. Agents Chemother.* 44: 382). Chromosomal walking from pBS1006 led to the isolation of an additional cosmid pBS1020, and together they covered 110-kb contiguous *S. globisporus* DNA, 85-kb of which was sequenced. orfs were identified by using the CODONPREFERENCE method in the GCG software. The overall GC content of the sequenced region is 70.1%. Functional assignments were made by comparison of the deduced gene products with proteins of known functions in the database and summarized in the GenBank under accession number AY048670 (see also, FIG. 12).

To determine the boundaries of the C-1027 gene cluster, orfs at both ends of the sequenced region were subjected to inactivation by gene disruptions—inactivation of genes within the C-1027 gene cluster, as exemplified by sgcA, sgcC, sgcC1, sgcD6, and sgcE, abolished C-1027 production (FIG. 15), while that of genes outside the C-1027 gene cluster, such as orf(−5), orf(−3), and orf54, had no effect on C-1027 production, leading to the assignment of the cluster boundaries at sgcB1 and sgcR3, respectively.

Inactivation by gene disruption of orf(−5), orf(−3), sgcC, sgcC1, sgcD6, and orf54 was carried out as reported herein for sgcA. Essentially a 0.5–1 kb fragment internal to the target gene was cloned into pOJ260, and the resulting construct was introduced into *S. globisporus* by conjugation. Recombinant strain was isolated by selection for apramycin resistance and confirmed by Southern analysis.

C-1027 production was monitored by bioassay against *Micrococcus luteus* (Liu and Shen (2000) *Antimicrobiol. Agents Chemother.* 44: 382) and high performance liquid chromatography (HPLC) analysis of 1 (15), which undergoes facile Bergman cyclization to yield the aromatized product (4) (FIGS. 18 and 15A) (Minami et al. (1993) *Tetrahetron Lett.* 34: 2633; Yoshida et al. (1993) *Tetrahedron Lett.* 34: 2637). The identities of 1 and 4 were confirmed by electrospray ionization-mass spectrometry (ESI-MS) analyses: 1 showed $(M+H)^+$ and $(M+Na)^+$ ions at m/z=844 and 866, consistent with the molecular formula of $C_{43}H_{42}N_3O_{13}Cl$, and 4 showed a $(M+H)^+$ ion at m/z=846, consistent with the molecular formula of $C_{43}H_{44}N_3O_{13}Cl$. Consistent with the structure of 1, those identified within the C-1027 cluster include thirteen genes, sgcE to sgcE11 and sgcF, encoding the enediyne core (5) biosynthesis, seven genes, sgcA to sgcA6, encoding deoxy aminosugar (6) biosynthesis, six genes, sgcC to sgcC5, encoding β-amino acid (7) biosynthesis, and seven genes, sgcD to sgcD6, encoding benzoxazolinate (8) biosynthesis (FIG. 12).

Three types of PKSs are known for polyketide biosynthesis in bacteria: type I and type II systems, both of which use acyl carrier protein (ACP) to activate substrates and channel the growing intermediates, for aliphatic (Staunton and Wilkinson (1998) *Top. Curr. Chem.* 195: 49) and aromatic polyketides (Shen (2000) *Top. Curr. Chem.* 209: 1), respectively, and the type III system that has no apparent amino acid sequence similarity to the former and acts directly on acyl CoAs, largely for monocyclic aromatic polyketides (Funa et al. (1999) *Nature* 400: 897). The enediyne cores bear no structural resemblance to any of the polyketides studied to date, failing to predict what type of PKS may be responsible for their biosynthesis. In fact, a controversy remains as to whether the enediyne cores are assembled via de novo polyketide biosynthesis or degradation from a fatty acid precursor, although feeding experiments with $^{13}C$-labeled precursors for neocarzinostatin (Hensens et al. (1989) *J. Am. Chem. Soc.* 111: 3295), dynemicin (Tokiwa et al.(1992) *J. Am. Chem. Soc.* 114: 4107), and esperamicin (Lam et al. (1993) *J. Am. Chem. Soc.* 115: 12340) unambiguously established that the enediyne cores were all derived from minimally eight head-to-tail acetate units. Strikingly, of the genes identified within the C-1027 cluster, there is only one, sgcE, that encodes a PKS. SgcE contains five domains—the ketoacyl synthase (KS), acyltransferase (AT), ketoreductase (KR), and dehydratase (DH) domains that are characteristic of known PKSs and a domain at the COOH-terminus (TD) that, unique only to enediyne PKSs, shows no sequence homology to any other proteins, as well as a region between AT and KR that might contain a putative ACP domain (FIG. 13A). SgcE could be envisaged to catalyze the assembly of a nascent linear polyunsaturated intermediate from acetyl and malonyl CoAs in an iterative process, which, upon action of other enzyme activities, is subsequently desaturated to furnish the two yne groups and cyclized to afford the enediyne core. An enzyme that catalyzes the formation of an acetylenic bond from a C—C double bond has been reported from the plant *Crepis alpina* and characterized as acetylenase that is a non-heme diiron protein (Lee et al. (1998) *Science* 280: 915). While no such homolog was found within the C-1027 cluster, close comparison of the C-1027 gene cluster with that for neocarzinostatin, another nine-membered enediyne antibiotic (the neocarzintostatin cluster was cloned, sequenced, and characterized from *Streptomyces carzinostaticus* ATCC15944), revealed a group of orfs (sgcE1 to sgcE11), in addition to sgcE, that are highly conserved. SgcE6, SgcE7, and SgcE9 resembles various oxidoreductases, SgcE1, SgcE2, SgcE3, SgcE4, SgcE5, SgcE8, or SgcE11 show no sequence homology or homology only to proteins of unknown functions, and SgcE10 is highly homologous to a family of thioesterases. These enzymes, together with the SgcF epoxide hydrolase, serve as candidates for processing the nascent linear polyunsaturated intermediate into an enediyne intermediate such as 5 (FIG. 12).

To experimentally test this hypothesis, we inactivated sgcE by replacing it with a mutant copy in which the KS domain is replaced with the erythromycin resistance gene, ermE. sgcE was mutated by replacing the 371-bp BamHI fragment that harbors the KS domain with the ermE resistance gene, and cloned into pOJ260 to yield pBS1019. The latter was introduced into *S. globisporus* by conjugation (Liu and Shen (2000) *Antimicrobiol. Agents Chemother.* 44: 382) and selected first for both erythromycin and apramycin resistance and then for the loss of apramycin resistance to isolate the *S. globisporus* SB1005 mutant strain whose genotype was confirmed by Southern analysis. To complement the sgcE mutation in SB1005, a 450-bp ErmE* fragment and a 6.2-kb sgcE fragment were cloned into pKC1139 to yield pBS1005, which was introduced into SB1005 by conjugation as described (Id.).

The resultant *S. globisporus* SB1005 mutant strain completely loses its ability to produce 1 (FIG. 15, panel B), and this phenotype can be complemented by introduction of pBS1019, in which the expression of sgcE is under the control of the constitutive ermE* promoter, into SB1005, restoring 1 production to a level comparable to the wild-type organism (FIG. 15, panel C). These findings unambiguously established that C-1027 enediyne core biosynthesis proceeds via a polyketide pathway.

Remarkably, the SgcE enediyne PKS exhibits head-to-tail sequence homology (56% identity and 67% similarity) with an identical domain organization to the CalE8 enediyne PKS that catalyzes the biosynthesis of the ten-membered enediyne core of 2 in *Micromonospora echinospora* (FIG. 13A). These results suggest that the nine- and ten-membered enediyne cores share a common polyketide pathway. Very recently, type I PKSs acting iteratively to synthesize polyunsaturated polyketides from acetyl and malonyl CoAs have been reported, such as the LNKS and LDKS enzymes that catalyze lovastatin biosynthesis in fungus *Aspergillus terreus* (Kennedy et al. (1999) *Science* 284: 1368) and the putative PKS enzymes that catalyze polyunsaturated fatty acid biosynthesis in the marine bacterium Shewanella and marine protist Schizochytrium (Metz et al. (2001) *Science* 293: 290). However, the enediyne PKSs as a family are apparently distinct in both structure and mechanism from any bacterial PKSs known to date.

The availability of the gene cluster has now set the stage to investigate the molecular basis for C-1027 biosynthesis and to engineer novel enediyne compounds by manipulating C-1027 biosynthesis genes. Thus, the seven deoxy aminosugar biosynthesis genes encode a TDP-glucose synthetase (SgcA1), a TDP-glucose 4,6-dehydratase (SgcA), a TDP-4-keto-6-deoxyglucose epimerase (SgcA2), a C-methyl transferase (SgcA3), an amino transferase (SgcA4), an N-methyl transferase (SgcA5), and a glycosyl transferase (SgcA6). Together, they are in an exact agreement with the enzyme functions that would be required for the biosynthesis of 6 from glucose-1-phosphate (FIG. 14B) and the attachment of 6 to 5 (FIG. 14A). This hypothesis was validated experimentally by inactivating sgcA (12), and the resultant *S. globisporus* SB1001 mutant strain completely loses its ability to produce 1 (FIG. 15, panel D). The six β-amino acid biosynthesis genes encode a phenol hydroxylase (SgcC), a nonribosomal peptide synthetase (NRPS) adenylation enzyme (SgcC1), an NRPS peptidyl carrier protein (PCP) (SgcC2), a halogenase (SgcC3), an aminomutase (SgcC4), and an NRPS condensation enzyme (SgcC5). These enzyme functions agree well with the proposed biosynthetic pathway for 7 from tyrosine (FIG. 14C), which is apparently activated as aminoacyl-S-PCP for its attachment to 5 by SgcC5 (FIG. 14A). Although the precise timing of each reaction in the proposed pathway remains unknown, i.e., the substrate for any of these reactions could be a free amino acid or aminoacyl-S-PCP, sequence analysis of SgcC1 suggests that it activates an α-amino acid (Stachelhaus et al. (1999) *Chem. Biol.* 6: 493; Challis et al. (2000) *Chem. Biol.* 7: 211). The latter prediction is consistent with the recent finding that covalent tethering of an amino acid as aminoacyl-S-PCP for modification is a general strategy to sequester, and thus divert, a fraction of the amino acid into secondary metabolism (29). Indeed, inactivation of sgcC1 resulted in the isolation of the *S. globisporus* SB1003 mutant strain (14) that completely loses its ability to produce 1 (FIG. 15, panel E). The seven benzoxazolinate biosynthesis genes encode the anthranilate synthase I and II subunits (SgcD and SgcD1), a monoxygenases (SgcD2), a P-450 hydroxylase (SgcD3), an O-methyl transferase (SgcD4), a coenzyme A (CoA) ligase (SgcD5), and an acyltransferase (SgcD6). These enzyme functions support the hypothesis that the biosynthesis of 8 starts from anthranilate, a commonly available intermediate from the shikimate pathway (FIG. 14D). The co-localization of SgcD and SgcD1 along with the rest C-1027 production genes assures the availability of anthranilate for secondary metabolite biosynthesis. Although it remains unclear what the origin of the $C_3$ unit is and how it is fused to the anthranilate intermediate to form the morpholinone moiety of 8, the latter is apparently activated as acyl-S-CoA for its attachement to 5 by SgcD6 (FIG. 14A). We inactivated sgcD6 to experimentally support this hypothesis (14), and the resultant *S. globisporus* SB1004 mutant strain completely loses its ability to produce 1 (FIG. 15, panel F). The fact that the biosynthetic building blocks are activated as aminoacy-S-ACP, acyl-S-CoA, and nucleotide diphosphosugar, and attached to the enediyne core by an NRPS condensation enzyme, an acyltransferase, and a glycosyl transferase, respectively, highlights once again nature's efficiency and versatility in synthesizing complex molecules.

Finally we inactivated the sgcC hydroxylase gene to demonstrate the production of novel enediyne metabolites by manipulating genes governing C-1027 biosynthesis (as described above). The resulting *S. globisporus* SB1006 mutant strain still produces a chromoprotein that is biologically active as judged by bioassay against *M. luteus* but is distinct from 1 upon HPLC analysis (FIG. 15, panel G). The new compounds were isolated as described above and subjected to ESI-MS analysis: 3 exhibited a (M+H)⁺ ion at m/z=828, consistent with the molecular formula of $C_{43}H_{42}N_3O_{12}Cl$, and 9 showed a (M+H)⁺ ion at m/z=830, consistent with the molecular formula of $C_{43}H44N_3O_{12}Cl$. By comparison with 1, the new compounds were deduced to be deshydroxy-C-1027 (3) and its aromatized product (9), as would be predicted according to FIG. 14C. Intriguingly, 3 is at least 5-fold more stable than 1 at 25° C. in respect to undergoing the Bergman cyclization, a property that could be potentially explored in developing C-1027 into a clinically useful drug. We envisage applying methods of combinatorial biosynthesis to the enediyne system for the production of novel polyketides.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated gene cluster comprising open reading frames encoding polypeptides sufficient to direct the assembly of a C-1027 enediyne, wherein said gene cluster comprises a sequence that encodes the proteins encoded by the nucleic acid of SEO ID NO: 1.

2. The gene cluster of claim 1, wherein one or more open reading frames is operatively linked to a heterologaus promoter.

3. An isolated gene cluster comprising open reading frames encoding polypeptides sufficient to direct the assembly of a C-1027 enediyne analogues, wherein said gene cluster comprises a sequence that encodes the proteins encoded by the nucleic acid of SEQ ID NO: 1, and wherein one or more genes selected from the group consisting of sgcN (nucleotides 51420 to 52341 of SEQ ID NO: 1), sgcD4 (nucleotides 46167 to 47171 of SEQ ID NO: 1), sgcC3 (nucleotide 12835 12835 to 11351 of SEQ ID NO: 1) and sgcC (nucleotides 32809 to 34392 of SEQ ID NO: 1) are inactivated.

4. The gene cluster of claim 3, wherein one or more open reading frames is linked to a heterologous promoter.

5. A bacterial host cell comprising the gene cluster of any one of claim 1, 2, 3, or 4.

6. A bacterial host cell comprising the gene cluster of any one of claim 1, 2, 3, or 4 wherein said bacterial host cell is selected from the group consisting of Actinomadura, Micromonospora, and Streptomyces.

7. A bacterial host cell comprising the gene cluster of any one of claim 1, 2, 3, or 4 wherein said bacterial host cell is selected from the group consisting Streptomyces globisporus, Streptomyces lividans, Streptomyces coeticolor, Micromonospora echinospora, Actinomadura verrucosospora, Micromonospora chersina, and Streptomyces carzinostaricus.

* * * * *